(12) United States Patent
Almassy et al.

(10) Patent No.: US 12,344,645 B2
(45) Date of Patent: Jul. 1, 2025

(54) PROTEIN CONJUGATES

(71) Applicant: Polaris Group, Grand Cayman, Grand Cayman (KY)

(72) Inventors: Robert J. Almassy, Vista, CA (US); Elena Brin, San Diego, CA (US); Richard E. Showalter, El Cajon, CA (US); James A. Thomson, San Diego, CA (US)

(73) Assignee: POLARIS GROUP, Grand Cayman (KY)

( * ) Notice: Subject to any disclaimer, the term of this patent is extended or adjusted under 35 U.S.C. 154(b) by 469 days.

(21) Appl. No.: 15/940,626

(22) Filed: Mar. 29, 2018

(65) Prior Publication Data

US 2018/0296690 A1    Oct. 18, 2018

Related U.S. Application Data

(60) Provisional application No. 62/478,398, filed on Mar. 29, 2017.

(51) Int. Cl.
| | | |
|---|---|---|
| C07K 14/525 | (2006.01) | |
| A61K 38/17 | (2006.01) | |
| A61K 38/50 | (2006.01) | |
| A61K 47/60 | (2017.01) | |
| A61K 47/64 | (2017.01) | |
| A61K 47/68 | (2017.01) | |
| A61P 35/00 | (2006.01) | |
| C07K 14/705 | (2006.01) | |
| C12N 9/78 | (2006.01) | |

(52) U.S. Cl.
CPC ........ *C07K 14/525* (2013.01); *A61K 38/1761* (2013.01); *A61K 38/50* (2013.01); *A61K 47/60* (2017.08); *A61K 47/642* (2017.08); *A61K 47/6815* (2017.08); *A61P 35/00* (2018.01); *C07K 14/70575* (2013.01); *C12N 9/78* (2013.01); *C12Y 305/03006* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 4,671,958 A | 6/1987 | Rodwell et al. |
| 4,751,180 A | 6/1988 | Cousens et al. |
| 4,873,192 A | 10/1989 | Kunkel |
| 4,904,584 A | 2/1990 | Shaw |
| 4,935,233 A | 6/1990 | Bell et al. |
| 5,428,128 A | 6/1995 | Mensi-Fattohi et al. |
| 5,621,039 A | 4/1997 | Hallahan et al. |
| 5,622,986 A | 4/1997 | Greenwald et al. |
| 5,643,575 A | 7/1997 | Martinez et al. |
| 5,728,560 A | 3/1998 | Shorr et al. |
| 5,730,990 A | 3/1998 | Greenwald et al. |
| 5,738,846 A | 4/1998 | Greenwald et al. |
| 5,811,076 A | 9/1998 | Brasch et al. |
| 5,824,701 A | 10/1998 | Greenwald et al. |
| 5,840,900 A | 11/1998 | Greenwald et al. |
| 5,880,131 A | 3/1999 | Greenwald et al. |
| 5,900,402 A | 5/1999 | Shorr |
| 5,902,588 A | 5/1999 | Greenwald et al. |
| 5,919,455 A | 7/1999 | Greenwald et al. |
| 5,951,974 A | 9/1999 | Gilbert et al. |
| 5,965,119 A | 10/1999 | Greenwald et al. |
| 5,965,566 A | 10/1999 | Greenwald et al. |
| 5,969,040 A | 10/1999 | Hallahan et al. |
| 5,981,709 A | 11/1999 | Greenwald et al. |
| 6,011,042 A | 1/2000 | Greenwald et al. |
| 6,042,822 A | 3/2000 | Gilbert et al. |
| 6,113,906 A | 9/2000 | Greenwald et al. |
| 6,127,355 A | 10/2000 | Greenwald et al. |
| 6,132,713 A | 10/2000 | Fiipula et al. |
| 6,177,087 B1 | 1/2001 | Greenwald et al. |
| 6,180,095 B1 | 1/2001 | Greenwald et al. |
| 6,448,369 B1 | 9/2002 | Bentley et al. |
| 6,495,659 B2 | 12/2002 | Bentley et al. |
| 6,602,498 B2 | 8/2003 | Shen |
| 6,828,401 B2 | 12/2004 | Nho et al. |
| 6,858,736 B2 | 2/2005 | Nho et al. |
| 7,026,440 B2 | 4/2006 | Bentley et al. |
| 7,029,872 B2 | 4/2006 | Gerngross |
| 7,230,068 B2 | 6/2007 | Wilson |

(Continued)

FOREIGN PATENT DOCUMENTS

| | | |
|---|---|---|
| EP | 0425235 A2 | 5/1991 |
| WO | 2012143477 A2 | 10/2012 |
| WO | WO2014/151982 | * 9/2014 |

OTHER PUBLICATIONS

Chen, X., et al. Fusion protein linkers: Property, design, and functionality. Adv. Drug Deliv. Rev., 2013, 65(10):1357-1369.*
Wangpaichitr, M., et al. Combination of arginine deprivation with Trail treatment as a targeted-therapy for mesothelioma. Anticancer Research, 2014, 34:6991-7000.*
You, M., etl al. Trail induces autophagic protein cleavage through caspase activation in melanoma cell lines under arginine deprivation. Mol. Cell. Biochem., 2013, 374(0):181-190.*
Skolnick et al (Trends Biotechnol. Jan. 2000;18(1):34-9) (Year: 2000).*
Burgess et al. (J. Cell Biol. 111:2129-2138, 1990) (Year: 1990).*
Miosge (Proc Natl Acad Sci U S A. Sep. 15, 2015;112(37):E5189-98) (Year: 2015).*

(Continued)

*Primary Examiner* — Brian Gangle
*Assistant Examiner* — Andrea K McCollum
(74) *Attorney, Agent, or Firm* — Carter, DeLuca & Farrell LLP; George Likourezos

(57) ABSTRACT

Provided are conjugates of an arginine deiminase (ADI) and a Tumor Necrosis Factor (TNF) superfamily ligand, and related compositions and methods of use thereof. Also provided are conjugates of a hexameric polypeptide and a trimeric polypeptide, conjugates of a first and second trimeric polypeptide, and related compositions and methods of use thereof.

20 Claims, 22 Drawing Sheets

Specification includes a Sequence Listing.

(56) References Cited

U.S. PATENT DOCUMENTS

| | | | |
|---|---|---|---|
| 7,326,681 | B2 | 2/2008 | Gerngross |
| 7,608,678 | B2 | 10/2009 | Harris et al. |
| 7,629,163 | B2 | 12/2009 | Gerngross |
| 7,632,924 | B2 | 12/2009 | Cho et al. |
| 7,638,299 | B2 | 12/2009 | Cho et al. |
| 7,655,747 | B2 | 2/2010 | Harris |
| 7,736,872 | B2 | 6/2010 | Paulsel et al. |
| 7,737,226 | B2 | 6/2010 | Wilson |
| 7,786,221 | B2 | 8/2010 | Harris et al. |
| 7,816,320 | B2 | 10/2010 | Hays et al. |
| 7,820,766 | B2 | 10/2010 | Wilson |
| 7,829,310 | B2 | 11/2010 | Paulsel et al. |
| 7,838,265 | B2 | 11/2010 | Paulsel et al. |
| 7,872,072 | B2 | 1/2011 | Bentley et al. |
| 7,883,866 | B2 | 2/2011 | Paulsel et al. |
| 7,910,661 | B2 | 3/2011 | Kozlowski et al. |
| 7,939,496 | B2 | 5/2011 | Cho et al. |
| 7,947,473 | B2 | 5/2011 | Buechler et al. |
| 2012/0165267 | A1 | 6/2012 | Kelley et al. |
| 2013/0165383 | A1 | 6/2013 | Kelley et al. |
| 2014/0031283 | A1* | 1/2014 | Pieczykolan ........ C07K 14/435 514/7.6 |
| 2016/0074487 | A1 | 3/2016 | Showalter et al. |
| 2017/0000862 | A1 | 1/2017 | Wu et al. |

OTHER PUBLICATIONS

Lazar et al. (Mol. Cell. Biol., 8:1247-1252, 1988) (Year: 1988).*
Bork (Genome Research, 2000,10:398-400) (Year: 2000).*
Kulmanov et al (Bioinformatics, 34(4), 2018, 660-668) (Year: 2018).*
Chu et al (Int. J. Mol. Sci. 2023, 24(13), 10668) (Year: 2023).*
You et al (Biochem Biophys Res Commun. Apr. 9, 2010; 394(3): 760-766) (Year: 2010).*
Penny et al (Chem. Soc. Rev., 2015, 44, 8836) (Year: 2015).*
Shankar et al (Front. Pharmacol. 12:809308) (Year: 2022).*
Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042 (Year: 1997).*
HogenEsch et al (J Control Release. Dec. 10, 2012; 164(2): 183-186.) (Year: 2012).*
Jain RK (Scientific American, Jul. 1994,58-65) (Year: 1994).*
George et al., "An analysis of protein domain linkers: their classification and role in protein folding," Protein Engineering, (2003), vol. 15, No. 11, pp. 871-879.
Head et al., "Crystal Structure of Trimeric Carbohydrate Recognition and Neck Domains of Surfactant Protein A," The Journal of Biological Chemistry, Oct. 31, 2003, vol. 278, No. 44; pp. 43254-43260.
Desjarlais et al., "Use of a zinc-finger consensus sequence framework and specificity rules to design specific DNA binding proteins," Proc. Natl. Acad. Sci. USA, Mar. 1993, vol. 90; pp. 2256-2260.
Desjarlais et al., "Length-encoded multiplex binding site determination: Application to zinc finger proteins," Proc. Natl. Acad. Sci. USA, Nov. 1994, vol. 91; pp. 11099-11103.
Kunkel, "Rapid and efficient site-specific mutagenesis without phenotypic selection," Proc. Natl. Acad. Sci., USA, Jan. 1985, vol. 82; pp. 488-492.
Kunkel et al., "[19] Rapid and Efficient Site-Specific Mutagenesis without Phenotypic Selection," Methods in Enzymology, (1987), vol. 154; pp. 367-382.
Arkin et al., "An algorithm for protein engineering: Simulations of recursive ensemble mutagenesis," Proc. Natl. Acad. Sci. USA, Aug. 1992, vol. 89; pp. 7811-7815.
Doherty et al., "Site-Specific PEGylation of Engineered Cysteine Analogues of Recombinant Human Granulocyte-Macrophage Colony-Stimulating Factor," Bioconjugate Chem., 2005, vol. 16, Issue 5; pp. 1291-1298.

Zucker, "Mfold web server for nucleic acid folding and hybridization prediction," Nucleic Acids Research, 2003, vol. 31, No. 13; pp. 3406-3415.
Kozak, "Adherence to the first-AUG rule when a second AUG codon follows closely upon the first," Proc. Natl. Acad. Sci. USA, Mar. 1995, vol. 92; pp. 2662-2666.
Structural Genomics Consortium et al., "Protein production and purification," Nature Methods, Feb. 2008, vol. 5, No. 2; pp. 135-146.
Hamilton et al., "Production of Complex Human Glycoproteins in Yeast", Science, Aug. 29, 2003, vol. 301; Issue 5637; pp. 1244-1246.
Hamilton et al., "Humanization of Yeast to Produce Complex Terminally Sialylated Glycoproteins" Science, Sep. 8, 2008, vol. 313, Issue 5792; pp. 1441-1443.
Takamatsu, et al., "Expression of bacterial chloramphenicol acetyltransferase gene in tobacco plants mediated by TMV-RNA," The EMBO Journal, 1987, vol. 6, No. 2, pp. 307-311.
Coruzzi et al., "Tissue-specific and light-regulated expression of a pea nuclear gene encoding the small subunit of ribulose-1,5-bisphosphate carboxylase," The EMBO Journal, 1984, vol. 3, No. 8; pp. 1671-1679.
Kolb et al., "Click Chemistry: Diverse Chemical Function from a Few Good Reactions," Angew. Chem. Int. Ed., 2001, vol. 40; pp. 2004-2021.
Hein et al., "Click Chemistry, a Powerful Tool for Pharmaceutical Sciences," Pharm Res., Oct. 2008, vol. 25, No. 10; pp. 2216-2230.
Henikoff et al., "Amino acid substitution matrices from protein blocks," Proc. Natl. Acad. Sci. USA, Nov. 1992, vol. 89; pp. 10915-10919.
Murphy et al., "Genetic construction, expression, and melanoma-selective cytotoxicity of a diphtheria toxin-related alpha-melanocyte-stimulating hormone fusion proten," Proc. Natl. Acad. Sci. UA, Nov. 1986, vol. 83; pp. 8258-8262.
Engelhard et al., "The insect tracheal system: A conduit for the systemic spread of Autographa californica M nuclear polyhedrosis virus," Proc. Natl. Acad. Sci. USA, Apr. 1994, vol. 91; pp. 3224-3227.
Logan et al., "Adenovirus tripartite leader sequence enhances translation of mRNAs late after infection," Proc. Natl. Acad. Sci. USA, Jun. 1984, vol. 81; pp. 3655-3659.
Mather, "Establishment and Characterization of Two Distinct Mouse Testicular Epithelial Cell Lines," Biology of Reproduction, 1980, vol. 23; pp. 243-252.
Graham et al., "Characteristics of a Human Cell Line Transformed by DNA from Human Adenovirus Type 5," J. Gen Viral., (1977), vol. 36; pp. 59-74.
Urlaub et al., "Isolation of Chinese hamster cell mutants deficient in dihydrofolate reductase activity," Proc. Natl. Acad. Sci. USA, Jul. 1980, vol. 77, No. 7; pp. 4216-4220.
Chari et al., "Immunoconjugates Containing Novel Maytansinoids: Promising Anticancer Drugs," Cancer Research, Jan. 1, 1992, vol. 52; pp. 127-131.
European Search Report dated Dec. 21, 2020, corresponding to counterpart European Application No. 18776452.7; 11 pages.
Han et al., "Arginine deiminase: recent advances in discovery, crystal structure, and protein engineering for improved properties as an anti-tumor drug," Appl. Microbiol. Biotechnol (2016), vol. 100; pp. 4747-4760.
Brin et al., "Abstract 3902: A novel biolotic ADI-Trail fusion proten benefits from structural and functional complementarity of its components arginine deiminase and Trail, induces cancer cell apoptosis in vitro, and inhibits tumor growth in vivo," Cancer Research, Jul. 2018, vol. 78, Issue 13 Supplement, 4 pages.
Brin et al., "Trail stabilization and cancer cell sensitization to its proapoptotic activity achieved through genetic fusion with arginine deiminase," Oncotarget, 2018, vol. 9, No. 97; pp. 36914-36928.
Wajant, "Molecular Mode of Action of Trail Receptor Agonists—Common Principles and Their Translational Exploitation," Cancers, 2019, vol. 11, 954; 26 pages.
Broglie et al., "Light-regulated expression of a pea ribulose-1,5-bisphosphate carboxylase small subunit gene in transformed plant cells," Science, (1984), vol. 224, Issue 4648; pp. 838-843.

(56) References Cited

OTHER PUBLICATIONS

Myers et al., "Optimal Alignments in Linear Space," Cabios, vol. 4, No. 1, 1988; pp. 11-17.
Weis et al., "Trimeric Structure of a C-type Mannose-Binding Protein," Structure, vol. 2, No. 12, Dec. 15, 1994; pp. 1227-1240.
Knipp et al., "A Colorimetric 96-Well Microtiter Plate Assay for the Determination of Enzymatically Formed Citrulline1," Analytical Biochemistry, vol. 286, Issue 2, Nov. 15, 2000; pp. 257-264.
Delagrave et al.,. ,"Recursive Ensemble Mutagenesis," Protein Engineering, vol. 6, No. 3, Apr. 1993; pp. 327-331.
De Graaf et al., "Nonnatural Amino Acids for Site-Specific Protein Conjugation," Bioconjugate Chemistry, vol. 20, No. 7, Jul. 2009; pp. 1281-1295.
Kameda et al., "A severed de novo methylation of episomal vectors by human ES cells," ScienceDirect, ElSevier, Biochemical and Biophysical Research Communications, vol. 349, No. 4, Nov. 3, 2006; pp. 1269-1277.
Needham et al. "Further Development of the Locus Control Region/ Murine Erythroleukemia Expression System: High Level Expression and Characterization of Recombinant Human Calcitonin Receptor," Protein Expr Purif, vol. 6, No. 2, Apr. 1995; pp. 124-131.
Shimp et al., "Production and characterization of clinical grade *Escherichia coli* derived Plasmodium falciparum 42 kDa merozoite surface protein 1 (MSP1(42)) in the absence of an affinity tag ," Protein Expr Purif., vol. 50, No. 1, Nov. 2006; pp. 58-67.
Qing et al., "Cold-shock induced high-yield protein production in *Escherichia coli*," Nature Biotechnology, vol. 22, No. 7, Jul. 2004; pp. 877-882.
Bitter et al., "[33] Expression and secretion vectors for yeast," Methods of Enzymology, vol. 153, (1987); pp. 516-544.
Li et al., "Optimization of humanized IgGs in glycoengineered Pichia pastoris," Nature Biotechnology, Feb. 2006, vol. 24, No. 2; pp. 210-215.
Wildt et al., "The humanization of N-glycosylation pathways in yeast", Nature Reviews Microbial, Feb. 2005, vol. 3; pp. 119-128.
Gemgross, "Advances in the production of human therapeutic proteins in yeasts and filamentous fungi," Nature-Biotechnology, Nov. 4, 2004, vol. 22, No. 11; pp. 1409-1414.
Murphy et al., "Overview of the Baculovirus Expression System," Current Protocols in Protein Science (1995), Chapter 5: Unit 5.4; 5 pages.
Winter et al., "The Expression of Heat Shock Protein and Cognate Genes During Plant Development. Results," Heat Shock and Development, 1991, vol. 17; pp. 85-105.
Yazaki et al., "Expression of Recombinant Antibodies in Mammalian Cell Lines," Methods in Molecular Biology, (2003), vol. 248; pp. 255-268.
Himo et al., "Copper(I)-Catalyzed Synthesis of Azoles. DFT Study Predicts Unprecedented Reactivity and Intermediates," J Am Chem Soc., 2005, vol. 127, No. 1; pp. 210-216.
Rausmussen et al., "Ruthenium-Catalyzed Cycloaddition of Aryl Azides and Alkynes," Organic Letters, (2007), vol. 9, No. 26; pp. 5337-5339.
Needleman et al., "A General Method Applicable to the Search for Similarities in the Amino Acid Sequence of Two Proteins," Journal of Molecular Biology, Mar. 28, 1970, vol. 48, Issue 3; pp. 443-453.
Brinkley "A Brief Survey of Methods for Preparing Protein Conjugates with Dyes, Haptens, and Crosslinking Reagents," Bioconjugate Chem., vol. 3, No. 1, (1992); pp. 2-13.
"Transcription and Translation—A Practical Approach," (B. Hames & S. Higgins, eds., 1984), Biochemical Education, vol. 13, No. 2, 1985; p. 328 (Abstract).
Freshney, Animal Cell Culture: A Practical Approach, 1986; p. 248 (Abstract).
J.M. Harris, "Poly(Ethylene Glycol) Chemistry," Biotechnical and Biomedical Applications, (1992); 1 page.
Kyte, et al., "A Simple Method for Displaying the Hydropathic Character of a Protein," J. Mol. Biol., 1982, vol. 157; pp. 105-132.
Maratea et al., "Deletion and fusion analysis of the phage ØX174 lysis gene E," Gene, 1985, vol. 40, Issue 1; pp. 39-49.
Mather et al., "Culture of Testicular Cells in Hormone-Supplemented Serum-Free Medium," Testicular Cell Culture, Annals New York Academy of Sciences, (1982), vol. 383; pp. 44-68.
Zalipsky et al., "Use of Functionalized Poly(Ethylene Glycol)s for Modification of Polypeptides, " Polyethylene Glycol Chemistry, 1992, pp. 347-370.
Zalipsky, "Chemistry of polyethylene glycol conjugates with biologically active molecules", Advanced Drug Delivery Reviews, Sep. 1995, vol. 16, Issue 2-3; pp. 157-182.
Roberts et al., "Chemistry for peptide and protein PEGylation," Adv. Drug Delivery Reviews, Jun. 17, 2002, vol. 54; pp. 459-476.
Qiu et al., "Targeting arginine metabolism pathway to treat arginine-dependent cancers," Cancer Lett., Aug. 1, 2015, vol. 364, No. 1; pp. 1-7.
Feun et al., "Arginine deprivation in cancer therapy," Current Opinion in Clinical Nutrition and Metabolic Care, Jan. 2015, vol. 18, Issue 1; pp. 78-82.
Palacios et al., "The Long and Winding Road to Cancer Treatment: The Trail System," Current Pharmaceutical Design, May 11, 2014, vol. 20, Issue 17; pp. 2819-2833.
Letarov et al., "The Carboxy-Terminal Domain Initiates Trimerization of Bacteriophage T4 Fibritin," Biochemistry (Moscow), Aug. 1999, vol. 64, No. 7; pp. 817-823.
Veronese et al., "Introduction and overview of peptide and protein pegylation," Advanced Drug Delivery Reviews, vol. 54, No. 4, (2002), pp. 453-456.
Taiwanese Search Report issued Apr. 16, 2022, corresponding to counterpart Taiwanese Application No. 107111070; 1 page.
Hobbs in McGraw Hill, Yearbook of Science and Technology, pp. 191-196, 1992.
Nakamura et al., "Codon usage tabulated from international DNA sequrnce databases: status for the year 2000," Nucleic Acids Research, 2000, vol. 28, No. 1; p. 292.
Altschul et al., "Gapped BLAST and PSI-BLAST: a new generation of protein database search programs," Nucleic Acids Research, 1997, vol. 25, No. 17; pp. 3389-3402.
Altschul et al. "Basic Local Alignment Search Tool," J. Mol. Biol., 1990, vol. 215; pp. 403-410.
European Communication from related case 18776452.7, Nov. 7, 2022, 5 pages.
You, Min, et al., "The combination of ADI-PEG20 and Trail effectively increases cell death in melanoma cell lines," Biochemical and biophysical research communications, Apr. 2010, pp. 760-766, 394.3.
Shin, Jin Na, et al., "Generation of a novel proform of tumor necrosis factor-related apoptosis-inducing ligand (Trail) protein that can be reactivated by matrix metalloproteinases," Experimental cell research, Nov. 2006, pp. 3892-3898, 312.19.
English Translation of Chinese Office Action for related application No. 201880021161.5, Nov. 24, 2022, 14 pages.
English translation of Decision issued in related Taiwanese application No. 107111070, Apr. 17, 2023, 9 pages.
English Translation of Chinese Office Action from application No. 201880021161.5, Aug. 16, 2023, 7 pages.
English Translation of Chinese Office Action from application No. 201880021161.5, Dec. 14, 2023, 11 pages.

* cited by examiner

PROTEIN CONJUGATES

CROSS-REFERENCE TO RELATED APPLICATIONS

This application claims priority under 35 U.S.C. § 119(e) to U.S. Provisional Application No. 62/478,398, filed Mar. 29, 2017, which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is TDWG_007_01US_ST25.txt. The text file is about 251 KB, was created on Mar. 28, 2018 and is being submitted electronically via EFS-Web

BACKGROUND

Technical Field

The present disclosure relates in part to conjugates of an arginine deiminase (ADI) and a Tumor Necrosis Factor (TNF) superfamily ligand, and related compositions and methods of use thereof. The present disclosure also relates to conjugates of a hexameric polypeptide and a trimeric polypeptide, conjugates of a first and second trimeric polypeptide, and related compositions and methods of use thereof.

Description of the Related Art

Arginine depletion therapy can be an effective treatment of certain forms of cancer, among other diseases. For instance, arginine deiminase can be used to deplete the bloodstream supply of arginine by converting it to citrulline and ammonia. ADI-PEG 20 is an exemplary ADI-PEG that is being investigated in the clinic for tumors deficient in the key enzyme argininosuccinate synthetase-1 (ASS1), which is involved in the conversion of citrulline to arginine. ADI-PEG 20 has been well-tolerated and showed promise in clinical studies (see, e.g., Qiu et al., Cancer Lett. 2015 Aug. 1; 364(1):1-7; Phillips et al., Cancer Res Treat. 2013 December; 45(4):251-62; Feun et al., Curr Pharm Des. 2008; 14(11):1049-57; Feun and Savaraj, Expert Opin Investig Drugs. 2006 July; 15(7):815-22; Feun et al., Curr Opin Clin Nutr Metab Care. 2015 January; 18(1):78-82).

Activation of cell surface death receptors of the tumor necrosis factor (TNF) receptor superfamily by the appropriate ligands represents an attractive therapeutic strategy to induce cell death by apoptosis in cancer cells (see, e.g., Palacios et al., Curr Pharm Des. 2014; 20(17):2819-33). As one example, TNF-related apoptosis-inducing ligand (TRAIL, also known as Apo2L) possesses the ability to induce apoptosis selectively in cancer cells, and has demonstrated robust anticancer activity in a number of preclinical studies.

However, there remains a need to optimize the pharmacokinetics and/or biological activities of these and other agents. The present disclosure provides these benefits and others.

BRIEF SUMMARY

Embodiments of the present disclosure include conjugates, comprising an arginine deiminase (ADI) that is covalently linked to a Tumor Necrosis Factor (TNF) superfamily ligand.

In some embodiments, the ADI comprises, consists, or consists essentially of an amino acid sequence that is at least 90%, 95%, 96%, 97%, 98%, or 99% identical to a sequence selected from Table A1. In some embodiments, the ADI is a hexameric ADI polypeptide, for example, a homohexameric polypeptide. In some embodiments, the hexameric or homohexameric ADI comprises, consists, or consists essentially of an amino acid sequence that is at least 90%, 95%, 96%, 97%, 98%, or 99% identical to SEQ ID NO: 9, 37, 38, 50, or 57-68.

In some embodiments, the TNF superfamily ligand is selected from Table T1. In some embodiments, the superfamily ligand is selected from TNF-related apoptosis-inducing ligand (TRAIL), TNF-α, and FasL. In some embodiments, the TNF superfamily ligand comprises, consists, or consists essentially of an amino acid sequence that is at least 90%, 95%, 96%, 97%, 98%, or 99% identical to a sequence selected from Table T2. In some embodiments, the TNF superfamily ligand is a trimeric or homotrimeric polypeptide.

In some embodiments, the ADI and the TNF superfamily ligand are separated by a linker, optionally a physiologically-stable linker. In some embodiments, the linker is a peptide linker, optionally a flexible peptide linker or a rigid peptide linker. In some embodiments, the peptide linker is about 1-100 amino acids, about 1-90 amino acids, about 1-80 amino acids, about 1-70 amino acids, about 1-80 amino acids, about 1-50 amino acids, about 1-40 amino acids, about 1-30 amino acids, about 1-20 amino acids, about 1-10 amino acids, or about 1-5 amino acids in length, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100 amino acids in length. In some embodiments, the peptide linker is selected from Table L1.

In some embodiments, the conjugate is a fusion polypeptide. In some embodiments, the ADI is fused to the N-terminus of the TNF superfamily ligand, optionally separated by a linker. In some embodiments, the ADI is fused to the C-terminus of the TNF superfamily ligand, optionally separated by a linker In some embodiments, the linker is a non-peptide linker.

In some embodiments, the conjugate has improved pharmacokinetic, physical, and/or biological properties relative to the ADI alone and/or the TNF superfamily ligand alone, optionally selected from one or more of increased stability, increased serum half-life, increased bioavailability, increased biological activity, increased exposure, and decreased clearance.

In some embodiments, the conjugate has increased stability and/or serum half-life relative to the ADI alone and/or the TNF superfamily ligand alone, optionally wherein the stability and/or serum half-life relative of the conjugate is increased by about or at least about 10, 20, 30, 40, 50, 60, 70, 80, 90, 100, 200, 300, 400, 500, 600, 700, 800, 900, or 1000% or more relative to the ADI alone and/or the TNF superfamily ligand alone.

In some embodiments, the conjugate has increased biological activity relative to the ADI alone and/or the TNF superfamily ligand alone, optionally wherein the biological activity of the conjugate is increased by about or at least about 10, 20, 30, 40, 50, 60, 70, 80, 90, 100, 200, 300, 400, 500, 600, 700, 800, 900, or 1000% or more relative to the ADI alone and/or the TNF superfamily ligand alone, or optionally wherein the biological activity is increased synergistically relative to the ADI alone and/or the TNF superfamily ligand alone. In some embodiments, the biological activity is induction of cell death or apoptosis in cancer cells, which is optionally increased synergistically relative to the ADI alone and/or the TNF superfamily ligand alone.

In some embodiments, the cancer cells are ADI-sensitive cells, which are optionally selected from one or more of breast cancer cells, hepatocellular carcinoma cells, Burkitt's Lymphoma cells, colon cancer cells, glioblastoma cancer cells, leukemic cells, melanoma cancer cells, non-small lung cell cancer (NSCLC) cells, ovarian cancer cells, pancreatic cancer cells, prostate cancer cells, and renal cancer cells.

In some embodiments, the cancer cells are ADI-non-sensitive cells, which are optionally selected from one or more of breast cancer cells, colon cancer cells, and NSCLC cells.

In some embodiments, the ADI increases the ability of the TNF superfamily ligand to induce cell death or apoptosis in cancer cells, optionally by about at least about 10, 20, 30, 40, 50, 60, 70, 80, 90, 100, 200, 300, 400, 500, 600, 700, 800, 900, or 1000% relative to the TNF superfamily ligand alone.

In some embodiments, the ADI upregulates expression of Death Receptor 5 (DR5) on the cancer cells.

In some embodiments, the ADI polypeptide is covalently bonded via a linking group to at least one polyethylene glycol (PEG) molecule, optionally wherein the TNF superfamily ligand is not covalently bonded to a PEG molecule.

Also included are conjugates, comprising (a) a hexameric polypeptide that is covalently linked to a trimeric polypeptide, or (b) a first trimeric polypeptide that is covalently linked to a second trimeric polypeptide which differs from the first trimeric polypeptide.

In some embodiments, the hexameric polypeptide is a homohexameric polypeptide. In some embodiments, the hexameric polypeptide is selected from an arginine deiminase, optionally as described herein, and adiponectin or a collagen-like domain thereof.

In some embodiments, the trimeric polypeptide is a homotrimeric polypeptide.

In some embodiments, the first trimeric polypeptide of (b) is selected from adiponectin or a collagen-like domain thereof, T4 fibritin or a trimerization domain thereof (foldon), C-propeptide of collagen, surfactant protein A (SP-A), and mannose-binding protein A (MBP-A).

In some embodiments, the trimeric polypeptide of (a) or the second trimeric polypeptide of (b) is selected from a Tumor Necrosis Factor (TNF) superfamily ligand, optionally as described herein. In some embodiments, for (a) the hexameric polypeptide of is covalently linked to the N-terminus of the trimeric polypeptide, or for (b) the first trimeric polypeptide is covalently linked to the N-terminus of the second trimeric polypeptide. In some embodiments, for (a) the hexameric polypeptide is covalently linked to the C-terminus of the trimeric polypeptide, or wherein for (b) the first trimeric polypeptide is covalently linked to the C-terminus of the second trimeric polypeptide. In some embodiments, for (a) the hexameric polypeptide and the trimeric polypeptide are separated by a linker, or for (b) the first and second trimeric polypeptide are separated by a linker, wherein the linker is optionally a physiologically-stable linker.

In some embodiments, the conjugate is a fusion polypeptide.

In some embodiments, the conjugate has increased physical, pharmacokinetic, and/or biological properties relative to the hexameric and/or trimeric polypeptide alone. In some embodiments, for (a) conjugation to the hexameric polypeptide increases the stability and/or serum half-life of the trimeric polypeptide, optionally by about or at least about 10, 20, 30, 40, 50, 60, 70, 80, 90, 100, 200, 300, 400, 500, 600, 700, 800, 900, or 1000% or more relative to the trimeric polypeptide alone, or for (b) conjugation to the first trimeric polypeptide increases the stability and/or serum half-life of the second trimeric polypeptide, optionally by about or at least about 10, 20, 30, 40, 50, 60, 70, 80, 90, 100, 200, 300, 400, 500, 600, 700, 800, 900, or 1000% or more relative to the second trimeric polypeptide alone.

Certain embodiments relate to isolated polynucleotides which encode a conjugate described herein, wherein the conjugate is a fusion protein. Also included are expression vectors that comprises the isolated polynucleotide, and host cells that comprise the isolated polynucleotide or the expression vector.

Also included are therapeutic compositions, comprising a conjugate described herein and a pharmaceutically-acceptable carrier or excipient. In particular embodiments, the conjugate forms a hexameric complex of six ADI-TRAIL and/or TRAIL-ADI conjugates, optionally as fusion proteins (see, for example, FIG. 4). In some embodiments, the conjugate or composition is at least about 95% pure and less than about 5% aggregated, and is substantially endotoxin-free.

Also included are methods of treating, ameliorating the symptoms of, or reducing the progression of a cancer in a subject in need thereof, comprising administering to the subject a conjugate or therapeutic composition as described herein.

In some embodiments, the cancer is selected from one or more of hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

BRIEF DESCRIPTION OF THE DRAWINGS

FIG. 2C), compared to each agent alone in Raji Burkitt's lymphoma cell line.

DETAILED DESCRIPTION

Definitions

Figure 1A:
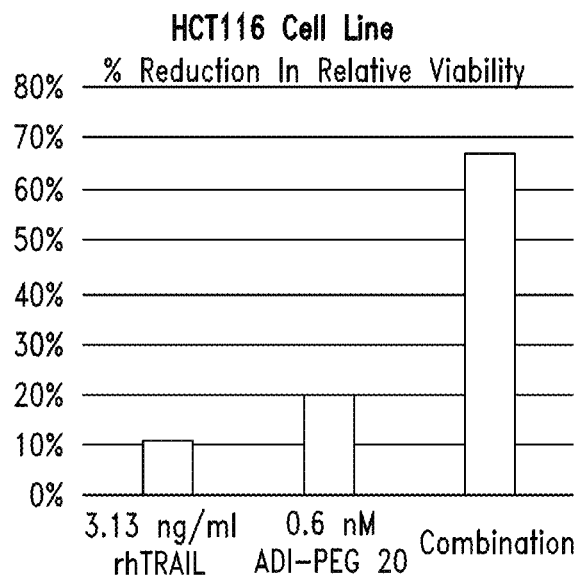
FIGS. 1A-1D illustrate the synergistic effects ADI-PEG 20 and rhTRAIL on the relative viability of various cancer cell lines, compared to each agent alone.

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology or Current Protocols in Immunology*, John Wiley & Sons, New York, N.Y. (2009); Ausubel et al., *Short Protocols in Molecular Biology*, 3rd ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

An "antagonist" refers to biological structure or chemical agent that interferes with or otherwise reduces the physiological action of another agent or molecule. In some instances, the antagonist specifically binds to the other agent or molecule. Included are full and partial antagonists.

An "agonist" refers to biological structure or chemical agent that increases or enhances the physiological action of another agent or molecule. In some instances, the agonist specifically binds to the other agent or molecule. Included are full and partial agonists.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Biocompatible" refers to materials or compounds which are generally not injurious to biological functions and which will not result in any degree of unacceptable toxicity, including allergenic and disease states.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "conjugate" refers to an entity formed as a result of covalent or non-covalent attachment or linkage of at least two separate polypeptides (for example, a first polypeptide and a second polypeptide), as described herein. One example of a conjugate polypeptide is a "fusion protein" or "fusion polypeptide," that is, a polypeptide that is created through the joining of two or more coding sequences, which originally coded for separate polypeptides; translation of the joined coding sequences results in a single, fusion polypeptide, typically with functional properties derived from each of the separate polypeptides.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the Limulus Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The "half-life" of a conjugate or polypeptide can refer to the time it takes for the conjugate or polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a conjugate or polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts, and with respect to ADI is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ADI enzymes/proteins described herein, or sequences that have deletions from, additions to, and/or substitutions of one or more amino acid of the ADI proteins. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, or may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (for example, a conjugate) in a composition may be specifically defined. For instance, certain compositions may comprise a conjugate that is at least 80, 85, 90, 91, 92, 93, 94, 95, 96, 97, 98, 99, or 100% pure, including all decimals and ranges in between, as measured, for example and by no means limiting, by high performance liquid chromatography (HPLC), a well-known form of column chromatography used frequently in biochemistry and analytical chemistry to separate, identify, and quantify compounds. In some instances, the purity of a composition is characterized by the degree of aggregation. For instance, the degree of aggregation of a conjugate (for example, fusion protein) can be determined by Size-exclusion chromatography (SEC), which separates particles on the basis of size. It is a generally accepted method for determining the tertiary structure and quaternary structure of purified proteins. SEC is used primarily for the analysis of large molecules such as proteins or polymers. SEC works by trapping these smaller molecules in the pores of a particle. The larger molecules simply pass by the pores as they are too large to enter the pores. Larger molecules therefore flow through the column quicker than smaller molecules, that is, the smaller the molecule, the longer the retention time. Certain compositions are also substantially free of aggregates (greater than about 95% appearing as a single peak by SEC HPLC). Certain embodiments are free of aggregates with greater than about 96%, about 97%, about 98%, or about 99%, appearing as a single peak by SEC HPLC.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (for example, a conjugate) described herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/mL at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents, for example, conjugates.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied *mutatis mutandis* to every other embodiment unless expressly stated otherwise.

Conjugates

Embodiments of the present disclosure relate in part to the unexpected discovery that conjugation (for example, fusion) of an arginine deiminase (ADI) to a Tumor Necrosis Factor (TNF) superfamily ligand, for example, TRAIL, improves the pharmacokinetics and/or biological activity of the conjugate relative to one or both of the components alone, and in many instances does so synergistically. Also related is the discovery that conjugation of a hexameric or homohexameric polypeptide to a trimeric or homotrimeric polypeptide improves the pharmacokinetics and/or biological activity of the conjugate relative to one or both of the components alone. Also related is the discovery that conjugation of a first trimeric polypeptide to a second trimeric polypeptide (which differs from the first) improves the pharmacokinetics and/or biological activity of the conjugate relative to one or both of the components alone. In some instances, each component of the conjugate potentiates (for example, synergistically potentiates) the pharmacokinetics and/or biological activity of the other component.

Thus, certain embodiments relate to conjugates, comprising an arginine deiminase ADI that is covalently linked to a TNF superfamily ligand (for example, TRAIL), each of which is described in greater detail herein. In some embodiments, the ADI is conjugated to the N-terminus of the TNF superfamily ligand. In some embodiments, the ADI is conjugated to the C-terminus of the TNF superfamily ligand.

Also included are conjugates, comprising (a) a hexameric polypeptide that is covalently linked to a trimeric polypeptide, or (b) a first trimeric polypeptide that is covalently linked to a second trimeric polypeptide which differs from the first trimeric polypeptide. In some instances, the hexameric polypeptide is a homohexameric polypeptide. Examples of the hexameric or homohexameric polypeptide of (a) include, for example, certain ADIs such as the native ADIs from *Mycoplasma columbinum, M. iners, M gallinarum*, and *M. meleagridis* (e.g., SEQ ID NOs: 9, 37, 38, 50, respectively), the chimeric ADIs from Table A1 (e.g., SEQ ID NOs: 57-68), and adiponectin or collagen-like domain thereof, which are described in greater detail herein. Adiponectin is a 244-amino acid protein composed of an amino-terminal signal peptide, a collagen-like domain at the N-terminus, and a globular domain at the C-terminus. Adiponectin self-associates into larger structures, for example, adiponectin molecules bind together via the collagen-like domain to form homotrimers, and in some instances the trimers continue to self-associate and form hexamers.

In some instances, the trimeric polypeptide is a homotrimeric polypeptide. Examples of the first trimeric or homotrimeric polypeptide of (b) include adiponectin or a collagen-like domain thereof, T4 fibritin or a trimerization domain thereof (foldon), C-propeptide of procollagen, surfactant protein A (SP-A), and mannose-binding protein A (MBP-A). As noted above, in some instances adiponectin or the collagen-liked domain thereof self-associates into trimers. Bacteriophage T4 fibritin is a triple-stranded, parallel, segmented alpha-helical coiled-coil protein. The C-terminal globular domain (foldon) of T4 fibritin is essential for correct trimerization and folding of the protein, however foldon is capable of trimerization in the absence of the coiled-coil part of fibritin (see Letarov et al., Biochemistry (Mosc). 64(7):817-23, 1999). The C-propeptides of fibrillar procollagens play crucial roles in tissue growth and repair by controlling both the intracellular assembly of procollagen molecules and the extracellular assembly of collagen fibrils, and are responsible for the selective formation of homotrimers and certain heterotrimers between various procollagens (see, e.g., Bourhis et al., Nat Struct Mol Biol. 19(10):1031-1036, 2012). Surfactant protein A (SP-A), one of four proteins associated with pulmonary surfactant, binds with high affinity to alveolar phospholipid membranes, positioning the protein at the first line of defense against inhaled pathogens. SP-A exhibits both calcium-dependent carbohydrate binding, a characteristic of the collectin family, and specific interactions with lipid membrane components. The carbohydrate recognition domain (CRD) of SP-A forms trimeric structure with the neck domain (see, e.g., J. Biol Chem. 278(44):43254-60, 2003) Mannose-binding proteins (MBPs) are C-type (Ca(2+)-dependent) animal lectins found in serum. They recognize cell-surface oligosaccharide structures characteristic of pathogenic bacteria and fungi, and trigger the neutralization of these organisms. The carbohydrate-recognition domain (CRD) of MBP and the neck domain that links the carboxy-terminal CRD to the collagen-like portion of the intact molecule form trimeric structures (see, e.g., Weis and Drickamer, Structure. 2(12):1227-40, 1994). Thus, any of the foregoing trimeric polypeptides or trimeric fragments/domains thereof can be employed as the first trimeric polypeptide of (b).

In some embodiments, the trimeric or homotrimeric polypeptide of (a), or the second trimeric or homotrimeric polypeptide of (b), is a TNF superfamily ligand or receptor, which are described in greater detail herein.

In some embodiments, for (a) the hexameric polypeptide is covalently linked to the N-terminus of the trimeric polypeptide, or for (b) the first trimeric polypeptide is covalently linked to the N-terminus of the second trimeric polypeptide. In some embodiments, for (a) the hexameric polypeptide is covalently linked to the C-terminus of the trimeric polypeptide, or for (b) the first trimeric polypeptide is covalently linked to the C-terminus of the second trimeric polypeptide.

In some instances, the conjugate is a fusion protein, for example, where the covalent linkage between the two components of the conjugate is composed entirely of peptide bonds. In some instances, the conjugate is a non-fusion protein, for example, where the covalent linkage between the components of the conjugate comprises at least one non-peptide bond, or where the covalent linkage is chemically-reacted after each polypeptide of the conjugate has been separately produced (e.g., recombinantly produced) and optionally purified.

In some embodiments, the conjugate comprises a linker between each component of the conjugate, for example, a physiologically-stable linker. General examples of linkers include peptide linkers (for example, flexible and rigid peptide linkers) and non-peptide linkers. Exemplary linkers are described in greater detail herein.

In some instances, as noted above, at least one component of the conjugate improves one or more properties of the other component of the conjugate, and in some instances, the conjugate does so synergistically. In some instances, each component improves one or more properties of the other component of the conjugate. In some instances, the conjugate has one or more improved properties relative to one or both of the components alone. Exemplary properties include physical and/or pharmacokinetic properties such as protein stability, solubility, serum half-life, bioavailability, exposure, and clearance. Also included are biological properties or activities.

In some instances, the conjugate has increased biological activity relative to one or both components alone. In some instances, the conjugate has an "additive" effect on a biological activity relative to each component alone. "Additivity" refers to increased conjugate activity that is about equal to the combined, additive activity of each component alone. In some instances, the conjugate has a "synergistic" effect on a biological activity relative to each component alone. "Synergy" or "synergism" refers to increased conjugate activity that is greater than the combined, additive activity of each component alone. In some instances, one component of the conjugate "potentiates" the biological activity of the other component (for example, in some instances, ADI potentiates the activity of TRAIL). "Potentiation" refers to increased conjugate activity in instances where only one component is active or significantly active alone. In some instances, there is "coalism" between the components of the conjugate, which refers to conjugate activity in instances where neither component is active by itself.

In specific embodiments, the conjugate comprises an ADI that is covalently linked to a TNF superfamily member ligand (for example, TRAIL, TNF-α, FasL) and the conjugate has improved pharmacokinetic, physical, and/or biological properties relative to the ADI alone and/or the TNF superfamily ligand alone. As noted above, exemplary pharmacokinetic and physical properties include increased stability, increased serum half-life, increased bioavailability, increased exposure, and decreased clearance. In some instances, the conjugate has increased stability and/or serum half-life relative to the ADI alone and/or the TNF superfamily ligand alone. In particular instances, the stability and/or serum half-life of the conjugate is increased by about or at least about 10, 20, 30, 40, 50, 60, 70, 80, 90, 100, 200, 300, 400, 500, 600, 700, 800, 900, or 1000% or more relative to the ADI alone and/or the TNF superfamily ligand alone.

In some instances, the conjugate has increased biological activity relative to the ADI alone and/or the TNF superfamily ligand alone. In particular instances, the biological activity of the conjugate is increased by about or at least about 10, 20, 30, 40, 50, 60, 70, 80, 90, 100, 200, 300, 400, 500, 600, 700, 800, 900, or 1000% or more relative to the ADI alone and/or the TNF superfamily ligand alone. In some instances, the increase in biological activity is a synergistic increase relative to the ADI alone and/or the TNF superfamily ligand alone. In some instances, the increase in biological activity is an additive increase relative to the ADI alone and/or the TNF superfamily ligand alone. In particular embodiments, the biological activity is induction of cell death or apoptosis in cancer cells and/or upregulation of TNF superfamily receptor expression, for example, Death Receptor 5 (DR5). In specific instances, the ADI component of the conjugate increases the ability of the TNF superfamily ligand to induce cell death or apoptosis in cancer cells, for example, by about at least about 10, 20, 30, 40, 50, 60, 70, 80, 90, 100, 200, 300, 400, 500, 600, 700, 800, 900, or 1000% relative to the TNF superfamily ligand alone, for example, by upregulating expression of DR5 on the cancer cells.

In specific instances, the conjugate has increased (for example, by about at least about 10, 20, 30, 40, 50, 60, 70, 80, 90, 100, 200, 300, 400, 500, 600, 700, 800, 900, or 1000% or more) or synergistically-increased tumor cell-killing and/or apoptosis-inducing activity relative to the ADI alone and/or the TNF superfamily ligand alone. In some instances, the cancer cells are ADI-sensitive cancer cells, or cancer cells that express low or undetectable levels of argininosuccinate synthetase-1 (ASS1). In particular instances, the cancer cells (for example, the ADI-sensitive cancer cells) are selected from one or more of breast cancer cells, hepatocellular carcinoma cells, Burkitt's Lymphoma cells, colon cancer cells, glioblastoma cancer cells, leukemic cells, melanoma cancer cells, non-small lung cell cancer (NSCLC) cells, ovarian cancer cells, pancreatic cancer cells, prostate cancer cells, and renal cancer cells. In some instances, the cancer cells are ADI-non-sensitive or ADI-resistant cancer cells, or cancer cells that express relatively high levels of ASS1. In particular instances, the cancer cells (for example, the ADI-non-sensitive cancer cells) are selected from one or more of breast cancer cells, colon cancer cells, and NSCLC cells.

In some embodiments, the conjugate comprises a hexameric (for example, homohexameric) polypeptide that is covalently linked to a trimeric (for example, homotrimeric) polypeptide, and in some instances conjugation to the hexameric polypeptide improves the physical, pharmacokinetic, and/or biological properties of the trimeric polypeptide relative to the latter alone, and/or vice versa. In some embodiments, the conjugate comprises a first trimeric (for example, homotrimeric) polypeptide that is covalently linked to a second trimeric (for example, homotrimeric) polypeptide, and in some instances conjugation to the first trimeric polypeptide improves the physical, pharmacokinetic, and/or biological properties of the second trimeric polypeptide relative to the latter alone, and/or vice versa. In some instances, the conjugate has increased physical, pharmacokinetic, and/or biological properties relative to one or both the components alone. In specific instances, the conjugate has increased stability and/or serum half-life relative to one or both the components alone, for example, where the stability and/or serum half-life of the conjugate is increased by about at least about 10, 20, 30, 40, 50, 60, 70, 80, 90, 100, 200, 300, 400, 500, 600, 700, 800, 900, or 1000% or more relative to one or both the components alone. In some instances, the conjugate has increased biological activity relative to one or both the components alone, for example, where the biological activity of the conjugate is increased by about at least about 10, 20, 30, 40, 50, 60, 70, 80, 90, 100, 200, 300, 400, 500, 600, 700, 800, 900, or 1000% or more relative to one or both the components alone.

The individual components of the conjugates are described in greater detail below.

Arginine Deiminases (ADIs). Certain conjugates comprise one or more arginine deiminases (ADIs), also referred to as ADI polypeptides or ADI enzymes. In some embodiments, the ADI polypeptide is from *M. hominis, M. arginini, M. arthritidis, M. phocicerebrale, M. gateae, M. phocidae, M. columbinum, M. iowae, M. crocodyli, M. alligatoris, H. orenii,* or *M. bovis*. In some embodiments, the ADI polypeptide is from *Mycoplasma salivarium, Mycoplasma spumans, Mycoplasma canadense, Mycoplasma auris, Mycoplasma hyosynoviae, Mycoplasma cloacale, Mycoplasma anseris, Mycoplasma alkalescens, Mycoplasma orale, Mycoplasma finers, Mycoplasma meleagridis, Mycoplasma alvi, Mycoplasma penetrans, Mycoplasma gallinarum, Mycoplasma pirum, Mycoplasma primatum, Mycoplasma fermentans, Mycoplasma lipofaciens, Mycoplasma felifaucium, Mycoplasma imitans, Mycoplasma opalescens, Mycoplasma moatsii, Mycoplasma elephantis, Mycoplasma pneumoniae, Mycoplasma testudinis, Mycoplasma* sp. CAG:877, or *Mycoplasma* sp. CAG:472.

The amino acid sequences of illustrative ADI polypeptides are provided in Table A1 below.

TABLE A1

ADI Polypeptide Sequences

| Source | Sequence | SEQ ID NO: |
|---|---|---|
| *Mycoplasma hominis* | MSVFDSKFNGIHVYSEIGELETVLVHEPGREIDYITPARLDELLFSAIL ESHDARKEHQSFVKIMKDRGINVVELTDLVAETYDLASKAAKEEFIETF LEETVPVLTEANKKAVRAFLLSKPTHEMVEFMMSGITKYELGVESENEL IVDPMPNLYFIRDPFASVGNGVIIHFMRYIVRRRETLFARFVFRNHPKL VKTPWYYDPAMKMPIEGGDVFIYNNETLVVGVSERIDLDTITLLAKNIK ANKEVEFKRIVAINVPKWINLMHLDTWLTMLDKNKFLYSPIANDVFKFW DYDLVNGGAEPQPQLNGLPLDKLLASIINKEPVLIPIGGAGATEMEIAR ETNEDGINYLAIKPGLVIGYDRNEKTNAALKAAGITVLPFHGNQLSLGM GNARCMSMPLSRKDVKW | 1 |
| PHX8 | MSVFDSKFNGIHVYSEIGELETVLVHEPGREIDYITPARLDELLFSAIL ESHDARKEHQSFVKIMKDRGINVVELTDLVAETYDLASKAAKEEFIETF LEETVPVLTEANKEAVRAFLLSKPTHEMVEFMMSGITKYELGVESENEL IVDPMPNLYFIRDPFASVGNGVIIHFMRYIVRRRETLFARFVFRNHPKL VKTPWYYDPAMKMSIEGGDVFIYNNETLVVGVSERIDLDTITLLAKNIK ANKEVEFKRIVAINVPKWINLMHLDTWLTMLDKNKFLYSPIANDVFKFW DYDLVNGGAEPQPQLNGLPLDKLLASIINKEPVLIPIGGAGATEMEIAR ETNEDGINYLAIKPGLVIGYDRNEKTNAALKAAGITVLPFHGNQLSLGM GNARCMSMPLSRKDVKW | 2 |

TABLE A1-continued

ADI Polypeptide Sequences

| Source | Sequence | SEQ ID NO: |
|---|---|---|
| *Mycoplasma phocicerebrale* | IHVYSEIGELETVLVHEPGREIDYITPARLDELLFSAILESHDARKEHQ SFVKQLKDNGINVVELTDLVAETFDLASKEEQEKLIEEFLEDSEPVLSE AHKTAVRKFLTSRKSTREMVEFMMAGITKYDLGIEADHELIVDPMPNLY FIRDPFASVGNGVIIHYMRYKVRQRETLFSRFVFSNHPKLVKTPWYYDP AMKMSIEGGDVFIYNNDTLVVGVSERIDLETITLLAKNIKANKEVEFKR IVAINVPKWINLMHLDTWLTMLDKDKFLYSPIANDVFKFWDYDLVNGGA EPQPKENGLPLEGLLQSIINKKPVLIPIAGNNASHIDIERETHFDGINY LAIKPGVVIGYARNEKTNAALAAAGIKVLPFHGNQLSLGMGNARCMSMP | 3 |
| *Mycoplasma arginini* | MSVFDSKFKGIHVYSEIGELESVLVHEPGREIDYITPARLDELLFSAIL ESHDARKEHKQFVAELKANDINVVELIDLVAETYDLASQEAKDKLIEEF LEDSEPVLSEEHKVVVRNFLKAKKISRELVEIMMAGITKYDLGIEADHE LIVDPMPNLYFIRDPFASVGNGVIIHYMRYKVRQRETLFSRFVFSNHPK LINTPWYYDPSLKLSIEGGDVFIYNNDTLVVGVSERIDLQTVILLAKNI VANKECEFKRIVAINVPKWINLMHLDTWLTMLDKDKFLYSPIANDVFKF WDYDLVNGGAEPQPVENGLPLEGLLQSIINKKPVLIPIAGEGASQMEIE RETHFDGINYLAIRPGVVIGYSRNEKTNAALEAAGIKVLPFHGNQLSLG MGNARCMSMPLSRKDVKW | 4 |
| *Mycoplasma arthritidis* | MSVFDSKFKGIHVYSEIGELETVLVHEPGKEIDYITPARLDELLFSAIL ESHDARKEHKEFVAELKKRGINVVELVDLIVETYDLASKEAKEKLLEEF LDDSVPVLSDEHRAAVKKFLQSQKSTRSLVEYMIAGITKHDLKIESDLE LIVDPMPNLYFIRDPFASVGNGVIIHYMRYKVRQRETLFSRFVFSNHPK LVNTPWYYDPAEGLSIEGGDVFIYNNDTLVVGVSERTDLQIITLLAKNI KANKECEFKRIVAINVPKWINLMHLDTWLTMLDKDKFLYSPIANDVFKF WDYDLVNGGDAPQPVDNGLPLEDLLKSIIGKKPTLIPIAGAGASQIDIE RETHFDGINYLAVAPGIVIGYARNEKTNAALEAAGITVLPFRGNQLSLG MGNARCMSMPLSRKDVK | 5 |
| *Mycoplasma orale* | SVFSDKFNGIHVYSEIGDLESVLVHEPGKEIDYITPARLDELLFSAILE STDARKEHKEFVEILKKQGINVVELVDLVVETYNLVDKKTQEKLLKDFL DDSEPVLSPEHRKAVEKFLKSLKSTKELIQYMMAGITKYDLGIKADKEL IVDPMPNLYFIRDPFASVGNGVIIHYMRYKVRQRETLFSKFIFINHPKL VKTPXYYDPAMKLSIEGGDVFIYNNDTLVVGVSERTDLETITLLAKNIK ANKECEFKRIVAINVPKXTNLMHLDTXLIMLDKDKFLYSPIANDVFKFX DYDLVNGGSNPEPVVNGLPLDKLLESIINKKPVLIPIAGKGATEIETAV ETHFDGINYLAIKPGVVVGYSRNVKINAALEANGIKVLPFKGNQLSLGM GNARCMSMPLSRKDVK | 6 |
| *Mycoplasma gateae* | IHVYSEIGELESVLVHEPGREIDYITPARLDELLFSAILESHDARKEHK LFVSELKANDINVVELTDLVTETYDLASQEAKDNLIEEFLEDSEPVLTE ELKSVVRTYLKSIKSTRELIQMMMAGITKYDLGIEADHELIVDPMPNLY FIRDPFASVGNGVIIHYMRYKVRQRETLFSRFVFSNHPKLVNTPWYYDP SLKLSIEGGDVFIYNNNTLVVGVSERIDLETVILLAKNIVANKECEFKR IVAINVPKWINLMHLDTWLTMLDKDKFLYSPIANDVFKFWDYDLVNGGE EPQPVENGLPLEGLLESIINKKPILIPIAGEGASQIDIERETHFDGINY LAIRPGVVIGYSRNEKTNAALEAAGIKVLPFHGNQLSLGMGNARCMSM | 7 |
| *Mycoplasma phocidae* | IHVYSEIGELQTVLVHEPGREIEYITPARLDELLFSAILESHDARKEHQ EFVAELKKNNINVVELTDLVSETYDMVSKEKQEKLIEEFLEDSEPVLSE EHKGLVRKFLKSLKSSKELIQYMMAGITKHDLNIEADHELIVDPMPNLY FIRDPFASVGNGVIIHYMRYKVRQRETLFSRFIFANHPKLMNIPLYYNP DMKLSIEGGDVFVYNNETLVVGVSERTDLDTITLLAKNIKANKEREFKR IVAINVPKWINLMHLDTWLTMLDKDKFLYSPIANDVFKFWDYDLVNGGD EPQPKVNGLPLEKLLESIINKKPILIPIAGTSASNIDVERETHFDGINY LAIAPGVVIGYSRNVKTNEALEAAGIKVLPFKGNQLSLGMGNARCMSMP | 8 |
| *Mycoplasma columbinum* | MSKINVYSEIGELKEVLVHTPGDEIRRISPSRLDELLFSAILEPNEAIK EHKGFLKILQDKGIKVIQLSDLVAETYTYHATQKEREAFIEKWLDEAEP ALTKDLRAKVKSYVLSKEGTPVAMVRTMMAGVSKQELNVESETELVVDP MPNLYFIRDPFASAGNGISLNNMKYVIRKRETIPAEFIFATHPDYKTIP HWFDRLDEGNIEGGDVFIYNKDILVIGVSERINKEAILTIAKKIKNNKE AKFKKIVAINVPPMPNLMHLDTWLTMVDKDKFLYSPNMLSVLKVWEIDL SKEIEMVETNKPLADVLESIIGVKPVLIPIAGKGATQLDIDIETHFDGT NYLTIAPGVVVGYSRNIKTEAALRAAGVTVLSFEGNQLSLGMGSARCMS MPLVREDVK | 9 |
| *Mycoplasma iowae* | MGNNIPKKINVFSEIGNLKRVLVHIPGKEIEYVTPQRLDELLFSAILDP VRAREEHKEFIKILESQGVEVVQLVDLTAETYDVAESQAKENFIQKWLD ESLPKLTDENRNKVYSLLKSLEKDPKEMIRKMMSGVLASEIGVKSDVEL IVDPMPNLYFIRDPFASVGNGITLHRMFRPTRRRETIFADFIFSNHPEY KSTQKYYEREDKESLEGGDVFIYNNKTLVVGVSERTEKGAIKALAKAVQ | 10 |

TABLE A1-continued

ADI Polypeptide Sequences

| Source | Sequence | SEQ ID NO: |
|---|---|---|
| | NNSNMSFEKIYAINVPKMSNLMHLDTWLTMLDTDKFLYSPNMMGVLKIW EIDLSDKSLKWKEIRDSLDHFLSTIIGKKAITVPVAGKDAMQFEIDIET HFDAINFIAVAPGVVIGYDRNKKINEALKEAGIKVLSWNGDQLSLGMGS ARCMTMPLYREELKK | |
| *Mycoplasma crocodyli* | MNKINVYSEVGKLKEVLVHTPGDEIRRISPSRLEELLFSAILEPDSAIE EHKRFLKILEDNNIKVIQLDQLVADTYELVNPSVRDAFIEKWLNESEPK LDKKLREKVKEYLLHIQKTVGIKRMVRIMMAGVDRVELGVELDRQLVVD PMPNLYFIRDPFASAGNGISLNNMKYVIRKRETIFSEFIFENHPDYKIT PHWFDRLDKGNIEGGDVFIYNRITLVIGISERINKDALLTIANNIKSNK ESKFERIVAVNVPPMPNLMHDTWLIMVDHDKFLYSPNMMKTLKEWTID LTKPIKMVELEESLSDMIETIIGKKPVLIPIAGHDASPLDVDIETHFDG TNYLTIAPGVVVGYSRNKLTEKALTKAGVKVLSFEGNQLSLGMGSARCM SMPLVREDIK | 11 |
| *Mycoplasma fermentans* | MQIIAKIDLLINMLIFMKIYFIGRLIMKKINVYSEYGKLKEVLVHIPGD EIRRIAPSRLDELLFSAILEPDSAIAEHKRFVQLLKDNGIKVIQLDELF AKTFDLVSESVKQSLIERWLDECEPKLDATLRAKVKEYILELKAKSSKK MVRVMMAGIDKKELGIELDRDLVVDPMPNLYFTRDPFASVGNGISLHHM KYVTRQRETIFSEFIFDNNLDYNTVPRWFDRKDEGRIEGGDVFIYSADT LVVGVSERTNKEAINVMARKIAADKEVKFKRIYAINVPPMPNLMHLDTW LTMLDKNKFLYSPNMLSVLKVWRIDLNDPDFVWHEIEGSLEEILEQIIG MKPILIPIAGKGASQLDIDIETHEDGINYLTIAPSVVVGYSRNEKTEKA LKAAKVKVLSFEGNQLSLGMGSARCMSMPLIREDIKKK | 12 |
| *Mycoplasma penetrans* | MVITIALNILNKIYFKPQNRSILKLYRLPSLCTQISIFIGGKMSSIDKN SLGNGINVYSEIGELKEVLVHIPGDEIRYTAPSRLEELLFSAVLKADTA IEEHKGFVKILQNNGIKVIQLCDLVAETYELCSKEVRNSFIEQYLDEAL PVLKKEIRPVVKDYLLSFPTVQMVRKMMSGILANELNIKQDNPLIIDGM PNLYFIRDPFASMGNGVSINCMKYPIRKREVIFSRFVFINNPKYKNIPR YFDIVGNNGTIEGGDIFIYNSKILVIGNSERINFAAIESVAKNIQANKD CIFERIVVINVPPMPNLMHLDTWLTMLDYDKFLYSPNMMNVLKIWEIDL NVKPVKFVEKKGTLEEVLYSIIDKKPILIPIAGKGANQLDIDIETHFDG TNYLTIAPGVVVGYERNEKTQKALVEAGIKVLSENGSQLSLGMGSARCM SMPLIRENLKK | 13 |
| *Mycoplasma gallisepticum* | MENKIRVYSEIGKLRKVLVHIPGKELDYVTPQRLDELLESSLLNPIKAR QEHETFIKLLEDHDVECVQLSTLTAQTFUNNSKIQEEFINRWLDECLP VLSEINRLKVYDYLKSLATNPQVMIRKMMSGILAKEVGIQSEVELVADP MPNLYFIRDPFASIGKGITLHSMFHPIRKRETIFADFIFSHHPEYKNAP KYYSREDKYSIEGGDLEVYDDKILVIGVSERTEKKAIQSLAEKLRQNDE TSFEKIYAINVPKMSNLMHLDTWLTMLDYDKFLYSPNMMGVLKIWEIDL IHPILIWRELNESLEGFLSMVIGKKATLIPVAGEDSTQIEIDVETNEDA INFLVIQPGVVVGYDRNYKINQALRDAGVKVISWNGDQLSLGMGSARCM SMPLYRDPIKK | 14 |
| *Mycoplasma alligatoris* | MSKINVYSEVGRLKEVLVHIPGDEIRRISPIRLEELLFSAILEPDTAIE EHKRFLNVLEKNGIKAIQLDELVAQTYDQVDQKIKDEFIDQWLQEAKPV LNDQLKKLVKNYLLKSQKEFSTKKMVRIMMAGIDKKEINIDLDRDLVVD PMPNLYFIRDPFASVGNGISLHNMKYQTRKRETIFAQFIFKYNKDYKIT PHWFDRFDHGSIEGGDVFVYTKDILVIGISERTIKEAVLNIAKKIKANT DSKFKKIVAINVPPMPNLMHLDTWITMVDHDKFLYSPNMMKSLKFWLID LSKEIKMVELEESLSNMLEAIIGKKPILIPIAGKNASQLDIDIETHFDG TNYLTIAPGVVVGYSRNKLIQKALEDAGVKVLSEDGNQLSLGMGSARCM SMPLVREDIK | 15 |
| *Mycoplasma pneumoniae* | MSKKQLVKIDGHNQLDQPNIKALQLKKKUNSGVRVISEISFLREVIAH HPGIETERVIDNQTFGSAMYLERAQKEHQLFIKILRQHGTKVHYLQDLL LEALSAADPNVRQDFIKNFLLESGIKSVSTFEACLNFFRSLDSLVDVIK VMFGGIKVSDVPPITPQRFADIHVSNSPFLIKPLSFSLYPHKFFNTLGT GVALFVINDSELKRHSLVYEYIMRFHPRFDGVKLYTNRDFKNCLINSSD IIQISNEILLIGISHDTDVLGIESLARNLLSDHINPIKQIIAINIHKFG AKTNLNKLIAMVDVDKFIIARKVLQATEIFELTATAQRDVDGLAQIKFK PLKFNFGEIIEAIIDKQPRFVIIGGGDEVAERKELLDCGMGVLNLSPGE IVVFDRNHYTNNLLNELGLIIHKIPASELSRGPSGPLEMVCSLWRE | 16 |
| *Mycoplasma mobile* | MKDTKDIINVFSEIGELKKVLIHTPGNELKYVSPYRLDELLFSNVLEWR EAKKEHNEFIQKLKSEGVEPVELTDLVAESFEESSIKVKNDFIRQYLDE ATPILDGLIKQKLLPFFLDIKHSTRKTIELMMSGITQKDISISHIEREL IIDPMPNLYFSRDNFISIGNSVIISNMKYKTRKRETIFTDFIFKNHPLY KKVNMAFERKDLNNQISIIEGGDVLVYSKEILIIGISERTTMSAILELA ENFKKTKRSPKKIYGVEVPKMKNLMHLDTWLIMIDYDKFIYSPNVLIDL KFWEINLDYEKISSKELHASLSEFLKLIIGKDPILIPIGGKGASQITID IETNEVAANYLVIRPGVVIGYSRNYETQKALEGHGVKVIAFEGNQLSLG MGSSRCMSMPLIRSNLK | 17 |

TABLE A1-continued

ADI Polypeptide Sequences

| Source | Sequence | SEQ ID NO: |
|---|---|---|
| Streptococcus pyogenes | MTAQTPIHVYSEIGKLKKVLLHRPGKEIENLMPDYLERLLFDDIPFLED AQKEHDAFAQALRDEGIEVLYLETLAAESLVTPEIREAFIDEYLSEANI RGRATKKAIRELLMAIEDNQELIEKTMAGVQKSELPEIPASEKGLIDLV ESNYPFAIDPMPNLYFIRDPFATIGTGVSLNHMFSETRNRETLYGKYIF THHPIYGGGKVPMVYDRNETTRIEGGDELVLSKDVLAVGISQRTDAASI EKLLVNIFKQNLGEKKVLAFEFANNRKFMHLDTVETMVDYDKFTIHPEI EGDLRVYSVTYDNEELHIVEEKGDLAELLAANLGVEKVDLIRCGGDNLV AAGREQWNDGSNTLTIAPGVVVVYNRNTITNAILESKGLKLIKIHGSEL VRGRGGPRCMSMPFEREDI | 18 |
| Enterococcus faecalis | MSHPINVESEIGKLKTVMLHRPGKELENLMPDYLERLLFDDIPFLEKAQ AEHDAFAELLRSKDIEVVYLEDLAAEALINEEVRRQFIDQFLEEANIRS ESAKEKVRELMLEIDDNEELIQKAIAGIQKQELPKYEQEFLTDMVEADY PFIIDPMPNLYFIRDNFATMGHGISLNHMYSVIRQRETIFGQYIFDYHP RFAGKEVPRVYDRSESTRIEGGDELILSKEVVAIGISQRTDAASIEKIA RNIFEQKLGFKNILAFDIGEHRKFMHLDTVFTMIDYDKFTIHPEIEGGL VVYSITEKADGDIQIIKEKDILDNILCKYLHLDNVQLIRCGAGNLTAAA REQWNDGSNTLAIAPGEVVVYDRNTITNKALEEAGVKLNYIPGSELVRG RGGPRCMSMPLYREDL | 19 |
| Mycoplasma capricolum | MEKKINVFSEIGILKTVLVHRPGDEIENLIPELLERLLFDDVPFKDVAV KEHDAFTKIMRDNGVEVLYIEKLAAETLDQHPDLREKFIDQFISEANIE DKYKEKYRDFISSLDNYRMIKKMIAGTKKLELGIDEGYKAYPFIADPLP NVLFQRDPFSSVGFGITMNRMWSVIRNRETIFPDLVFKHHNRFANQVPY YYERDWKEETIEGGDILVLNKETLIIGVTQRTILKAIEKFSERLFNDPE SSYSKVIALDLPKSRAFMHLDTVFTNIDYDKFIAHPLIFDCIDEFKIYE VSKQGTKEVKKILIELLSDAAGREVQIIRCGNDVVGASREQWNDGINV VALRPGKVIAYERNWITIDLLRKAGVEVLTIASSELSRGRGGPRCMTMP LWREDLQEIKR | 20 |
| Halothermothrix orenii | MFKKSPLNVISEIGKLKKVLLHRPGHEIENLTPDLLERLLFDDIPYLKV AQEEHDAFAQTLRDNGVEVLYLHELAAEAIQEDEIRKKFIEQFLDEAGV IGKGARQVLKEYFADMDNETLIRKMMAGVRKKEIPAIEKVASLNDMVEE DYPFVLDPMPNLYFIRDPFATIGIGITLNHMRTETRNREVIFAEYIFSY HPDFKDTEIPFWFDRNETTSIEGGDELILSDKVLAMGISERTDAASIEK VARNIFIDGQPFETILAFKIPEKRAFMHLDTVFTMVDYDKFTIHAEIEG PLKVYSITKGDNDELKIDEEKATLEDILKKYLGLDEVTLIRCAGGDYID AGREQWNDGSNTLAIAPGEVVVYNRNHTTNRLLEEHGIKLHVIPSSELS RGRGGPRCMSMPLVREDI | 21 |
| Staphylococcus aureus | MIDGPIKVNSEIGALKTVLLKRPGKELENLVPDYLDGLLFDDIPYLEVA QKEHDHFAQVLREEGVEVLYLEKLAAESIENPQVRSEFIDDVLAESKKT ILGHEEEIKALFATLSNQELVDKIMSGVRKEEINPKCTHLVEYMDDKYP FYLDPMPNLYFTRDPQASIGHGITINRMFWRARRRESIFIQYIVKHHPR FKDANIPIWLDRDCPFNIEGGDELVLSKDVLAIGVSERTSAQAIEKLAR RIFENPQATFKKVVAIEIPTSRTFMHLDTVFTMIDYDKFTMHSAILKAE GNMNIFIIEYDDVNKDIAIKQSSHLKDTLEDVLGIDDIQFIPTGNGDVI DGAREQWNDGSNTLCIRPGVVVTYDRNYVSNDLLRQKGIKVIEISGSEL VRGRGGPRCMSQPLFREDI | 22 |
| Pseudomonas plecoglossicida | MSAEKQKYGVHSEAGKLRKVMVCAPGLAHKRLTPSNCDELLFDDVIWVD QAKRDHFDFVTKMRERGVDVLEMHNLLTDIVQNPEALKWILDRKITPDT VGVGLTNEVRSWLEGQEPRHLAEFLIGGVAGQDLPESEGASVVKMYNDY LGHSSFILPPLPNTQFIRDITCWIYGGVILNPMYWPARRQETLLITAIY KFHPEFTKADFQVWYGDPDQEHGQATLEGGDVMPIGKGIVLIGMGERTS RQAIGQLAQNLFAKGAVEQVIVAGLPKSRAAMHLDTVFSFCDRDLVTVF PEVVREIVPFIIRPDESKPYGMDVRRENKSFIEVVGEQLGVKLRVVETG GNSFAAEREQWDDGNNVVALEPGVVIGYDRNTYTNILLRKAGIEVITIS AGELGRGRGGGHCMTCPIVRDPINY | 23 |
| Pseudomonas putida | MSAEKQKYGVHSEAGKLRKVMVCAPGLAHKRLTPSNCDELLFDDVIWVD QAKRDHFDFVTKMRERGVDVLEMHNLLTDIVQNKDALKWILDRKITPDT VGVGLTNEVRSWLEGLEPRHLAEFLIGGVAGQDLPQSEGADVVKMYNDY LGHSSFILPPLPNTQFIRDITCWIYGGVILNPMYWPARRQETLLITAIY KFHPQFTGADFQVWYGDPDKDHGNATLEGGDVMPIGKGIVLIGMGERTS RQAIGQLAQNLFAKGAVEKVIVAGLPKSRAAMHLDTVFSFCDRDLVTIF PEVVKEIVPFIIRPDESKPYGMDVRRENKSFIEVVGEQLGVKLRVVETG GNSFAAEREQWDDGNNVVAVEPGVVIGYDRNTYTNILLRKAGIEVITIS AGELGRGRGGGHCMTCPIVRDPIDY | 24 |
| Pseudomonas aeruginosa | MSTEKTKLGVHSEAGKLRKVMVCSPGLAHQRLIPSNCDELLFDDVIWVN QAKRDHFDFVTKMRERGIDVLEMHNLLTETIQNPEALKWILDRKITADS VGLGLTSELRSWLESLEPRKLAEYLIGGVAADDLPASEGANILKMYREY LGHSSFLLPPLPNTQFIRDITCWIYGGVILNPMYWPARRQETLLITAIY | 25 |

TABLE A1-continued

ADI Polypeptide Sequences

| Source | Sequence | SEQ ID NO: |
|---|---|---|
| | KFHPEFANAEFEIWYGDPDKDHGSSTLEGGDVMPIGNGVVLIGMGERSS<br>RQAIGQVAQSLFAKGAAERVIVAGLPKSRAAMHLDTVFSFCDRDLVIVF<br>PEVVKEIVPFSLRPDASSPYGMSIRREEKTFLEVVAESLGLKKLRVVET<br>GGNSFAAEREQWDDGNNVVCLEPGVVVGYDRNTYTNILLRKAGVEVITI<br>SASELGRGRGGGHCMTCPIIRDPIDY | |
| Mycobacterium tuberculosis complex | MGVELGSNSEVGALRVVILHRPGAELRRLTPRNIDQLLFDGLPWVSRAQ<br>DEHDEFAELLASRGAEVLLLSDLLTEALHHSGAARMQGIAAAVDAPRLG<br>LPLAQELSAYLRSLDPGRLAHVLTAGMTFNELPSDTRTDVSLVLRMHHG<br>GDFVIEPLPNLVFIRDSSIWIGPRVVIPSLALRARVREASLIDLIYAHH<br>PRFTGVRRAYESRTAPVEGGDVLLLAPGVVAVGVGERTTPAGAEALARS<br>LFDDDLAHTVLAVPIAQQRAQMHLDTVCIMVDTDTMVMYANVVDTLEAF<br>TIQRTPDGVTIGDAAPFAEAAAKAMGIDKLRVIHIGMDPVVAEREQWDD<br>GNNTLALAPGVVVAYERNVQTNARLQDAGIEVLTIAGSELGTGRGGPRC<br>MSCPAARDPL | 26 |
| Mycoplasma arthritidis | MSVFDSKFKGIHVYSEIGELETVLVHEPGKEIDYITPARLDELLFSAIL<br>ESHDARKEHKEFVAELKKRGINVVELVDLIVETYDLASKEAKEKLLEEF<br>LDDSVPVLSDEHRAAVKKFLQSQKSTRSLVEYMIAGITKHDLKIESDLE<br>LIVDPMPNLYFIRDPFASVGNGVIIHYMRYKVRQRETLFSRFVFSNHPK<br>LVNTPWYYDPAEGLSIEGGDVFIYNNDTLVVGVSERTDLQIITLLAKNI<br>KANKECEFKRIVAINVPKWINLMHLDTWLTMLDKDKFLYSPIANDVFKF<br>WDYDLVNGGDAPQPVDNGLPLEDLLKSIIGKKPTLIPIAGAGASQIDIE<br>RETHFDGINYLAVAPGIVIGYARNEKTNAALEAAGITVLPFRGNQLSLG<br>MGNARCMSMPLSRKDVK | 27 |
| Mycoplasma phocicerebrale Artificial full length | MSVFDSKFNGIHVYSEIGELETVLVHEPGREIDYITPARLDELLFSAIL<br>ESHDARKEHQSFVKQLKDNGINVVELTDLVAETFDLASKEEQEKLIEEF<br>LEDSEPVLSEAHKTAVRKFLTSRKSTREMVEFMMAGITKYDLGIEADHE<br>LIVDPMPNLYFIRDPPASVGNGVIIHYMRYKVRQRETLFSRFVFSNHPK<br>LVKIPWYYDPAMKMSIEGGDVFIYNNDILVVGVSERTDLETITLLAKNI<br>KANKEVEFKRIVAINVPKWINLMHLDTWLTMLDKDKFLYSPIANDVFKF<br>WDYDLVNGGAEPQPKENGLPLEGLLQSIINKKPVLIPIAGNNASHIDIE<br>RETHFDGINYLAIKPGVVIGYARNEKTNAALAAAGIKVLPFHGNQLSLG<br>MGNARCMSMPLSRKDVKW | 28 |
| Mycoplasma gateae Artificial full length | MSVFDSKFNGIHVYSEIGELESVLVHEPGREIDYITPARLDELLFSAIL<br>ESHDARKEHKLEVSELKANDINVVELTDLVTETYDLASQEAKDNLIEEF<br>LEDSEPVLTEELKSVVRTYLKSIKSTRELIQMMMAGITKYDLGIEADHE<br>LIVDPMPNLYFIRDPFASVGNGVIIHYMRYKVRQRETLFSRFVFSNHPK<br>LVNTPWYYDPSLKLSIEGGDVFIYNNNTLVVGVSERIDLETVILLAKNI<br>VANKECEFKRIVAINVPKWINLMHLDTWLTMLDKDKFLYSPIANDVFKF<br>WDYDLVNGGEEPQPVENGLPLEGLLESIINKKPILIPIAGEGASQIDIE<br>RETHFDGINYLAIRPGVVIGYSRNEKTNAALEAAGIKVLPFHGNQLSLG<br>MGNARCMSMPLSRKDVKW | 29 |
| Mycoplasma Phocidae Artificial full length | MSVFDSKFNGIHVYSEIGELQTVLVHEPGREIEYITPARLDELLFSAIL<br>ESHDARKEHQEFVAELKKNNINVVELTDLVSETYDMVSKEKQEKLIEEF<br>LEDSEPVLSEEHKGLVRKFLKSLKSSKELIQYMMAGITKHDLNIEADHE<br>LIVDPMPNLYFIRDPFASVGNGVIIHYMRYKVRQRETLFSRFIFANHPK<br>LMNIPLYYNPDMKLSIEGGDVFVYNNETLVVGVSERIDLDTITLLAKNI<br>KANKEREFKRIVAINVPKWINLMHLDTWLTMLDKDKFLYSPIANDVFKF<br>WDYDLVNGGDEPQPKVNGLPLEKLLESIINKKPILIPIAGTSASNIDVE<br>RETHFDGINYLAIAPGVVIGYSRNVKINEALEAAGIKVLPFKGNQLSLG<br>MGNARCMSMPLSRKDVKW | 30 |
| Mycoplasma salivarium | MSVFSSKFNGIHVYSEIGELETVLVHEPGKEIDYITPSRLDELLFSAIL<br>ESHDARKEHQEFVAILKKEKINVVELTDLVIETYDLVDQKTKDKLIDEF<br>LEDSEPVLTAELKATVKKFLKSFKETRKLIEVMMAGITKYDLGIKADRE<br>LIVDPMPNLYFIRDPFASVGNGVIIHYMRYKVRQRETLFSRFIFNNHPK<br>LVKTPWYYDPAMKMSIEGGDVFIYNNDTLVVGVSERTDLDTITLLAKNI<br>KANKECEFKRIVAINVPKWINLMHLDTWLTMLDKDKFLYSPIANDIFKF<br>WDYDLVNGGANPQPKDNGLPLDKLLKSIIGKEPVLIPIAGHHATEIEVA<br>RETHFDGINYLAIRPGVVIGYARNEKTNEALKDAGITVLPFKGNQLSLG<br>MGNARCMSMPLSRKDVKW | 31 |
| Mycoplasma spumans | MSVFDSKFKGIHVYSEIGELESVLVHEPGREIDYITPARLDELLFSAIL<br>ESHDARKEHKGFVAELKKQNVNVIELTDLVAETYELASKEAQAKLIEDF<br>IEDSEPVLNAEEEAQAVRKFLSERKSTREMVEYMMSGLTKYELGLESADR<br>ELIVDPMPNLYFIRDPFASVGNGVIIHYMKYKVRQRETLFSRFVFSNHPK<br>KLVNTPRYYDPSMKLPIEGGDVFIYNNETLVVGCSERTELETITLLAKN<br>IKANKEVEFKRIVAINVPKWINLMHLDTWLTMLDKDKFLYSPIANDVFK<br>FWDYDLVNGGEEPQPVENGLPLEELLASIINKKPTLIPIAGEGATHIDV<br>ERETHEDGINYLAIAPALIIGYSRNEKTNAALEKAGITVLPFHGNQLSL<br>GMGNARCMSMPLSRKDVKW | 32 |

TABLE A1-continued

ADI Polypeptide Sequences

| Source | Sequence | SEQ ID NO: |
|---|---|---|
| Mycoplasma auris | MSVFDSKFKGIHVYSEIGELETVLVHEPGREIDYITPKRLDELLFSAIL ESHEARKEHKQFVAELKANDINVVELTDLVAETYDLVSQELKDKLIEEF LDDSYPVLTEEHKKAVRSFLKSRSSTRELIEYMMAGITKYDLGIEAEGD LIVDPMPNLYFIRDPFASVGNGVIIHYMRYKVRQRETLFSRFIFDNHPK LVNTPRYYDPSLKLSIEGGDVFIYNNDTLVMGVSERIDLETVILLAKNI VANKECEFKRIVAINVPHWINLMHLDTWLTMLDKDKFLYSPIANDYFKF WDYDLVNGGAEPQPVVNELPLDKLLESIIHKKPILIPIAGEGASQIDLE RETHFDGINYLVLRPGVVVGYARNEKTNAALEAVGIKVLPFYGNQLSLG MGNSRCMSMPLSRKDVKW | 33 |
| Mycoplasma hyosynoviae | MSVFNSKFKGIHVYSEIGDLESVLVHEPGKEIDYITPSRLDELLFSAIL ESNDARKEHKEFVEILKKEGVNVVELVDLIAETIDLVDAKKKEALIDEY IEDSEPVVDAKVKPLVKKLLLGIKDTKELVKLMMAGITKYDLEIESEKE LIIDPMPNLYFIRDPFASVGNGVIIHYMRYKVRQRETLFSRFVFRNHPK LTSTPWYYDPAMKLSIEGGDVFIYNNDTLVVGVSERTDLDTITLLAKNI KANKECEFKRIVAINVPKWINLMHLDTWLTMLDKDKFLYSPIANDIFKF WDYDLVNGGSEPQPKDNGLPLEKLLESIIGKKPVLIPIAGCCASDIEIA RETHEDGINYLAIKPGVVIGYARNEKINKALEKAGIKVLPFKGNQLSLG MGNARCMSMPLSRKDVKW | 34 |
| Mycoplasma cloacale | MSVFDKRFKGIHVYSEIGELQTVLVHEPGREIDYITPARLDELLFSAIL ESHDARKEHKEFVKILESQGINVVELTDLIAETYELASEEAKDNLIEEF LDESEPVLSEEEHRILVRNFLKGITKTKELVKMMMAGITKYDLGIEADRE LIVDPMPNLYFIRDPFASVGNGVIIHYMRYKVRQRETLFSRFIFENHPK LVSTPIYYHPSQGLSIEGGDVFIYNNDTLVVGVSERIDLQIITLLAKNI KANEECEFKRIVAINVPKWINLMHLDTWLTMLDKNKFLYSPIANDVFKF WDYDLVNGGDEPQPVDNGLPLNELLASIIGEEPVLVPIAGEGASKMDIE RETHEDGINYLAIAPGVVVGYSRNEKTNAALEKAGIKVLPFKGHQLSLG MGNARCMSMPLYRKDVK | 35 |
| Mycoplasma alkalescens | MSVFDSKFKGIHVYSEIGELESVLVHEPGHEIDYITPSRLDELLFSAML ESHDARKEHKQFVAELKANNNVIELTDLVAETYDLASQEAKDKLIEEF LEDSEPVLSEENKIAVRDFLKSRKTTRELIEVMMAGITKYDLGIKNCKC QDLVVDPMPNLYFTRDPFASVGNGITIHYMRYKVRQRETLFSRFIFANH PKLVNTPIYYHPSLKLSIEGGDVFIYNNDTLVVGVSERTDLETITLLAK NIVANKECEFKRIVAINVPKWINLMHLDTWLTMLDKDKFLYSPIANDVF KFWDYDLVNGGAEPKPVENGSSLEAILESIIHKKPILIPIGGDSASQIE VERETHFDGINYLAIRPGVVIGYSRNVKINAALEAAGIKVIPFHGNQLS LGMGNARCMSMPLSRKDVKW | 36 |
| Mycoplasma iners | MSKINVYSEIGVLKEVLVHTPGDEIRRIAPSRLDELLFSAILEPSAAIQ EHKSFLKILQDRGIKTIQLSDLVAETYKHYASEAEKEAFIEKYLDEATP VLSKDMRAKVKNYILSMQGEPVKMVRTMMAGVSKQELNVESEVELIVDP MPNLYFIRDPFASAGNGISLNNMKYVVRKRETIFAEFIFSIHPEYKKTP HWFDRLDNGSIEGGDVFIYNKDILVIGVSERINKEAIITIAKHIQDNKE AQFKKIVAINVPPMPNLMHLDTWLTMVDKNKFLYSPNMLSVLKVWEIDL SKPIEMVETNKPLAEVLESIIGEKPILIPIAGKDATQLDIDIETHFDGT NYLTIAPGVVVGYSRNVKTEAALRAAGVTVLSFEGNQLSLGMGSARCMS MPLVREDVK | 37 |
| Mycoplasma gallinarum | MSKIRVYSEIGNLKKVLVHTPGDEIRRISPSRLEELLFSAVLEPNAAIE EHKRFVKLLEDRGIQAIQLSDLVAETYVKYATAEQKAAFIEKYLDEATP ALSAENRERAKKYILSLEMQPVKMIRTMMAGLSKYELNVESNIELIIDP MPNLYFTRDPFASAGNGISLNNMKYVVRKRETIFAEFIFAIHPEYKETP HWFDRLDHGSIEGGDVFVYNKDILVIGVSERINKEAIITIAKHIQDNKE AEFKKIVAINVPPMPNLMHLDTWLTMVDKNKFIYSPNMLSVLKIWEIDL AKPIEMVESNKSLTEVLESIIGEKPILIPIAGEGASQLDIDIETHFDGT NYLTIAPGVVVGYSRNEKTEKALKAAGITVLSFEGNQLSLGMGSARCMS MPLVREDVK | 38 |
| Mycoplasma pirum | MNSNQKGIHVYSEIGKLKEVLVHRPGRELDFLDPIRLDELLFAATLEAE TARLEHDNFTNALKNQGVIVIELADLVAQTYSSSTPTIKAAFINKYLDE ATPALTIKLRILVKDFLIKQKSVRKMVDYMIGGILSIDLNIKGKPELIV EPMPNAYFTHDPFASVGNGVTLHYMKHNVRRREVLFSEFIFNNNERFQN TPRYIVPIKGLDIEGGDVFVYNKNILVVGVSERTKMVTIKELAKNILKN KECLFKKIYAINVPKMPNLMHLDTWLTMLDHNKFLYSPNMLSVLKIWEI DISSGKSISSPKELNMDLSKALSIIIGKKPILIPVAGENASQIDINIET NFDATNYLVTQPGVVVGYSRNKKTEAALIKAGIEVIPFQGNQLSLGMGS ARCMSMPLIREDV | 39 |
| Mycoplasma primatum | MSKSKINVYSEYGNLKEVLVHTPGDEIRRITPSRLDELLFSAILEPKSA IAEHKSFCQILKDNKVKAIQLDELVAATYKGVSESVQNSFVERWLDECE PKLENNVRPIVKEYLLKAAEQSVKKMIRIMMAGIDKREIGVESEVDFIV DPMPNLYFTRDPFASVGNGITLHHMKYVVRQRETLFSEFIFDNHPDYKF | 40 |

TABLE A1-continued

ADI Polypeptide Sequences

| Source | Sequence | SEQ ID NO: |
|---|---|---|
| | VPRYFDRDDEGKIEGGDVFIYNSKILVVGISERINKDAIRIVAKKIQAN<br>ADAKFEKIFAINVPPMPNLMHLDTWLTMLDSNKFLYSPNMLSVLKVWEI<br>NLDDPALEWKEISGSLEEILTYIIGKKPILIPIAGKGASQFEIDIETHF<br>DGTNYLAIAPSVVIGYSRNELTEKALKKAGVKVLSLDGNQLSLGMGSAR<br>CMSMPLIREDVK | |
| Mycoplasma lipofaciens | MSKINVYSEVGVLKEVLVHTPGDEIRRVAPSRLDELLFSAILEPQDAIA<br>EHKRFIKILEDNNIKVIQLDELVSETWEKATAEQRDAFIEKWLDEAEPV<br>LDAKLRETVKKYLLSLNPVKKMVRTMMAGIDKKELKIELDRDLVVDPMP<br>NLYFIRDPFASAGNGISLNNMKYVIRKRETIFAEFIFNIHPDYKTIPHW<br>FDRLDKGNIEGGDVFIYNKDILVLGVSERINKDAYMTIAKHIQSNEQAK<br>FKKLVAINVPPMPNLMHLDTWLIMVDHDKFLYSPNMLSVLKIWEIDLTP<br>GKEIEMVESTKSLSDMLESIIGKKPVLIPIAGKDASQLDIDIETHFDGT<br>NYLTIRPGVVVGYSRNCLTEQALKDAGVIVLSFDGNQLSLGMGSARCMS<br>MPLVREDIK | 41 |
| Mycoplasma felifaucium | MNKINVYSEIGKLKEVLVHTPGNEIRRISPSRLDELLFSALLEPNFAAK<br>EHTAFCEILKENGIKAIQLVDLVSDTWRIASEKAKTEFIERWLDECEPK<br>LDSNLREIVRKHIYAIEKRSVKRMVKIMMAGIERRELPVISKEVARELV<br>VDPMPNLYFIRDPFASVGNGISLHHMKYVTRQRETIFAEFVFGNHPDYI<br>DTPRWFDRSDDGRIEGGDVFIYGSKILVIGVSERINKEAIKVMAKKIQA<br>NKEATFEKIYAINVPPMPNLMHLDTWLTMLDKNKFLYSPNMLAVLQVWE<br>IDLKDPELTWHELSGSLEEILHKIIGRKPILIPIAGHGAQQIDIDIETH<br>FDGINYLAIAPGVVVGYNRNVLTERALKKAGIKVLSFEGNQLSLGMGSA<br>RCMSMPLIRENLK | 42 |
| Mycoplasma imitans | MFNKIKVYSEIGRLRKVLVHIPGKELEYVTPQRLDELLFSSLLNPVKAR<br>QEHEAFIKILQDGVECVQLTTLTAQTFQSATSEVKEKFINRWLDECLP<br>KLSDDNRIKVYAYLKDLSSDPEVMIRKMMSGILAKEVNVQSDVELIADP<br>MPNLYFIRDPFASIGKGVILHSMFHPIRKRETIFADFVFSHHPEYKQTP<br>KYYSRLNEYSIEGGDLFVYDDKILVIGVSERTEKKAIQFLAEKLRENYE<br>TIFEKIYAINVPKMSNLMHLDTWLTMLDYDKFLYSPNMMGVLKIWEIDL<br>THEQLSWRELNESLEEFLSMVIGKKATTIPVAGEDSTQIEIDVETNFDA<br>INFLVIQPGVVVGYDRNYKINQALVNAGIKVLSWNGDQLSLGMGSARCM<br>SMPLYRDPIKKG | 43 |
| Mycoplasma opalescens | MSKINVYSEIGILKEVLVHIPGDEIRRVAPARLDELLFSAILEPNHAIA<br>EHKAFIKILEDNGIKVIQLDELVVQTWNQVDEATRKAFVTKWLDECEPK<br>LESNVRVEVEKYIYSLAKEPKKMVRTMMAGISKEELPLNVNRPLVVDPM<br>PNLYFIRDPFASVGIGISLHHMKYVTRQRETIFAQFVFDNHKDYNTVPR<br>WFDNKDQGRIEGGDVFIYNTKILVIGVSERTDKAIKIMAKKIQADKNC<br>KFEKIFAINVPPMPNLMHLDTWLTMVDRNKFLYSPNMLSVLKVWEIDLK<br>DASLAWKEIEGSLSQILEKIIGEKPILIPIAGENASQLDIDIETHFDGT<br>NYLTIAPGVVVGYSRNVKTEQALKAAGVKVLSFEGNQLSLGMGSARCMS<br>MPLIREDLK | 44 |
| Mycoplasma moatsii | MKKNAINVYSEIGKLKKVLVHRPGDELKYVTPQRMDELLMSAIIELEQA<br>KEEHDAFTKILRDNGVEVIELADLTAEMYDSLTPSEKDAFLNQWVKEAS<br>WGKKSSIDALKIKKNLSKKVFDYVKSIKPTRKMIDKLMAGVLLSEIGEK<br>SIILNKDKKNEMVIDLVVDPMPNLYFIRDPFASVGNGITLHNMKYPIRK<br>RETIFAQWIFNKHPEYKDVPQFISKRDGKETIEGGDVFIYTKDVLAIGV<br>SERTNMEAILRIATNIKKDKNCEFKKIVAINVPPMGNLMHLDTWLTMLD<br>KDLFLYSGNIKSALKVWEIDLTKPITPKSPKLSTAKLADILAKIYGKKV<br>RMIPIGGKDGNQMDIDIETHEDGINYLAIAPGVVVGYHRNRKTQKALEE<br>AGVKVLAFQGNQLSLGMGSARCMSMPLVREEVK | 45 |
| Mycoplasma elephantis | MSQINVFSEIGQLKEVLVHTPGDEIRRISPKRYNELLFSAILEADVAIK<br>EHKSFVKILEENNVKVIQLKDILLETWNICSKEAKNIFINKWIEEAQPV<br>IHSSSLKEKIKLFLKSKTPLEIIDIMMKGILKQELGIEYKHELIIDPMP<br>NLYFIRDPFTSMGSGITINNMKYQTRKRETIFSEFIFNNHPKYKNIPRW<br>FDREDSGNIEGGDLEVYTKETIVVGVSERIKKKAILKIAKNIQENNNSF<br>KKIVVIKVPIMQNLMHLDTWIVMVDFDKFIYSPNVIKSLKFWEIDLIKK<br>PKFIQLKNETLEDVLYRVIGKKPILIPVAGENANQIDIDVETHFDATNY<br>LTIRPGVVVGYSRNKKTEEALINAGVKVYAFEGNQLSLGMGSARCMSMP<br>LIREDII | 46 |
| Mycoplasma testudinis | MKNINVYSEVGKLKEVVVHIPGEELHNVAPSRLQELLTSAVLEPEVARK<br>EHLKFIKILNDYGVKVIQIVDLITETYEAVDSNKKEAFINNWLDNSVPK<br>LTDKNRMILRNYLTQFSTKAMIRKMISGIRAKELNLKTPSALLVDPMPN<br>LCFARDTFACVGSAISLSTMKHPIRRREALLTEFIFQNHPKYKDVIKYF<br>DSKNSKATIEGGDIFVYNPKTLVVGNSERTNMQACLLLAKKIQSNPNNK<br>FEKIVIVNVPPLPHLMHLDTWLIMVDYDKFIYSPNILHILKFWVIDLKK<br>RKLEAVEKHNTLKAMLRMIIKKEPILIPVGDVGADQLDIDLETHFDATN<br>YLALAPGVVVGYDRNIKTQRALEKAGVKVLSFGNQLSLAMGSARCLSM<br>PLIREEN | 47 |

TABLE A1-continued

ADI Polypeptide Sequences

| Source | Sequence | SEQ ID NO: |
|---|---|---|
| Mycoplasma canadense | MSVFDSKFKGIHVYSEIGELESVLVHEPGREIDYITPARLDELLFSAIL ESHDARKEHKQFVSELKANDINVVELTDLVAETYDLASQEAKDKLIEEF LEDSEPVLSEEHKAIVRKYLKGIQPIRKLIEMMMAGITKYDLGIEADHE LIVDPMPNLYFIRDPPFASVGNGVIIHYMRYKVRQRETLFSRFVFSNHPK LVNTPWYYDPSLKLSIEGGDVFVYNNDTLVVGVSERTDLQTVILLAKNI VANKECEFKRIVAINVPKWINLMHLDTWLTMLDKDKFLYSPIANDVFKF WDYDLVNGGSEPQPVENGLPLEGLLESIINKKPILIPIAGEGASQMEIE RETHFDGINYLAIRPGVVIGYSRNEKTNAALEAAGIKVLPFHGNQLSLG MGNARCMSMPLSRKDVKW | 48 |
| Mycoplasma anseris | MSVFDKRFKGIHVYSEIGELQTVLVHEPGREIDYITPARLDELLFSAIL ESHDARAEHKKEVAILKEQGINTVELTDLVAETYDLASQEARDNLLEEF LDDSAPVLSEEHKEIVRTYLKGIKGTRKLIETMMAGITKYDLGIEAEQE LIVDPMPNLYFIRDPPFASVGNGVIIHYMRYKVRQRETLFSRFIFSNHPQ LVNTPWYYNPAEGLSIEGGDVFIYNNDTLVVGVSERTDLQIITLLAKNI KANEECEFKRIVAINVPKWINLMHLDTWLTMLDINKFLYSPIANDVFKF WDYDLVNGGDEPQPVDNGLPLNELLKSIIGEEPILIPIAGDGATQIEIE RETHFDGINYLAIAPGVVIGYSRNEKTNAALEAAGIKVLPFKGHQLSLG MGNARCMSMPLYRKDVK | 49 |
| Mycoplasma meleagridis | MSKINVYSEIGVLKEVLVHTPGDEIRRISPSRLDELLFSAILQPEQAIK EHQSFVKILQDRGIKVIQLSDLVAETYVKYATSKEKESFIEKWLDEATP ALNSENRARVKNYITAMQGQPVKMVRAMMAGVSKQELNIESDVELIVDP MPNLYFTRDPFASAGNGISLNNMKYVVRKRETIFAEFIFSIHPEYKQTP HWFDRLDKGNIEGGDVFIYNKDILVIGVSERINKEAILTIAEHIKNNKE AKFKKIVAINVPPMPNLMHLDTWLTMVDKNKFLYSPNMLSVLKIWEIDL SKEIKMVETSKPLADVLESIIGEKPILIPIAGENASQLDIDIETHFDGT NYLTIAPGVVVGYSRNVKTEAALKAAGVIVYSEDGNQLSLGMGSGRCMS MPLVREDVK | 50 |
| Mycoplasma alvi | MSIKENGIHVYSEIGKLRDVLVHRPGRELNFLDPSRLDELLFAATLEPE TARLEHDNFTTVLKNQGVNVIELADLVSQTYSKVDSKVKKEFIDQYLNE ATPKLISELSKKVYDFLIKQKSNREMVDFMMGGILSSDLNIKGQPYLIV EPMPNLYFTRDPFASVGNGATIHWMKHNVRRREVLFANFIFKYNERFQN TPKYITPTKGLDIEGGDVFVYNKKILVVGVSERTKMETIKELAKNISKN KECTFTKIYAINVPKMPNLMHLDTWLTMLDYNKFLYSPNMLSVLKVWEI NISNNKVSAPKELNVNLEKALSMIIGKKPILIPVAGANASQIDINIETN FDATNYLVIEPGVVVGYSRNKKTEEALVKAGIKVLPFHGNQLSLGMGSA RCMSMPLYREDV | 51 |
| Mycoplasma penetrans | MSSIDKNSLGNGINVYSEIGELKEVLVHTPGDEIRYTAPSRLEELLFSA VLKADTAIEEHKGFVKILQNNGIKVIQLCDLVAETYELCSKEVRNSFIE QYLDEALPVLKKEIRPVVKDYLLSFPTVQMVRKMMSGILANELNIKQDN PLIIDGMPNLYFIRDPFASMGNGVSINCMKYPIRKREVIFSRFVFINNP KYKNIPRYFDIVGNNGTIEGGDIFIYNSKILVIGNSERTNFAAIESVAK NIQANKDCTFERIVVINVPPMPNLMHLDTWLTMLDYDKFLYSPNMMNVL KIWEIDLNVKPVKFVEKKGTLEEVLYSIIDKKPILIPIAGKGANQLDID IETHEDGINYLTIAPGVVVGYERNEKTQKALVEAGIKVLSENGSQLSLG MGSARCMSMPLIRENLKK | 52 |
| Mycoplasma fermentans | MKKINVYSEYGKLKEVLVHTPGDEIRRIAPSRLDELLFSAILEPDSAIA EHKRFVQLLKDNGIKVIQLDELFAKTFDLVSESVKQSFIERWLDECEPK LDATLRAKVKEYILELKAKSSKKMVRVMMAGIDKKELGIELDRDLVVDP MPNLYFIRDPFASVGNGISLHHMKYVTRQRETIFSEFIFDNNLDYNTVP RWFDRKDEGRIEGGDVFIYSADTLVVGVSERTNKEAINVMARKIAADKE VKFKRIYAINVPPMPNLMHLDTWLTMLDKNKFLYSPNMLSVLKVWRIDL NDPDFVWHEIEGSLEEILEQIIGMKPILIPIAGKGASQLDIDIETHEDG TNYLTIAPSVVVGYSRNEKTEKALKAAKVKVLSFEGNQLSLGMGSARCM SMPLIREDIKKK | 53 |
| Mycoplasma pneumoniae | MKYNINVHSEIGQLQTVLVHTPGNEIRRISPRRLDDLLFSAVIEPDTAI QEHQTFCQLLEQNIEVVQLTDLTATTFDKANATAQNQFIETWLDQAEP KLIPEHRKVAKQYLLEQKAKSTLSMVRSMMGGIDKRKVAAANTINGDFL VDPMPNLYFIRDPFASIGHGISINRMKYLTRRRETLFASFIFANHPIIA ARKEYFKPIDMGTIEGGDIFVYDQQTVVMGLSERTTEAAINVLAKKIQQ DSSTSFKRIEVINVPQLPNLMHLDTWLTMLDRNKFLYSPNMLAVLKAWR IDFTDPALKWNEIAGDLSTILHTIIGQKPMLIPIAGADANQTEIDIETH FDGTNYLTIAPSVVVGYARNKLTHQTLEAAGVKVIAFKGNQLSLGMGSA RCMSMPLVRKPL | 54 |
| Mycoplasma sp. CAG: 877 | MEKIHVISEIGPLKKVLLHRPGNELLNLTPDTLSRLLFDDIPYLPDAIK EHDEFADALRANGVEVVYLENLMADVLDLSDEIRDKFIKQFIYEAGIRT PKYKYLVFDYLDQIINSKKLVLKTMEGIQISDIPRRKREIEKSLVDLIE TEDEFIADPMPNLYFIRDPFASVGEGISLNKMYSVIRNRETIYAEYIFK | 55 |

TABLE A1-continued

ADI Polypeptide Sequences

| Source | Sequence | SEQ ID NO: |
|---|---|---|
| | YHPDYKDQARLYYDRYNPYHIEGGDVLNINDHVLAIGISQRTTAEAIDQ<br>LAKNLEKDPECKIDTILAFNIPESRAFMHLDTVETQVDYDKFTYHPGIM<br>GILQVFEITEGDDPNSDEDLIVTEINAPLEEILIKYVGRKVILIPCAGG<br>DKVSAEREQWNDGSNTLCIAPGVVVVYDRNNLINAVLRSYGLKVIEIHG<br>AELSRGRGGPRCMSMPLVREDI | |
| Mycoplasma sp. CAG: 472 | MHVISEIKKLKKVLVHRPGKELLNLTPDTLGRLLFDDIPYLKDAILEHD<br>EFCQILRDNDVEVVYLEDLMAETLDENPQVKPSFIRQFIYEAGVRTPKY<br>KDLLFDYLMSYTNNKELVLKTMEGIKVSEVHRNKQDSEYSLVDQISEET<br>KFLAEPMPNLYFIRDPFASVGDGIILNKMHSVIRSRETIYAYYIFNYHP<br>DYMDKVPKYYDRENPFSIEGGDVLNLNEHTLAIGISQRTSAEAIDLVAK<br>NMENDEKCNIDTILAFKIPECRAFMHLDTVFIQIDIDKFTYHPGIMDTL<br>EVFEITKNEDDLDEVRVIKKEGSLENILEEYLGIDITLIPCAGGDKIAS<br>EREQWNDGINTLCIAPGVVVVYNRNNITNEVLREKGIKVIEMNSAELSR<br>GRGGPRCMSMPLERED | 56 |
| M. columbinum-<br>M. gallinarum<br>chimeric ADI | MSKINVYSEIGELKEVLVHTPGDEIRRISPSRLDELLFSAILEPNEAIK<br>EHKGFLKILQDKGIKVIQLSDLVAETYVKYATAEQKAAFIEKYLDEATP<br>ALSAENRERAKKYILSLEMQPVKMIRTMMAGLSKYELNVESNIELIIDP<br>MPNLYFIRDPFASAGNGISLNNMKYVIRKRETIFAEFIFATHPDFIP<br>HWFDRLDEGNIEGGDVFIYNKDILVIGVSERINKEAILTIAKKIKNNKE<br>AKFKKIVAINVPPMPNLMHLDTWLTMVDKDKFLYSPNMLSVLKVWEIDL<br>SKEIEMVETNKPLADVLESIIGVKPVLIPIAGKGATQLDIDIETHFDGT<br>NYLTIAPGVVVGYSRNIKTEAALRAAGVTVLSFEGNQLSLGMGSARCMS<br>MPLVREDVK | 57 |
| M. columbinum-<br>M. iners<br>chimeric ADI | MSKINVYSEIGELKEVLVHTPGDEIRRISPSRLDELLFSAILEPNEAIK<br>EHKGFLKILQDKGIKVIQLSDLVAETYKHYASEAEKEAFIEKYLDEATP<br>VLSKDMRAKVKNYILSMQGEPVKMVRTMMAGVSKQELNVESEVELIVDP<br>MPNLYFIRDPFASAGNGISLNNMKYVIRKRETIFAEFIFATHPDYKTIP<br>HWFDRLDEGNIEGGDVFIYNKDILVIGVSERINKEAILTIAKKIKNNKE<br>AKFKKIVAINVPPMPNLMHLDTWLTMVDKDKFLYSPNMLSVLKVWEIDL<br>SKEIEMVETNKPLADVLESIIGVKPVLIPIAGKGATQLDIDIETHFDGT<br>NYLTIAPGVVVGYSRNIKTEAALRAAGVTVLSFEGNQLSLGMGSARCMS<br>MPLVREDVK | 58 |
| M. columbinum-<br>M. meleagridis<br>chimeric ADI | MSKINVYSEIGELKEVLVHTPGDEIRRISPSRLDELLFSAILEPNEAIK<br>EHKGFLKILQDKGIKVIQLSDLVAETYVKYATSKEKESFIEKWLDEATP<br>ALNSENRARVKNYITAMQGQPVKMVRAMMAGVSKQELNIESDVELIVDP<br>MPNLYFIRDPFASAGNGISLNNMKYVIRKRETIFAEFIFATHPDYKTIP<br>HWFDRLDEGNIEGGDVFIYNKDILVIGVSERINKEAILTIAKKIKNNKE<br>AKFKKIVAINVPPMPNLMHLDTWLTMVDKDKFLYSPNMLSVLKVWEIDL<br>SKEIEMVETNKPLADVLESIIGVKPVLIPIAGKGATQLDIDIETHFDGT<br>NYLTIAPGVVVGYSRNIKTEAALRAAGVTVLSFEGNQLSLGMGSARCMS<br>MPLVREDVK | 59 |
| M. gallinarum-<br>M. columbinum<br>chimeric ADI | MSKIRVYSEIGNLKKVLVHTPGDEIRRISPSRLEELLFSAVLEPNAAIE<br>EHKRFVKLLEDRGIQAIQLSDLVAETYTYHATQKEREAFIEKWLDEAEP<br>ALTKDLRAKVKSYVLSKEGTPVAMVRTMMAGVSKQELNVESETELVVDP<br>MPNLYFTRDPFASAGNGISLNNMKYVVRKRETIFAEFIFAIHPEYKETP<br>HWFDRLDHGSIEGGDVFVYNKDILVIGVSERINKEAIITIAKHIQDNKE<br>AEFKKIVAINVPPMPNLMHLDTWLTMVDKNKFIYSPNMLSVLKIWEIDL<br>AKPIEMVESNKSLTEVLESIIGEKPILIPIAGEGASQLDIDIETHFDGT<br>NYLTIAPGVVVGYSRNEKTEKALKAAGITVLSFEGNQLSLGMGSARCMS<br>MPLVREDVK | 60 |
| M. gallinarum-<br>M. iners<br>chimeric ADI | MSKIRVYSEIGNLKKVLVHTPGDEIRRISPSRLEELLFSAVLEPNAAIE<br>EHKRFVKLLEDRGIQAIQLSDLVAETYKHYASEAEKEAFIEKYLDEATP<br>VLSKDMRAKVKNYILSMQGEPVKMVRTMMAGVSKQELNVESEVELIVDP<br>MPNLYFTRDPFASAGNGISLNNMKYVVRKRETIFAEFIFAIHPEYKETP<br>HWFDRLDHGSIEGGDVFVYNKDILVIGVSERINKEAIITIAKHIQDNKE<br>AEFKKIVAINVPPMPNLMHLDTWLTMVDKNKFIYSPNMLSVLKIWEIDL<br>AKPIEMVESNKSLTEVLESIIGEKPILIPIAGEGASQLDIDIETHFDGT<br>NYLTIAPGVVVGYSRNEKTEKALKAAGITVLSFEGNQLSLGMGSARCMS<br>MPLVREDVK | 61 |
| M. gallinarum-<br>M. meleagridis<br>chimeric ADI | MSKIRVYSEIGNLKKVLVHTPGDEIRRISPSRLEELLFSAVLEPNAAIE<br>EHKRFVKLLEDRGIQAIQLSDLVAETYVKYATSKEKESFIEKWLDEATP<br>ALNSENRARVKNYITAMQGQPVKMVRAMMAGVSKQELNIESDVELIVDP<br>MPNLYFTRDPFASAGNGISLNNMKYVVRKRETIFAEFIFAIHPEYKETP<br>HWFDRLDHGSIEGGDVFVYNKDILVIGVSERINKEAIITIAKHIQDNKE<br>AEFKKIVAINVPPMPNLMHLDTWLTMVDKNKFIYSPNMLSVLKIWEIDL<br>AKPIEMVESNKSLTEVLESIIGEKPILIPIAGEGASQLDIDIETHFDGT<br>NYLTIAPGVVVGYSRNEKTEKALKAAGITVLSFEGNQLSLGMGSARCMS<br>MPLVREDVK | 62 |

TABLE A1-continued

ADI Polypeptide Sequences

| Source | Sequence | SEQ ID NO: |
|---|---|---|
| M. iners-<br>M. columbinum<br>chimeric ADI | MSKINVYSEIGVLKEVLVHTPGDEIRRIAPSRLDELLFSAILEPSAAIQ<br>EHKSFLKILQDRGIKTIQLSDLVAETYTYHATQKEREAFIEKWLDEAEP<br>ALTKDLRAKVKSYVLSKEGTPVAMVRTMMAGVSKQELNVESETELVVDP<br>MPNLYFIRDPFASAGNGISLNNMKYVVRKRETIFAEFIFSIHPEYKKTP<br>HWFDRLDNGSIEGGDVFIYNKDILVIGVSERINKEAIITIAKHIQDNKE<br>AQFKKIVAINVPPMPNLMHLDTWLTMVDKNKFLYSPNMLSVLKVWEIDL<br>SKPIEMVETNKPLAEVLESIIGEKPILIPIAGKDATQLDIDIETHFDGT<br>NYLTIAPGVVVGYSRNVKTEAALRAAGVTVLSFEGNQLSLGMGSARCMS<br>MPLVREDVK | 63 |
| M. iners-<br>M. gallinarum<br>chimeric ADI | MSKINVYSEIGVLKEVLVHTPGDEIRRIAPSRLDELLFSAILEPSAAIQ<br>EHKSFLKILQDRGIKTIQLSDLVAETYVKYATAEQKAAFIEKYLDEATP<br>ALSAENRERAKKYILSLEMQPVKMIRTMMAGLSKYELNVESNIELIIDP<br>MPNLYFIRDPFASAGNGISLNNMKYVVRKRETIFAEFIFSIHPEYKKTP<br>HWFDRLDNGSIEGGDVFIYNKDILVIGVSERINKEAIITIAKHIQDNKE<br>AQFKKIVAINVPPMPNLMHLDTWLTMVDKNKFLYSPNMLSVLKVWEIDL<br>SKPIEMVETNKPLAEVLESIIGEKPILIPIAGKDATQLDIDIETHFDGT<br>NYLTIAPGVVVGYSRNVKTEAALRAAGVTVLSFEGNQLSLGMGSARCMS<br>MPLVREDVK | 64 |
| M. iners-<br>M. meleagridis<br>chimeric ADI | MSKINVYSEIGVLKEVLVHTPGDEIRRIAPSRLDELLFSAILEPSAAIQ<br>EHKSFLKILQDRGIKTIQLSDLVAETYVKYATSKEKESFIEKWLDEATP<br>ALNSENRARVKNYITAMQGQPVKMVRAMMAGVSKQELNIESDVELIVDP<br>MPNLYFIRDPFASAGNGISLNNMKYVVRKRETIFAEFIFSIHPEYKKTP<br>HWFDRLDNGSIEGGDVFIYNKDILVIGVSERINKEAIITIAKHIQDNKE<br>AQFKKIVAINVPPMPNLMHLDTWLTMVDKNKFLYSPNMLSVLKVWEIDL<br>SKPIEMVETNKPLAEVLESIIGEKPILIPIAGKDATQLDIDIETHFDGT<br>NYLTIAPGVVVGYSRNVKTEAALRAAGVTVLSFEGNQLSLGMGSARCMS<br>MPLVREDVK | 65 |
| M. meleagridis-<br>M. columbinum<br>chimeric ADI | MSKINVYSEIGVLKEVLVHTPGDEIRRISPSRLDELLFSAILQPEQAIK<br>EHQSFVKILQDRGIKVIQLSDLVAETYTYHATQKEREAFIEKWLDEAEP<br>ALTKDLRAKVKSYVLSKEGTPVAMVRTMMAGVSKQELNVESETELVVDP<br>MPNLYFTRDPFASAGNGISLNNMKYVVRKRETIFAEFIFSIHPEYKQTP<br>HWFDRLDKGNIEGGDVFIYNKDILVIGVSERINKEAILTIAEHIKNNKE<br>AKFKKIVAINVPPMPNLMHLDTWLTMVDKNKFLYSPNMLSVLKIWEIDL<br>SKEIKMVETSKPLADVLESIIGEKPILIPIAGENASQLDIDIETHFDGT<br>NYLTIAPGVVVGYSRNVKTEAALKAAGVIVYSEDGNQLSLGMGSGRCMS<br>MPLVREDVK | 66 |
| M. meleagridis-<br>M. gallinarum<br>chimeric ADI | MSKINVYSEIGVLKEVLVHTPGDEIRRISPSRLDELLFSAILQPEQAIK<br>EHQSFVKILQDRGIKVIQLSDLVAETYVKYATAEQKAAFIEKYLDEATP<br>ALSAENRERAKKYILSLEMQPVKMIRTMMAGLSKYELNVESNIELIIDP<br>MPNLYFTRDPFASAGNGISLNNMKYVVRKRETIFAEFIFSIHPEYKQTP<br>HWFDRLDKGNIEGGDVFIYNKDILVIGVSERINKEAILTIAEHIKNNKE<br>AKFKKIVAINVPPMPNLMHLDTWLTMVDKNKFLYSPNMLSVLKIWEIDL<br>SKEIKMVETSKPLADVLESIIGEKPILIPIAGENASQLDIDIETHFDGT<br>NYLTIAPGVVVGYSRNVKTEAALKAAGVIVYSEDGNQLSLGMGSGRCMS<br>MPLVREDVK | 67 |
| M. meleagridis-<br>M. iners<br>chimeric ADI | MSKINVYSEIGVLKEVLVHTPGDEIRRISPSRLDELLFSAILQPEQAIK<br>EHQSFVKILQDRGIKVIQLSDLVAETYKHYASEAEKEAFIEKYLDEATP<br>VLSKDMRAKVKNYILSMQGEPVKMVRTMMAGVSKQELNVESEVELIVDP<br>MPNLYFTRDPFASAGNGISLNNMKYVVRKRETIFAEFIFSIHPEYKQTP<br>HWFDRLDKGNIEGGDVFIYNKDILVIGVSERINKEAILTIAEHIKNNKE<br>AKFKKIVAINVPPMPNLMHLDTWLTMVDKNKFLYSPNMLSVLKIWEIDL<br>SKEIKMVETSKPLADVLESIIGEKPILIPIAGENASQLDIDIETHEDGT<br>NYLTIAPGVVVGYSRNVKTEAALKAAGVTVYSFDGNQLSLGMGSGRCMS<br>MPLVREDVK | 68 |

Hence, in some embodiments, the ADI component of the conjugate comprises, consists, or consists essentially of an amino acid sequence selected from Table A1 (SEQ ID NOs:1-68), or an active variant or fragment thereof. Particular examples of active variants and fragments comprise, consist, or consist essentially of an amino acid sequence that is at least 80%, 95%, 90%, 95%, 96%, 97%, 98%, or 99% identical to a sequence selected from Table A1. Additional examples of polypeptide "variants" and "fragments" are described elsewhere herein.

In certain embodiments, the ADI has an "ADI activity", or the ability to convert or metabolize arginine into citrulline and ammonia. ADI activity can be measured according to routine techniques in the art. For instance, the amount of L-citrulline can be detected by a colorimetric endpoint assay (see, for example, Knipp and Vasak, Analytical Biochem. 286:257-264, 2000) and compared to a standard curve of known amounts of L-citrulline in order to calculate the specific activity of ADI, which can be expressed as IU/mg of protein. In some embodiments, one IU of ADI enzyme activity is defined as the amount of enzyme that produces 1 µmol of citrulline per minute at the pH and temperature being tested.

In some embodiments, the ADI is a hexameric or homohexameric ADI, for example, an ADI is capable of forming a hexameric or homohexameric structure in its natural state and/or upon conjugation to the TNF Superfamily ligand component of the conjugate. Without being bound by any one theory, it is hypothesized that the hexameric or homohexameric structure of the ADI component of the conjugate can stabilize the TNF superfamily ligand component of the conjugate, especially where the latter forms a trimeric or homotrimeric structure in its natural state and/or upon conjugation to the ADI component of the conjugate. Particular examples of hexameric or homohexameric ADIs include the native ADIs derived from *Mycoplasma columbinum, M iners, M gallinarum*, and *M. meleagridis* (e.g., SEQ ID NOs: 9, 37, 38, 50, respectively), and the chimeric ADIs from Table A1 (e.g., SEQ ID NOs: 57-68), including active variants and fragments thereof.

Any one or more of the ADI polypeptides described herein can be combined with any one or more of the TNF superfamily ligands or trimeric (for example, homotrimeric) polypeptides described herein, to form a conjugate, for example, a fusion protein.

TNF Superfamily Ligands. Certain conjugates comprise one or more Tumor Necrosis Factor (TNF) superfamily ligands, also referred to as TNF superfamily ligand polypeptides. The Tumor Necrosis Factor receptor superfamily (TNFRSF) is a protein superfamily of cytokine receptors characterized by the ability to bind tumor necrosis factors (TNFs) via an extracellular cysteine-rich domain. With the exception of nerve growth factor (NGF), all TNFs are homologous to the archetypal TNF-α. TNF receptors are primarily involved in apoptosis and inflammation, but also regulate other signal transduction pathways, such as cell proliferation, survival, and differentiation. The term death receptor refers to those members of the TNF receptor superfamily that contain a death domain, examples of which include TNFR1, the Fas receptor, Death Receptor 4 (DR4), and Death Receptor 5 (DR5).

An illustrative list of TNF superfamily receptors and their corresponding ligands is provided in Table T1 below.

TABLE T1

Exemplary TNF Superfamily Members

| Receptor(s) | Synonyms | Ligand(s) |
| --- | --- | --- |
| Death receptor 4 | TRAILR1, Apo-2, CD261 | TRAIL |
| Death receptor 5 | TRAILR2, CD262 | |
| Decoy receptor 1 | TRAILR3, LIT, TRID, CD263 | |
| Decoy receptor 2 | TRAILR4, TRUNDD, CD264 | |
| Tumor necrosis factor receptor 1 | CD120a | TNF-α |
| Tumor necrosis factor receptor 2 | CD120b | |
| Fas receptor | Apo-1, CD95 | FasL |
| Lymphotoxin beta receptor | CD18 | Lymphotoxin beta (TNF-C) |
| OX40 | CD134 | OX40L |
| CD40 | Bp50 | CD154 |
| Decoy receptor 3 | TR6, M68 | FasL, LIGHT, TL1A |
| CD27 | S152, Tp55 | CD70, Siva |
| CD30 | Ki-1 | CD153 |
| 4-1BB (9) | CD137 | 4-1BB ligand |
| RANK | CD265 | RANKL |
| Osteoprotegerin | OCIF, TR1 | |
| TWEAK receptor | Fn14, CD266 | TWEAK |
| TACI | IGAD2, CD267 | APRIL, BAFF, CAMLG |
| BAFF receptor | CD268 | BAFF |
| Herpesvirus entry mediator | ATAR, TR2, CD270 | LIGHT |
| Nerve growth factor receptor | p75NTR, CD271 | NGF, BDNF, NT-3, NT-4 |
| B-cell maturation antigen | TNFRSF13A, CD269 | BAFF |
| Glucocorticoid-induced TNFR-related | AITR, CD357 | GITR ligand |
| Death receptor 3 | Apo-3, TRAMP, LARD, WS-1 | TL1A |
| Ectodysplasin A2 receptor | XEDAR | EDA-A2 |

Thus, in certain embodiments, the TNF superfamily ligand component of the conjugate is selected from a ligand polypeptide in Table T1. In certain embodiments, the TNF superfamily ligand is a human polypeptide ligand selected from Table T1.

In some embodiments, the TNF superfamily ligand is a trimeric or homotrimeric polypeptide. As noted above, according to one non-limiting theory the hexameric or homohexameric structure of the ADI component of the conjugate can stabilize the trimeric or homotrimeric TNF superfamily ligand component of the conjugate. In certain embodiments, the TNF superfamily ligand is a trimeric or homotrimeric polypeptide ligand selected from Table T1.

In some embodiments, the TNF superfamily ligand induces apoptosis in cancer cells, for example, by binding to a death domain or death receptor of a TNF superfamily receptor. Thus, in some embodiments, TNF superfamily ligand (e.g., trimeric or homotrimeric ligand) binds to at least one TNF death receptor, or a TNF superfamily receptor that contains at least one death domain. Examples of TNF superfamily death receptors include TNFR1, Fas receptor, DR4, and DR5. Particular examples of death receptor ligands include TRAIL, TNF-α, and FasL. Thus, in certain embodiments, the TNF superfamily ligand component of the conjugate is selected from one or more of TRAIL, TNF-α, and FasL, optionally a human TRAIL, human TNF-α, or human FasL.

The amino acid sequences of human TRAIL, human TNF-α, and human FasL are provided in Table T2 below.

I266L, D267Q; Y189Q, R191K, Q193R; and Y189Q, R191K, Q193R, I266L (see U.S. Application Nos. 2013/0165383; and 2012/0165267, incorporated by reference). Particular examples of TRAIL fragments include residues 114-281 (extracellular domain), residues 95-281, residues

TABLE T2

Exemplary TNF Superfamily Ligand Sequences

| Name | Sequence | SEQ ID NO. |
|---|---|---|
| FL TRAIL (1-281) | MAMMEVQGGPSLGQICVLIVIFTVLLQSLCVAVTYVYFTNELKQMQDKYSKS GIACFLKEDDSYWDPNDEESMNSPCWQVKWQLRQLVRKMILRISEETISTVQ EKQQNISPLVRERGPQRVAAHITGIRGRSNILSSPNSKNEKALGRKINSWES SRSGHSFLSNLHLRNGELVIHEKGFYYIYSQTYFRFQEEIKENTKNDKQMVQ YIYKYTSYPDPILLMKSARNSCWSKDAEYGLYSIYQGGIFELKENDRIFVSV TNEHLIDMDHEASFFGAFLVG | 69 |
| TRAIL extracellular region (114-281) | VRERGPQRVAAHITGIRGRSNILSSPNSKNEKALGRKINSWESSRSGHSFLS NLHLRNGELVIHEKGFYYIYSQTYFRFQEEIKENTKNDKQMVQYIYKYTSYP DPILLMKSARNSCWSKDAEYGLYSIYQGGIFELKENDRIFVSVINEHLIDMD HEASFFGAFLVG | 70 |
| TNF-α | MSTESMIRDVELAEEALPKKIGGPQGSRRCLFLSLFSFLIVAGATTLFCLLH FGVIGPQREEFPRDLSLISPLAQAVRSSSRIPSDKPVAHVVANPQAEGQLQW LNRRANALLANGVELRDNQLVVPSEGLYLIYSQVLFKGQGCPSTHVLLTHTI SRIAVSYQTKVNLLSAIKSPCQRETPEGAEAKPWYEPIYLGGVFQLEKGDRL SAEINRPDYLDFAESGQVYFGIIAL | 71 |
| FasL | MQQPFNYPYPQIYWVDSSASSPWAPPGIVLPCPTSVPRRPGQRRPPPPPPPP PLPPPPPPPLPPLPLPPLKKRGNHSTGLCLLVMFFMVLVALVGLGLGMFQL FHLQKELAELRESTSQMHTASSLEKQIGHPSPPPEKKELRKVAHLIGKSNSR SMPLEWEDTYGIVLLSGVKYKKGGLVINETGLYFVYSKVYFRGQSCNNLPLS HKVYMRNSKYPQDLVMMEGKMMSYCITGQMWARSSYLGAVFNLISADHLYVN VSELSLVNFEESQTFFGLYKL | 72 |

In some embodiments, the TNF superfamily ligand component of the conjugate comprises, consists, or consists essentially of an amino acid sequence selected from Table T2 (SEQ ID NOs: 69-72), or an active variant or fragment thereof. Particular examples of variants and fragments comprise, consist, or consist essentially of an amino acid sequence that is at least 80%, 95%, 90%, 95%, 96%, 97%, 98%, or 99% identical to a sequence selected from Table T2. Additional examples of active polypeptide "variants" and "fragments" are described elsewhere herein.

In specific embodiments, the TNF superfamily ligand component of the conjugate is a human TNF-related apoptosis-inducing ligand (TRAIL) polypeptide, or a variant or fragment thereof. TRAIL is a cytokine that is produced and secreted by most normal tissue cells. It causes apoptosis in tumor cells, for example, by binding to certain death receptors. The predicted 281 amino acid TRAIL protein has the characteristic structure of a type II membrane protein, with a single internal hydrophobic domain and no signal sequence. The extracellular C-terminal domain of TRAIL shares 22 to 28% identity with the C-terminal domains of other TNF family members. Formation of a complex between TRAIL and its signaling receptors, DR4 and DR5, triggers apoptosis by inducing the oligomerization of intracellular death domains.

In certain embodiments, the TRAIL component of the conjugate comprises, consists, or consists essentially of a TRAIL sequence from Table T2 (SEQ ID NOs: 69 and 70), or a variant or fragment thereof. Specific examples of TRAIL variants include those having any one or more of the following substitutions; S96C, S101C, S111C, R170C, and K179C. In some embodiments, the TRAIL variant has a set of amino acid substitutions at the residue position selected from one or more of Y189Q, R191K, Q193R; H264R, 92-281, residues 91-281, residues 41-281, residues 39-281, residues 15-281, residues 119-281, and residues 1-281 of the full-length sequence (SEQ ID NO:69). Additional examples of polypeptide "variants" and "fragments" are described elsewhere herein.

Any one or more of the TNF superfamily ligands described herein can be combined with any one or more of the ADI polypeptides or hexameric (e.g., homohexameric) polypeptides described herein, to form a conjugate, for example, a fusion protein.

Linkers. Certain conjugates comprise one or more linker groups. The term "linkage," "linker," "linker moiety," or "L" is used herein to refer to a linker that can be used to separate one polypeptide component of a conjugate from another polypeptide component, for example, an ADI polypeptide from a TNF superfamily ligand, or a hexameric polypeptide from a trimeric polypeptide. The linker may be physiologically stable or may include a releasable linker such as a labile linker or an enzymatically degradable linker (e.g., proteolytically cleavable linkers). In certain aspects, the linker is a peptide linker. In some aspects, the linker is a non-peptide linker or non-proteinaceous linker.

Certain embodiments comprise one or more peptide linkers. Such a peptide linker sequence can be incorporated into a conjugate, for example, a fusion polypeptide, using standard techniques in the art.

Certain peptide linker sequences may be chosen based on the following exemplary factors: (1) their ability to adopt a flexible extended conformation; (2) their inability to adopt a secondary structure that could interact with functional epitopes on the first and second polypeptides; (3) their physiological stability; and (4) the lack of hydrophobic or charged residues that might react with the polypeptide functional epitopes, or other features. See, e.g., George and Heringa, J Protein Eng. 15:871-879, 2002. In some embodiments, the peptide linker is a rigid linker. In some embodiments, the peptide linker is a flexible linker. In particular embodiments, flexible linkers can be rationally designed using a computer program capable of modeling the peptides themselves (Desjarlais & Berg, PNAS. 90:2256-2260, 1993; and PNAS. 91:11099-11103, 1994) or by phage display methods.

In some embodiments, the peptide linker sequence is from 1 to about 200 amino acids in length. Exemplary linkers can have an overall amino acid length of about 1-200 amino acids, 1-150 amino acids, 1-100 amino acids, 1-90 amino acids, 1-80 amino acids, 1-70 amino acids, 1-60 amino acids, 1-50 amino acids, 1-40 amino acids, 1-30 amino acids, 1-20 amino acids, 1-10 amino acids, 1-5 amino acids, 1-4 amino acids, 1-3 amino acids, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 110, 120, 130, 140, 150, 160, 170, 180, 190, or 200 or more amino acids.

A peptide linker may employ any one or more naturally-occurring amino acids, non-naturally occurring amino acid(s), amino acid analogs, and/or amino acid mimetics as described elsewhere herein and known in the art. Certain amino acid sequences which may be usefully employed as linkers include those disclosed in Maratea et al., Gene 40:39-46, 1985; Murphy et al., PNAS USA. 83:8258-8262, 1986; U.S. Pat. Nos. 4,935,233 and 4,751,180. Particular peptide linker sequences contain Gly, Ser, and/or Asn residues. Other near neutral amino acids, such as Thr and Ala may also be employed in the peptide linker sequence, if desired.

Certain exemplary peptide linkers are provided in Table L1 below.

TABLE L1

Exemplary Peptide Linkers

| Sequence | SEQ ID NO: |
|---|---|
| $[G]_x$ | |
| $[S]_x$ | |
| $[N]_x$ | |
| $[GS]_x$ | |
| $[GGS]_x$ | |
| $[GSS]_x$ | |
| $[GSGS]_x$ | 73 |
| $[GGSG]_x$ | 74 |
| $[GGGS]_x$ | 75 |
| $[GGGGS]_x$ | 76 |
| $[GN]_x$ | |
| $[GNN]_x$ | |
| $[GNN]_x$ | |
| $[GNGN]_x$ | 77 |
| $[GGNG]_x$ | 78 |
| $[GGGN]_x$ | 79 |

TABLE L1-continued

Exemplary Peptide Linkers

| Sequence | SEQ ID NO: |
|---|---|
| $[GGGGN]_x$ | 80 |
| $A(EAAAK)_xA$ | 81 |
| AEAAAKA | 81 |
| AEAAAKEAAAKA | 82 |
| $(XP)_x$ | |
| APAPKP | 83 |
| APAPKPEPAPKP | 84 |
| GGGGS | 76 |
| GGGGSGGGGS | 85 |
| DGGGS | 86 |
| TGEKP | 87 |
| GGRR | 88 |
| EGKSSGSGSESKVD | 89 |
| KESGSVSSEQLAQFRSLD | 90 |
| GGRRGGGS | 91 |
| LRQRDGERP | 92 |
| LRQKDGGGSERP | 93 |
| $LRQKd(GGGS)_2ERP$ | 94 |

Where "X" is any amino acid; and Where "x" is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or 100

Thus, in certain embodiments, a conjugate, for example, a fusion polypeptide, comprises one or more peptide linkers selected from Table P1.

In some embodiments, for example, in non-fusion or chemically-linked conjugates, the linker is a non-peptide linker. For example, in some embodiments the linker is an organic moiety constructed to contain an alkyl, or aryl backbone, and contains an amide, ether, ester, hydrazone, disulphide linkage or any combination thereof. Linkages containing amino acid, ether and amide bound components are stable under conditions of physiological pH, normally 7.4 in serum. Also included are linkages that contain esters or hydrazones and are stable at serum pH.

In some instances, a linker includes a spacer that increases the distance between the two joined atoms. A spacer may further add flexibility and/or length to the linker. Spacers may include, but are not be limited to, alkyl groups, alkenyl groups, alkynyl groups, aryl groups, aralkyl groups, aralkenyl groups, aralkynyl groups; each of which can contain one or more heteroatoms, heterocycles, amino acids, nucleotides, and saccharides.

In some embodiments, the linker is about 1 to about 30 atoms in length, or about 1, 2, 3, 4, 5, 6, 7, 8, 9, 0, 11, 12, 13, 14, 15, 16, 17, 18, 19, 20, 21, 22, 23, 24, 25, 26, 27, 28, 29, or 30 atoms in length, including all ranges in between. In certain embodiments, the linker is about 1 to 30 atoms in length with carbon chain atoms which may be substituted by heteroatoms independently selected from the group consisting of O, N. or S. In some embodiments, from 1-4 or from 5 to 15 of the C atoms are substituted with a heteroatom independently selected from O, N, S.

In certain embodiments, the linker comprises or consists of a structure selected from the following: —O—, —NH—, —S—, —C(O)—, C(O)—NH, NH—C(O)—NH, O—C(O)—NH, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$-, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —NH—C(O)—CH$_2$—, —CH$_2$—NH—C(O)—CH$_2$—, —CH$_2$—NH—C(O)—CH$_2$—, —NH—C(O)—CH$_2$—CH$_2$—, —CH$_2$—NH—C(O)—CH$_2$—CH$_2$, —CH$_2$—CH$_2$—NH—C(O)—CH$_2$—CH$_2$, —C(O)—NH—CH$_2$—, —C(O)—NH—CH$_2$—CH$_2$—, —O—C(O)—NH—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, bivalent cycloalkyl group, —N(R$^6$)—, R$^6$ is H or an organic radical selected from the group consisting of alkyl, substituted alkyl, alkenyl, substituted alkenyl, alkynyl, substituted alkynyl, aryl and substituted aryl.

In some embodiments, the linker is a stable linker. In some embodiments, the stable linker is selected from the group consisting of: succinimide, propionic acid, carboxymethylate linkages, ethers, carbamates, amides, amines, carbamides, imides, aliphatic C—C bonds, and thio ethers. In some embodiments, the linker group is hydrophilic, for instance, to enhance the solubility of the conjugate in body fluids.

In some embodiments, the linker comprises or consists of polymer such as a polyethylene glycol or polypropylene glycol. The terms "PEG," "polyethylene glycol" and "poly(ethylene glycol)" as used herein, are interchangeable and meant to encompass any water-soluble poly(ethylene oxide) derivative. PEG is a well-known polymer with good solubility in many aqueous and organic solvents, which exhibits low toxicity, lack of immunogenicity, and is clear, colorless, odorless, and stable. Similar products may be obtained with other water-soluble polymers, as described herein, including without limitation; polyvinyl alcohol, other poly(alkylene oxides) such as poly(propylene glycol) and the like, poly(oxyethylated polyols) such as poly(oxyethylated glycerol) and the like, carboxymethylcellulose, dextran, polyvinyl alcohol, polyvinyl purrolidone, poly-1,3-dioxolane, poly-1,3,6-trioxane, ethylene/maleic anhydride, and polyaminoacids. One skilled in the art will be able to select the desired polymer based on the desired dosage, circulation time, resistance to proteolysis, and other considerations.

Typically, PEGs for use in accordance with the conjugates described herein comprise the following structure "—(OCH2CH2)n-" where (n) is about 1 to 4000, about 20 to 1400, or about 20-800. In particular embodiments, PEG also includes "—O—(CH2CH2O)n-CH2CH2-" and "—(OCH2CH2)n-O—" depending upon whether or not the terminal oxygens have been displaced. The term "PEG" includes structures having various terminal or "end capping" groups. The term "PEG" also includes a polymer that contains a majority, that is to say, greater than 50%, of —OCH2CH2-repeating subunits. With respect to specific forms, the PEG can take any number of a variety of molecular weights, as well as structures or geometries such as "branched," "linear," "forked," "multifunctional" PEG molecules.

Representative polymeric reagents and methods for conjugating such polymers to an active moiety are described in Harris, J. M. and Zalipsky, S., Eds, Poly(ethylene glycol), Chemistry and Biological Applications, ACS, Washington, 1997; Veronese, F., and J. M. Harris, Eds., Peptide and Protein PEGylation, Advanced Drug Delivery Reviews, 54(4); 453-609 (2002); Zalipsky, S., et al., "Use of Functionalized Poly Ethylene Glycols) for Modification of Polypeptides" in Polyethylene Glycol Chemistry: Biotechnical and Biomedical Applications, J. M. Harris, ed., Plenus Press, New York (1992); Zalipsky (1995) Advanced Drug Reviews 16:157-182; and in Roberts et al., Adv. Drug Delivery Reviews, 54, 459-476 (2002).

A wide variety of PEG derivatives are both commercially available and suitable for use in the preparation of the PEG-conjugates of the disclosure. For example, NOF Corp.'s SUNBRIGHT® Series provides numerous PEG derivatives, including methoxypolyethylene glycols and activated PEG derivatives such as succinimidyl ester, methoxy-PEG amines, maleimides, and carboxylic acids, for coupling by various methods to polypeptides and polynucleotides and Nektar Therapeutics' Advanced PEGylation also offers diverse PEG-coupling technologies to improve the safety and efficacy of therapeutics. Additional PEGs for use in forming conjugates include those available from Polypure (Norway), from QuantaBioDesign LTD (Ohio) JenKem Technology, Nanocs Corporation, and Sunbio, Inc (South Korea). Further PEG reagents suitable for use in forming a conjugate, and methods of conjugation are described, for example, in Pasut et al., Expert Opin. Ther. Patents. 14(6) 859-893, 2004.

The preparation of linear or branched PEG polymers and derivatives or conjugates thereof is described, for example, in U.S. Pat. Nos. 4,904,584; 5,428,128; 5,621,039; 5,622,986; 5,643,575; 5,728,560; 5,730,990; 5,738,846; 5,811,076; 5,824,701; 5,840,900; 5,880,131; 5,900,402; 5,902,588; 5,919,455; 5,951,974; 5,965,119; 5,965,566; 5,969,040; 5,981,709; 6,011,042; 6,042,822; 6,113,906; 6,127,355; 6,132,713; 6,177,087; 6,180,095; 6,448,369; 6,495,659; 6.602,498; 6,858,736; 6,828,401; 7,026,440; 7,608,678; 7,655,747; 7,786,221; 7,872,072; and 7,910,661, each of which is incorporated herein by reference in its entirety.

In certain embodiments, the foregoing linkers are optional.

Polypeptide Variants. Certain embodiments include "variants" and "fragments" of the reference sequences described herein, whether described by name or by reference to a Table or sequence identifier. Examples include any of the ADI polypeptides, TNF superfamily ligand polypeptides, and fusion polypeptides described herein. A "variant" sequence refers to a polypeptide or polynucleotide sequence that differs from a reference sequence by one or more substitutions, deletions (e.g., truncations), additions, and/or insertions. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of interactive binding capacity. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Tables or the Sequence Listing).

In some embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Tables or the Sequence Listing).

In certain embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In certain instances, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In certain embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdn CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (Cabios. 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (Nucleic Acids Res. 25: 3389-3402, 1997). When utilizing BLAST and Gapped BLAST programs, the default parameters of the respective programs (e.g., XBLAST and NBLAST) can be used.

In some embodiments, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In some embodiments, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA*. 89:10915-10919, 1992). GAP uses the algorithm of Needleman and Wunsch (*J Mol Biol*. 48:443-453, 1970) to find the alignment of two complete sequences that maximizes the number of matches and minimizes the number of gaps.

In particular embodiments, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (PNAS USA. 82: 488-492, 1985); Kunkel et al., (Methods in Enzymol. 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, PNAS USA 89: 7811-7815, 1992; Delgrave et al., Protein Engineering. 6: 327-331, 1993).

Polypeptide Modifications. Certain embodiments include conjugates that comprise at least one "modifying agent," examples of which included but are not limited to macromolecule polymers, proteins, peptides, polysaccharides, and other compounds. In some instances, the modifying agent is attached to the ADI component of a conjugate, the TNF superfamily ligand component of a conjugate, or both. In some embodiments, the modifying agent is attached only to the ADI component of a conjugate, that is, the modifying agent is not attached to the TNF superfamily ligand (for example, TRAIL) component of the conjugate. The conjugate and the modifying agent may be linked by either covalent bonds or non-covalent interaction to form a stable conjugate or a stable composition to achieve a desired effect. In certain embodiments, the modified conjugate retains the biological activity of a corresponding unmodified conjugate (e.g., of the same or similar sequence) and has a longer half-life in vivo, and lower antigenicity than the corresponding unmodified conjugate. In certain embodiments, the modified conjugate retains at least 30%, 35%, 40%, 45%, 50%, 55%, 60%, 65%, 70%, 75%, 80%, 85%, 90%, 95%, 96%, 97%, 98%, 99% or more of the biological activity of the corresponding unmodified conjugate. Generally, the modified conjugate retains biological activity sufficient for therapeutic use.

In some embodiments, the modifying agent is a polymer or a protein or a fragment thereof that is biocompatible and increases the half-life of the conjugate in blood. The modifying agent can be either chemically coupled to the conjugate or a component thereof or where applicable, linked to the conjugate or a component thereof via fusion protein expression.

Macromolecule polymers may include a non-peptide macromolecule polymer, which in certain embodiments, may have its own bioactivity. Suitable polymers include, but are not limited to, polyenol compounds, polyether compounds, polyvinylpyrrolidone, poly amino acids, copolymer of divinyl ether and maleic anhydride, N-(2-hydroxypropyl)-methacrylamide, polysaccharide, polyoxyethylated polyol, heparin or its fragment, poly-alkyl-ethylene glycol and its derivatives, copolymers of poly-alkyl-ethylene glycol and its derivatives, poly(vinyl ethyl ether), a,P-Poly[(2-hydroxyethyl)-DL-aspartamide], polycarboxylates, poly oxyethylene-oxymethylenes, polyacryloyl morpholines, copolymer of amino compounds and oxyolefin, poly hyaluronic acid, polyoxiranes, copolymer of ethanedioic acid and malonic acid, poly (1,3-dioxolane), ethylene and maleic hydrazide copolymer, poly sialic acid, cyclodextrin, etc. In certain embodiments, the polymer is polyethylene glycol.

The polyenol compounds as used herein include, but are not limited to, polyethylene glycol (including monomethoxy polyethylene glycol, monohydroxyl polyethylene glycol), polyvinyl alcohol, polyallyl alcohol, polybutenol and the like, and their derivatives, such as lipids.

The polyether compounds include, but are not limited to poly alkylene glycol $(HO((CH2)_x(O)_nH)$, polypropylene glycol, polyoxyrehylene $(HO((CH_2)_2O)_nH)$, polyvinyl alcohol $((CH_2CHOH)_n)$.

Poly amino acids include, but are not limited to, polymers of one type of amino acid or copolymers of two or more types of amino acids, for example, polyalanine or polylysine, or block co-polymers thereof.

Polysaccharides include but are not limited to, glucosan and its derivatives, for example dextran sulfate, cellulose and its derivatives (including methyl cellulose and carboxymethyl cellulose), starch and its derivatives, polysucrose, etc.

In particular embodiments, the modifying agent is a PEG molecule. "Polyethylene glycol" or "PEG" refers to mixtures of condensation polymers of ethylene oxide and water, in a branched or straight chain, represented by the general formula $H(OCH_2CH_2)_nH$, wherein n is at least 4. In some instances, the PEG is attached to the ADI component of a conjugate, the TNF superfamily ligand component of a conjugate, or both. In some embodiments, the PEG is attached only to the ADI component of a conjugate, that is, the PEG is not attached to the TNF superfamily ligand (for example, TRAIL) component of the conjugate.

"Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In some embodiments, the PEG has a total weight average molecular weight of about 1,000 to about 50,000; about 3,000 to about 40,000; about 5,000 to about 30,000; about 8,000 to about 30,000; about 11,000 to about 30,000; about 12,000 to about 28,000; about 16,000 to about 24,000; about 18,000 to about 22,000; or about 19,000 to about 21,000. In some embodiments, the PEG has a total weight average molecular weight of about 1,000 to about 50,000; about 3,000 to about 30,000; about 3,000 to about 20,000; about 4,000 to about 12,000; about 4,000 to about 10,000; about 4,000 to about 8,000; about 4,000 to about 6,000; or about 5,000. In specific embodiments, the PEG has a total weight average molecular weight of about 20,000. Generally, PEG with a molecular weight of 30,000 or more is difficult to dissolve, and yields of the formulated product may be reduced. The PEG may be a branched or straight chain. The PEG may be a branched or straight chain, and in certain embodiments is a straight chain. The PEG having a molecular weight described herein may be used in conjunction with the conjugate or a component thereof, and optionally, a biocompatible linker.

Certain embodiments employ thiol, sulfhydryl, or cysteine-reactive PEG(s). In some embodiments, the thiol, sulfhydryl, or cysteine-reactive PEG(s) are attached to one or more naturally-occurring cysteine residues, one or more introduced cysteine residues (e.g., substitution of one or more wild-type residues with cysteine residue(s)), insertion of one or more cysteine residues), or any combination thereof (see, e.g., Doherty et al., Bioconjug Chem. 16:1291-98, 2005). In specific embodiments, the ADI component of the conjugate has one or both of K192C and/or K287C substitutions for attachment to cysteine-reactive PEG(s). In certain embodiments, one more of the wild-type cysteines residues of the conjugate are substituted with another amino acid to prevent attachment of the PEG polymer to wild-type cysteines, for example, to prevent the PEG(s) from disrupting an otherwise desirable biological activity. Some embodiments employ one or more non-natural cysteine derivatives (e.g., homocysteine) instead of cysteine.

Non-limiting examples of thiol, sulfhydryl, or cysteine-reactive PEGs include Methoxy PEG Maleimides (M-PEG-MAL) (e.g., MW 2000, MW 5000, MW 10000, MW 20000, MW 30000, MW 40000). M-PEG-MALs react with the thiol groups on cysteine side chains in proteins and peptides to generate a stable 3-thiosuccinimidyl ether linkage. This reaction is highly selective and can take place under mild conditions at about pH 5.0-6.5 in the presence of other functional groups. Thus, in certain embodiments, the conjugate or a component thereof is conjugated to any one or more of the thiol, sulfhydryl, or cysteine-reactive PEG molecules described herein.

The conjugate or a component thereof may be covalently bonded to a modifying agent, such as PEG, with or without a linker. In some instances, the conjugate or a component thereof may be coupled directly (i.e., without a linker) to a modifying agent such as PEG, for example, through an amino group, a sulfhydryl group, a hydroxyl group, a carboxyl group, or other group.

The linker used to covalently attach the conjugate or a component thereof to a modifying agent (e.g. PEG) can be any biocompatible linker. "Biocompatible" indicates that the compound or group is non-toxic and may be utilized in vitro or in vivo without causing injury, sickness, disease, or death. A modifying agent such as PEG can be bonded to the linker, for example, via an ether bond, a thiol bond, an amide bond, or other bond.

In some embodiments, suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, for example, wherein the atoms in the chain comprise C, S, N, P, and/or O. In some instances, a linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. Particular examples of stable linkers include succinimide, propionic acid, carboxymethylate linkages, ethers, carbamates, amides, amines, carbamides, imides, aliphatic C—C bonds, and thio ethers. In certain embodiments, the biocompatible linker is a succinimidyl succinate (SS) group.

Other suitable linkers include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In certain embodiments, the linker is derived from SS, SPA, SCM, or NHS; in certain embodiments, SS, SPA, or NHS are used, and in some embodiments, SS or SPA are used. Thus, in certain embodiments, potential linkers can be formed from methoxy-PEG succinimidyl succinate(SS), methoxy-PEG succinimidyl glutarate(SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and/or methoxy-PEG succinimidyl succinimide.

Additional examples of linkers include, but are not limited to, one or more of the following: —O—, —NH—, —S—, —C(O)—, C(O)—NH, NH—C(O)—NH, —O—C(O)—NH, —C(S)—, —CH$_2$—, —CH2-CH2-, —CH2-CH2-CH2-, —CH2-CH2-CH2-CH2-, —O—CH2-, —CH2-O—, —O—CH2-CH2-, —CH2-O—CH2-, —CH2-CH2-O—, —O—CH2-CH2-CH2-, —CH2-O—CH2-CH2-, —CH2-CH2-O—CH2-, —CH2-CH2-CH2-O—, —O—CH2-CH2-CH2-CH2-, —CH2-O—CH2-CH2-CH2-, —CH2-CH2-O—CH2-CH2-, —CH2-CH2-CH2-O—CH2-, —CH2-CH2-CH2-CH2-O—, —C(O)—NH—CH2-, —C(O)—NH—CH2-CH2-, —CH2-C(O)—NH—CH2-, —CH2-CH2-C(O)—NH—, —C(O)—NH—CH2-CH2-CH2-, —CH2-C(O)—NH—CH2-CH2-, —CH2-CH2-C(O)—NH—CH2-, —CH2-CH2-C(O)—NH—CH2-, —CH2-CH2-CH2-C(O)—NH—, —C(O)—NH—CH2-CH2-CH2-CH2-, —CH2-C(O)—NH—CH2-CH2-CH2-, —CH2-CH2-C(O)—NH—CH2-CH2-, —CH2-CH2-CH2-C(O)—NH—CH2-, —CH2-CH2-CH2-CH2-C(O)—NH—NH—C(O)—CH2-, —CH2-NH—C(O)—CH2-, —CH2-CH2-NH—C(O)—CH2-, —NH—C(O)—CH2-CH2-, —CH2-NH—C(O)—CH2-CH2, —CH2-CH2-NH—C(O)—CH2-CH2, —C(O)—NH—CH2-, —C(O)—NH—CH2-CH2-, —O—C(O)—NH—CH2-, —O—C(O)—NH—CH2-CH2-, —NH—CH2-, —NH—CH2-CH2-, —CH2-NH—CH2-, —CH2-CH2-NH—CH2-, —C(O)—CH2-, —C(O)—CH2-CH2-, —CH2-C(O)—CH2-, —CH2-CH2-C(O)—CH2-, —CH2-CH2-C(O)—CH2-CH2-, —CH2-CH2-C(O)—, —CH2-CH2-CH2-C(O)—NH—CH2-CH2-NH—, —CH2-CH2-CH2-C(O)—NH—CH2-CH2-NH—C(O)—, —CH2-CH2-CH2-C(O)—NH—CH2-CH2-NH—C(O)—CH2-, bivalent cycloalkyl group, —N(R6)-, R6 is H or an organic radical selected from the group consisting of alkyl, substituted alkyl, alkenyl, substituted alkenyl, alkynyl, substituted alkynyl, aryl and substituted aryl. Additionally, any of the linker moieties described herein may further include an ethylene oxide oligomer chain comprising 1 to 20 ethylene oxide monomer units [i.e., —(CH$_2$CH$_2$O)$_{1-20}$—]. That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

Specific exemplary PEG molecules and linkers are described in Table P1 below.

TABLE P1

PEG and Linkers

| PEG | Linker | Comments |
|---|---|---|
| Methoxy-PEG succinimidyl hexanoate | amide | pH 7-8, lower reactivity |
| Methoxy-PEG succinimidyl butanoate (SBA) | amide | pH 7-8, longer hydrolysis time than SPA (~23 min) |
| Methoxy-PEG succinimidyl propionate (SPA) | amide | Tan, 1998, Metase; Basu, IFN; Games, Phe Am. Lyase; better than SCM (~16 min) |
| Methoxy-PEG succinimidyl carboxymethyl ester (SCM) | amide | pH 7-8, RT, 1 hr rxn time, extremely reactive, 0.75 min at pH 8, 25° C., arginase |
| Methoxy-PEG succinimidyl glutaramide | amide | pH 7-8, RT, 90% complete |
| Methoxy-PEG succinimidyl succinamide | amide | pH 7-8, RT, 95% complete |
| MethoxyPEG2 NHS | | Gamez, Phe Am. Lyase; Basu, IFNa2a40K, Nulasta (G-CSF), |
| Methoxy-PEG succinimidyl carbonate (SC) | urethane | Hydrolysis ½ longer than SCM, Wang, 2006 |
| Methoxy-PEG succinimidyl glutarate (SG) | ester | Yang, 2004, Metase |
| Methoxy-PEG succinimidyl succinate (SS) | ester | |
| PEG-maleimide | | |
| PEG-vinylsulfone | | |
| PEG-iodoacetamide | | |
| orthopyridyl disulfide-PEG | | |

In certain embodiments, the conjugate or a component thereof comprises one or more PEG molecules and/or linkers as described herein (e.g., in Table P1).

From 1 to about 30 PEG molecules may be covalently bonded to the conjugate or a component thereof. In certain embodiments, the conjugate or a component thereof is modified with (i.e., comprises) one PEG molecule. In some embodiments, the conjugate or a component thereof is modified with more than one PEG molecule. In particular embodiments, the conjugate or a component thereof is modified with about 1 to about 10, or from about 7 to about 15 PEG molecules, or from about 2 to about 8 or about 9 to about 12 PEG molecules. In some embodiments, the conjugate or a component thereof is modified with about 2, 3, 4, 5, 6, 7, 8, 9, 10, 11, 12, 13, 14, or 15 PEG molecules. In specific embodiments, the conjugate or a component thereof is modified with 4.5-5.5 PEG molecules per conjugate. In some embodiment, the conjugate or a component thereof is modified with 5±1.5 PEG molecules.

In certain embodiments, about 15% to about 70% of the primary amino groups in the conjugate or a component thereof are modified with PEG, in some embodiments about 20% to about 65%, about 25% to about 60%, or in certain embodiments about 30% to about 55%, or 45% to about 50%, or in some embodiments about 50% of the primary amino groups in arginine deiminase are modified with PEG.

PEG which is attached to the conjugate may be either a straight chain, as with SS-PEG, SPA-PEG and SC-PEG, or a branched chain of PEG may be used, as with PEG2-NHS.

In some embodiments, for example, as noted above, the amino acid substitutions employ non-natural amino acids for conjugation to PEG or other modifying agent (see, e.g., de Graaf et al., Bioconjug Chem. 20:1281-95, 2009). Certain embodiments thus include a conjugate or a component thereof that is conjugated to one or more PEGs via one or more non-natural amino acids. In some embodiments the non-natural amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxyl amide, and an organosilane group. In some embodiments, the non-natural amino acid is selected from the group consisting of: p-acetyl-L-phenylalanine, O-methyl-L-tyrosine, L-3-(2-naphthyl)alanine, 3-methyl-phenylalanine, O-4-allyl-L-tyrosine, homocysteine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

Polynucleotides, Expression Vectors, and Host Cells. Certain embodiments relate to polynucleotides that encode a conjugate, for example, a fusion polypeptide, as described herein. Also included are polynucleotides that encode any one or more of the individual ADI or hexameric polypeptides described herein, alone or in combination with polynucleotides that encode any one or more of the individual TNF superfamily ligand or trimeric polypeptides described herein. Thus, certain embodiments include a polynucleotide that encodes any one or more of the individual ADI polypeptides in Table A1, any one or more of the individual TNF superfamily ligands in Table T1 or Table T2, or a fusion polypeptide described herein, for example, a fusion polypeptide that comprise any one or more of the ADI polypeptides of Table A1 fused to any one or more of the TNF superfamily ligands in Table T1 or Table T2.

Among other uses, these and related embodiments may be utilized to recombinantly produce a fusion polypeptide or an individual component thereof (ADI, TNF superfamily ligand, hexameric polypeptide, trimeric polypeptide) in a host cell. It will be appreciated by those of ordinary skill in the art that, as a result of the degeneracy of the genetic code, there are many nucleotide sequences that encode a polypeptide described herein. Some of these polynucleotides may bear minimal homology to the nucleotide sequence of any native gene. Nonetheless, polynucleotides that vary due to differences in codon usage are specifically contemplated, for example, polynucleotides that are optimized for human, yeast or bacterial codon selection.

As will be recognized by the skilled artisan, polynucleotides may be single-stranded (coding or antisense) or double-stranded, and may be DNA (genomic, cDNA or synthetic) or RNA molecules. Additional coding or non-coding sequences may, but need not, be present within a polynucleotide of the present disclosure, and a polynucleotide may, but need not, be linked to other molecules and/or support materials.

Polynucleotides may comprise a native sequence (i.e., an endogenous sequence that encodes a fusion polypeptide or a component thereof) or may comprise a variant, or a biological functional equivalent of such a sequence. Polynucleotide variants may contain one or more substitutions, additions, deletions and/or insertions, as described herein, preferably such that the activity of the variant polypeptide is not substantially diminished relative to the unmodified polypeptide.

Additional coding or non-coding sequences may, but need not, be present within a polynucleotide, and a polynucleotide may, but need not, be linked to other molecules and/or support materials. Hence, the polynucleotides, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably.

The polynucleotide sequences may also be of mixed genomic, cDNA, RNA, and that of synthetic origin. For example, a genomic or cDNA sequence encoding a leader peptide may be joined to a genomic or cDNA sequence encoding the polypeptide, after which the DNA or RNA sequence may be modified at a site by inserting synthetic oligonucleotides encoding the desired amino acid sequence for homologous recombination in accordance with well-known procedures or preferably generating the desired sequence by PCR using suitable oligonucleotides. In some embodiments a signal sequence can be included before the coding sequence. This sequence encodes a signal peptide N-terminal to the coding sequence which communicates to the host cell to direct the polypeptide to the cell surface or secrete the polypeptide into the media. Typically the signal peptide is clipped off by the host cell before the protein leaves the cell. Signal peptides can be found in variety of proteins in prokaryotes and eukaryotes.

One or multiple polynucleotides can encode the ADI, TNF superfamily ligand, hexameric, trimeric, and/or fusion polypeptides described herein. Moreover, the polynucleotide sequence can be manipulated for various reasons. Examples include but are not limited to the incorporation of preferred codons to enhance the expression of the polynucleotide in various organisms (see generally Nakamura et al., Nuc. Acid. Res. 28:292, 2000). In addition, silent mutations can be incorporated in order to introduce, or eliminate restriction sites, decrease the density of CpG dinucleotide motifs (see for example, Kameda et al., Biochem. Biophys. Res. Commun. 349:1269-1277, 2006) or reduce the ability of single stranded sequences to form stem-loop structures: (see, e.g., Zuker M., Nucl. Acid Res. 31:3406-3415, 2003). In addition, mammalian expression can be further optimized by including a Kozak consensus sequence (i.e., (a/g)cc(a/g) ccATGg) (SEQ ID NO:95) at the start codon. Kozak consensus sequences useful for this purpose are known in the art (Mantyh et al., PNAS 92: 2662-2666, 1995; Mantyh et al., Prot. Exp. & Purif. 6:124, 1995).

Also included are expression vectors that comprise the polynucleotides, and host cells that comprise the polynucleotides and/or expression vectors. Polypeptides and conjugates, for example, fusion polypeptides, can be produced by expressing a DNA or RNA sequence encoding the polypeptide in a suitable host cell by well-known techniques. The term "host cell" is used to refer to a cell into which has been introduced, or which is capable of having introduced into it, a nucleic acid sequence encoding one or more of the polypeptides described herein, and which further expresses or is capable of expressing a polypeptide of interest, such as a polynucleotide encoding any herein described polypeptide. The term includes the progeny of the parent cell, whether or not the progeny are identical in morphology or in genetic make-up to the original parent, so long as the selected gene is present. Host cells may be chosen for certain characteristics, for instance, the expression of a formylglycine generating enzyme (FGE) to convert a cysteine or serine residue within a sulfatase motif into a formylglycine (FGly) residue, or the expression of aminoacyl tRNA synthetase(s) that can incorporate unnatural amino acids into the polypeptide, including unnatural amino acids with an azide side-chain, alkyne side-chain, or other desired side-chain, to facilitate chemical conjugation or modification.

In some instances, a polynucleotide or expression vector comprises additional non-coding sequences. For example, the "control elements" or "regulatory sequences" present in an expression vector are non-translated regions of the vector, including enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

A variety of expression vector/host systems are known and may be utilized to contain and express polynucleotide sequences. These include, but are not limited to, microorganisms such as bacteria transformed with an expression vector, for example, a recombinant bacteriophage, plasmid, or cosmid DNA expression vector; yeast transformed with yeast expression vectors; insect cell systems infected with viral expression vectors (e.g., baculovirus); plant cell systems transformed with viral expression vectors (e.g., cauliflower mosaic virus, CaMV; tobacco mosaic virus, TMV) or with bacterial expression vectors (e.g., Ti or pBR322 plasmids); or animal cell systems, including mammalian cell and more specifically human cell systems transformed with viral, plasmid, episomal, integrating, or other expression vectors. Certain embodiments therefore include an expression vector, comprising a polynucleotide sequence that encodes a polypeptide described herein, for example, a fusion polypeptide. Also included are host cells that comprise the polynucleotides and/or expression vectors.

Certain embodiments may employ *E. coli*-based expression systems (see, e.g., Structural Genomics Consortium et al., Nature Methods. 5:135-146, 2008). These and related embodiments may rely partially or totally on ligation-independent cloning (LIC) to produce a suitable expression vector. In specific embodiments, protein expression may be controlled by a T7 RNA polymerase (e.g., pET vector series), or modified pET vectors with alternate promoters, including for example the TAC promoter. These and related embodiments may utilize the expression host strain BL21 (DE3), a λDE3 lysogen of BL21 that supports T7-mediated expression and is deficient in lon and ompT proteases for improved target protein stability. Also included are expression host strains carrying plasmids encoding tRNAs rarely used in *E. coli*, such as ROSETTA™ (DE3) and Rosetta 2 (DE3) strains. In some embodiments other *E. coli* strains may be utilized, including other *E. coli* K-12 strains such as W3110 (F⁻ lambda⁻ IN(rnD-rrnE)1 rph-1), and UT5600 (F, araC14, leuB6(Am), secA206(aziR), lacY1, proC14, tsx67, Δ(ompTfepC)266, entA403, glnX44(AS), λ⁻, trpE38, rfbC1, rpsL109(strR), xylA5, mtl-1, thiE1), which can result in reduced levels of post-translational modifications during fermentation. Cell lysis and sample handling may also be improved using reagents sold under the trademarks BENZONASE® nuclease and BUGBUSTER® Protein Extraction Reagent. For cell culture, auto-inducing media can improve the efficiency of many expression systems, including high-throughput expression systems. Media of this type (e.g., OVERNIGHT EXPRESS™ Autoinduction System) gradually elicit protein expression through metabolic shift without the addition of artificial inducing agents such as IPTG.

Particular embodiments employ hexahistidine tags (such as those sold under the trademark HIS·TAG® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., Protein Expr Purif. 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., Nature Biotechnology. 22:877-882, 2004).

Also included are high-density bacterial fermentation systems. For example, high cell density cultivation of Ralstonia eutropha allows protein production at cell densities of over 150 g/L, and the expression of recombinant proteins at titers exceeding 10 g/L. In the yeast Saccharomyces cerevisiae, a number of vectors containing constitutive or inducible promoters such as alpha factor, alcohol oxidase, and PGH may be used. For reviews, see Ausubel et al. (supra) and Grant et al., Methods Enzymol. 153:516-544, 1987. Also included are Pichia pandoris expression systems (see, e.g., Li et al., Nature Biotechnology. 24, 210-215, 2006; and Hamilton et al., Science, 301:1244, 2003). Certain embodiments include yeast systems that are engineered to selectively glycosylate proteins, including yeast that have humanized N-glycosylation pathways, among others (see, e.g., Hamilton et al., Science. 313:1441-1443, 2006; Wildt et al., Nature Reviews Microbiol. 3:119-28, 2005; and Gerngross et al., Nature-Biotechnology. 22:1409-1414, 2004; U.S. Pat. Nos. 7,629,163; 7,326,681; and 7,029,872). Merely by way of example, recombinant yeast cultures can be grown in Fernbach Flasks or 15 L, 50 L, 100 L, and 200 L fermentors, among others.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311, 1987). Alternatively, plant promoters such as the small subunit of RUBISCO or heat shock promoters may be used (Coruzzi et al., EMBO J. 3:1671-1680, 1984; Broglie et al., Science. 224:838-843, 1984; and Winter et al., Results Probl. Cell Differ. 17:85-105, 1991). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196, 1992).

An insect system may also be used to express a polypeptide of interest. For example, in one such system, Autographa californica nuclear polyhedrosis virus (AcNPV) is used as a vector to express foreign genes in *Spodoptera frugiperda* cells or in *Trichoplusia* cells. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* cells in which the polypeptide of interest may be expressed (Engelhard et al., PNAS USA. 91:3224-3227, 1994). Also included are baculovirus expression systems, including those that utilize SF9, SF21, and T. ni cells (see, e.g., Murphy and Piwnica-Worms, Curr Protoc Protein Sci. Chapter 5:Unit5.4, 2001). Insect systems can provide post-translation modifications that are similar to mammalian systems.

In mammalian host cells, a number of expression systems are well known in the art and commercially available. Exemplary mammalian vector systems include for example, pCEP4, pREP4, and pREP7 from Invitrogen, the PerC6 system from Crucell, and Lentiviral based systems such as pLP1 from Invitrogen, and others. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, PNAS USA. 81:3655-3659, 1984). In addition, transcription enhancers, such as the Rous sarcoma virus (RSV) enhancer, may be used to increase expression in mammalian host cells.

Examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., J. Gen Virol. 36:59, 1977); baby hamster kidney cells (BHK, ATCC CCL 10); mouse sertoli cells (TM4, Mather, Biol. Reprod. 23:243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68, 1982); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA. 77:4216, 1980); and myeloma cell lines such as NSO and Sp2/0. For a review of certain mammalian host cell lines suitable for protein production, see, e.g., Yazaki and Wu, Methods in Molecular Biology, Vol. 248 (B. K. C Lo, ed., Humana Press, Totowa, N.J., 2003), pp. 255-268. Certain preferred mammalian cell expression systems include CHO and HEK293-cell based expression systems. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation, or the insertion of non-naturally occurring amino acids (see generally U.S. Pat. Nos. 7,939,496; 7,816,320; 7,947,473; 7,883,866; 7,838,265; 7,829,310; 7,820,766; 7,820,766; 7,7737,226, 7,736,872; 7,638,299; 7,632,924; and 7,230,068). Post-translational processing which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the foreign protein.

Exemplary Methods for Conjugation. Conjugation or coupling of a first polypeptide (e.g., ADI, hexameric polypeptide) to a second polypeptide (e.g., TNF superfamily ligand, trimeric polypeptide) or more can be carried out using standard chemical, biochemical, and/or molecular techniques. It will be apparent how to make a conjugate in light of the present disclosure using available art-recognized methodologies. In some instances, it will generally be preferred when coupling the primary components of a conjugate that the techniques employed and the resulting linking chemistries do not substantially disturb the desired functionality or activity of the individual components of the conjugate.

In certain embodiments, the conjugate is a fusion polypeptide or fusion protein. In some instances, a fusion polypeptide is expressed as a recombinant polypeptide in an expression system, as described herein and known in the art. Fusion polypeptides can contain one or multiple copies of a polypeptide sequence and may contain one or multiple copies of a polypeptide-based agent of interest, present in any desired arrangement.

For fusion proteins, DNA sequences encoding the fusion polypeptide components and optionally the peptide linker components may be assembled separately, and then ligated into an appropriate expression vector. The 3' end of the DNA sequence encoding one polypeptide component is ligated, with or without a peptide linker, to the 5' end of a DNA sequence encoding the other polypeptide component(s) so that the reading frames of the sequences are in phase. The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the most C-terminal polypeptide. This permits translation into a single fusion polypeptide that retains the biological activity of both component polypeptides.

Similar techniques, mainly the arrangement of regulatory elements such as promoters, stop codons, and transcription termination signals, can be applied to the recombinant production of non-fusion polypeptides, for instance, polypeptides for the production of non-fusion conjugates (e.g., chemically-coupled conjugates).

Polynucleotides and fusion polynucleotides of the disclosure can contain one or multiple copies of a nucleic acid encoding a polypeptide sequence, and/or may contain one or multiple copies of a nucleic acid encoding a polypeptide agent.

In some embodiments, a polynucleotide encoding a polypeptide and/or fusion polypeptide are introduced directly into a host cell, and the cell incubated under conditions sufficient to induce expression of the encoded polypeptide(s). The polypeptide sequences of this disclosure may be prepared using standard techniques well known to those of skill in the art in combination with the polypeptide and nucleic acid sequences provided herein.

Therefore, according to certain embodiments, there is provided a recombinant host cell that comprises a polynucleotide or a fusion polynucleotide which encodes a polypeptide or fusion polypeptide described herein. Expression of a polypeptide or a fusion polypeptide in the host cell may be achieved by culturing under appropriate conditions recombinant host cells containing the polynucleotide. Following production by expression, the polypeptide(s) may be isolated and/or purified using any suitable technique, and then used as desired. Exemplary polynucleotides, expression vectors, and host cells are described elsewhere herein.

The polypeptides, for example, fusion polypeptides, produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-performance liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HYPERD® ion exchange chromatography, and hydrophobic interaction columns (HIC), among others known in the art.

In some embodiments, the conjugate is a non-fusion polypeptide, for example, a conjugate produced by chemically-linking or coupling a first polypeptide (e.g., ADI, hexameric polypeptide) to a second polypeptide (e.g., TNF superfamily ligand, trimeric polypeptide) or more. The particular coupling chemistry employed will depend upon the structure of the polypeptides, the potential presence of multiple functional groups within the biologically active agent, the need for protection/deprotection steps, chemical stability of the agent, and the like, and will be readily determined by one skilled in the art. Illustrative coupling chemistry useful for preparing the conjugates of the disclosure can be found, for example, in Wong (1991), "Chemistry of Protein Conjugation and Crosslinking", CRC Press, Boca Raton, Fla.; and Brinkley "A Brief Survey of Methods for Preparing Protein Conjugates with Dyes, Haptens, and Crosslinking Reagents," in Bioconjug. Chem., 3:2013, 1992. Preferably, the binding ability and/or activity of the conjugate is not substantially reduced as a result of the conjugation technique employed, for example, relative to the unconjugated polypeptides.

In certain embodiments, a first polypeptide (e.g., ADI, hexameric polypeptide) is coupled to a second polypeptide (e.g., TNF superfamily ligand, trimeric polypeptide) either directly or indirectly. A direct reaction between two polypeptides of interest is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to indirectly couple a first polypeptide (e.g., ADI, hexameric polypeptide) and a second polypeptide (e.g., TNF superfamily ligand, trimeric polypeptide) of interest via a linker group, as described herein, including non-peptide linkers and peptide linkers, as described herein. A linker group can also function as a spacer to distance a first and second polypeptide in order to avoid interference with binding capabilities, targeting capabilities or other functionalities. A linker group can also serve to increase the chemical reactivity of a substituent on a polypeptide, and thus increase the coupling efficiency. An increase in chemical reactivity may also facilitate the use of agents, or functional groups on agents, which otherwise would not be possible. Examples of linking groups include, for example, disulfide groups, thioether groups, acid labile groups, photolabile groups, peptidase labile groups and esterase labile groups. In other illustrative embodiments, the conjugates include linking groups such as those disclosed in U.S. Pat. No. 5,208,020 or EP Patent 0 425 235 B1, and Chari et al., Cancer Research. 52: 127-131, 1992. Additional exemplary linkers are described herein.

In certain exemplary embodiments, a reaction between a polypeptide comprising a succinimidyl ester functional group and a polypeptide comprising an amino group forms an amide linkage; a reaction between a polypeptide comprising a oxycarbonylimidizaole functional group and a polypeptide comprising an amino group forms an carbamate linkage; a reaction between a polypeptide comprising a p-nitrophenyl carbonate functional group and a polypeptide comprising an amino group forms an carbamate linkage; a reaction between a polypeptide comprising a trichlorophenyl carbonate functional group and a polypeptide comprising an amino group forms an carbamate linkage; a reaction between a polypeptide comprising a thio ester functional group and a polypeptide comprising an n-terminal amino group forms an amide linkage; a reaction between a polypeptide comprising a proprionaldehyde functional group and a polypeptide comprising an amino group forms a secondary amine linkage.

In some exemplary embodiments, a reaction between a polypeptide comprising a butyraldehyde functional group and a polypeptide comprising an amino group forms a secondary amine linkage; a reaction between a polypeptide comprising an acetal functional group and a polypeptide comprising an amino group forms a secondary amine linkage; a reaction between a polypeptide comprising a piperidone functional group and a polypeptide comprising an amino group forms a secondary amine linkage; a reaction between a polypeptide comprising a methylketone functional group and a polypeptide comprising an amino group forms a secondary amine linkage; a reaction between a polypeptide comprising a tresylate functional group and a polypeptide comprising an amino group forms a secondary amine linkage; a reaction between a polypeptide comprising a maleimide functional group and a polypeptide comprising an amino group forms a secondary amine linkage; a reaction between a polypeptide comprising a aldehyde functional group and a polypeptide comprising an amino group forms a secondary amine linkage; and a reaction between a polypeptide comprising a hydrazine functional group and a polypeptide comprising an carboxylic acid group forms a secondary amine linkage.

In particular exemplary embodiments, a reaction between a polypeptide comprising a maleimide functional group and a polypeptide comprising a thiol group forms a thio ether linkage; a reaction between a polypeptide comprising a vinyl sulfone functional group and a polypeptide comprising a thiol group forms a thio ether linkage; a reaction between a polypeptide comprising a thiol functional group and a polypeptide comprising a thiol group forms a di-sulfide linkage; a reaction between a polypeptide comprising a orthopyridyl disulfide functional group and a polypeptide comprising a thiol group forms a di-sulfide linkage; and a reaction between a polypeptide comprising an iodoacetamide functional group and a polypeptide comprising a thiol group forms a thio ether linkage.

In a specific embodiment, an amine-to-sulfhydryl crosslinker is used for preparing a conjugate. In one preferred embodiment, for example, the crosslinker is succinimidyl-4-(N-maleimidomethyl)cyclohexane-1-carboxylate (SMCC) (Thermo Scientific), which is a sulfhydryl crosslinker containing NHS-ester and maleimide reactive groups at opposite ends of a medium-length cyclohexane-stabilized spacer arm (8.3 angstroms). SMCC is a non-cleavable and membrane permeable crosslinker that can be used to create sulfhydryl-reactive, maleimide-activated agents (e.g., polypeptides) for subsequent reaction with the components of the conjugate. NHS esters react with primary amines at pH 7-9 to form stable amide bonds. Maleimides react with sulfhydryl groups at pH 6.5-7.5 to form stable thioether bonds. Thus, the amine reactive NHS ester of SMCC crosslinks rapidly with primary amines of a polypeptide and the resulting sulfhydryl-reactive maleimide group is then available to react with cysteine residues of the other polypeptide to yield specific conjugates of interest.

In certain specific embodiments, a polypeptide is modified to contain exposed sulfhydryl groups to facilitate crosslinking, e.g., to facilitate crosslinking to a maleimide-activated polypeptide. In some specific embodiments, a polypeptide is modified with a reagent which modifies primary amines to add protected thiol sulfhydryl groups. In some embodiments, the reagent N-succinimidyl-S-acetylthioacetate (SATA) (Thermo Scientific) is used to produce thiolated polypeptides.

In certain embodiments, a maleimide-activated polypeptide is reacted under suitable conditions with a thiolated polypeptides to produce a conjugate. It will be understood that by manipulating the ratios of SMCC, SATA, agent, and polypeptides in these reactions it is possible to produce conjugates having differing stoichiometries, molecular weights and properties.

In some illustrative embodiments, conjugates are made using bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio)propionate (SPDP) (Carlsson et al., Biochem. J. 173:723-737 [1978]) and N-succinimidyl-4-(2-pyridylthio)pentanoate (SPP) to provide for a disulfide linkage.

The specific crosslinking strategies discussed herein are but a few of many examples of suitable conjugation strategies that may be employed in producing the conjugates described herein. It will be evident to those skilled in the art that a variety of other bifunctional or polyfunctional reagents, both homo- and hetero-functional (such as those described in the catalog of the Pierce Chemical Co., Rockford, IL), may be employed as the linker group. Coupling may be affected, for example, through amino groups, carboxyl groups, sulfhydryl groups or oxidized carbohydrate residues. There are numerous references describing such methodology, e.g., U.S. Pat. No. 4,671,958, to Rodwell et al.

Conjugates can also be prepared by a various "click chemistry" techniques, including reactions that are modular, wide in scope, give very high yields, generate mainly inoffensive byproducts that can be removed by non-chromatographic methods, and can be stereospecific but not necessarily enantioselective (see Kolb et al., Angew Chem Int Ed Engl. 40:2004-2021, 2001). Particular examples include conjugation techniques that employ the Huisgen 1,3-dipolar cycloaddition of azides and alkynes, also referred to as "azide-alkyne cycloaddition" reactions (see Hein et al., Pharm Res. 25:2216-2230, 2008). Non-limiting examples of azide-alkyne cycloaddition reactions include copper-catalyzed azide-alkyne cycloaddition (CuAAC) reactions and ruthenium-catalyzed azide-alkyne cycloaddition (RuAAC) reactions.

CuAAC works over a broad temperature range, is insensitive to aqueous conditions and a pH range over 4 to 12, and tolerates a broad range of functional groups (see Himo et al, J Am Chem Soc. 127:210-216, 2005). The active Cu(I) catalyst can be generated, for example, from Cu(I) salts or Cu(II) salts using sodium ascorbate as the reducing agent. This reaction forms 1,4-substituted products, making it region-specific (see Hein et al., supra).

RuAAC utilizes pentamethylcyclopentadienyl ruthenium chloride [Cp*RuCl] complexes that are able to catalyze the cycloaddition of azides to terminal alkynes, regioselectively leading to 1,5-disubstituted 1,2,3-triazoles (see Rasmussen et al., Org. Lett. 9:5337-5339, 2007). Further, and in contrast to CuAAC, RuAAC can also be used with internal alkynes to provide fully substituted 1,2,3-triazoles.

Any one or more of the fusion or non-fusion techniques can be employed in the preparation of a conjugate, as described herein.

Methods of Use and Compositions

Also included are methods of using the conjugates described herein for treating a subject in need thereof, and compositions comprising the conjugates. For example, certain embodiments include methods of treating, ameliorating the symptoms of, or inhibiting the progression of, a cancer in a subject in need thereof, comprising administering to the subject a conjugate described herein, or a composition comprising the conjugate.

The methods and compositions described herein can be used in the treatment of any variety of cancers. In some embodiments, the cancer is selected from one or more of hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell glioblastoma or a gliosarcoma), meningioma, pituitary adenoma, vestibular schwannoma, primary CNS lymphoma, primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

In some embodiments, the cancer exhibits reduced expression and/or activity of argininosuccinate synthetase-1 (ASS-1), or is otherwise argininosuccinate synthetase-1-deficient. In some of these and related embodiments, the cancer is ADI-sensitive or substantially ADI-sensitive. In some instances, reduced ASS-1 expression or activity is a reduction in expression and/or activity of about 5%, 10%, 15%, 20%, 25%, 30%, 35%, 40%, 45%, 50%, 55%, 60%, 65%, 70%, or more, relative to expression and/or activity in an appropriate control sample, for example, a normal cell or tissue. In certain embodiments, ASS or ASL expression or activity is reduced by at least two-fold relative to expression or activity in a control sample.

In some embodiments, the cancer exhibits normal or increased expression and/or activity of argininosuccinate synthetase-1 (ASS-1). In certain of these and related embodiments, the cancer is ADI-resistant or substantially ADI-resistant, or ADI-non-sensitive.

ASS-1 expression or activity can be measured according to routine techniques the art, including, for example, quantitative PCR, immunohistochemistry, Western Blotting, enzyme activity assays (e.g., ADI activity assays to measure conversion of citrulline into argininosuccinate or conversion of argininosuccinate into arginine and fumarate), and the like.

In some embodiments, the methods or compositions described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods or compositions described herein increase median survival time of a patient by 1 year, 2 years, 3 years, or longer. In some embodiments, the methods or compositions described herein increase progression-free survival by 2 weeks, 3 weeks, 4 weeks, 5 weeks, 6 weeks, 7 weeks, 8 weeks, 9 weeks, 10 weeks or longer. In certain embodiments, the methods or compositions described herein increase progression-free survival by 1 year, 2 years, 3 years, or longer.

In certain embodiments, the composition administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the composition administered is sufficient to result in stable disease. In certain embodiments, the composition administered is sufficient to result in stabilization or clinically relevant reduction in symptoms of a particular disease indication known to the skilled clinician.

The methods or compositions for treating cancers can be combined with other therapeutic modalities. For example, a compositions described herein can be administered to a subject before, during, or after other therapeutic interventions, including symptomatic care, chemotherapy, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions described herein are known in the art.

For in vivo use, for instance, for the treatment of human disease or testing, the conjugates described herein are generally incorporated into one or more pharmaceutical or therapeutic compositions prior to administration. In some instances, a pharmaceutical or therapeutic composition comprises one or more of the conjugates described herein in combination with a physiologically acceptable carrier or excipient.

To prepare a pharmaceutical or therapeutic composition, an effective or desired amount of one or more conjugates is mixed with any pharmaceutical carrier(s) or excipient known to those skilled in the art to be suitable for the particular conjugate and/or mode of administration. A pharmaceutical carrier may be liquid, semi-liquid or solid. Solutions or suspensions used for parenteral, intradermal, subcutaneous or topical application may include, for example, a sterile diluent (such as water), saline solution (e.g., phosphate buffered saline; PBS), fixed oil, polyethylene glycol, glycerin, propylene glycol or other synthetic solvent; antimicrobial agents (such as benzyl alcohol and methyl parabens); antioxidants (such as ascorbic acid and sodium bisulfate) and chelating agents (such as ethylenediaminetetraacetic acid (EDTA)); buffers (such as acetates, citrates and phosphates). If administered intravenously (e.g., by IV infusion), suitable carriers include physiological saline or phosphate buffered saline (PBS), and solutions containing thickening and solubilizing agents, such as glucose, polyethylene glycol, polypropylene glycol and mixtures thereof.

In certain aspects, the pH of the composition is near physiological pH or about pH 7.4, including about pH 6.5, about 7.0, about 7.1, about 7.2, about 7.3, about 7.4, about 7.5, about 7.6, about 7.7, about 7.8, about 7.9, about 8.0, about 8.5, or any range thereof. In specific embodiments, the composition has one or more of the following determinations of purity: less than about 1 EU endotoxin/mg protein, less that about 100 ng host cell protein/mg protein, less than about 10 pg host cell DNA/mg protein, and/or greater than about 95% single peak purity by SEC HPLC.

Administration may be achieved by a variety of different routes, including oral, parenteral, intranasal, intravenous, intradermal, intramuscular, intrathecal, subcutaneous, sublingual, buccal, rectal, vaginal, and topical. Preferred modes of administration depend upon the nature of the condition to be treated or prevented. Particular embodiments include administration by IV infusion.

Carriers can include, for example, pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, one or more conjugates can be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980). The particle(s) or liposomes may further comprise other therapeutic or diagnostic agents.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Certain pharmaceutical or therapeutic compositions are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described conjugate in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will typically contain a therapeutically effective amount of a conjugate described herein, for treatment of a disease or condition of interest.

A pharmaceutical or therapeutic composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical or therapeutic composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical or therapeutic compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminenetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical or therapeutic composition intended for either parenteral or oral administration should contain an amount of a conjugate such that a suitable dosage will be obtained. Typically, this amount is at least 0.01% of the conjugate of interest in the composition. When intended for oral administration, this amount may be varied to be between 0.1 and about 70% of the weight of the composition. Certain oral pharmaceutical compositions contain between about 4% and about 75% of the conjugate of interest. In certain embodiments, pharmaceutical compositions and preparations are prepared so that a parenteral dosage unit contains between 0.01 to 10% by weight of the conjugate of interest prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include a component that binds to the conjugate and thereby assists in the delivery of the conjugate. Suitable components that may act in this capacity include monoclonal or polyclonal antibodies, one or more proteins or a liposome.

The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The compositions described herein may be prepared with carriers that protect the conjugates against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others known to those of ordinary skill in the art.

The pharmaceutical compositions may be prepared by methodology well known in the pharmaceutical art. For example, a pharmaceutical composition intended to be administered by injection may comprise one or more of salts, buffers and/or stabilizers, with sterile, distilled water so as to form a solution. A surfactant may be added to facilitate the formation of a homogeneous solution or suspension. Surfactants are compounds that non-covalently interact with the conjugate so as to facilitate dissolution or homogeneous suspension of the conjugate in the aqueous delivery system.

The compositions may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

In some embodiments, a therapeutically effective amount or therapeutic dosage of a composition described herein is an amount that is effective to reduce or stabilize tumor growth. In certain instances, treatment is initiated with small dosages which can be increased by small increments until the optimum effect under the circumstances is achieved. In some instances, a therapeutically effective daily dose is (for a 70 kg mammal) from about 0.001 mg/kg (i.e., ~0.07 mg) to about 100 mg/kg (i.e., ~7.0 g); preferably a therapeutically effective dose is (for a 70 kg mammal) from about 0.01 mg/kg (i.e., ~0.7 mg) to about 50 mg/kg (i.e., ~3.5 g); more preferably a therapeutically effective dose is (for a 70 kg mammal) from about 1 mg/kg (i.e., ~70 mg) to about 25 mg/kg (i.e., ~1.75 g).

In some embodiments, a dosage is administered from about once a day to about once every two or three weeks. For example, in certain embodiments, a dosage is administered about once every 1, 2, 3, 4, 5, 6, or 7 days, or about once a week, or about twice a week, or about three times a week, or about once every two or three weeks.

In some embodiments, the dosage is from about 0.1 mg/kg to about 20 mg/kg, or to about 10 mg/kg, or to about 5 mg/kg, or to about 3 mg/kg. In some embodiments, the dosage is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg. 7.0 mg/kg, 7.5 mg/kg, 8.0 mg/kg, 8.5 mg/kg, 9.0 mg/kg, 9.5 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg, including all integers and ranges in between. In specific embodiments, the dosage is about 1 mg/kg once a week as a 2 ml intravenous injection to about 20 mg/kg once every 3 days.

Also included are patient care kits, comprising one or more conjugates or compositions described herein. Certain kits also comprise one or more pharmaceutically-acceptable diluents or solvents, such as water (e.g., sterile water). In some embodiments, the conjugates are stored in vials, cartridges, dual chamber syringes, and/or pre-filled mixing systems.

The kits herein may also include a one or more additional therapeutic agents (e.g., conjugates) or other components suitable or desired for the indication being treated, or for the desired diagnostic application. The kits herein can also include one or more syringes or other components necessary or desired to facilitate an intended mode of delivery (e.g., stents, implantable depots, etc.).

All publications, patent applications, and issued patents cited in this specification are herein incorporated by reference as if each individual publication, patent application, or issued patent were specifically and individually indicated to be incorporated by reference.

Although the foregoing has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Combinations of ADI-PEG 20 and TRAIL

The ability of ADI to increase the anti-cancer activity of TRAIL, and in some instances vice versa, was tested by treating various cancer cell lines with ADI-PEG 20 (pegylated arginine deiminase from Mycoplasma hominis that is modified with K112E and P210S substitutions), human rhTRAIL, or a combination thereof. The cellular assays were performed as described in Example 1.

The results for ADI-sensitive (most have low or undetectable expression of ASS1) cancer cell lines are shown in Table E1 below.

TABLE E1

Effect on Cell Viability in ADI-Sensitive Cell Lines

| Cancer | Cell Line | Individual Agent Potency | | ADI-PEG 20 and rhTRAIL Combination Potency |
|---|---|---|---|---|
| | | ADI-PEG 20 IC50 (nM) | rhTRAIL IC50 (ng/ml) | |
| Prostate | PC3 | 1.3 | >100 | ** |
| Ovarian | SKOV-3 | 0.7 | >100 | ** |
| Pancreatic | Mia-Paca-2 | 1.0 | 30.0 | * |
| | Panc-1 | 0.3 | 100.0 | *** |
| Colon | HCT116 | 0.9 | 5.8 | *** |
| | HT29 | 0.5 | >100 | ** |
| Breast | MDA-MB-231 | 0.7 | 120.0 | ** |
| NSCLC | H1299 | 1.2 | >100 | ** |
| Renal | 786-O | 1.4 | >100 | ** |
| | ACHN | 0.8 | >100 | *** |
| | Caki-1 | 0.4 | 27.5 | *** |
| | Caki-2 | 0.7 | >100 | *** |
| Melanoma | A375 | 0.9 | >100 | ** |
| | SK-MEL-3 | 0.6 | >100 | ** |
| | SK-MEL-24 | 1.0 | >100 | — |
| | MeWO | 1.0 | >100 | — |
| | WM-115 | 2.0 | >100 | *** |
| Glioblastoma | U87MG | 0.8 | >100 | ** |
| Burkitt's | Ramos | 1.5 | >100 | — |
| Lymphoma | Raji | 0.4 | 80.0 | *** |
| | Daudi | 0.2 | >100 | — |
| | NAMALWA | 0.6 | 16.8 | * |
| Leukemia | K562 | 0.3 | >100 | *** |
| | MOLT4 | 0.9 | >100 | — |
| | HL60 | 10 | >100 | ** |
| | Jurkat | 0.9 | 1.9 | * |

*** Strong synergy relative to each agent alone (CI = 0.4-0.74 by Bliss Independence Model)
** Synergy relative to each agent alone (CI = 0.75-0.9 by Bliss Independence Model)
* Additive relative to each agent alone (CI = 0.9-1 by Bliss Independence Model and <0.9 by Highest Single Agent Model)
— Combination had same activity as the highest agent alone These results illustrate a synergistic or additive effect between the ADI-PEG 20 and rhTRAIL combination relative to ADI-PEG 20 and/or rhTRAIL alone in the cell-killing of a variety of cancer cell lines. These results also illustrate that ADI-PEG 20 potentiates the activity of rhTRAIL in cancer cell lines that are otherwise resistant to rhTRAIL. Significantly or synergistically increased cell-killing activity was observed in a variety of cancer cell lines, including breast cancer cells, Burkitt's Lymphoma cells, colon cancer cells, glioblastoma cancer cells, leukemic cells, melanoma cancer cells, non-small lung cell cancer (NSCLC) cells, ovarian cancer cells, pancreatic cancer cells, prostate cancer cells, and renal cancer cells.

Figure 1B:
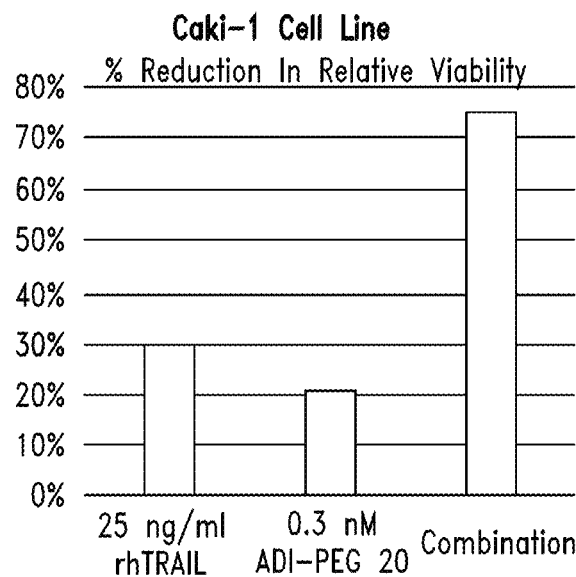
Figure 1C:
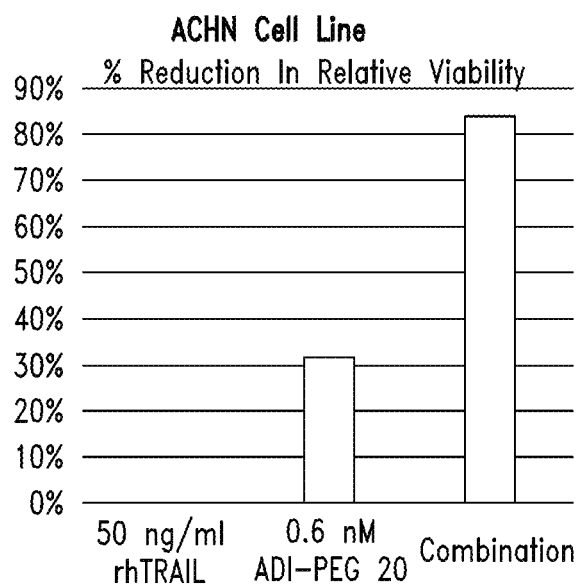
Figure 1D:
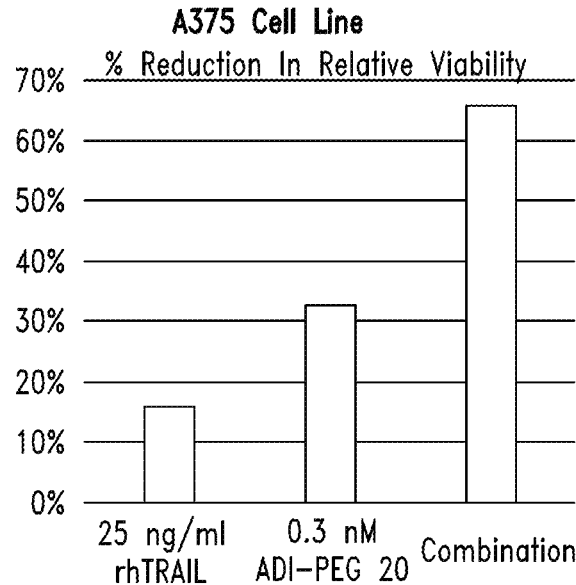

FIGS. 1A-1D further illustrate the synergistic effects of the ADI-PEG 20 and rhTRAIL combination on the relative viability of various cancer cell lines, relative to ADI-PEG 20 and/or rhTRAIL alone. FIG. 1A shows synergy in the HCT116 colon cancer cell line, FIG. 1B shows synergy in the Caki-1 renal cancer cell line, FIG. 1C shows synergy in the ACHN renal cancer cell line, and FIG. 1D shows synergy in the A375 melanoma cell line.

Figure 2A:
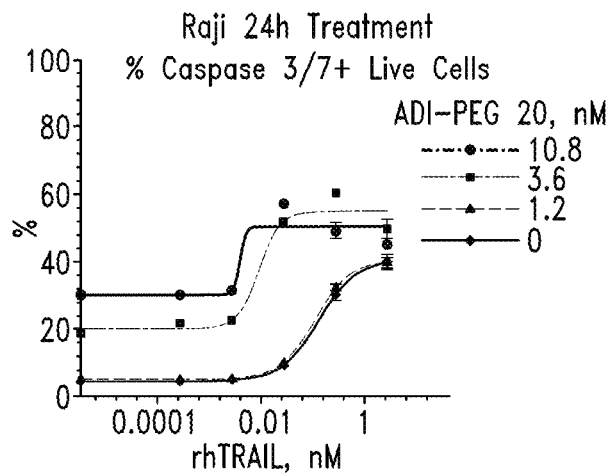
FIGS. 2A-2C demonstrate the synergistic effects ADI-PEG 20 and rhTRAIL on caspase 3/7 activation (FIG. 2A), induction of cell death (FIG. 2B), and reduction in the percentage of viable cells that are not committed to apoptosis (cells in which caspase 3/7 is not activated.
Figure 2B:
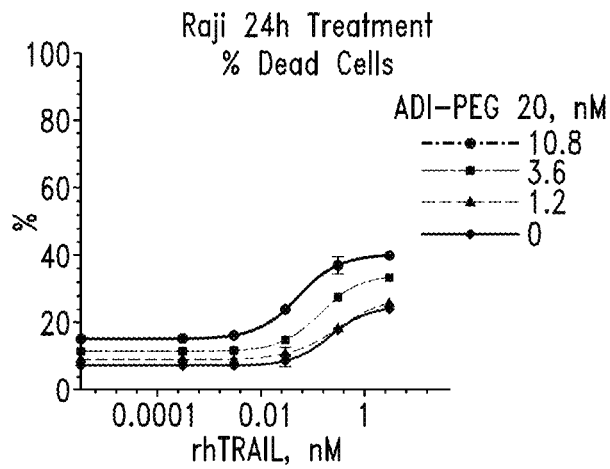
Figure 2C:
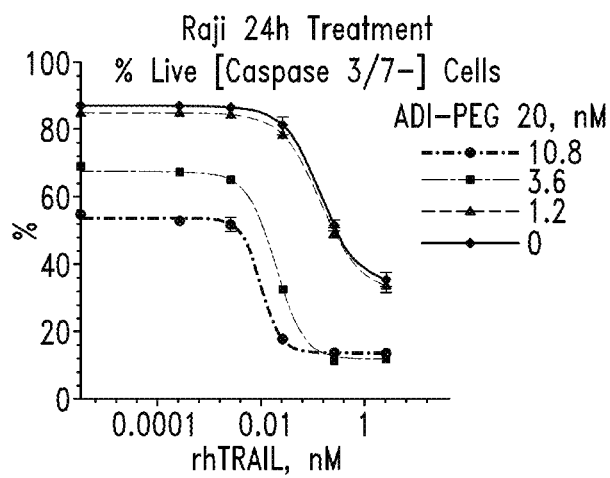
Figure 3A:
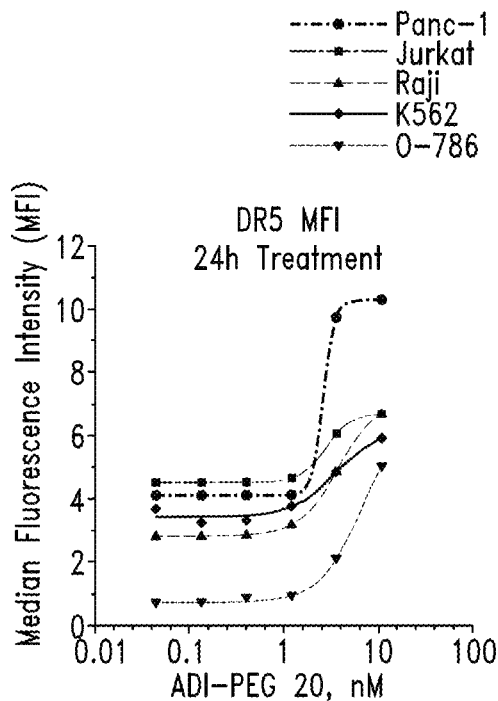
FIGS. 3A-3D show up-regulated expression of TRAIL receptor DR5 in various cancer cell lines following treatment with ADI-PEG 20.
Figure 3B:
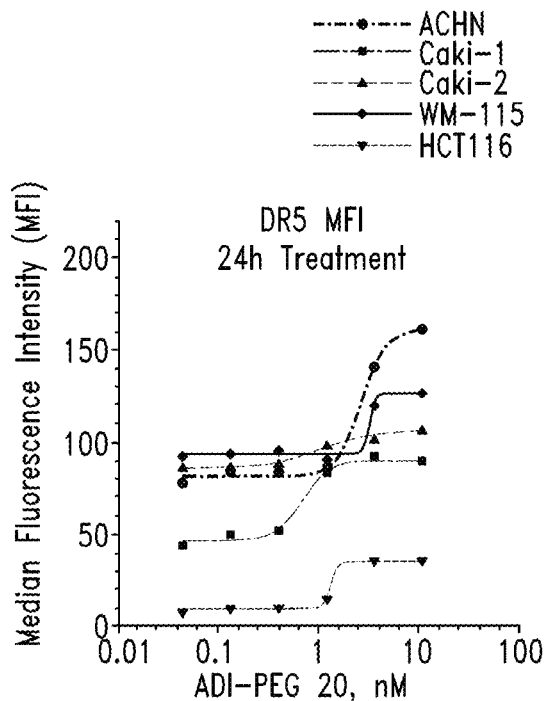
Figure 3C:
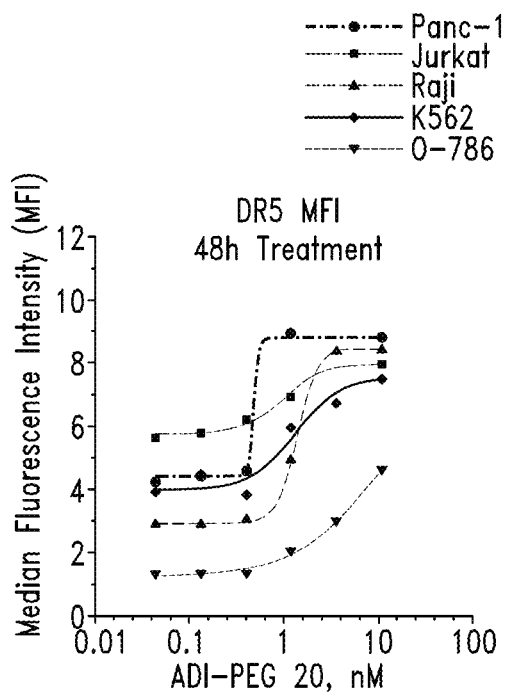
Figure 3D:
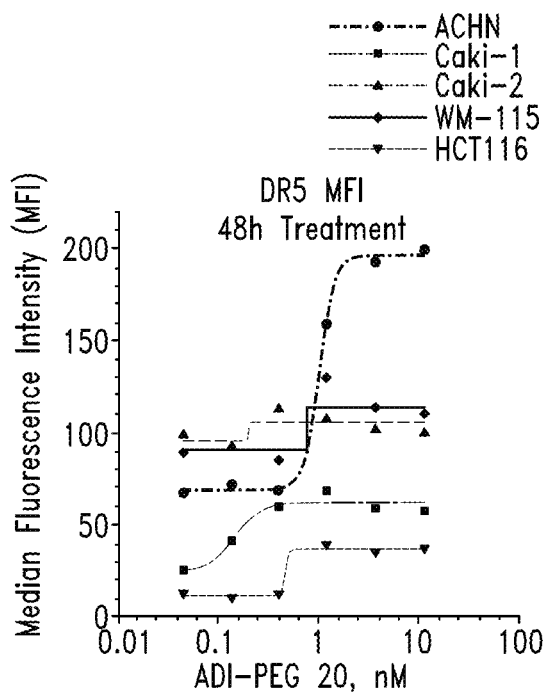

FIGS. 2A-2C demonstrate the synergistic effects ADI-PEG 20 and rhTRAIL on caspase 3/7 activation (FIG. 2A), induction of cell death (FIG. 2B), and reduction in the percentage of viable cells that are not committed to apoptosis (cells in which caspase 3/7 is not activated; FIG. 2C), compared to each agent alone in Raji Burkitt's lymphoma cell line. Percentages of dead cells or cells with and without activated caspase 3/7 were determined by flow cytometry analysis after staining with fluorescent reagents detecting activated caspase 3/7 and dead cells (CellEvent Caspase 3/7 kit from ThermoFisher Scientific).

The results for ADI-resistant (relatively high expression of ASS1) cancer cell lines are shown in Table E2 below.

TABLE E2

Effect on Cell Viability in ADI-Resistant Cell Lines (ADI-PEG 20 IC50 >10 nM)

| Cancer | Cell Line | rhTRAIL IC50 (ng/ml) | ADI-PEG 20 and rhTRAIL Combination Potency |
|---|---|---|---|
| Prostate | LnCap | >100 | — |
| Ovarian | OVCAR-3 | 21.4 | — |
| | Caov-3 | 6.4 | — |
| Pancreatic | BxPC3 | 54.6 | — |
| Colon | Colo205 | 3.8 | — |
| | LoVo | 6.0 | — |
| | DLD-1 | 7.5 | — |
| Breast | SkBr-3 | >100 | — |
| | BT-20 | >100 | — |
| | BT-474 | >100 | — |
| | ZR-75-1 | >100 | — |
| | T47D | >100 | — |
| | MCF7 | >100 | — |
| | MDA-MB-157 | >100 | — |
| | MDA-MB-453[a] | >100 | **** |
| NSCLC | A549 | >100 | — |
| | H460 | >100 | — |
| | H1975[a] | 2.9 | * |
| | H23 | >100 | — |
| | H2122 | 2.9 | — |
| Multiple myeloma | U266 | >100 | — |
| | RPMI8226 | 9.9 | — |
| Leukemia | EOL-1 | >100 | — |

[a] ADI had some activity at 10 nM
**** Strongest synergy relative to each agent alone (CI <0.4 by Bliss Independence Model)
*** Strong synergy relative to each agent alone (CI = 0.4-0.74 by Bliss Independence Model)
** Synergy relative to each agent alone (CI = 0.75-0.9 by Bliss Independence Model)
* Additive relative to each agent alone (CI = 0.9-1 by Bliss Independence Model and <0.9 by Highest Single Agent Model)
— Combination had same activity as the highest agent alone The results in Table E2 show that ADI-PEG 20 does not necessary potentiate the cancer cell-killing activity of rhTRAIL (or vice versa) in certain ADI-resistant cell lines (due to high ASS1). However, in some ADI-resistant cancer cell lines (for example, MDA-MB-453 and H1975, where ADI has at least some minimal activity), the combination of ADI-PEG 20 and rhTRAIL shows synergism, potentiation, and/or coalism in cancer cell-killing activity relative to ADI-PEG 20 and/or TRAIL alone. Examples 2 and 3 show some of the biological activities of ADI that are likely to contribute to its ability to potentiate or synergize with TRAIL.

Example 2

ADI-PEG 20 Upregulates DR5 Receptor

To explore potential mechanisms by which ADI increases or potentiates the activity of rhTRAIL, the expression of DR4 and DR5 receptors was measured by flow cytometry following treatment of cancer cell lines with ADI-PEG 20.

The experimental workflow consisted of cell treatment, collection, and staining with fixable Live/Dead stain (ThermoFisher) and antibodies recognizing TRAIL receptors for 30 minutes on ice. This was followed by washing away unincorporated Live/Dead dye and unbound antibodies and analysis by a multi-color flow cytometer. Live/dead stain and antibodies were labeled with distinct fluorophores detected in different channels of a flow cytometerlsotype control antibodies were used to assess and control for non-specific binding. Receptor expression was analyzed in a cell population gated on singlet and live cells.

FIGS. 3A-3D show that expression of the DR5 receptor was upregulated by ADI-PEG 20 in the Panc-1, Jurkat, Raji, K562, O-786, ACHN, Caki-1, Caki-2, WM-115 and HCT116 cell lines. Expression of the DR4 receptor was low or undetectable in these cell lines and was not noticeably affected by ADI-PEG 20 treatment.

Example 3

ADI-PEG 20 Downregulates Survivin

Figure 4:
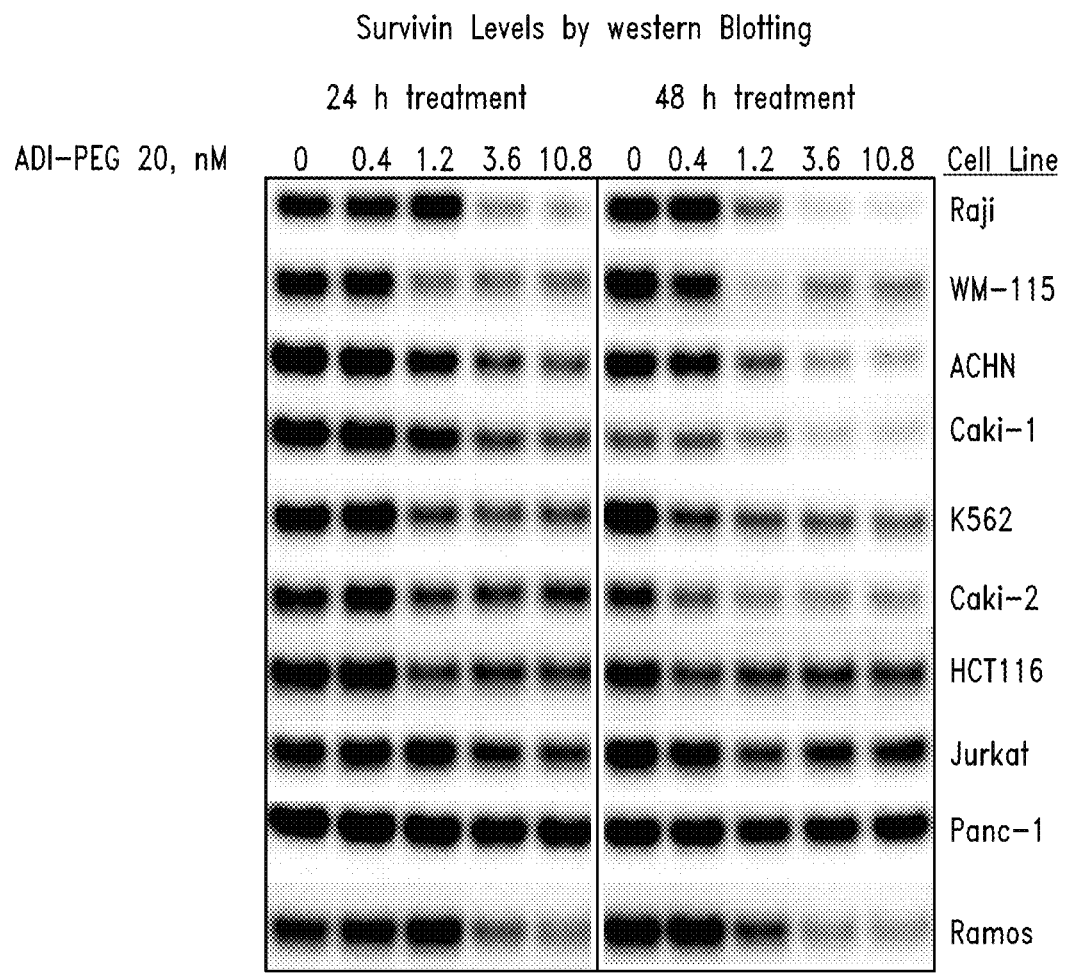
FIG. 4 demonstrates reduction in survivin protein levels after treatment with ADI-PEG 20 of ADI-sensitive cell lines. Survivin has been shown to impede activity of TRAIL. Thus, lowering survivin levels (along with DR5 upregulation) may contribute to the ability of ADI to potentiate and/or increase apoptotic activity of TRAIL in cancer cell lines.

FIG. 4 demonstrates reduction in survivin protein levels after treatment with ADI-PEG 20 of ADI-sensitive cell lines. Survivin has been shown to impede activity of TRAIL. Thus, lowering survivin levels (along with DR5 upregulation) may contribute to the ability of ADI to potentiate and/or increase apoptotic activity of TRAIL in cancer cell lines.

Example 4

Conjugates of ADI and TRAIL

Fusion proteins between the arginine deiminase (ADI) from *M. columbinum* and the extracellular domain (residues 114-281) of human TNF-related apoptosis-inducing ligand (TRAIL) were cloned, expressed, and purified according to routine techniques, and then tested for anti-cancer activity. Table E3 below provides a summary of the ADI-TRAIL fusion proteins tested.

TABLE E3

Exemplary ADI-TRAIL Fusion Polypeptides

| Construct | Size (a.a) | MW (kDA) | Linker Type | Linker Flexibility | Linker Sequence | Protein Production Yield mg | Protein Production Yield mg/L | ADI Activity IU/mg | ADI Activity IU/μ mol |
|---|---|---|---|---|---|---|---|---|---|
| Mcol-6H ADI | 407 | 44.97 | | | | | | 84.4 | 3888 |
| Mcol-hr-TRAIL (114-281) | 574 | 64.77 | $(GGGGS)_{x1}$ (SEQ ID NO: 76) | Flexible (L1 linker) | GGGGS (SEQ ID NO: 76) | 6 | 3 | 71.3 | 4615 |
| Mcol-hr-TRAIL (114-281) | 579 | 65.08 | $(GGGGS)_{x2}$ (SEQ ID NO: 85) | Flexible (L2 Linker) | GGGGSGGGGS (SEQ ID NO: 85) | 2.2 | 1.1 | 69.5 | 4526 |
| Mcol-hr-TRAIL (114-281) | 576 | 65.07 | $A(EAAAK)_{x1}A$ (SEQ ID NO: 81) | Rigid L3 (Linker) | AEAAAKA (SEQ ID NO: 81) | 10 | 2.5 | 63.6 | 4137 |
| Mcol-hr-TRAIL (114-281) | 581 | 65.54 | $A(EAAAK)_{x2}A$ (SEQ ID NO: 82) | Rigid L4 (Linker) | AEAAAKEAAAKA (SEQ ID NO: 82) | 13.1 | 3.3 | 68.6 | 4493 |
| Mcol-hr-TRAIL (114-281) | 575 | 65.02 | $(XP)_{x3}$ (SEQ ID NO: 96) | Rigid L5 (Linker) | APAPKP (SEQ ID NO: 83) | 9.4 | 2.4 | 71.1 | 4622 |
| Mcol-hr-TRAIL (114-281) | 581 | 65.64 | $(XP)_{x6}$ (SEQ ID NO: 97) | Rigid L6 (Linker) | APAPKPEPAPKP (SEQ ID NO: 84) | 16.3 | 4.1 | 71.2 | 4672 |

In addition, ADI from other hexameric species as well as their swap domains were used to make fusion proteins with human TRAIL (aa 114-281) using the GGGGS linker (SEQ ID NO:76). Table E4 below provides a summary of the generated hexameric ADI-TRAIL fusion proteins as well as the activity of ADI hexamer as part of the ADI-TRAIL fusion protein.

E3) on caspase 3/7 induction (FIG. 6A) and relative cell viability (FIGS. 6B and 6C) in the ADI-resistant Colo 205 cancer cell line, relative to rhTRAIL alone, M.col.ADI alone and the combination of rhTRAIL and M.col.ADI as separate polypeptides. In this cell line (high ASS1 expression), ADI is not significantly active, and the cancer cell-killing activity

TABLE E4

Enzymatic activity of exemplary ADI and ADI-TRAIL fusion proteins

| | ADI protein | | | ADI-TRAIL fusion protein | | | Fold Increase in ADI enzymatic activity in the ADI-TRAIL fusion protein |
|---|---|---|---|---|---|---|---|
| ADI derived from | Monomer, MW | IU/ mg | IU/μmol (monomer) | Monomer, MW | IU/ mg | IU/μmol (monomer) | versus ADI protein |
| M. columbinum | 46044.3 | 88.9 | 4095 | 64769.7 | 69.4 | 4498 | 1.1 |
| M. columbinum-M. gallinarum chimeric | 46127.5 | 50.5 | 2329 | 64853.0 | 72.4 | 4694 | 2.0 |
| M. columbinum-M. iners chimeric | 46094.4 | 90.7 | 4181 | 64819.9 | 69.6 | 4509 | 1.1 |
| M. columbinum-M. meleagridis chimeric | 46048.3 | 82.5 | 3801 | 64773.8 | 67.2 | 4354 | 1.1 |
| M. gallinarum | 46287.6 | 94.4 | 4369 | 64697.7 | 74.6 | 4825 | 1.1 |
| M. gallinarum-M. columbinum chimeric | 46204.3 | 86.6 | 4002 | 64929.7 | 68.8 | 4469 | 1.1 |
| M. gallinarum-M. iners chimeric | 46254.5 | 83.5 | 3862 | 64979.9 | 69.4 | 4507 | 1.2 |
| M. gallinarum-M. meleagridis chimeric | 46208.4 | 93.1 | 4302 | 64933.8 | 71.5 | 4641 | 1.1 |
| M. iners | 46127.5 | 82.1 | 3788 | 64852.9 | 68.4 | 4434 | 1.2 |
| M. iners-M. columbinum chimeric | 46077.3 | 74.6 | 3436 | 64802.7 | 65.4 | 4240 | 1.2 |
| M. iners-M. gallinarum chimeric | 46160.6 | 45.7 | 2111 | 64886.0 | 57.2 | 3709 | 1.8 |
| M. iners-M. meleagridis chimeric | 46081.4 | 80.1 | 3692 | 64806.8 | 65.8 | 4266 | 1.2 |
| M. meleagridis | 46204.4 | 67.4 | 3114 | 64929.9 | 59.7 | 3874 | 1.2 |
| M. meleagridis-M. columbinum chimeric | 46200.4 | 4.8 | 221 | 64925.8 | 53.8 | 3491 | 15.8 |
| M. meleagridis-M. gallinarum chimeric | 46283.7 | 11.8 | 544 | 65009.1 | 63 | 4098 | 7.5 |
| M. meleagridis-M. iners chimeric | 46250.5 | 10.4 | 480 | 64976.0 | 65 | 4221 | 8.8 |

To assess effect of the fusion proteins on cancer cell growth, viability, and apoptosis induction, various cancer cell lines were plated in 96-well plates and exposed to the fusion proteins. The suspension cell lines were treated right after plating, while the adherent cells were allowed to attach overnight prior to addition of an investigational protein therapeutic to the cultures.

Relative cell viability was calculated by dividing the cell viability signal from a test sample by that of a non-treated control. Cell viability was determined with a reagent that detects viable cells such as resazurin or CellTiter-Glo (Promega) and measured using a plate reader (colorimetric, fluorescent or luminescent signal). For apoptosis, Caspase 3/7 activation was assessed using Promega's caspase 3/7 Glo reagent and luminescence readout by a plate reader. Caspase 3/7 activation and cell viability were also assessed by flow cytometry analysis of cells stained with fluorescent reagents detecting activated caspase 3/7 and dead cells (CellEvent Caspase 3/7 kit from ThermoFisher Scientific).

Figure 5:
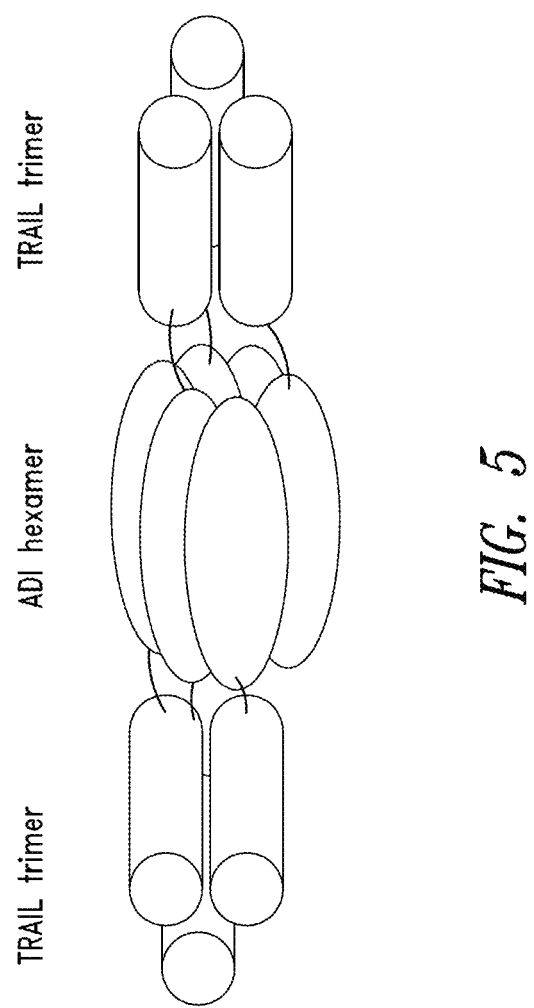
FIG. 5 illustrates a hexameric complex composed of six ADI-TRAIL and/or TRAIL-ADI conjugates, for example, fusion proteins.

FIG. 5 depicts an exemplary ADI-TRAIL or TRAIL-ADI fusion protein schematic.

Figure 6A:
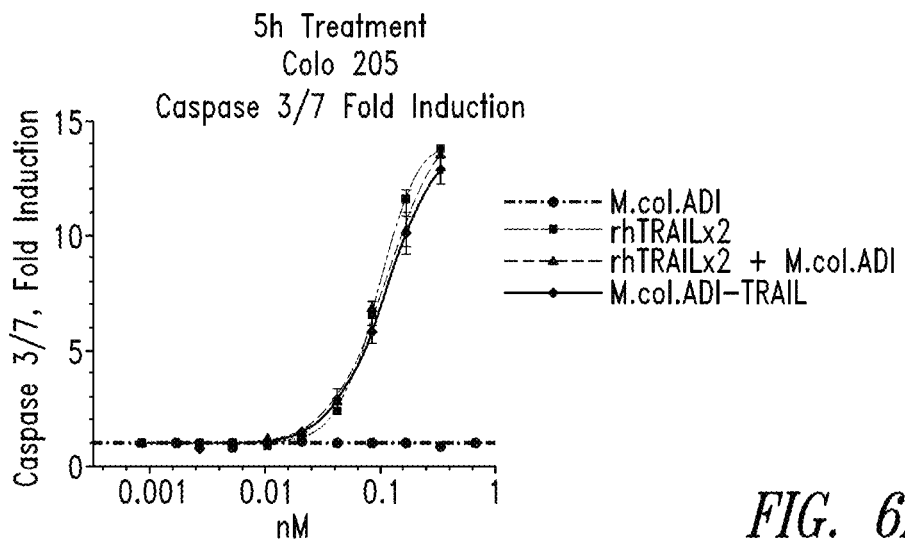
FIGS. 6A-6C show the effects of the exemplary M.col.ADI-TRAIL fusion polypeptide with L1 linker (see Table E3) on caspase 3/7 induction (FIG. 6A) and relative cell viability (FIGS. 6B and 6C) in the ADI-resistant Colo 205 cancer cell line, relative to rhTRAIL alone, M.col.ADI alone and the combination of rhTRAIL and M.col.ADI as separate polypeptides.
Figure 6B:
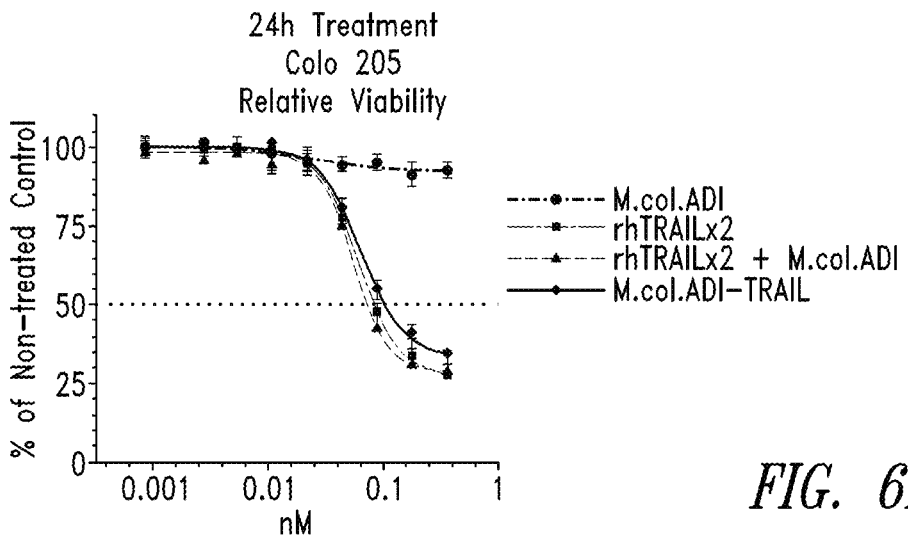
Figure 6C:
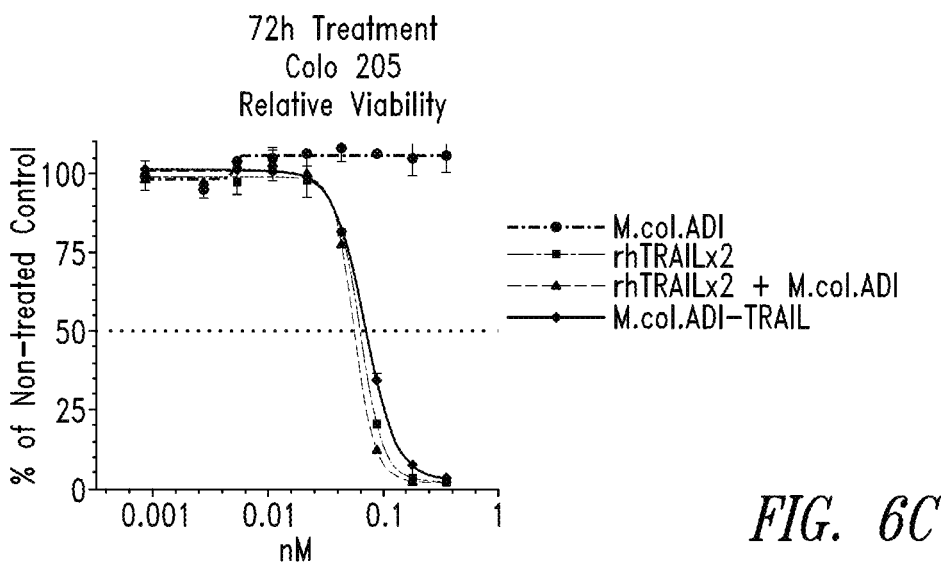

FIGS. 6A-6C show the effects of the exemplary M.col.ADI-TRAIL fusion polypeptide with L1 Linker (see Table is due to the TRAIL component of the ADI-TRAIL fusion polypeptide.

Figure 7A:
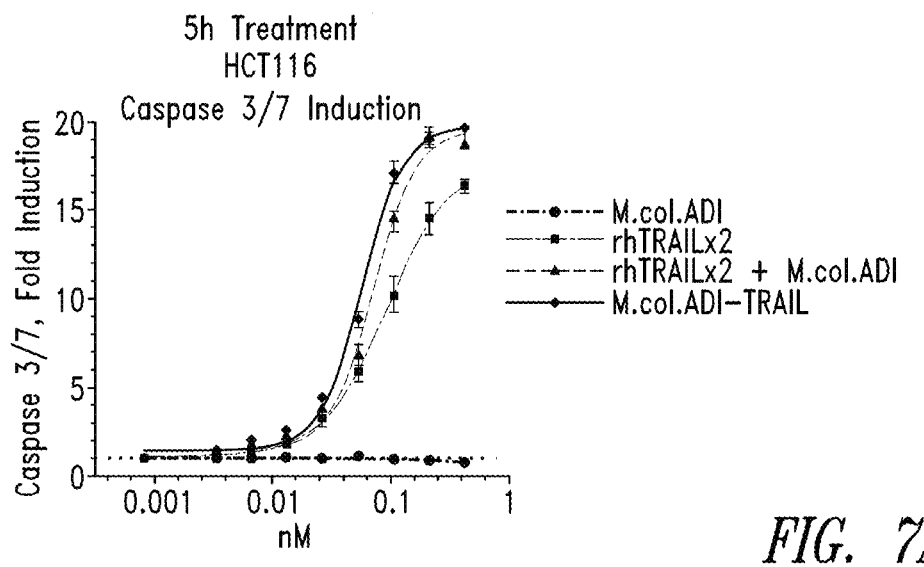
FIGS. 7A-7C show the effects of the exemplary M.col.ADI-TRAIL fusion polypeptide with L1 linker (see Table E3) on caspase 3/7 induction (FIG. 7A) and relative cell viability (FIGS. 7B and 7C) in the ADI-sensitive HCT116 tumor cell line, relative to rhTRAIL alone, M.col.ADI alone, and the combination of rhTRAIL and M.col.ADI as separate polypeptides.
Figure 7B:
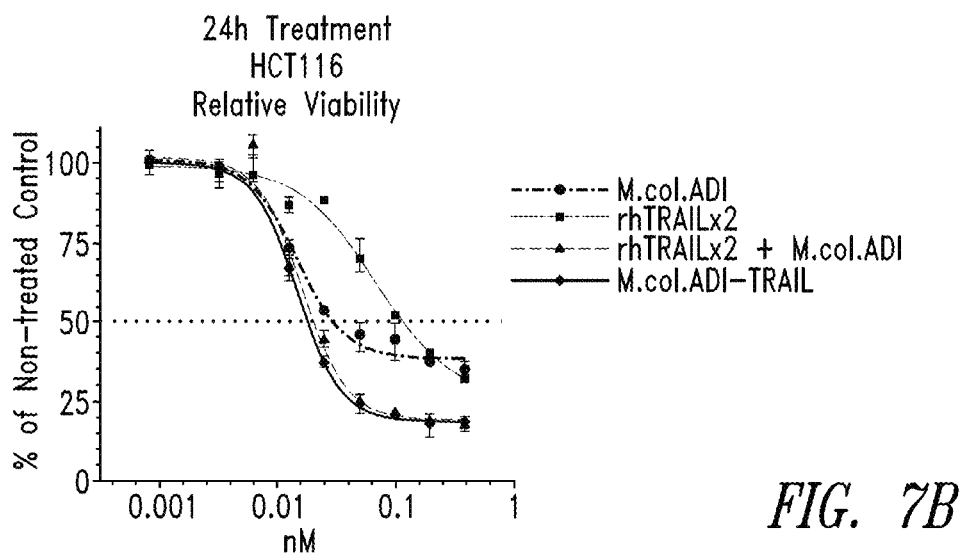
Figure 7C:
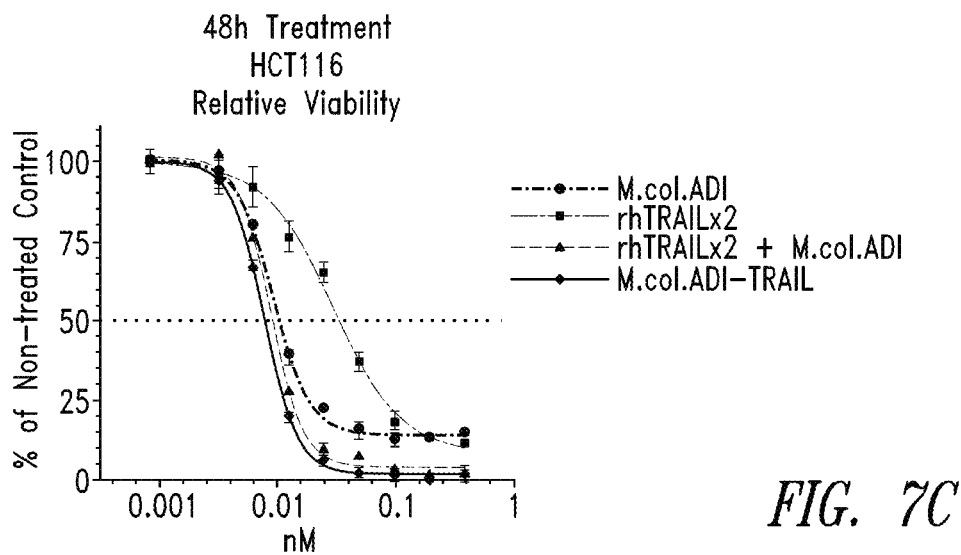

FIGS. 7A-7C show the effects of the exemplary M.col.ADI-TRAIL fusion polypeptide with L1 linker (see Table E3) on caspase 3/7 induction (FIG. 7A) and relative cell viability (FIGS. 7B and 7C) in the ADI-sensitive HCT116 tumor cell line, relative to rhTRAIL alone, M.col.ADI alone, and the combination of rhTRAIL and M.col.ADI as separate polypeptides.

Figure 8A:
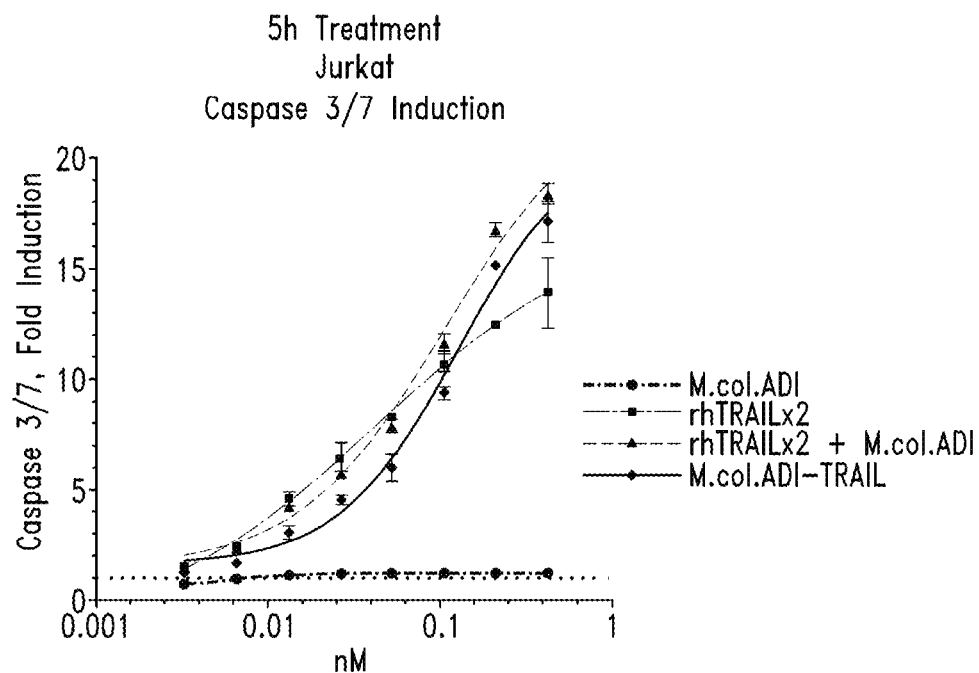
FIGS. 8A-8B show the effects of the exemplary M.col.ADI-TRAIL fusion polypeptide with L1 linker (see Table E3) on caspase 3/7 induction (FIG. 8A) and relative cell viability (FIG. 8B) in the ADI-sensitive Jurkat tumor cell line, relative to rhTRAIL alone, M.col.ADI alone and the combination of rhTRAIL and M.col.ADI as separate polypeptides.
Figure 8B:
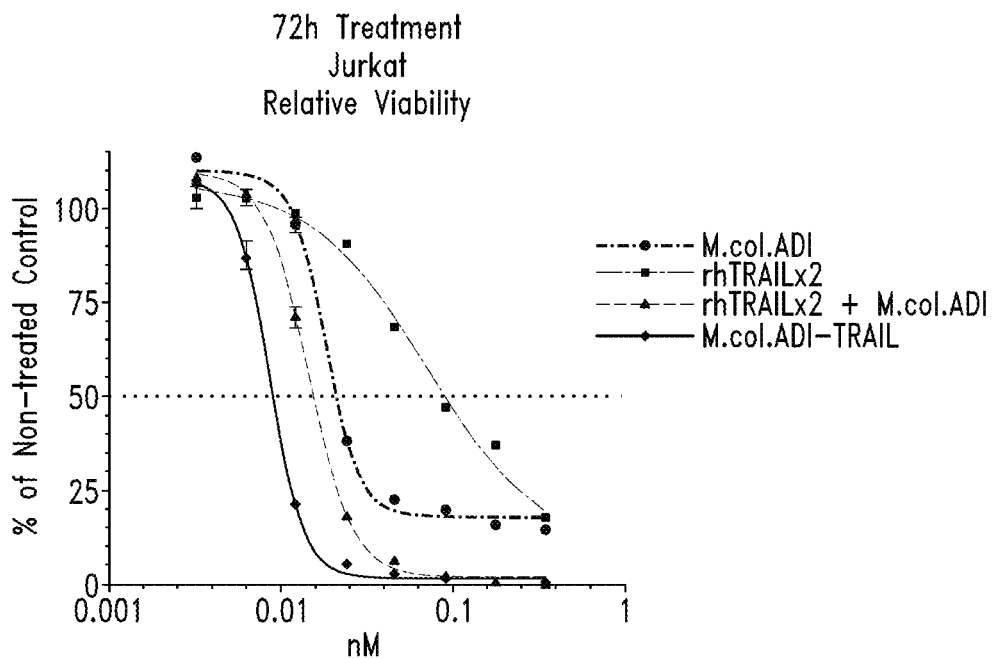
Figure 9A:
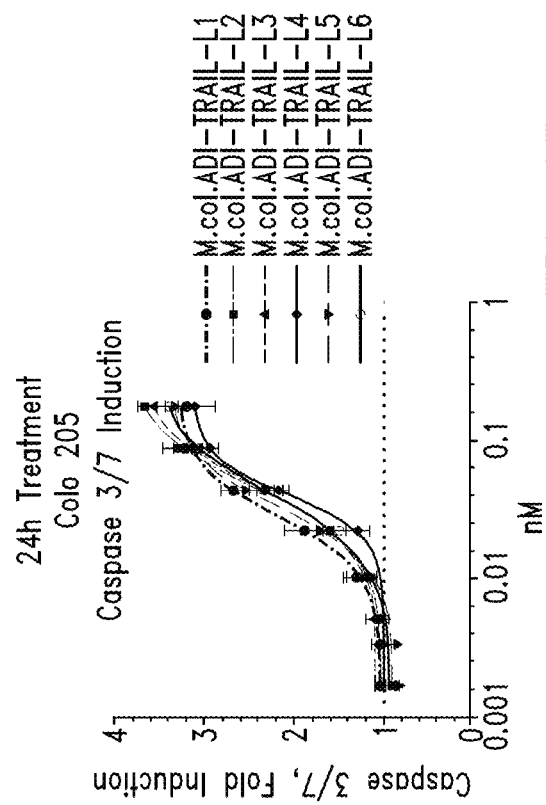
FIGS. 9A-9D show the effects of the exemplary ADI-TRAIL fusion polypeptides from Table E1 on caspase 3/7 induction (FIGS. 9A and 9B) and relative cell viability (FIGS. 9C and 9D) in the ADI-resistant Colo 205 cancer cell line.
Figure 9B:
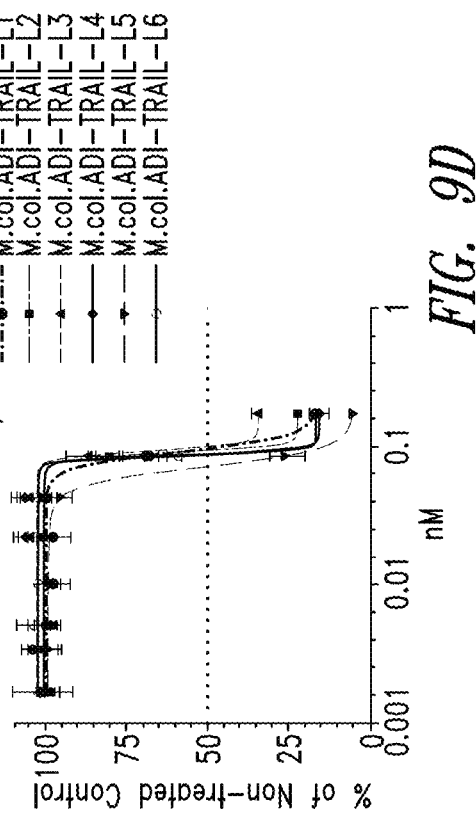
Figure 9C:
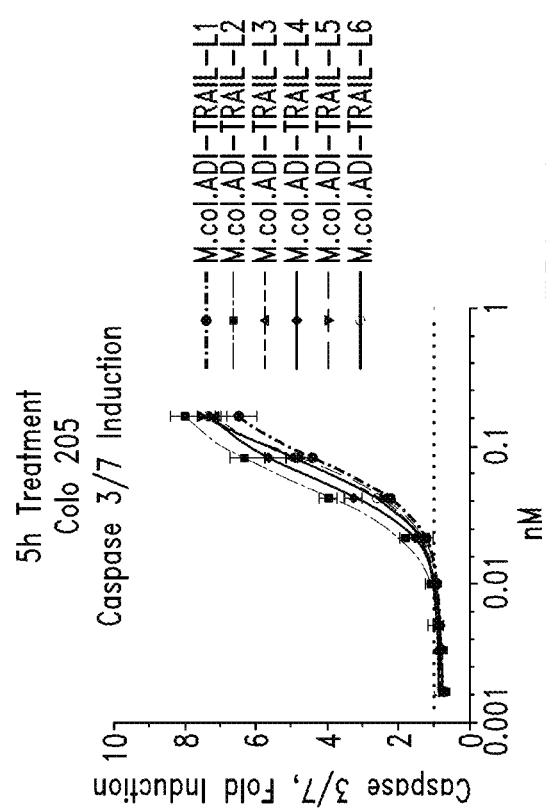
Figure 9D:
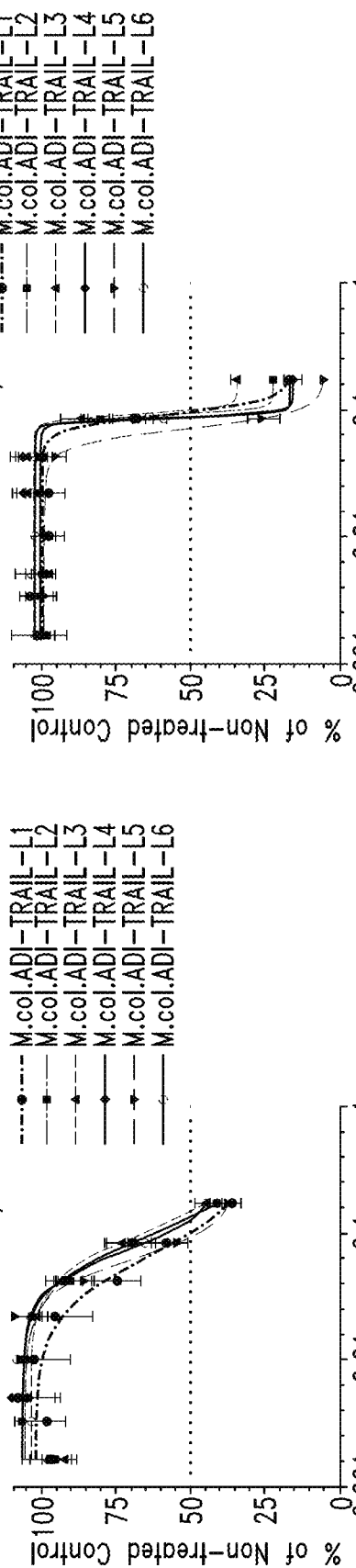
Figure 10A:
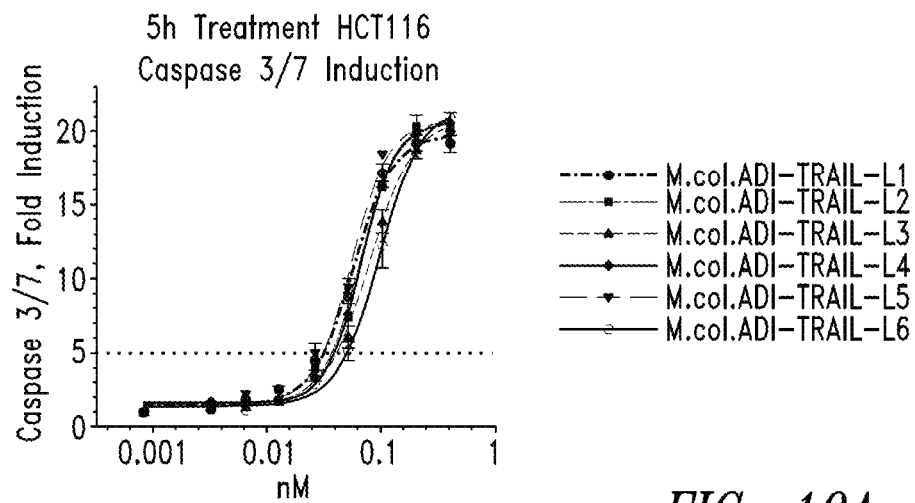
FIGS. 10A-10C show the effects of exemplary ADI-TRAIL fusion polypeptides on caspase 3/7 induction (FIG. 10A) and relative cell viability (FIGS. 10B-10C) in the ADI-sensitive HCT116 cell line.
Figure 10B:
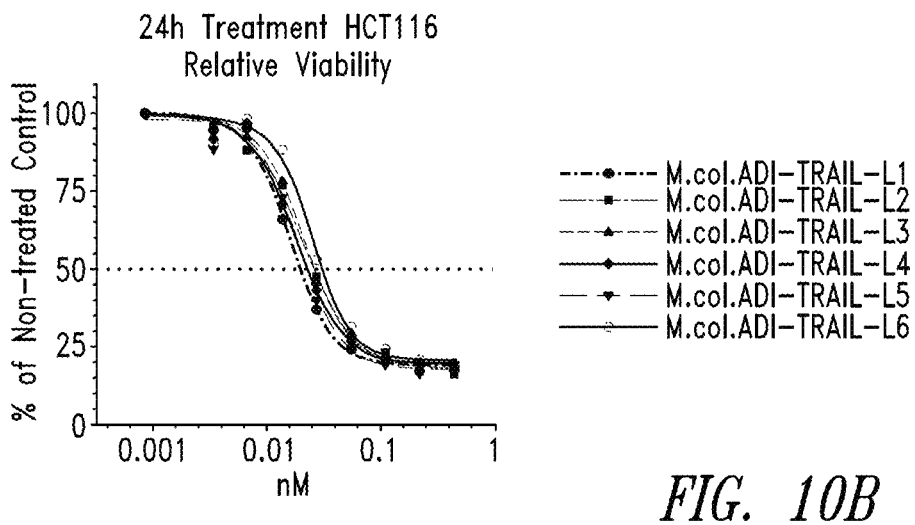
Figure 10C:
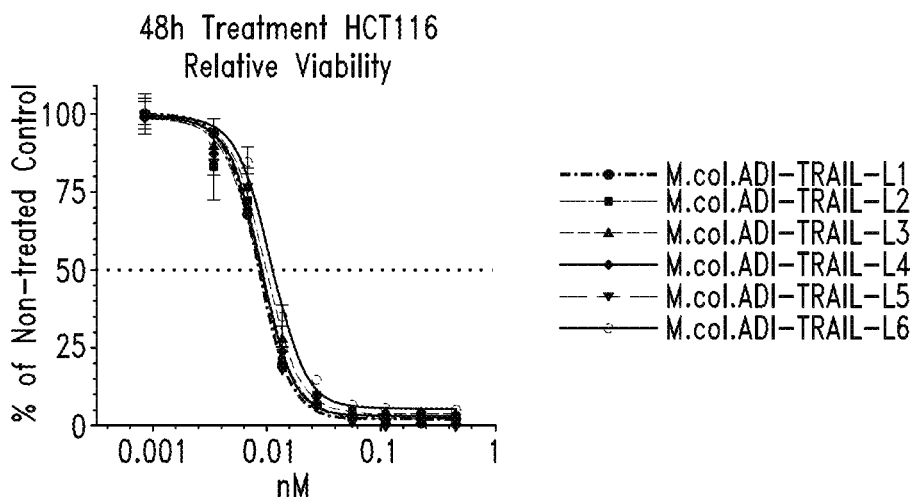
Figure 11A:
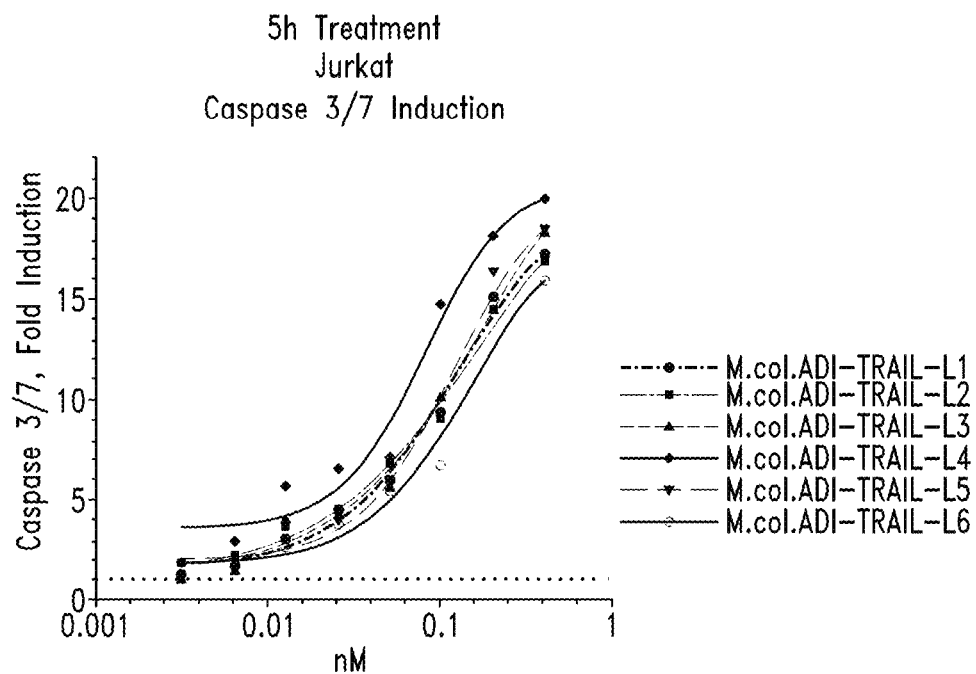
FIGS. 11A-11B show the effects of exemplary ADI-TRAIL fusion polypeptides on caspase 3/7 induction (FIG. 11A) and relative cell viability (FIG. 11B) in the ADI-sensitive Jurkat cell line.
Figure 11B:
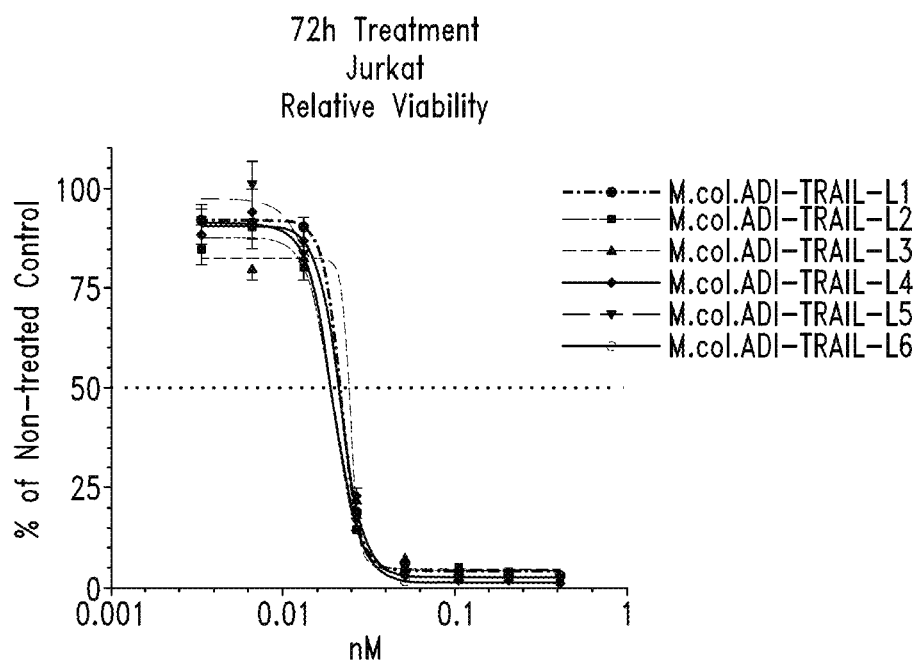

FIGS. 8A-8B show the effects of the exemplary M.col.ADI-TRAIL fusion polypeptide with L1 linker (see Table E3) on caspase 3/7 induction (FIG. 8A) and relative cell viability (FIG. 8B) in the ADI-sensitive Jurkat tumor cell line, relative to rhTRAIL alone, M.col.ADI alone and the combination of of rhTRAIL and M.col.ADI as separate polypeptides. FIGS. 9A-9D show the effects of the exemplary M.col.ADI-TRAIL fusion polypeptides from Table E3 on caspase 3/7 induction (FIGS. 9A and 9B) and relative cell viability (FIGS. 9C and 9D) in the ADI-resistant Colo 205 cancer cell line. FIGS. 10A-10C show the effects of exemplary M.col.ADI-TRAIL fusion polypeptides from Table E3 on caspase 3/7 induction (FIG. 10A) and relative cell viability (FIGS. 10B-10C) in the ADI-sensitive HCT116 cell line. FIGS. 11A-11B show the effects of exemplary M.col.ADI-TRAIL fusion polypeptides from Table E3 on caspase 3/7 induction (FIG. 11A) and relative cell viability (FIG. 11B) in the ADI-sensitive Jurkat cell line.

FIGS. 9-11 show that exemplary M.col.ADI-TRAIL fusion polypeptides from Table E1 have similar activities in three different cell lines, both ADI-sensitive and resistant.

Table E5 below summarizes the $IC_{50}$ values of exemplary ADI-TRAIL fusion polypeptides from Table E4 on caspase 3/7 induction and relative cell viability reduction in the ADI-resistant Colo 205 cell line and the ADI-sensitive HCT116 cell line. These data show that the exemplary ADI-TRAIL fusion polypeptides have similar activities.

Figure 15A:
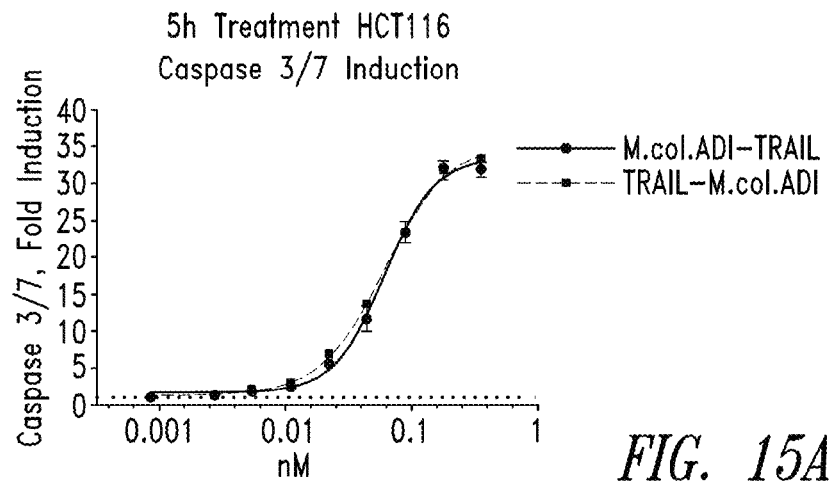
FIGS. 15A-15C show the effects of exemplary TRAIL-M.cob.ADI versus M.cob.ADI-TRAIL fusion polypeptides on caspase 3/7 induction (FIG. 15A) and relative cell viability (FIGS. 15B-15C) in the ADI-sensitive HCT116 cell line.
Figure 15B:
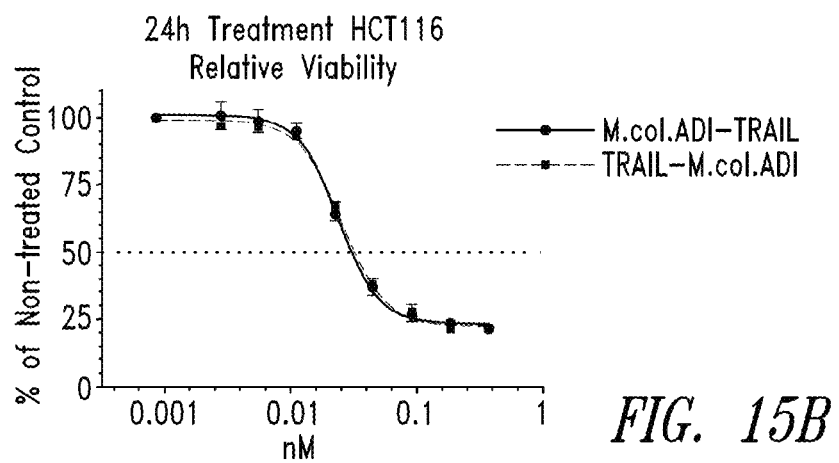
Figure 15C:
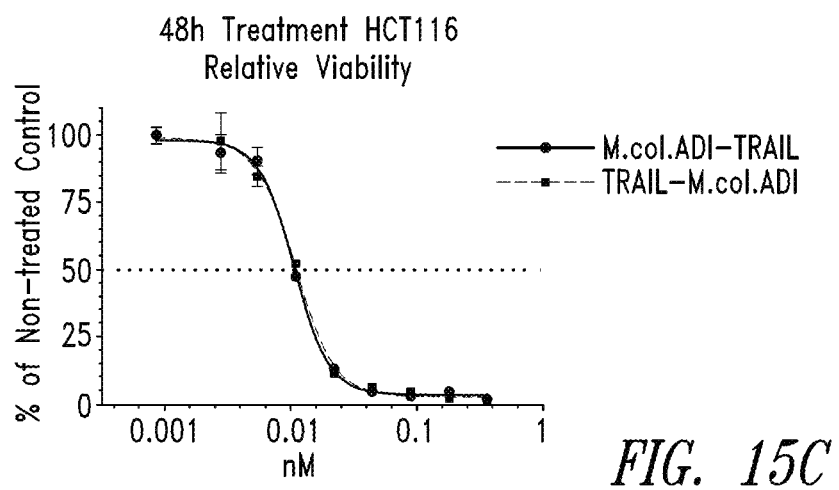

FIGS. 15A-15C show the effects of exemplary TRAIL-M.cob.ADI versus M.cob.ADI-TRAIL fusion polypeptides on caspase 3/7 induction (FIG. 15A) and relative cell viability (FIGS. 15B-15C) in the ADI-sensitive HCT116 cell line. In this cell line, the two fusion proteins have the same potencies for inducing caspase mediated apoptosis. ADI and TRAIL are synergistic in the HCT116 cell line. From this and other experiments (data not shown), it appears that ADI can enhance TRAIL effect to a certain level and that the combined effect of ADI and TRAIL is not significantly affected by small changes in the potency of the TRAIL moiety. In other words, a stronger synergy of ADI with a less potent preparation of TRAIL has been observed, and the

TABLE E5

Cell-based activity of exemplary ADI-TRAIL fusion proteins

| | IC50 (pM) | | | | | |
|---|---|---|---|---|---|---|
| | HCT116 | | | Colo 205 | | |
| ADI derived from | 5 h caspase 3/7 | 24 h Relative Viability | 48 h Relative Viability | 5 h caspase 3/7 | 24 h Relative Viability | 48 h Relative Viability |
| M. columbinum | 64.5 | 22.7 | 10.0 | 60.0 | 41.3 | 31.5 |
| M. columbinum-M. gallinarum chimeric | 50.9 | 22.6 | 10.3 | 37.7 | 35.7 | 36.6 |
| M. columbinum-M. iners chimeric | 51.5 | 22.9 | 11.0 | 33.2 | 34.4 | 35.1 |
| M. columbinum-M. meleagridis chimeric | 54.4 | 26.7 | 12.1 | 39.7 | 38.1 | 38.6 |
| M. gallinarum | 60.9 | 17.7 | 8.2 | 52.7 | 46.2 | 55.8 |
| M. gallinarum-M. columbinum chimeric | 64.2 | 25.4 | 9.3 | 45.3 | 40.5 | 57.7 |
| M. gallinarum-M. iners chimeric | 68.6 | 20.3 | 9.3 | 43.9 | 39.1 | 53.8 |
| M. gallinarum-M. meleagridis chimeric | 64.4 | 21.7 | 9.4 | 53.1 | 46.0 | 58.0 |
| M. iners | 56.2 | 20.4 | 9.1 | 48.4 | 42.2 | 50.4 |
| M. iners-M. columbinum chimeric | 78.7 | 24.3 | 10.3 | 50.4 | 45.4 | 64.0 |
| M. iners-M. gallinarum chimeric | 114.8 | 28.5 | 12.6 | 84.7 | 80.8 | 114.9 |
| M. iners-M. meleagridis chimeric | 80.2 | 23.4 | 10.4 | 73.7 | 68.0 | 85.0 |
| M. meleagridis | 57.6 | 24.3 | 11.0 | 30.1 | 30.9 | 34.0 |
| M. meleagridis-M. columbinum chimeric | 57.6 | 28.7 | 14.6 | 19.0 | 21.5 | 24.6 |
| M. meleagridis-M. gallinarum chimeric | 54.3 | 26.5 | 11.3 | 23.3 | 28.8 | 31.2 |
| M. meleagridis-M. iners chimeric | 45.2 | 23.2 | 11.2 | 20.3 | 24.1 | 25.1 |

Figure 12A:
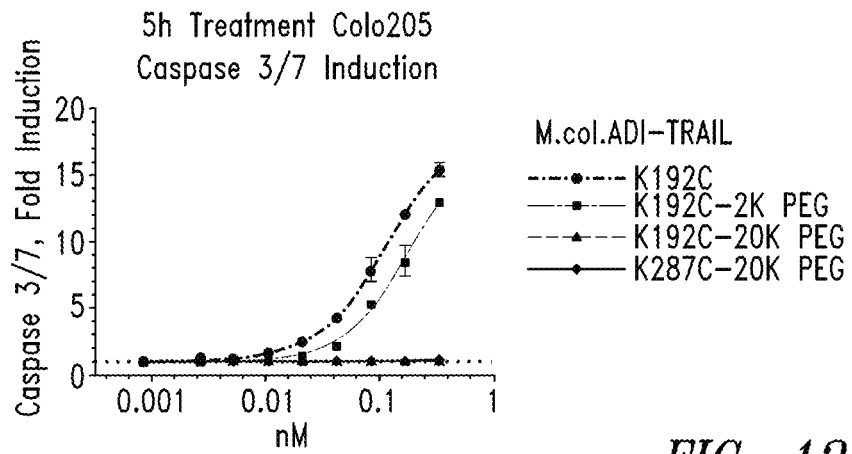
FIGS. 12A-12C show the effects of exemplary M.col.ADI-TRAIL fusion polypeptides with point mutation in M.col.ADI (K192C or K287C), including non-PEGylated versus PEGylated with 2K or 20K PEG, on caspase 3/7 induction (FIG. 12A) and relative cell viability (FIGS. 12B-12C) in the ADI-resistant Colo 205 cell line.
Figure 12B:
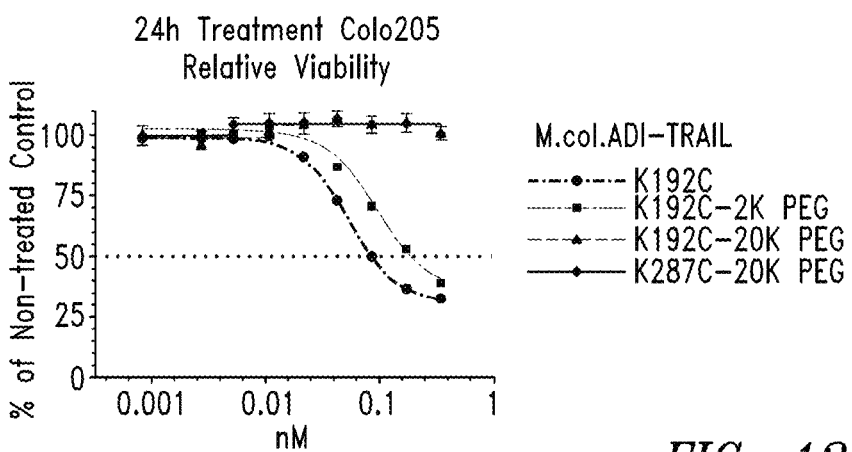
Figure 12C:
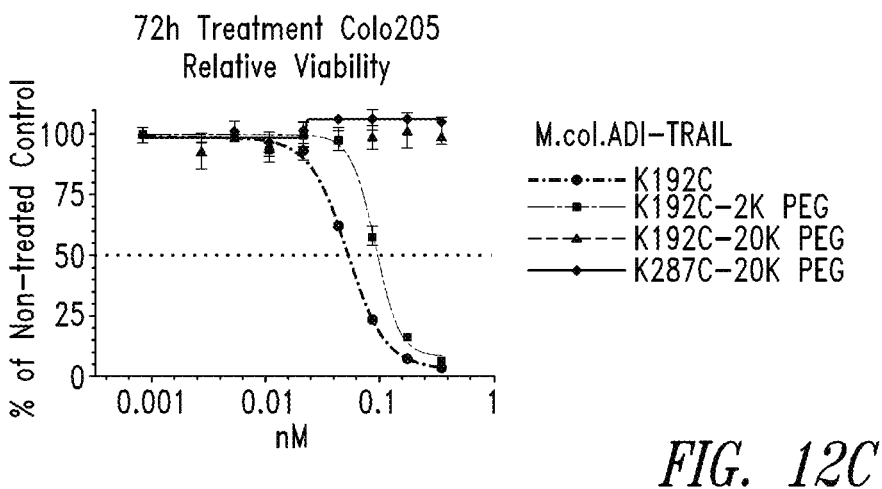
Figure 13A:
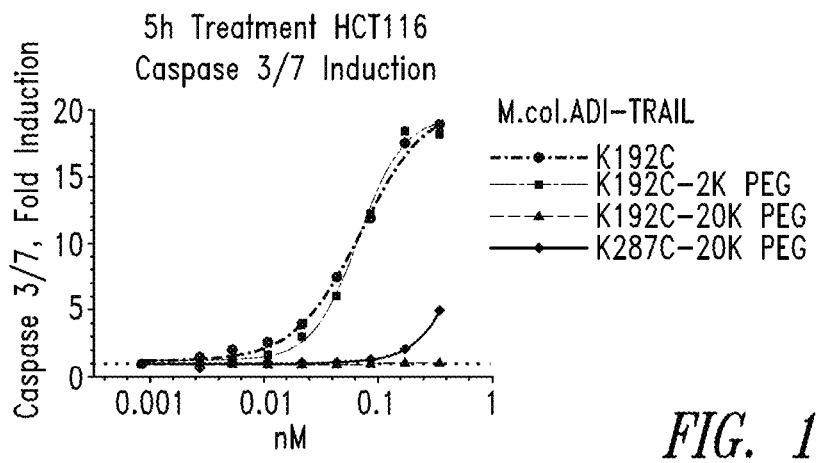
FIGS. 13A-13C show the effects of exemplary M.col.ADI-TRAIL fusion polypeptides with point mutation in M.col.ADI (K192C or K287C), including non-PEGylated versus PEGylated with 2K or 20K PEG, on caspase 3/7 induction (FIG. 13A) and relative cell viability (FIGS. 13B-13C) in the ADI-sensitive HCT116 cell line.
Figure 13B:
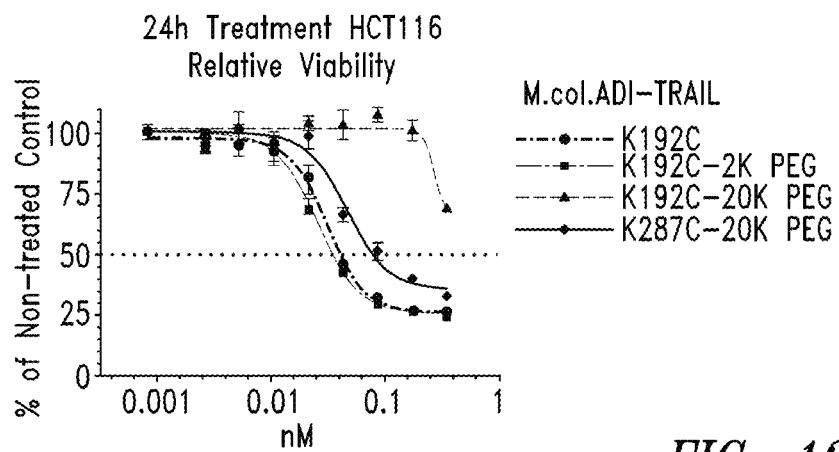
Figure 13C:
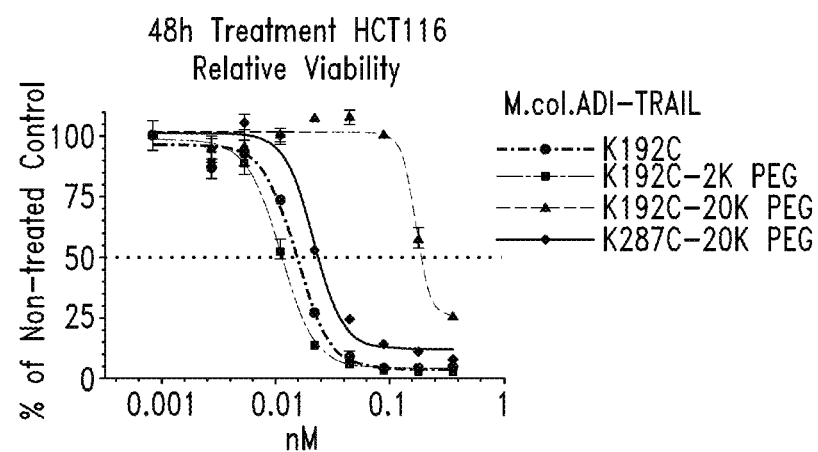

FIGS. 12A-12C show the effects of exemplary M.col.ADI-TRAIL fusion polypeptides with point mutation(s) in M.col.ADI (K192C or K287C), including non-PEGylated versus PEGylated with 2K or 20K PEG, on caspase 3/7 induction (FIG. 12A) and relative cell viability (FIGS. 12B-12C) in the ADI-resistant Colo 205 cell line. FIGS. 13A-13C show the effects of exemplary M.col.ADI-TRAIL fusion polypeptides with point mutation in M.col.ADI (K192C or K287C), including non-PEGylated versus PEGylated with 2K or 20K PEG, on caspase 3/7 induction (FIG. 13A) and relative cell viability (FIGS. 13B-13C) in the ADI-sensitive HCT116 cell line. ADI enzymatic activity was similar in the PEGylated versus non-PEGylated constructs described above.

Figure 14A:
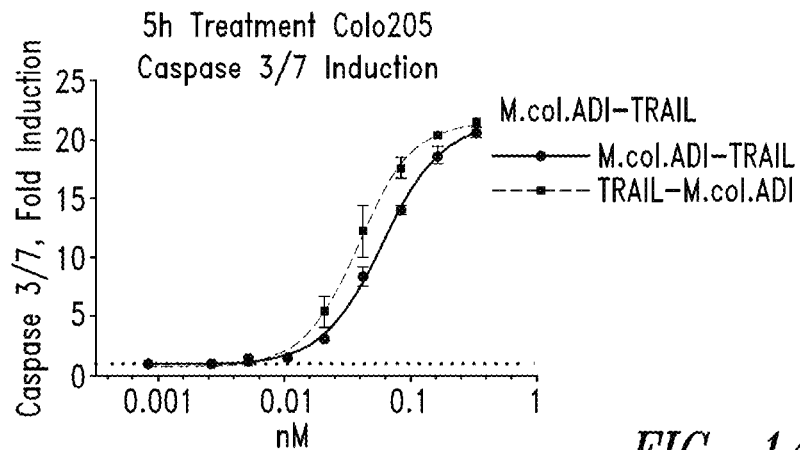
FIGS. 14A-14C show the effects of exemplary TRAIL-M.col.ADI versus M.col.ADI-TRAIL fusion polypeptides on caspase 3/7 induction (FIG. 14A) and relative cell viability (FIGS. 14B-14C) in the ADI-resistant Colo 205 cell line.
Figure 14B:
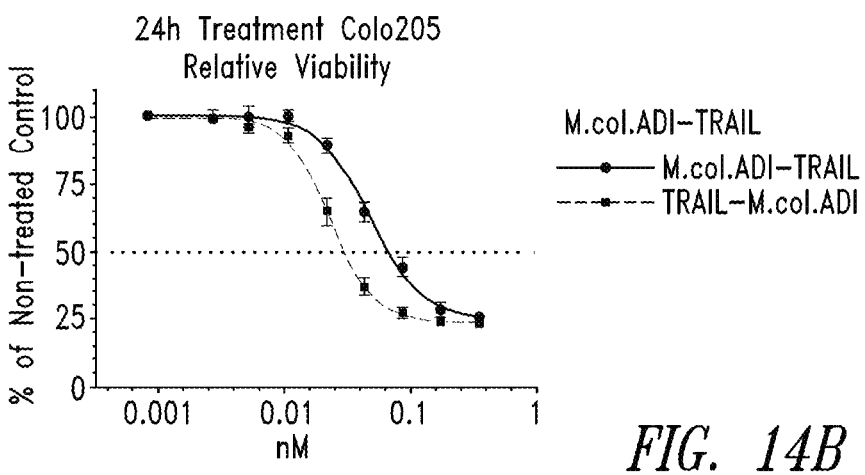
Figure 14C:
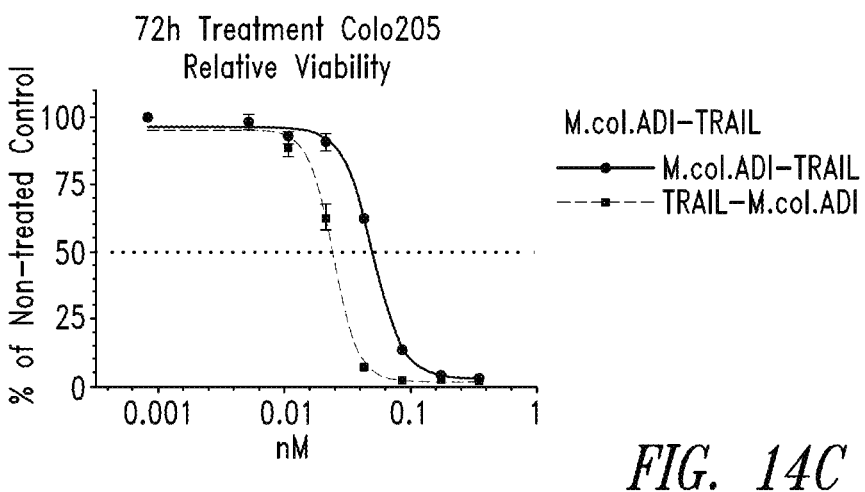

FIGS. 14A-14C show the effects of exemplary TRAIL-M.col.ADI versus M.col.ADI-TRAIL fusion polypeptides on caspase 3/7 induction (FIG. 14A) and relative cell viability (FIGS. 14B-14C) in the ADI-resistant Colo 205 cell line. Because this Colo 205 cell line is resistant to ADI activity, the observed caspase 3/7 activation and subsequent reductions in viability are due to the pro-apoptotic activity of the TRAIL moiety. As shown in the FIGS. 14A-14C, TRAIL activity is somewhat improved (approximately 2-fold) in TRAIL-M.cob.ADI fusion protein versus M.cob.ADI-TRAIL fusion proteins.

effect of the combination has a certain threshold which it reaches even with optimal or suboptimal preparations of TRAIL.

Figure 16A:
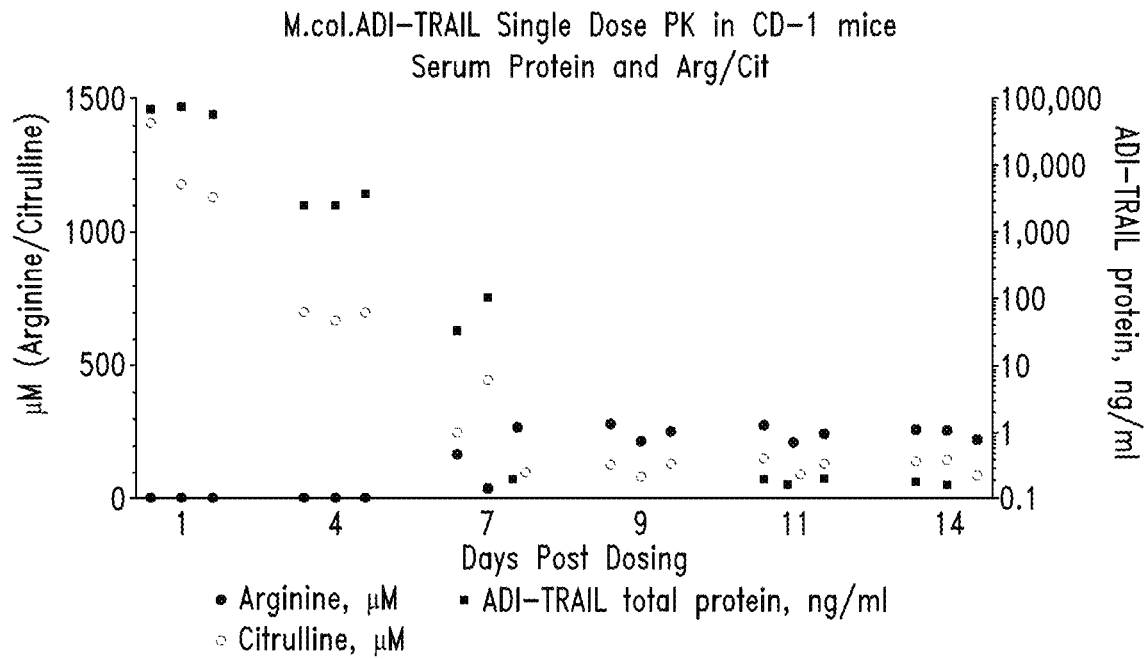
FIGS. 16A-16B display pharmacokinetics (PK) of M.cob.ADI-TRAIL over time in serum of CD-1 mice after a single dose of 30 mg/kg administered intravenously. M.col.ADI-TRAIL protein level (FIGS. 16A-16B), arginine and citrulline levels (FIG. 16A) as well as antibody titers against the fusion protein M.col.ADI-TRAIL, M.cob.ADI and rhTRAIL (assessed by ELISA, FIG. 16B) were measured in serum of CD-1 mice animals after a single injection of the fusion protein.
Figure 16B:
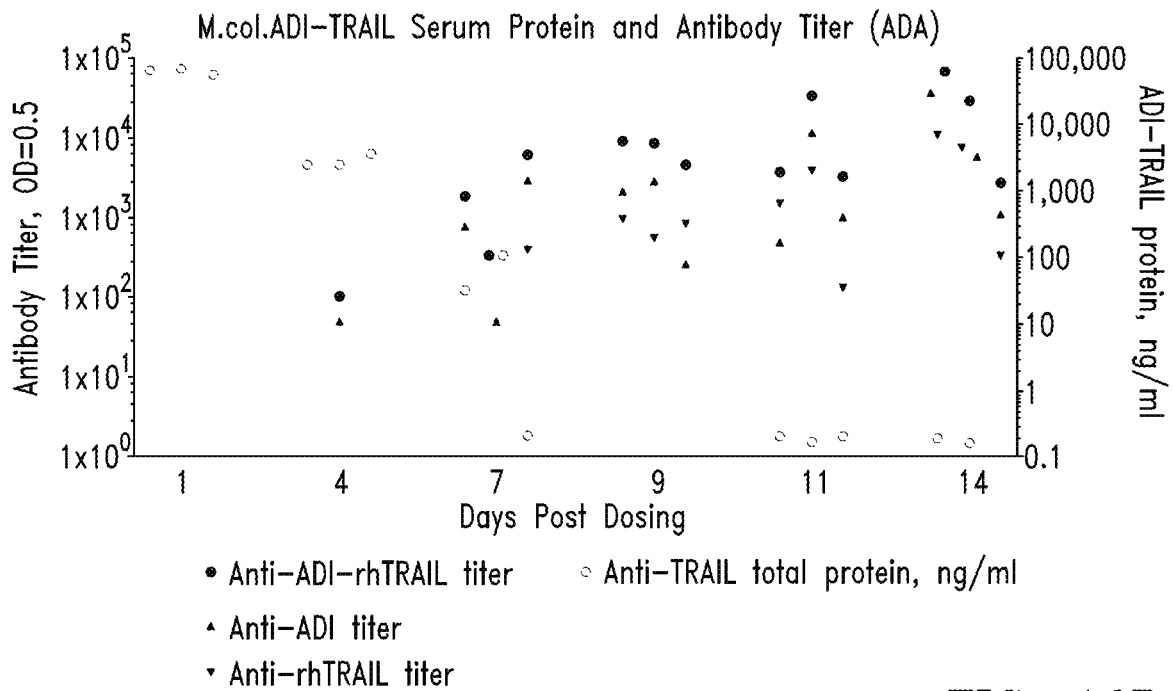
Figure 17A:
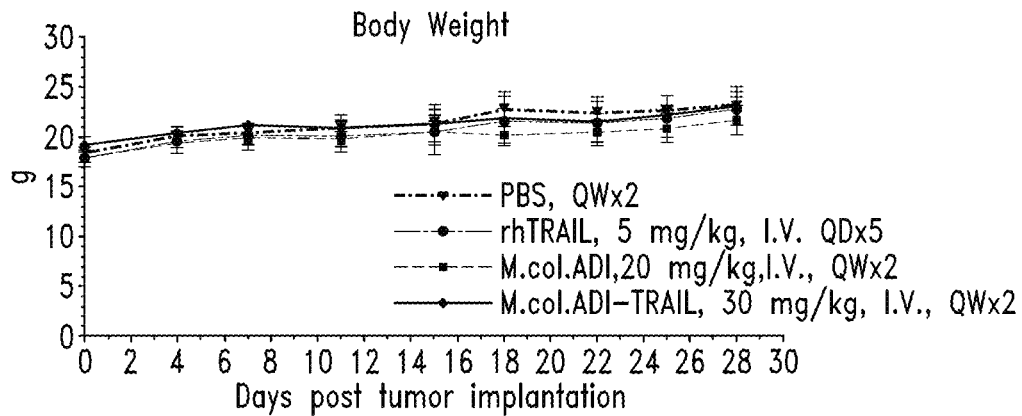
FIGS. 17A-17F demonstrate efficacy of the M.col.ADI-TRAIL in HCT116 xenograft model. The fusion protein did not cause any noticeable weight loss (FIG. 17A) and reduced tumor growth (FIGS. 17B-17F). *p<0.05, p<0.01, *p<0.001. The statistical significance of the tumor reduction in the fusion protein treated group as compared to the vehicle treated control group was assessed by the 2-way ANOVA.
Figure 17B:
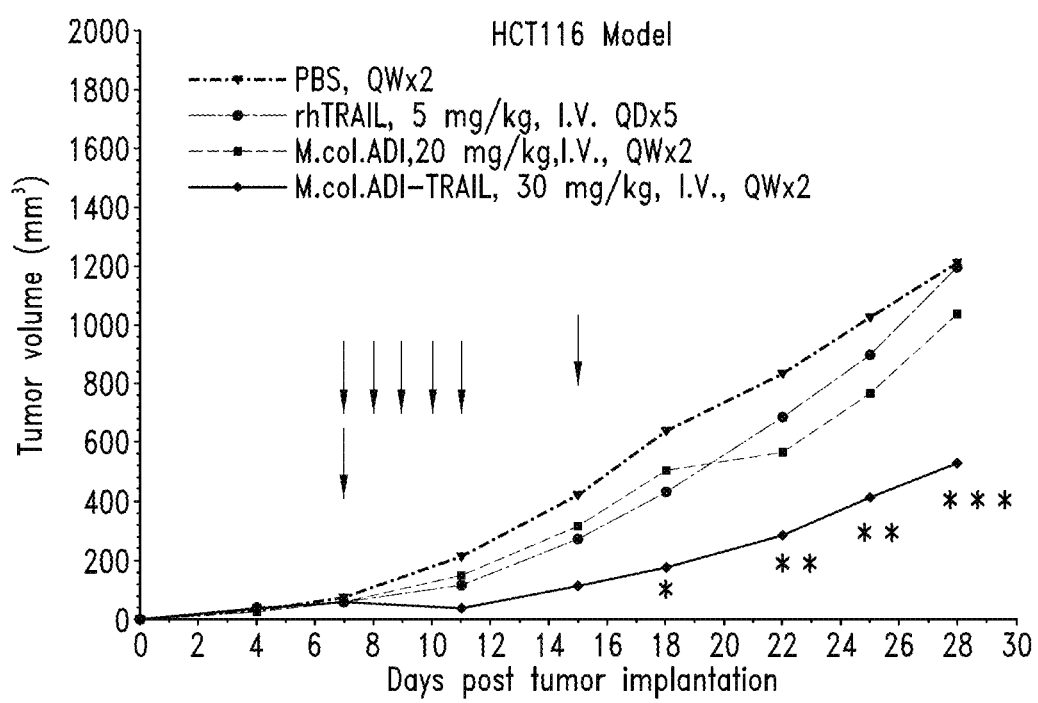
Figure 17C:
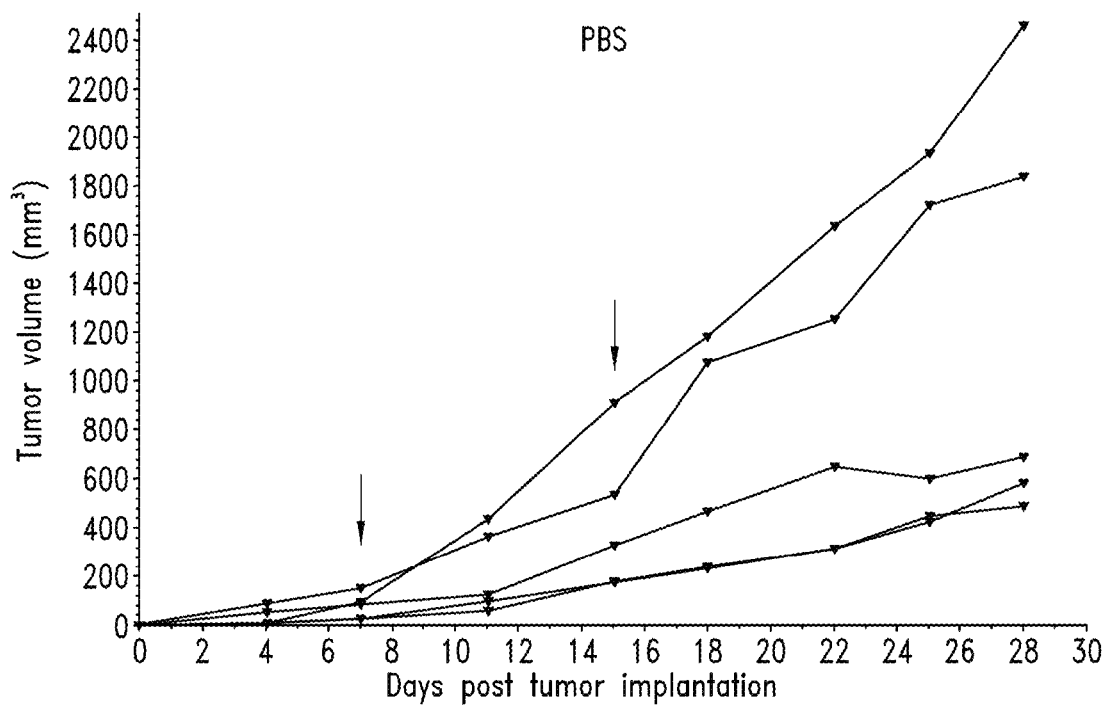
Figure 17D:
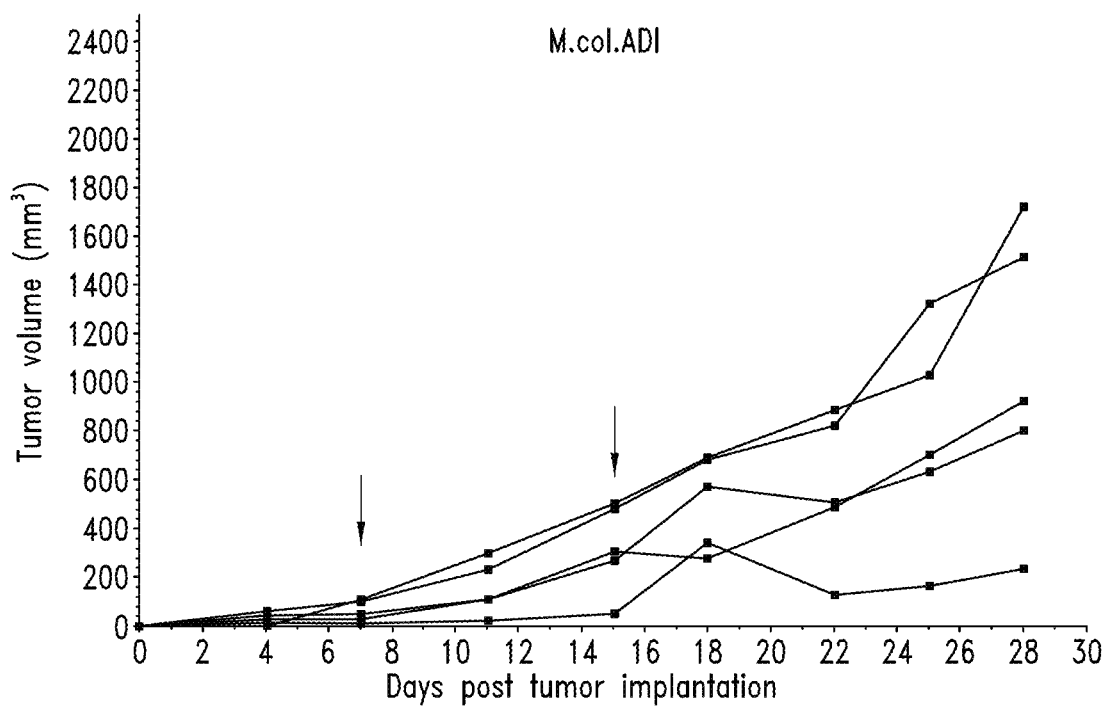
Figure 17E:
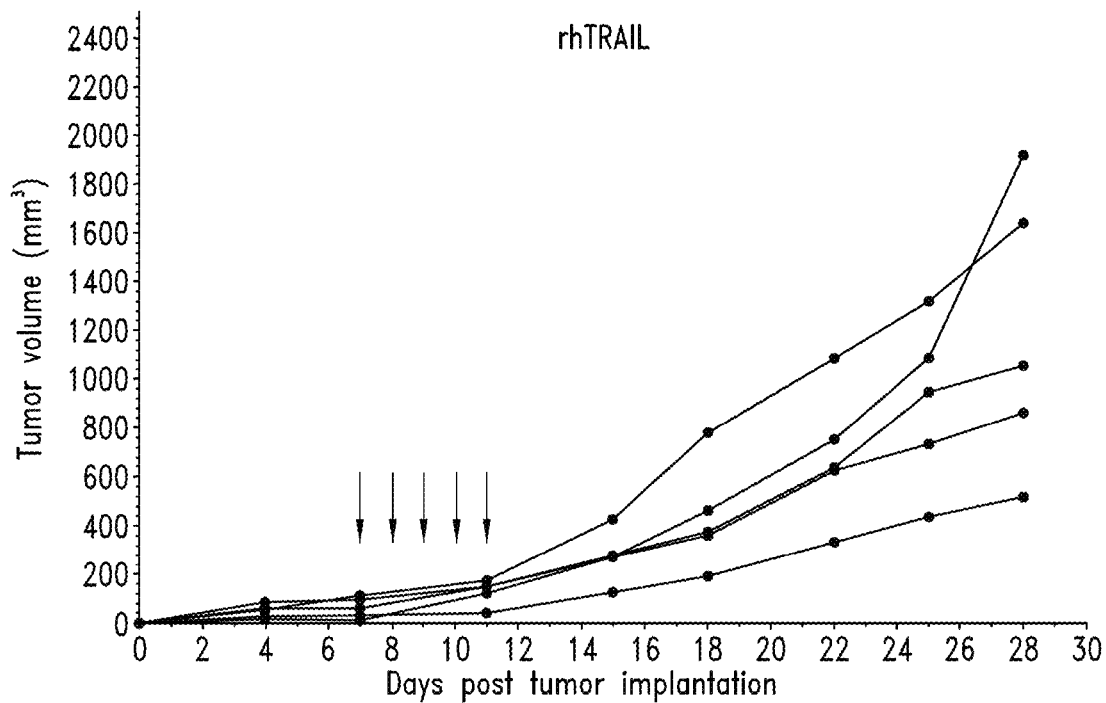
Figure 17F:
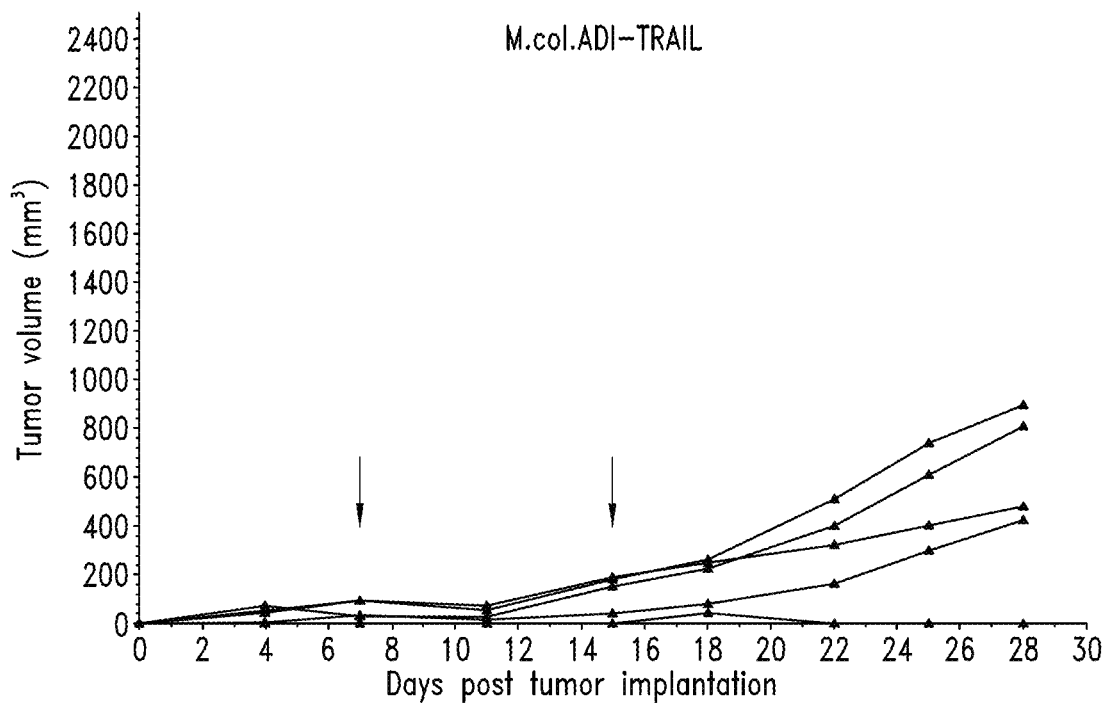

FIGS. 16A-16B display PK profiles of M.col.ADI-TRAIL over time in serum of CD-1 mice after a single dose of 30 mg/kg administered intravenously. M.col.ADI-TRAIL protein level (FIGS. 16A-16B), arginine and citrulline levels (FIG. 16A) as well as antibody titers against the fusion protein M.col.ADI-TRAIL, and its components M.col.ADI and rhTRAIL (FIG. 16B) were measured in serum of CD-1 mice after a single injection of the fusion protein.

The fusion protein concentration in serum was assessed by ELISA (FIGS. 16A-16B). Biological activity of ADI and TRAIL moieties in the serum samples were also assessed and concentrations of biologically active protein were determined based on a standard spiked into naïve sera. Concentration of biologically active protein (based on both ADI and TRAIL activities) was very similar to the total ADI-TRAIL protein determined by the ELISA method.

FIGS. 17A-17F demonstrate the efficacy of the M.col.ADI-TRAIL in HCT116 xenograft model. Female athymic Nude mice were inoculated with HCT116 cells subcutaneously. On day 7 post inoculation mice were randomized into the treatment groups (to have similar starting tumor volumes between the groups) and administered rhTRAIL, M.col.ADI, M.col.ADI-TRAIL fusion protein or vehicle control (PBS buffer) by intravenous injection. Treatment with rhTRAIL was performed daily for 5 consecutive days (days 7-11 post tumor implantation). M.col.ADI and M.col.ADI-TRAIL fusion proteins were injected on days 7 and 15 post tumor implantation. The fusion protein did not cause any noticeable weight loss (FIG. 17A) and was able to reduce tumor growth (FIGS. 17B-17F). *p<0.05, p<0.01, * p<0.001. The statistical significance of the tumor reduction in the fusion protein treated group as compared to the vehicle treated control group was assessed by the 2-way ANOVA.

Figure 18B:
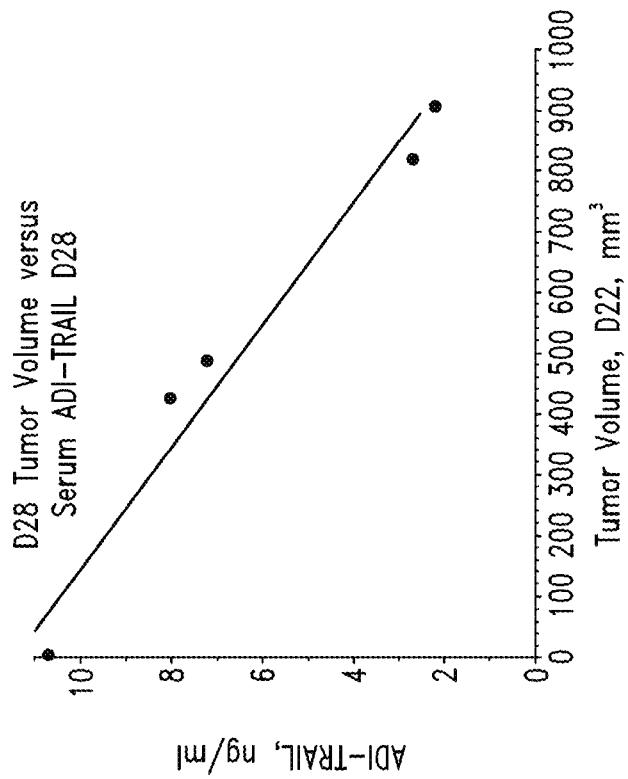
FIGS. 18A-18D show that serum ADI-TRAIL inversely correlates with tumor volume (FIGS. 18B-18C). Concentrations of fusion protein measured by ELISA (total protein) and in a biological assay (active protein) by were similar to one another. Serum was taken from tumor bearing mice on days 21 and 28 post tumor implantation. Treatment schedule and tumor growth are shown in FIGS. 17A-17F. Arginine and citrulline levels in these serums samples are shown in FIG. 18D.
Figure 18A:
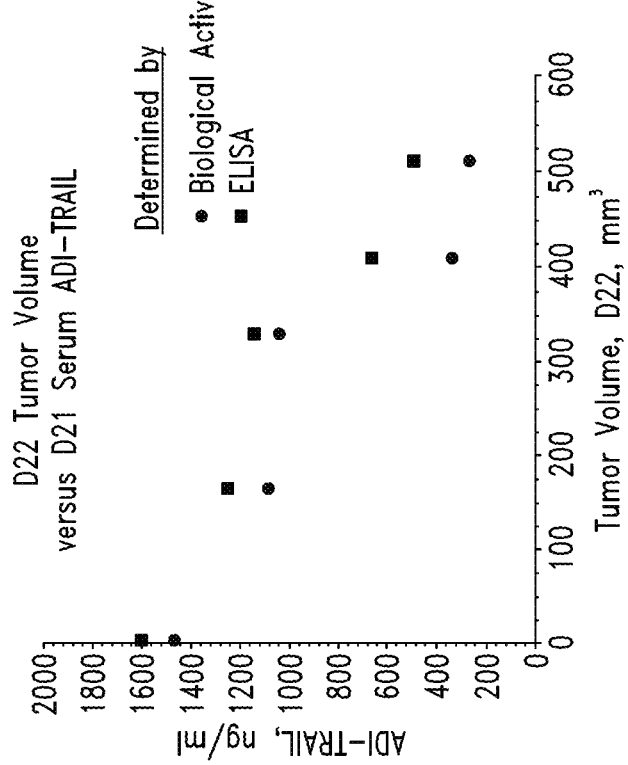
Figures 18C, 18D:
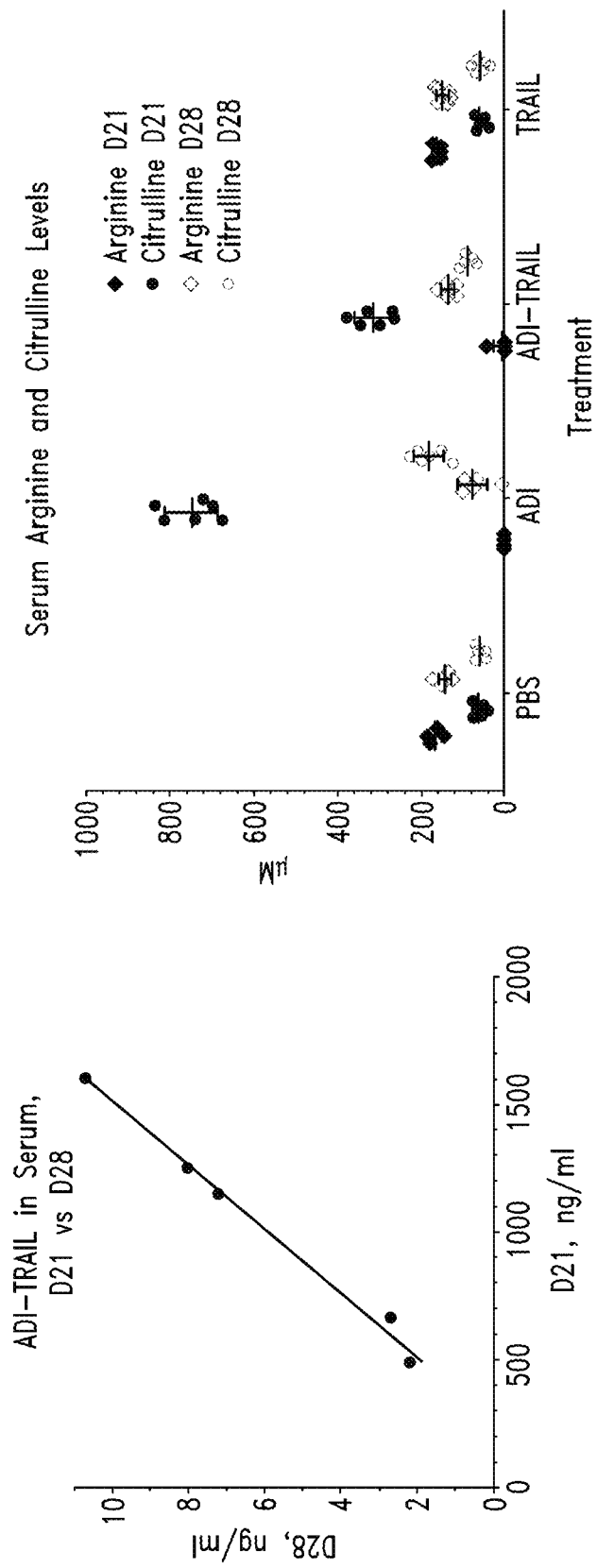

Serum M.col.ADI-TRAIL inversely correlated with the tumor volume as shown in FIGS. 18A-18B. Concentrations of fusion protein measured by ELISA (total protein) and in a biological assay (active protein) by were similar to one another. Serum was taken on days 21 and 28 post tumor implantation. The serum total fusion protein detected correlated between the two time points. Arginine and citrulline levels in these serums samples are shown in FIG. 18D. Serum citrulline levels were higher and arginine levels were lower in M.col.ADI group compared to M.col.ADI-TRAIL group. This is likely due to the fusion protein localization to the tumor site due to its TRAIL moiety thereby decreasing its serum levels. Reverse correlation between the tumor volume and serum M.col.ADI-TRAIL supports this hypothesis.

Figure 19:
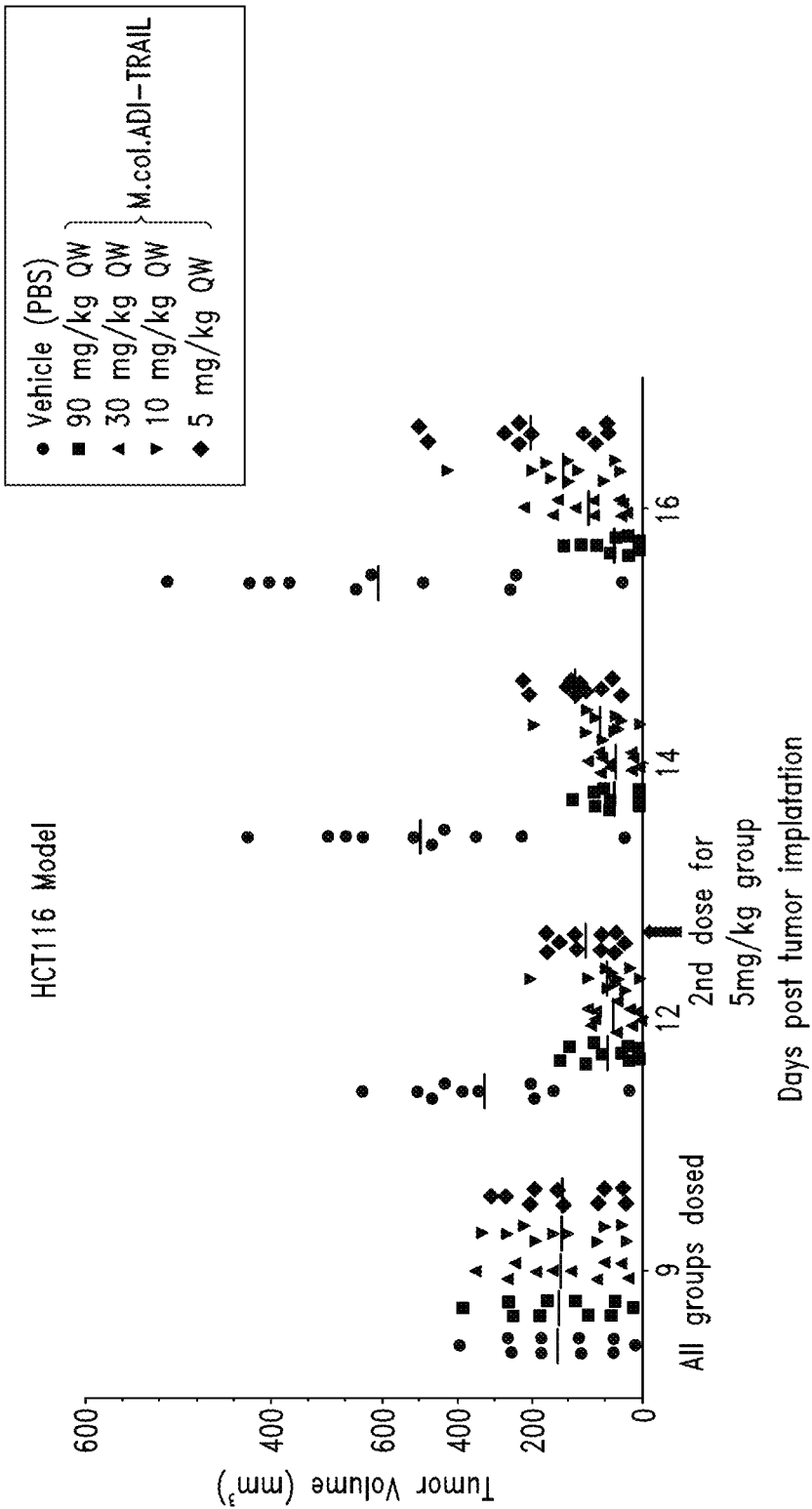
FIG. 19 demonstrates dose-dependent tumor growth reduction in HCT116 xenograft model after treatment with M.col.ADI-TRAIL.

FIG. 19 demonstrates dose-dependent tumor growth reduction in the HCT116 xenograft model after treatment with M.col.ADI-TRAIL. Female athymic Nude mice were inoculated with HCT116 cells subcutaneously. On day 9 post inoculation mice were randomized into the treatment groups (to have similar starting tumor volumes between the groups) and administered M.col.ADI-TRAIL fusion protein or vehicle control (PBS buffer) by intravenous injection. M.col.ADI-TRAIL dose groups were as follows: 90 mg/kg, 30 mg/kg, 10 mg/kg and 5 mg/kg. The first three groups were dosed only on day 9 and the 5 mg/kg group was dosed on day 9 and day 12 post tumor implantation.

2-way ANOVA analysis revealed statistical significance of tumor volume reduction after M.col.ADI-TRAIL treatment. P values for treatment group versus vehicle control were as follows:

Day 12 p<0.0001 for 10 mg/kg, 30 mg/kg and 90 mg/kg groups, p=0.0001 for 5 mg/kg group.
Day 14 p<0.0001 for all groups
Day 16 p<0.0001 for all groups On Day 16 (day 7 post treatment initiation) there were also statistically significant differences between high and low dose groups:

90 mg/kg group versus 10 mg/kg group p=0.0477
90 mg/kg group versus 5 mg/kg group p=0.0014
30 mg/kg group versus 5 mg/kg group p=0.0247

The invention claimed is:

1. A conjugate protein, wherein said conjugate protein is a single protein comprising a first polypeptide that is at least 95% identical to SEQ ID NO: 9, 37, 38, 50, or 57-68, that is covalently linked to a second polypeptide, wherein the second polypeptide comprises an amino acid sequence that is at least 95% identical to SEQ ID NO: 69 or SEQ ID NO: 70.

2. The conjugate protein of claim 1, wherein the first polypeptide comprises the amino acid sequence of SEQ ID NO: 9, 37, 38, 50, or 57-68 and the second polypeptide comprises the amino acid sequence of SEQ ID NO: 69 or SEQ ID NO: 70.

3. The conjugate protein of claim 1, wherein the first polypeptide is a hexameric polypeptide.

4. The conjugate protein of claim 1, wherein the second polypeptide is a trimeric polypeptide.

5. The conjugate protein of claim 1, wherein the first polypeptide and the second polypeptide are separated by a linker.

6. The conjugate protein of claim 5, wherein the linker is a peptide linker.

7. The conjugate protein of claim 6, wherein the peptide linker is 1-100 amino acids in length.

8. The conjugate protein of claim 6, wherein the peptide linker is selected from $[G]_x$, $[S]_x$, $[N]_x$, $[GS]_x$, $[GGS]_x$, $[GSS]_x$, $[GSGS \text{ (SEQ ID NO: 73)}]_x$, $[GGSG \text{ (SEQ ID NO: 74)}]_x$, $[GGGS \text{ (SEQ ID NO: 75)}]_x$, $[GGGGS \text{ (SEQ ID NO: 76)}]_x$, $[GN]_x$, $[GNN]_x$, $[GNGN \text{ (SEQ ID NO: 77)}]_x$, $[GGNG \text{ (SEQ ID NO: 78)}]_x$, $[GGGN \text{ (SEQ ID NO: 79)}]_x$, $[GGGGN \text{ (SEQ ID NO: 80)}]_x$, $A(EAAAK)_xA$ (SEQ ID NO: 81), AEAAAAKA (SEQ ID NO: 81), AEAAAKEAAAKA (SEQ ID NO: 82), $(XP)_x$, APAPKP (SEQ ID NO: 83), APAPKPEPAPKP (SEQ ID NO: 94), GGGGS (SEQ ID NO: 76), GGGGSGGGGS (SEQ ID NO: 85), DGGGS (SEQ ID N: 86), TGEKP (SEQ ID NO: 87), GGRR (SEQ ID NO: 88), EGKSSGSGSESKVD (SEQ ID NO: 89), KESGSVSSEQLAQFRSLD (SEQ ID NO: 90), GGRRGGGS (SEQ ID NO: 91), LRQRDGERP (SEQ ID NO: 92), LRQKDGGGSERP (SEQ ID NO: 93), LRQKD $(GGGS)_2$ ERP (SEQ ID NO: 94)

wherein x is 1-50, 60, 70, 80, 90, or 100.

9. The conjugate protein of claim 1, wherein the conjugate protein is a fusion polypeptide.

10. The conjugate protein of claim 9, wherein the first polypeptide is fused to the N-terminus of the second polypeptide.

11. The conjugate protein of claim 1, wherein the first polypeptide is covalently bonded via a linking group to at least one polyethylene glycol (PEG) molecule.

12. An isolated polynucleotide which encodes a conjugate protein of claim 1, wherein the conjugate protein is a fusion protein, or an expression vector that comprises the isolated polynucleotide, or an isolated host cell that comprises the isolated polynucleotide or the expression vector.

13. A therapeutic composition, comprising a conjugate protein of claim 1 and a pharmaceutically acceptable carrier or excipient.

14. The therapeutic composition of claim 13, wherein the conjugate protein forms a protein complex of one hexamer of six first polypeptides and two trimers of three second polypeptides.

15. The therapeutic composition of claim 13, where the conjugate protein as is at least 95% pure and less than 5% aggregated, and wherein the composition is substantially endotoxin-free.

16. The conjugate protein of claim 5, wherein the linker is a physiologically-stable linker.

17. The conjugate protein of claim 6, wherein the peptide linker is a flexible peptide linker or a rigid peptide linker.

18. The conjugate protein of claim 10, wherein the first polypeptide is separated from the second polypeptide by a linker.

19. The conjugate protein of claim 11, wherein the second polypeptide is not covalently bonded to a PEG molecule.

20. The conjugate protein of claim 4, wherein the trimeric polypeptide is a homotrimeric polypeptide.

* * * * *

SEQUENCE LISTING

```
<160> NUMBER OF SEQ ID NOS: 97

<210> SEQ ID NO 1
<211> LENGTH: 409
<212> TYPE: PRT
<213> ORGANISM: Mycoplasma hominis

<400> SEQUENCE: 1

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
```

```
                    180                 185                 190
His Pro Lys Leu Val Thr Pro Trp Tyr Tyr Asp Pro Ala Met Lys
                195                 200                 205

Met Pro Ile Glu Gly Gly Asp Val Phe Ile Tyr Asn Glu Thr Leu
    210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 2
<211> LENGTH: 409
<212> TYPE: PRT
<213> ORGANISM: Artificial Sequence
<220> FEATURE:
<223> OTHER INFORMATION: Mutated arginine deaminase

<400> SEQUENCE: 2

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Glu
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
```

```
            130                 135                 140
Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
                    180                 185                 190

His Pro Lys Leu Val Lys Thr Pro Trp Tyr Tyr Asp Pro Ala Met Lys
                195                 200                 205

Met Ser Ile Glu Gly Gly Asp Val Phe Ile Tyr Asn Asn Glu Thr Leu
            210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
                260                 265                 270

Leu Thr Met Leu Asp Lys Asn Lys Phe Leu Tyr Ser Pro Ile Ala Asn
                275                 280                 285

Asp Val Phe Lys Phe Trp Asp Tyr Asp Leu Val Asn Gly Gly Ala Glu
290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
                340                 345                 350

Leu Ala Ile Lys Pro Gly Leu Val Ile Gly Tyr Asp Arg Asn Glu Lys
                355                 360                 365

Thr Asn Ala Ala Leu Lys Ala Ala Gly Ile Thr Val Leu Pro Phe His
                370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405

<210> SEQ ID NO 3
<211> LENGTH: 392
<212> TYPE: PRT
<213> ORGANISM: Mycoplasma phocicerebrale

<400> SEQUENCE: 3

Ile His Val Tyr Ser Glu Ile Gly Glu Leu Glu Thr Val Leu Val His
1               5                   10                  15

Glu Pro Gly Arg Glu Ile Asp Tyr Ile Thr Pro Ala Arg Leu Asp Glu
                20                  25                  30

Leu Leu Phe Ser Ala Ile Leu Glu Ser His Asp Ala Arg Lys Glu His
                35                  40                  45

Gln Ser Phe Val Lys Gln Leu Lys Asp Asn Gly Ile Asn Val Val Glu
        50                  55                  60

Leu Thr Asp Leu Val Ala Glu Thr Phe Asp Leu Ala Ser Lys Glu Glu
65                  70                  75                  80

Gln Glu Lys Leu Ile Glu Glu Phe Leu Glu Asp Ser Glu Pro Val Leu
                85                  90                  95
```

```
Ser Glu Ala His Lys Thr Ala Val Arg Lys Phe Leu Thr Ser Arg Lys
            100                 105                 110

Ser Thr Arg Glu Met Val Glu Phe Met Met Ala Gly Ile Thr Lys Tyr
        115                 120                 125

Asp Leu Gly Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Lys Thr Pro Trp
            180                 185                 190

Tyr Tyr Asp Pro Ala Met Lys Met Ser Ile Glu Gly Gly Asp Val Phe
        195                 200                 205

Ile Tyr Asn Asn Asp Thr Leu Val Val Gly Val Ser Glu Arg Thr Asp
    210                 215                 220

Leu Glu Thr Ile Thr Leu Leu Ala Lys Asn Ile Lys Ala Asn Lys Glu
225                 230                 235                 240

Val Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Ala Glu Pro Gln Pro Lys Glu Asn Gly Leu Pro
    290                 295                 300

Leu Glu Gly Leu Leu Gln Ser Ile Ile Asn Lys Lys Pro Val Leu Ile
305                 310                 315                 320

Pro Ile Ala Gly Asn Asn Ala Ser His Ile Asp Ile Glu Arg Glu Thr
                325                 330                 335

His Phe Asp Gly Thr Asn Tyr Leu Ala Ile Lys Pro Gly Val Val Ile
            340                 345                 350

Gly Tyr Ala Arg Asn Glu Lys Thr Asn Ala Ala Leu Ala Ala Ala Gly
        355                 360                 365

Ile Lys Val Leu Pro Phe His Gly Asn Gln Leu Ser Leu Gly Met Gly
    370                 375                 380

Asn Ala Arg Cys Met Ser Met Pro
385                 390

<210> SEQ ID NO 4
<211> LENGTH: 410
<212> TYPE: PRT
<213> ORGANISM: Mycoplasma arginini

<400> SEQUENCE: 4

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
    50                  55                  60

Leu Lys Ala Asn Asp Ile Asn Val Val Glu Leu Ile Asp Leu Val Ala
65                  70                  75                  80
```

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Val Glu Asn Gly Leu Pro Leu Glu Gly Leu Leu Gln
305                 310                 315                 320

Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 5
<211> LENGTH: 409
<212> TYPE: PRT
<213> ORGANISM: Mycoplasma arthritidis

<400> SEQUENCE: 5

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile

```
              35                  40                  45
Leu Glu Ser His Asp Ala Arg Lys Glu His Lys Glu Phe Val Ala Glu
 50                  55                  60
Leu Lys Lys Arg Gly Ile Asn Val Val Glu Leu Val Asp Leu Ile Val
 65                  70                  75                  80
Glu Thr Tyr Asp Leu Ala Ser Lys Glu Ala Lys Glu Lys Leu Leu Glu
                 85                  90                  95
Glu Phe Leu Asp Asp Ser Val Pro Val Leu Ser Asp Glu His Arg Ala
            100                 105                 110
Ala Val Lys Lys Phe Leu Gln Ser Gln Lys Ser Thr Arg Ser Leu Val
        115                 120                 125
Glu Tyr Met Ile Ala Gly Ile Thr Lys His Asp Leu Lys Ile Glu Ser
130                 135                 140
Asp Leu Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
            180                 185                 190
Asn His Pro Lys Leu Val Asn Thr Pro Trp Tyr Tyr Asp Pro Ala Glu
        195                 200                 205
Gly Leu Ser Ile Glu Gly Gly Asp Val Phe Ile Tyr Asn Asn Asp Thr
210                 215                 220
Leu Val Val Gly Val Ser Glu Arg Thr Asp Leu Gln Thr Ile Thr Leu
225                 230                 235                 240
Leu Ala Lys Asn Ile Lys Ala Asn Lys Glu Cys Glu Phe Lys Arg Ile
                245                 250                 255
Val Ala Ile Asn Val Pro Lys Trp Thr Asn Leu Met His Leu Asp Thr
            260                 265                 270
Trp Leu Thr Met Leu Asp Lys Asp Lys Phe Leu Tyr Ser Pro Ile Ala
        275                 280                 285
Asn Asp Val Phe Lys Phe Trp Asp Tyr Asp Leu Val Asn Gly Gly Asp
290                 295                 300
Ala Pro Gln Pro Val Asp Asn Gly Leu Pro Leu Glu Asp Leu Leu Lys
305                 310                 315                 320
Ser Ile Ile Gly Lys Lys Pro Thr Leu Ile Pro Ile Ala Gly Ala Gly
                325                 330                 335
Ala Ser Gln Ile Asp Ile Glu Arg Glu Thr His Phe Asp Gly Thr Asn
            340                 345                 350
Tyr Leu Ala Val Ala Pro Gly Ile Val Ile Gly Tyr Ala Arg Asn Glu
        355                 360                 365
Lys Thr Asn Ala Ala Leu Glu Ala Ala Gly Ile Thr Val Leu Pro Phe
370                 375                 380
Arg Gly Asn Gln Leu Ser Leu Gly Met Gly Asn Ala Arg Cys Met Ser
385                 390                 395                 400
Met Pro Leu Ser Arg Lys Asp Val Lys
                405

<210> SEQ ID NO 6
<211> LENGTH: 408
<212> TYPE: PRT
<213> ORGANISM: Mycoplasma orale
<220> FEATURE:
<221> NAME/KEY: misc_feature
<222> LOCATION: (201)..(201)
```

<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid

<400> SEQUENCE: 6

```
Ser Val Phe Ser Asp Lys Phe Asn Gly Ile His Val Tyr Ser Glu Ile
1               5                   10                  15

Gly Asp Leu Glu Ser Val Leu Val His Glu Pro Gly Lys Glu Ile Asp
                20                  25                  30

Tyr Ile Thr Pro Ala Arg Leu Asp Glu Leu Leu Phe Ser Ala Ile Leu
            35                  40                  45

Glu Ser Thr Asp Ala Arg Lys Glu His Lys Glu Phe Val Glu Ile Leu
        50                  55                  60

Lys Lys Gln Gly Ile Asn Val Val Glu Leu Val Asp Leu Val Val Glu
65                  70                  75                  80

Thr Tyr Asn Leu Val Asp Lys Lys Thr Gln Glu Lys Leu Leu Lys Asp
                85                  90                  95

Phe Leu Asp Asp Ser Glu Pro Val Leu Ser Pro Glu His Arg Lys Ala
            100                 105                 110

Val Glu Lys Phe Leu Lys Ser Leu Lys Ser Thr Lys Glu Leu Ile Gln
        115                 120                 125

Tyr Met Met Ala Gly Ile Thr Lys Tyr Asp Leu Gly Ile Lys Ala Asp
130                 135                 140

Lys Glu Leu Ile Val Asp Pro Met Pro Asn Leu Tyr Phe Thr Arg Asp
145                 150                 155                 160

Pro Phe Ala Ser Val Gly Asn Gly Val Thr Ile His Tyr Met Arg Tyr
                165                 170                 175

Lys Val Arg Gln Arg Glu Thr Leu Phe Ser Lys Phe Ile Phe Thr Asn
            180                 185                 190

His Pro Lys Leu Val Lys Thr Pro Xaa Tyr Tyr Asp Pro Ala Met Lys
        195                 200                 205

Leu Ser Ile Glu Gly Gly Asp Val Phe Ile Tyr Asn Asn Asp Thr Leu
210                 215                 220

Val Val Gly Val Ser Glu Arg Thr Asp Leu Glu Thr Ile Thr Leu Leu
225                 230                 235                 240

Ala Lys Asn Ile Lys Ala Asn Lys Glu Cys Glu Phe Lys Arg Ile Val
                245                 250                 255

Ala Ile Asn Val Pro Lys Xaa Thr Asn Leu Met His Leu Asp Thr Xaa
            260                 265                 270

Leu Thr Met Leu Asp Lys Asp Lys Phe Leu Tyr Ser Pro Ile Ala Asn
        275                 280                 285

Asp Val Phe Lys Phe Xaa Asp Tyr Asp Leu Val Asn Gly Gly Ser Asn
290                 295                 300

Pro Glu Pro Val Val Asn Gly Leu Pro Leu Asp Lys Leu Leu Glu Ser
305                 310                 315                 320

Ile Ile Asn Lys Lys Pro Val Leu Ile Pro Ile Ala Gly Lys Gly Ala
                325                 330                 335
```

```
Thr Glu Ile Glu Thr Ala Val Glu Thr His Phe Asp Gly Thr Asn Tyr
            340                 345                 350

Leu Ala Ile Lys Pro Gly Val Val Gly Tyr Ser Arg Asn Val Lys
            355                 360                 365

Thr Asn Ala Ala Leu Glu Ala Asn Gly Ile Lys Val Leu Pro Phe Lys
370                 375                 380

Gly Asn Gln Leu Ser Leu Gly Met Gly Asn Ala Arg Cys Met Ser Met
385                 390                 395                 400

Pro Leu Ser Arg Lys Asp Val Lys
            405

<210> SEQ ID NO 7
<211> LENGTH: 391
<212> TYPE: PRT
<213> ORGANISM: Mycoplasma gateae

<400> SEQUENCE: 7

Ile His Val Tyr Ser Glu Ile Gly Glu Leu Glu Ser Val Leu Val His
1               5                   10                  15

Glu Pro Gly Arg Glu Ile Asp Tyr Ile Thr Pro Ala Arg Leu Asp Glu
            20                  25                  30

Leu Leu Phe Ser Ala Ile Leu Glu Ser His Asp Ala Arg Lys Glu His
        35                  40                  45

Lys Leu Phe Val Ser Glu Leu Lys Ala Asn Asp Ile Asn Val Val Glu
    50                  55                  60

Leu Thr Asp Leu Val Thr Glu Thr Tyr Asp Leu Ala Ser Gln Glu Ala
65                  70                  75                  80

Lys Asp Asn Leu Ile Glu Glu Phe Leu Glu Asp Ser Glu Pro Val Leu
                85                  90                  95

Thr Glu Glu Leu Lys Ser Val Val Arg Thr Tyr Leu Lys Ser Ile Lys
            100                 105                 110

Ser Thr Arg Glu Leu Ile Gln Met Met Met Ala Gly Ile Thr Lys Tyr
        115                 120                 125

Asp Leu Gly Ile Glu Ala Asp His Glu Leu Ile Val Asp Pro Met Pro
130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Asn Thr Pro Trp
            180                 185                 190

Tyr Tyr Asp Pro Ser Leu Lys Leu Ser Ile Glu Gly Asp Val Phe
        195                 200                 205

Ile Tyr Asn Asn Asn Thr Leu Val Val Gly Val Ser Glu Arg Thr Asp
210                 215                 220

Leu Glu Thr Val Thr Leu Leu Ala Lys Asn Ile Val Ala Asn Lys Glu
225                 230                 235                 240

Cys Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Glu Glu Pro Gln Pro Val Glu Asn Gly Leu Pro
290                 295                 300
```

```
Leu Glu Gly Leu Leu Glu Ser Ile Ile Asn Lys Lys Pro Ile Leu Ile
305                 310                 315                 320

Pro Ile Ala Gly Glu Gly Ala Ser Gln Ile Asp Ile Glu Arg Glu Thr
                325                 330                 335

His Phe Asp Gly Thr Asn Tyr Leu Ala Ile Arg Pro Gly Val Val Ile
            340                 345                 350

Gly Tyr Ser Arg Asn Glu Lys Thr Asn Ala Ala Leu Glu Ala Ala Gly
        355                 360                 365

Ile Lys Val Leu Pro Phe His Gly Asn Gln Leu Ser Leu Gly Met Gly
370                 375                 380

Asn Ala Arg Cys Met Ser Met
385                 390

<210> SEQ ID NO 8
<211> LENGTH: 392
<212> TYPE: PRT
<213> ORGANISM: Mycoplasma phocidae

<400> SEQUENCE: 8

Ile His Val Tyr Ser Glu Ile Gly Glu Leu Gln Thr Val Leu Val His
1               5                   10                  15

Glu Pro Gly Arg Glu Ile Glu Tyr Ile Thr Pro Ala Arg Leu Asp Glu
            20                  25                  30

Leu Leu Phe Ser Ala Ile Leu Glu Ser His Asp Ala Arg Lys Glu His
        35                  40                  45

Gln Glu Phe Val Ala Glu Leu Lys Lys Asn Asn Ile Asn Val Val Glu
    50                  55                  60

Leu Thr Asp Leu Val Ser Glu Thr Tyr Asp Met Val Ser Lys Glu Lys
65                  70                  75                  80

Gln Glu Lys Leu Ile Glu Glu Phe Leu Glu Asp Ser Glu Pro Val Leu
                85                  90                  95

Ser Glu Glu His Lys Gly Leu Val Arg Lys Phe Leu Lys Ser Leu Lys
            100                 105                 110

Ser Ser Lys Glu Leu Ile Gln Tyr Met Met Ala Gly Ile Thr Lys His
        115                 120                 125

Asp Leu Asn Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Ile Phe Ala Asn His Pro Lys Leu Met Asn Thr Pro Leu
            180                 185                 190

Tyr Tyr Asn Pro Asp Met Lys Leu Ser Ile Glu Gly Gly Asp Val Phe
        195                 200                 205

Val Tyr Asn Asn Glu Thr Leu Val Val Gly Val Ser Glu Arg Thr Asp
    210                 215                 220

Leu Asp Thr Ile Thr Leu Leu Ala Lys Asn Ile Lys Ala Asn Lys Glu
225                 230                 235                 240

Arg Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
```

```
                275                 280                 285
Leu Val Asn Gly Gly Asp Glu Pro Gln Pro Lys Val Asn Gly Leu Pro
290                 295                 300

Leu Glu Lys Leu Leu Glu Ser Ile Ile Asn Lys Lys Pro Ile Leu Ile
305                 310                 315                 320

Pro Ile Ala Gly Thr Ser Ala Ser Asn Ile Asp Val Glu Arg Glu Thr
                325                 330                 335

His Phe Asp Gly Thr Asn Tyr Leu Ala Ile Ala Pro Gly Val Val Ile
                340                 345                 350

Gly Tyr Ser Arg Asn Val Lys Thr Asn Glu Ala Leu Glu Ala Ala Gly
                355                 360                 365

Ile Lys Val Leu Pro Phe Lys Gly Asn Gln Leu Ser Leu Gly Met Gly
370                 375                 380

Asn Ala Arg Cys Met Ser Met Pro
385                 390

<210> SEQ ID NO 9
<211> LENGTH: 401
<212> TYPE: PRT
<213> ORGANISM: Mycoplasma columbinum

<400> SEQUENCE: 9

Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
                20                  25                  30

Leu Asp Glu Leu Leu Phe Ser Ala Ile Leu Glu Pro Asn Glu Ala Ile
                35                  40                  45

Lys Glu His Lys Gly Phe Leu Lys Ile Leu Gln Asp Lys Gly Ile Lys
            50                  55                  60

Val Ile Gln Leu Ser Asp Leu Val Ala Glu Thr Tyr Thr Tyr His Ala
65                  70                  75                  80

Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
                100                 105                 110

Leu Ser Lys Glu Gly Thr Pro Val Ala Met Val Arg Thr Met Met Ala
            115                 120                 125

Gly Val Ser Lys Gln Glu Leu Asn Val Glu Ser Glu Thr Glu Leu Val
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
                180                 185                 190

Lys Thr Thr Pro His Trp Phe Asp Arg Leu Asp Glu Gly Asn Ile Glu
            195                 200                 205

Gly Gly Asp Val Phe Ile Tyr Asn Lys Asp Thr Leu Val Ile Gly Val
210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255
```

-continued

```
Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
    290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 10
<211> LENGTH: 407
<212> TYPE: PRT
<213> ORGANISM: Mycoplasma iowae

<400> SEQUENCE: 10

Met Gly Asn Asn Ile Pro Lys Lys Ile Asn Val Phe Ser Glu Ile Gly
1               5                   10                  15

Asn Leu Lys Arg Val Leu Val His Thr Pro Gly Lys Glu Ile Glu Tyr
            20                  25                  30

Val Thr Pro Gln Arg Leu Asp Glu Leu Leu Phe Ser Ala Ile Leu Asp
        35                  40                  45

Pro Val Arg Ala Arg Glu Glu His Lys Glu Phe Ile Lys Ile Leu Glu
    50                  55                  60

Ser Gln Gly Val Glu Val Val Gln Leu Val Asp Leu Thr Ala Glu Thr
65                  70                  75                  80

Tyr Asp Val Ala Glu Ser Gln Ala Lys Glu Asn Phe Ile Gln Lys Trp
                85                  90                  95

Leu Asp Glu Ser Leu Pro Lys Leu Thr Asp Glu Asn Arg Asn Lys Val
            100                 105                 110

Tyr Ser Leu Leu Lys Ser Leu Glu Lys Asp Pro Lys Glu Met Ile Arg
        115                 120                 125

Lys Met Met Ser Gly Val Leu Ala Ser Glu Ile Gly Val Lys Ser Asp
    130                 135                 140

Val Glu Leu Ile Val Asp Pro Met Pro Asn Leu Tyr Phe Thr Arg Asp
145                 150                 155                 160

Pro Phe Ala Ser Val Gly Asn Gly Ile Thr Leu His Arg Met Phe Arg
                165                 170                 175

Pro Thr Arg Arg Arg Glu Thr Ile Phe Ala Asp Phe Ile Phe Ser Asn
            180                 185                 190

His Pro Glu Tyr Lys Ser Thr Gln Lys Tyr Tyr Glu Arg Glu Asp Lys
        195                 200                 205

Phe Ser Leu Glu Gly Gly Asp Val Phe Ile Tyr Asn Asn Lys Thr Leu
    210                 215                 220
```

```
Val Val Gly Val Ser Glu Arg Thr Glu Lys Gly Ala Ile Lys Ala Leu
225                 230                 235                 240

Ala Lys Ala Val Gln Asn Asn Ser Asn Met Ser Phe Glu Lys Ile Tyr
            245                 250                 255

Ala Ile Asn Val Pro Lys Met Ser Asn Leu Met His Leu Asp Thr Trp
                260                 265                 270

Leu Thr Met Leu Asp Thr Asp Lys Phe Leu Tyr Ser Pro Asn Met Met
        275                 280                 285

Gly Val Leu Lys Ile Trp Glu Ile Asp Leu Ser Asp Lys Ser Leu Lys
        290                 295                 300

Trp Lys Glu Ile Arg Asp Ser Leu Asp His Phe Leu Ser Thr Ile Ile
305                 310                 315                 320

Gly Lys Lys Ala Ile Thr Val Pro Val Ala Gly Lys Asp Ala Met Gln
                325                 330                 335

Phe Glu Ile Asp Ile Glu Thr His Phe Asp Ala Thr Asn Phe Ile Ala
                340                 345                 350

Val Ala Pro Gly Val Val Ile Gly Tyr Asp Arg Asn Lys Lys Thr Asn
            355                 360                 365

Glu Ala Leu Lys Glu Ala Gly Ile Lys Val Leu Ser Trp Asn Gly Asp
    370                 375                 380

Gln Leu Ser Leu Gly Met Gly Ser Ala Arg Cys Met Thr Met Pro Leu
385                 390                 395                 400

Tyr Arg Glu Glu Leu Lys Lys
                405

<210> SEQ ID NO 11
<211> LENGTH: 402
<212> TYPE: PRT
<213> ORGANISM: Mycoplasma crocodyli

<400> SEQUENCE: 11

Met Asn Lys Ile Asn Val Tyr Ser Glu Val Gly Lys Leu Lys Glu Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Ile Leu Glu Pro Asp Ser Ala Ile
        35                  40                  45

Glu Glu His Lys Arg Phe Leu Lys Ile Leu Glu Asp Asn Asn Ile Lys
    50                  55                  60

Val Ile Gln Leu Asp Gln Leu Val Ala Asp Thr Tyr Glu Leu Val Asn
65                  70                  75                  80

Pro Ser Val Arg Asp Ala Phe Ile Glu Lys Trp Leu Asn Glu Ser Glu
                85                  90                  95

Pro Lys Leu Asp Lys Lys Leu Arg Glu Lys Val Lys Glu Tyr Leu Leu
            100                 105                 110

His Thr Gln Lys Thr Val Gly Thr Lys Arg Met Val Arg Ile Met Met
        115                 120                 125

Ala Gly Val Asp Arg Val Glu Leu Gly Val Glu Leu Asp Arg Gln Leu
    130                 135                 140

Val Val Asp Pro Met Pro Asn Leu Tyr Phe Thr Arg Asp Pro Phe Ala
145                 150                 155                 160

Ser Ala Gly Asn Gly Ile Ser Leu Asn Asn Met Lys Tyr Val Thr Arg
                165                 170                 175

Lys Arg Glu Thr Ile Phe Ser Glu Phe Ile Phe Glu Asn His Pro Asp
            180                 185                 190
```

```
Tyr Lys Thr Thr Pro His Trp Phe Asp Arg Leu Asp Lys Gly Asn Ile
            195                 200                 205

Glu Gly Gly Asp Val Phe Ile Tyr Asn Arg Thr Thr Leu Val Ile Gly
210                 215                 220

Ile Ser Glu Arg Thr Asn Lys Asp Ala Leu Leu Thr Ile Ala Asn Asn
225                 230                 235                 240

Ile Lys Ser Asn Lys Glu Ser Lys Phe Glu Arg Ile Val Ala Val Asn
                245                 250                 255

Val Pro Pro Met Pro Asn Leu Met His Leu Asp Thr Trp Leu Thr Met
            260                 265                 270

Val Asp His Asp Lys Phe Leu Tyr Ser Pro Asn Met Met Lys Thr Leu
            275                 280                 285

Lys Phe Trp Thr Ile Asp Leu Thr Lys Pro Ile Lys Met Val Glu Leu
        290                 295                 300

Glu Glu Ser Leu Ser Asp Met Ile Glu Thr Ile Ile Gly Lys Lys Pro
305                 310                 315                 320

Val Leu Ile Pro Ile Ala Gly His Asp Ala Ser Pro Leu Asp Val Asp
                325                 330                 335

Ile Glu Thr His Phe Asp Gly Thr Asn Tyr Leu Thr Ile Ala Pro Gly
            340                 345                 350

Val Val Val Gly Tyr Ser Arg Asn Lys Leu Thr Glu Lys Ala Leu Thr
            355                 360                 365

Lys Ala Gly Val Lys Val Leu Ser Phe Glu Gly Asn Gln Leu Ser Leu
        370                 375                 380

Gly Met Gly Ser Ala Arg Cys Met Ser Met Pro Leu Val Arg Glu Asp
385                 390                 395                 400

Ile Lys

<210> SEQ ID NO 12
<211> LENGTH: 430
<212> TYPE: PRT
<213> ORGANISM: Mycoplasma fermentans

<400> SEQUENCE: 12

Met Gln Ile Ile Ala Lys Ile Asp Leu Leu Thr Asn Met Leu Ile Phe
1               5                   10                  15

Met Lys Ile Tyr Phe Ile Gly Arg Leu Ile Met Lys Lys Ile Asn Val
            20                  25                  30

Tyr Ser Glu Tyr Gly Lys Leu Lys Glu Val Leu Val His Thr Pro Gly
        35                  40                  45

Asp Glu Ile Arg Arg Ile Ala Pro Ser Arg Leu Asp Glu Leu Leu Phe
50                  55                  60

Ser Ala Ile Leu Glu Pro Asp Ser Ala Ile Ala Glu His Lys Arg Phe
65                  70                  75                  80

Val Gln Leu Leu Lys Asp Asn Gly Ile Lys Val Ile Gln Leu Asp Glu
                85                  90                  95

Leu Phe Ala Lys Thr Phe Asp Leu Val Ser Glu Ser Val Lys Gln Ser
            100                 105                 110

Leu Ile Glu Arg Trp Leu Asp Glu Cys Glu Pro Lys Leu Asp Ala Thr
        115                 120                 125

Leu Arg Ala Lys Val Lys Glu Tyr Ile Leu Glu Leu Lys Ala Lys Ser
    130                 135                 140

Ser Lys Lys Met Val Arg Val Met Met Ala Gly Ile Asp Lys Lys Glu
145                 150                 155                 160
```

```
Leu Gly Ile Glu Leu Asp Arg Asp Leu Val Val Asp Pro Met Pro Asn
            165                 170                 175

Leu Tyr Phe Thr Arg Asp Pro Phe Ala Ser Val Gly Asn Gly Ile Ser
            180                 185                 190

Leu His His Met Lys Tyr Val Thr Arg Gln Arg Glu Thr Ile Phe Ser
            195                 200                 205

Glu Phe Ile Phe Asp Asn Asn Leu Asp Tyr Asn Thr Val Pro Arg Trp
            210                 215                 220

Phe Asp Arg Lys Asp Glu Gly Arg Ile Glu Gly Asp Val Phe Ile
225                 230                 235                 240

Tyr Ser Ala Asp Thr Leu Val Val Gly Val Ser Glu Arg Thr Asn Lys
            245                 250                 255

Glu Ala Ile Asn Val Met Ala Arg Lys Ile Ala Ala Asp Lys Glu Val
            260                 265                 270

Lys Phe Lys Arg Ile Tyr Ala Ile Asn Val Pro Pro Met Pro Asn Leu
            275                 280                 285

Met His Leu Asp Thr Trp Leu Thr Met Leu Asp Lys Asn Lys Phe Leu
            290                 295                 300

Tyr Ser Pro Asn Met Leu Ser Val Leu Lys Val Trp Arg Ile Asp Leu
305                 310                 315                 320

Asn Asp Pro Asp Phe Val Trp His Glu Ile Glu Gly Ser Leu Glu Glu
            325                 330                 335

Ile Leu Glu Gln Ile Ile Gly Met Lys Pro Ile Leu Ile Pro Ile Ala
            340                 345                 350

Gly Lys Gly Ala Ser Gln Leu Asp Ile Asp Ile Glu Thr His Phe Asp
            355                 360                 365

Gly Thr Asn Tyr Leu Thr Ile Ala Pro Ser Val Val Gly Tyr Ser
            370                 375                 380

Arg Asn Glu Lys Thr Glu Lys Ala Leu Lys Ala Ala Lys Val Lys Val
385                 390                 395                 400

Leu Ser Phe Glu Gly Asn Gln Leu Ser Leu Gly Met Gly Ser Ala Arg
            405                 410                 415

Cys Met Ser Met Pro Leu Ile Arg Glu Asp Ile Lys Lys Lys
            420                 425                 430

<210> SEQ ID NO 13
<211> LENGTH: 452
<212> TYPE: PRT
<213> ORGANISM: Mycoplasma penetrans

<400> SEQUENCE: 13

Met Val Ile Thr Ile Ala Leu Asn Ile Leu Asn Lys Ile Tyr Phe Lys
1               5                   10                  15

Pro Gln Asn Arg Ser Ile Leu Lys Leu Tyr Arg Leu Pro Ser Leu Cys
            20                  25                  30

Thr Gln Ile Ser Ile Phe Ile Gly Gly Lys Met Ser Ser Ile Asp Lys
            35                  40                  45

Asn Ser Leu Gly Asn Gly Ile Asn Val Tyr Ser Glu Ile Gly Glu Leu
            50                  55                  60

Lys Glu Val Leu Val His Thr Pro Gly Asp Glu Ile Arg Tyr Thr Ala
65                  70                  75                  80

Pro Ser Arg Leu Glu Glu Leu Leu Phe Ser Ala Val Leu Lys Ala Asp
            85                  90                  95

Thr Ala Ile Glu Glu His Lys Gly Phe Val Lys Ile Leu Gln Asn Asn
```

```
                100             105             110
Gly Ile Lys Val Ile Gln Leu Cys Asp Leu Val Ala Glu Thr Tyr Glu
            115             120             125

Leu Cys Ser Lys Glu Val Arg Asn Ser Phe Ile Glu Gln Tyr Leu Asp
            130             135             140

Glu Ala Leu Pro Val Leu Lys Lys Glu Ile Arg Pro Val Val Lys Asp
145             150             155             160

Tyr Leu Leu Ser Phe Pro Thr Val Gln Met Val Arg Lys Met Met Ser
            165             170             175

Gly Ile Leu Ala Asn Glu Leu Asn Ile Lys Gln Asp Asn Pro Leu Ile
            180             185             190

Ile Asp Gly Met Pro Asn Leu Tyr Phe Thr Arg Asp Pro Phe Ala Ser
            195             200             205

Met Gly Asn Gly Val Ser Ile Asn Cys Met Lys Tyr Pro Thr Arg Lys
            210             215             220

Arg Glu Val Ile Phe Ser Arg Phe Val Phe Thr Asn Asn Pro Lys Tyr
225             230             235             240

Lys Asn Thr Pro Arg Tyr Phe Asp Ile Val Gly Asn Asn Gly Thr Ile
            245             250             255

Glu Gly Gly Asp Ile Phe Ile Tyr Asn Ser Lys Thr Leu Val Ile Gly
            260             265             270

Asn Ser Glu Arg Thr Asn Phe Ala Ala Ile Glu Ser Val Ala Lys Asn
            275             280             285

Ile Gln Ala Asn Lys Asp Cys Thr Phe Glu Arg Ile Val Val Ile Asn
            290             295             300

Val Pro Pro Met Pro Asn Leu Met His Leu Asp Thr Trp Leu Thr Met
305             310             315             320

Leu Asp Tyr Asp Lys Phe Leu Tyr Ser Pro Asn Met Met Asn Val Leu
            325             330             335

Lys Ile Trp Glu Ile Asp Leu Asn Val Lys Pro Val Lys Phe Val Glu
            340             345             350

Lys Lys Gly Thr Leu Glu Glu Val Leu Tyr Ser Ile Ile Asp Lys Lys
            355             360             365

Pro Ile Leu Ile Pro Ile Ala Gly Lys Gly Ala Asn Gln Leu Asp Ile
            370             375             380

Asp Ile Glu Thr His Phe Asp Gly Thr Asn Tyr Leu Thr Ile Ala Pro
385             390             395             400

Gly Val Val Val Gly Tyr Glu Arg Asn Glu Lys Thr Gln Lys Ala Leu
            405             410             415

Val Glu Ala Gly Ile Lys Val Leu Ser Phe Asn Gly Ser Gln Leu Ser
            420             425             430

Leu Gly Met Gly Ser Ala Arg Cys Met Ser Met Pro Leu Ile Arg Glu
            435             440             445

Asn Leu Lys Lys
    450

<210> SEQ ID NO 14
<211> LENGTH: 403
<212> TYPE: PRT
<213> ORGANISM: Mycoplasma gallisepticum

<400> SEQUENCE: 14

Met Phe Asn Lys Ile Arg Val Tyr Ser Glu Ile Gly Lys Leu Arg Lys
1               5               10              15
```

Val Leu Val His Thr Pro Gly Lys Glu Leu Asp Tyr Val Thr Pro Gln
            20                  25                  30

Arg Leu Asp Glu Leu Leu Phe Ser Ser Leu Leu Asn Pro Ile Lys Ala
        35                  40                  45

Arg Gln Glu His Glu Thr Phe Ile Lys Leu Leu Glu Asp His Asp Val
    50                  55                  60

Glu Cys Val Gln Leu Ser Thr Leu Thr Ala Gln Thr Phe Gln Ala Val
65                  70                  75                  80

Asn Ser Lys Ile Gln Glu Glu Phe Ile Asn Arg Trp Leu Asp Glu Cys
                85                  90                  95

Leu Pro Val Leu Ser Glu Ile Asn Arg Leu Lys Val Tyr Asp Tyr Leu
            100                 105                 110

Lys Ser Leu Ala Thr Asn Pro Gln Val Met Ile Arg Lys Met Met Ser
        115                 120                 125

Gly Ile Leu Ala Lys Glu Val Gly Ile Gln Ser Glu Val Glu Leu Val
    130                 135                 140

Ala Asp Pro Met Pro Asn Leu Tyr Phe Thr Arg Asp Pro Phe Ala Ser
145                 150                 155                 160

Ile Gly Lys Gly Ile Thr Leu His Ser Met Phe His Pro Thr Arg Lys
                165                 170                 175

Arg Glu Thr Ile Phe Ala Asp Phe Ile Phe Ser His His Pro Glu Tyr
            180                 185                 190

Lys Asn Ala Pro Lys Tyr Tyr Ser Arg Glu Asp Lys Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Ser Leu Ala Glu Lys Leu
225                 230                 235                 240

Arg Gln Asn Asp Glu Thr Ser Phe Glu Lys Ile Tyr Ala Ile Asn Val
                245                 250                 255

Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
        275                 280                 285

Ile Trp Glu Ile Asp Leu Ile His Pro Thr Leu Ile Trp Arg Glu Leu
    290                 295                 300

Asn Glu Ser Leu Glu Gly Phe Leu Ser Met Val Ile Gly Lys Lys Ala
305                 310                 315                 320

Thr Leu Ile Pro Val Ala Gly Glu Asp Ser Thr Gln Ile Glu Ile Asp
                325                 330                 335

Val Glu Thr Asn Phe Asp Ala Thr Asn Phe Leu Val Ile Gln Pro Gly
        340                 345                 350

Val Val Val Gly Tyr Asp Arg Asn Tyr Lys Thr Asn Gln Ala Leu Arg
    355                 360                 365

Asp Ala Gly Val Lys Val Ile Ser Trp Asn Gly Asp Gln Leu Ser Leu
370                 375                 380

Gly Met Gly Ser Ala Arg Cys Met Ser Met Pro Leu Tyr Arg Asp Pro
385                 390                 395                 400

Ile Lys Lys

<210> SEQ ID NO 15
<211> LENGTH: 402
<212> TYPE: PRT
<213> ORGANISM: Mycoplasma alligatoris

<400> SEQUENCE: 15

```
Met Ser Lys Ile Asn Val Tyr Ser Glu Val Gly Arg Leu Lys Glu Val
1               5                   10                  15

Leu Val His Thr Pro Gly Asp Glu Ile Arg Arg Ile Ser Pro Thr Arg
                20                  25                  30

Leu Glu Glu Leu Leu Phe Ser Ala Ile Leu Glu Pro Asp Thr Ala Ile
            35                  40                  45

Glu Glu His Lys Arg Phe Leu Asn Val Leu Glu Lys Asn Gly Ile Lys
        50                  55                  60

Ala Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
                100                 105                 110

Lys Ser Gln Lys Glu Phe Ser Thr Lys Lys Met Val Arg Ile Met Met
            115                 120                 125

Ala Gly Ile Asp Lys Lys Glu Ile Asn Ile Asp Leu Asp Arg Asp Leu
        130                 135                 140

Val Val Asp Pro Met Pro Asn Leu Tyr Phe Thr Arg Asp Pro Phe Ala
145                 150                 155                 160

Ser Val Gly Asn Gly Ile Ser Leu His Asn Met Lys Tyr Gln Thr Arg
                165                 170                 175

Lys Arg Glu Thr Ile Phe Ala Gln Phe Ile Phe Lys Tyr Asn Lys Asp
            180                 185                 190

Tyr Lys Thr Thr Pro His Trp Phe Asp Arg Phe Asp His Gly Ser Ile
        195                 200                 205

Glu Gly Gly Asp Val Phe Val Tyr Thr Lys Asp Thr Leu Val Ile Gly
210                 215                 220

Ile Ser Glu Arg Thr Thr Lys Glu Ala Val Leu Asn Ile Ala Lys Lys
225                 230                 235                 240

Ile Lys Ala Asn Thr Asp Ser Lys Phe Lys Lys Ile Val Ala Ile Asn
                245                 250                 255

Val Pro Pro Met Pro Asn Leu Met His Leu Asp Thr Trp Ile Thr Met
                260                 265                 270

Val Asp His Asp Lys Phe Leu Tyr Ser Pro Asn Met Met Lys Ser Leu
            275                 280                 285

Lys Phe Trp Leu Ile Asp Leu Ser Lys Glu Ile Lys Met Val Glu Leu
        290                 295                 300

Glu Glu Ser Leu Ser Asn Met Leu Glu Ala Ile Ile Gly Lys Lys Pro
305                 310                 315                 320

Ile Leu Ile Pro Ile Ala Gly Lys Asn Ala Ser Gln Leu Asp Ile Asp
                325                 330                 335

Ile Glu Thr His Phe Asp Gly Thr Asn Tyr Leu Thr Ile Ala Pro Gly
                340                 345                 350

Val Val Val Gly Tyr Ser Arg Asn Lys Leu Thr Gln Lys Ala Leu Glu
            355                 360                 365

Asp Ala Gly Val Lys Val Leu Ser Phe Asp Gly Asn Gln Leu Ser Leu
        370                 375                 380

Gly Met Gly Ser Ala Arg Cys Met Ser Met Pro Leu Val Arg Glu Asp
385                 390                 395                 400

Ile Lys
```

<210> SEQ ID NO 16
<211> LENGTH: 438
<212> TYPE: PRT
<213> ORGANISM: Mycoplasma pneumoniae

<400> SEQUENCE: 16

```
Met Ser Lys Lys Gln Leu Val Lys Thr Asp Gly His Asn Gln Leu Asp
1               5                   10                  15

Gln Pro Asn Thr Lys Ala Leu Gln Leu Lys Lys Gln Phe Asn Ser
            20                  25                  30

Gly Val Arg Val Thr Ser Glu Ile Ser Phe Leu Arg Glu Val Ile Ala
        35                  40                  45

His His Pro Gly Ile Glu Thr Glu Arg Val Ile Asp Asn Gln Thr Phe
    50                  55                  60

Gly Ser Ala Met Tyr Leu Glu Arg Ala Gln Lys Glu His Gln Leu Phe
65                  70                  75                  80

Ile Lys Ile Leu Arg Gln His Gly Thr Lys Val His Tyr Leu Gln Asp
                85                  90                  95

Leu Leu Leu Glu Ala Leu Ser Ala Ala Asp Pro Asn Val Arg Gln Asp
            100                 105                 110

Phe Ile Lys Asn Phe Leu Leu Glu Ser Gly Ile Lys Ser Val Ser Thr
        115                 120                 125

Phe Glu Ala Cys Leu Asn Phe Phe Arg Ser Leu Asp Ser Leu Val Asp
    130                 135                 140

Val Ile Lys Val Met Phe Gly Gly Ile Lys Val Ser Asp Val Pro Pro
145                 150                 155                 160

Ile Thr Pro Gln Arg Phe Ala Asp Ile His Val Ser Asn Ser Pro Phe
                165                 170                 175

Leu Ile Lys Pro Leu Ser Phe Ser Leu Tyr Pro His Lys Phe Phe Asn
            180                 185                 190

Thr Leu Gly Thr Gly Val Ala Leu Phe Val Thr Asn Asp Ser Glu Leu
        195                 200                 205

Lys Arg His Ser Leu Val Tyr Glu Tyr Ile Met Arg Phe His Pro Arg
    210                 215                 220

Phe Asp Gly Val Lys Leu Tyr Thr Asn Arg Asp Phe Lys Asn Cys Leu
225                 230                 235                 240

Ile Asn Ser Ser Asp Ile Ile Gln Ile Ser Asn Glu Ile Leu Leu Ile
                245                 250                 255

Gly Ile Ser His Asp Thr Asp Val Leu Gly Ile Glu Ser Leu Ala Arg
            260                 265                 270

Asn Leu Leu Ser Asp His Thr Asn Pro Ile Lys Gln Ile Ile Ala Ile
    275                 280                 285

Asn Ile His Lys Phe Gly Ala Lys Thr Asn Leu Asn Lys Leu Ile Ala
        290                 295                 300

Met Val Asp Val Asp Lys Phe Ile Ile Ala Arg Lys Val Leu Gln Ala
305                 310                 315                 320

Thr Glu Ile Phe Glu Leu Thr Ala Thr Ala Gln Arg Asp Val Asp Gly
                325                 330                 335

Leu Ala Gln Ile Lys Phe Lys Pro Leu Lys Phe Asn Phe Gly Glu Ile
            340                 345                 350

Ile Glu Ala Ile Ile Asp Lys Gln Pro Arg Phe Val Ile Ile Gly Gly
        355                 360                 365

Gly Asp Glu Val Ala Glu Arg Lys Glu Leu Leu Asp Cys Gly Met Gly
```

```
            370                 375                 380
Val Leu Asn Leu Ser Pro Gly Glu Ile Val Val Phe Asp Arg Asn His
385                 390                 395                 400

Tyr Thr Asn Asn Leu Leu Asn Glu Leu Gly Leu Ile Ile His Lys Ile
                405                 410                 415

Pro Ala Ser Glu Leu Ser Arg Gly Pro Ser Gly Pro Leu Glu Met Val
                420                 425                 430

Cys Ser Leu Trp Arg Glu
            435

<210> SEQ ID NO 17
<211> LENGTH: 409
<212> TYPE: PRT
<213> ORGANISM: Mycoplasma mobile

<400> SEQUENCE: 17

Met Lys Asp Thr Lys Asp Ile Ile Asn Val Phe Ser Glu Ile Gly Glu
1               5                   10                  15

Leu Lys Lys Val Leu Ile His Thr Pro Gly Asn Glu Leu Lys Tyr Val
                20                  25                  30

Ser Pro Tyr Arg Leu Asp Glu Leu Leu Phe Ser Asn Val Leu Glu Trp
            35                  40                  45

Arg Glu Ala Lys Lys Glu His Asn Glu Phe Ile Gln Lys Leu Lys Ser
        50                  55                  60

Glu Gly Val Glu Pro Val Leu Thr Asp Leu Val Ala Glu Ser Phe
65                  70                  75                  80

Glu Glu Ser Ser Ile Lys Val Lys Asn Asp Phe Ile Arg Gln Tyr Leu
                85                  90                  95

Asp Glu Ala Thr Pro Ile Leu Asp Gly Leu Thr Lys Gln Lys Leu Leu
            100                 105                 110

Pro Phe Phe Leu Asp Ile Lys His Ser Thr Arg Lys Thr Ile Glu Leu
        115                 120                 125

Met Met Ser Gly Ile Thr Gln Lys Asp Ile Ser Ile Ser His Ile Glu
130                 135                 140

Arg Glu Leu Ile Ile Asp Pro Met Pro Asn Leu Tyr Phe Ser Arg Asp
145                 150                 155                 160

Asn Phe Ile Ser Ile Gly Asn Ser Val Ile Ile Ser Asn Met Lys Tyr
                165                 170                 175

Lys Thr Arg Lys Arg Glu Thr Ile Phe Thr Asp Phe Ile Phe Lys Asn
            180                 185                 190

His Pro Leu Tyr Lys Lys Val Asn Met Ala Phe Glu Arg Lys Asp Leu
        195                 200                 205

Asn Asn Gln Ile Ser Ile Ile Glu Gly Gly Asp Val Leu Val Tyr Ser
    210                 215                 220

Lys Glu Ile Leu Ile Ile Gly Ile Ser Glu Arg Thr Thr Met Ser Ala
225                 230                 235                 240

Ile Leu Glu Leu Ala Glu Asn Phe Lys Lys Thr Lys Arg Ser Phe Lys
                245                 250                 255

Lys Ile Tyr Gly Val Glu Val Pro Lys Met Lys Asn Leu Met His Leu
            260                 265                 270

Asp Thr Trp Leu Thr Met Ile Asp Tyr Asp Lys Phe Ile Tyr Ser Pro
        275                 280                 285

Asn Val Leu Thr Asp Leu Lys Phe Trp Glu Ile Asn Leu Asp Tyr Glu
    290                 295                 300
```

```
Lys Ile Ser Ser Lys Glu Leu His Ala Ser Leu Ser Glu Phe Leu Lys
305                 310                 315                 320

Leu Ile Ile Gly Lys Asp Pro Ile Leu Ile Pro Ile Gly Gly Lys Gly
                325                 330                 335

Ala Ser Gln Ile Thr Ile Asp Ile Glu Thr Asn Phe Val Ala Ala Asn
            340                 345                 350

Tyr Leu Val Ile Arg Pro Gly Val Val Ile Gly Tyr Ser Arg Asn Tyr
        355                 360                 365

Glu Thr Gln Lys Ala Leu Glu Gly His Gly Val Lys Val Ile Ala Phe
    370                 375                 380

Glu Gly Asn Gln Leu Ser Leu Gly Met Gly Ser Ser Arg Cys Met Ser
385                 390                 395                 400

Met Pro Leu Ile Arg Ser Asn Leu Lys
                405

<210> SEQ ID NO 18
<211> LENGTH: 411
<212> TYPE: PRT
<213> ORGANISM: Streptococcus pyogenes

<400> SEQUENCE: 18

Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
            20                  25                  30

Pro Asp Tyr Leu Glu Arg Leu Leu Phe Asp Asp Ile Pro Phe Leu Glu
        35                  40                  45

Asp Ala Gln Lys Glu His Asp Ala Phe Ala Gln Ala Leu Arg Asp Glu
    50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95

Asn Ile Arg Gly Arg Ala Thr Lys Lys Ala Ile Arg Glu Leu Leu Met
            100                 105                 110

Ala Ile Glu Asp Asn Gln Glu Leu Ile Glu Lys Thr Met Ala Gly Val
        115                 120                 125

Gln Lys Ser Glu Leu Pro Glu Ile Pro Ala Ser Glu Lys Gly Leu Thr
    130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270
```

-continued

```
Phe Met His Leu Asp Thr Val Phe Thr Met Val Asp Tyr Asp Lys Phe
            275                 280                 285

Thr Ile His Pro Glu Ile Glu Gly Asp Leu Arg Val Tyr Ser Val Thr
290                 295                 300

Tyr Asp Asn Glu Glu Leu His Ile Val Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
                340                 345                 350

Gly Ser Asn Thr Leu Thr Ile Ala Pro Gly Val Val Val Tyr Asn
                355                 360                 365

Arg Asn Thr Ile Thr Asn Ala Ile Leu Glu Ser Lys Gly Leu Lys Leu
370                 375                 380

Ile Lys Ile His Gly Ser Glu Leu Val Arg Gly Arg Gly Pro Arg
385                 390                 395                 400

Cys Met Ser Met Pro Phe Glu Arg Glu Asp Ile
                405                 410
```

<210> SEQ ID NO 19
<211> LENGTH: 408
<212> TYPE: PRT
<213> ORGANISM: Enterococcus faecalis

<400> SEQUENCE: 19

```
Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
                20                  25                  30

Tyr Leu Glu Arg Leu Leu Phe Asp Asp Ile Pro Phe Leu Glu Lys Ala
            35                  40                  45

Gln Ala Glu His Asp Ala Phe Ala Glu Leu Leu Arg Ser Lys Asp Ile
        50                  55                  60

Glu Val Val Tyr Leu Glu Asp Leu Ala Ala Glu Ala Leu Ile Asn Glu
65                  70                  75                  80

Glu Val Arg Arg Gln Phe Ile Asp Gln Phe Leu Glu Glu Ala Asn Ile
                85                  90                  95

Arg Ser Glu Ser Ala Lys Glu Lys Val Arg Glu Leu Met Leu Glu Ile
            100                 105                 110

Asp Asp Asn Glu Glu Leu Ile Gln Lys Ala Ile Ala Gly Ile Gln Lys
        115                 120                 125

Gln Glu Leu Pro Lys Tyr Glu Gln Glu Phe Leu Thr Asp Met Val Glu
    130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Gln Tyr Ile Phe
            180                 185                 190

Asp Tyr His Pro Arg Phe Ala Gly Lys Glu Val Pro Arg Val Tyr Asp
        195                 200                 205

Arg Ser Glu Ser Thr Arg Ile Glu Gly Gly Asp Glu Leu Ile Leu Ser
    210                 215                 220

Lys Glu Val Val Ala Ile Gly Ile Ser Gln Arg Thr Asp Ala Ala Ser
```

```
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
        275                 280                 285

Glu Ile Glu Gly Gly Leu Val Val Tyr Ser Ile Thr Glu Lys Ala Asp
    290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Ala Arg Glu Gln Trp Asn Asp Gly Ser Asn
            340                 345                 350

Thr Leu Ala Ile Ala Pro Gly Glu Val Val Val Tyr Asp Arg Asn Thr
        355                 360                 365

Ile Thr Asn Lys Ala Leu Glu Glu Ala Gly Val Lys Leu Asn Tyr Ile
    370                 375                 380

Pro Gly Ser Glu Leu Val Arg Gly Arg Gly Gly Pro Arg Cys Met Ser
385                 390                 395                 400

Met Pro Leu Tyr Arg Glu Asp Leu
                405

<210> SEQ ID NO 20
<211> LENGTH: 403
<212> TYPE: PRT
<213> ORGANISM: Mycoplasma capricolum

<400> SEQUENCE: 20

Met Glu Lys Lys Ile Asn Val Phe Ser Glu Ile Gly Thr Leu Lys Thr
1               5                   10                  15

Val Leu Val His Arg Pro Gly Asp Glu Ile Glu Asn Leu Thr Pro Glu
            20                  25                  30

Leu Leu Glu Arg Leu Leu Phe Asp Asp Val Pro Phe Lys Asp Val Ala
        35                  40                  45

Val Lys Glu His Asp Ala Phe Thr Lys Ile Met Arg Asp Asn Gly Val
    50                  55                  60

Glu Val Leu Tyr Ile Glu Lys Leu Ala Ala Glu Thr Leu Asp Gln His
65                  70                  75                  80

Pro Asp Leu Arg Glu Lys Phe Ile Asp Gln Phe Ile Ser Glu Ala Asn
                85                  90                  95

Ile Glu Asp Lys Tyr Lys Glu Lys Tyr Arg Asp Phe Ile Ser Ser Leu
            100                 105                 110

Asp Asn Tyr Arg Met Ile Lys Lys Met Ile Ala Gly Thr Lys Lys Leu
        115                 120                 125

Glu Leu Gly Ile Asp Glu Gly Tyr Lys Ala Tyr Pro Phe Ile Ala Asp
    130                 135                 140

Pro Leu Pro Asn Val Leu Phe Gln Arg Asp Pro Phe Ser Ser Val Gly
145                 150                 155                 160

Phe Gly Ile Thr Met Asn Arg Met Trp Ser Val Thr Arg Asn Arg Glu
                165                 170                 175

Thr Ile Phe Pro Asp Leu Val Phe Lys His His Asn Arg Phe Ala Asn
            180                 185                 190
```

```
Gln Val Pro Tyr Tyr Tyr Glu Arg Asp Trp Lys Glu Thr Ile Glu
            195                 200                 205

Gly Gly Asp Ile Leu Val Leu Asn Lys Glu Thr Leu Ile Ile Gly Val
210                 215                 220

Thr Gln Arg Thr Thr Leu Lys Ala Ile Glu Lys Phe Ser Glu Arg Leu
225                 230                 235                 240

Phe Asn Asp Pro Glu Ser Ser Tyr Ser Lys Val Ile Ala Leu Asp Leu
                245                 250                 255

Pro Lys Ser Arg Ala Phe Met His Leu Asp Thr Val Phe Thr Asn Ile
            260                 265                 270

Asp Tyr Asp Lys Phe Ile Ala His Pro Leu Ile Phe Asp Cys Ile Asp
        275                 280                 285

Glu Phe Lys Ile Tyr Glu Val Ser Lys Gln Gly Thr Lys Glu Val Lys
    290                 295                 300

Lys Thr Leu Ile Glu Leu Leu Ser Asp Ala Ala Gly Arg Glu Val Gln
305                 310                 315                 320

Ile Ile Arg Cys Gly Gly Asn Asp Val Val Gly Ala Ser Arg Glu Gln
                325                 330                 335

Trp Asn Asp Gly Thr Asn Val Val Ala Leu Arg Pro Gly Lys Val Ile
            340                 345                 350

Ala Tyr Glu Arg Asn Trp Ile Thr Ile Asp Leu Leu Arg Lys Ala Gly
        355                 360                 365

Val Glu Val Leu Thr Ile Ala Ser Ser Glu Leu Ser Arg Gly Arg Gly
    370                 375                 380

Gly Pro Arg Cys Met Thr Met Pro Leu Trp Arg Glu Asp Leu Gln Glu
385                 390                 395                 400

Ile Lys Arg

<210> SEQ ID NO 21
<211> LENGTH: 410
<212> TYPE: PRT
<213> ORGANISM: Halothermothrix orenii

<400> SEQUENCE: 21

Met Phe Lys Lys Ser Pro Leu Asn Val Thr Ser Glu Ile Gly Lys Leu
1               5                   10                  15

Lys Lys Val Leu Leu His Arg Pro Gly His Glu Ile Glu Asn Leu Thr
            20                  25                  30

Pro Asp Leu Leu Glu Arg Leu Leu Phe Asp Asp Ile Pro Tyr Leu Lys
        35                  40                  45

Val Ala Gln Glu Glu His Asp Ala Phe Ala Gln Thr Leu Arg Asp Asn
    50                  55                  60

Gly Val Glu Val Leu Tyr Leu His Glu Leu Ala Ala Glu Ala Ile Gln
65                  70                  75                  80

Glu Asp Glu Ile Arg Lys Lys Phe Ile Glu Gln Phe Leu Asp Glu Ala
                85                  90                  95

Gly Val Ile Gly Lys Gly Ala Arg Gln Val Leu Lys Glu Tyr Phe Ala
            100                 105                 110

Asp Met Asp Asn Glu Thr Leu Ile Arg Lys Met Met Ala Gly Val Arg
        115                 120                 125

Lys Lys Glu Ile Pro Ala Ile Glu Lys Val Ala Ser Leu Asn Asp Met
    130                 135                 140

Val Glu Glu Asp Tyr Pro Phe Val Leu Asp Pro Met Pro Asn Leu Tyr
145                 150                 155                 160
```

```
Phe Thr Arg Asp Pro Phe Ala Thr Ile Gly Thr Gly Ile Thr Leu Asn
                165                 170                 175

His Met Arg Thr Glu Thr Arg Asn Arg Glu Val Ile Phe Ala Glu Tyr
            180                 185                 190

Ile Phe Ser Tyr His Pro Asp Phe Lys Asp Thr Glu Ile Pro Phe Trp
        195                 200                 205

Phe Asp Arg Asn Glu Thr Thr Ser Ile Glu Gly Gly Asp Glu Leu Ile
    210                 215                 220

Leu Ser Asp Lys Val Leu Ala Met Gly Ile Ser Glu Arg Thr Asp Ala
225                 230                 235                 240

Ala Ser Ile Glu Lys Val Ala Arg Asn Ile Phe Thr Asp Gly Gln Pro
                245                 250                 255

Phe Glu Thr Ile Leu Ala Phe Lys Ile Pro Glu Lys Arg Ala Phe Met
            260                 265                 270

His Leu Asp Thr Val Phe Thr Met Val Asp Tyr Asp Lys Phe Thr Ile
        275                 280                 285

His Ala Glu Ile Glu Gly Pro Leu Lys Val Tyr Ser Ile Thr Lys Gly
    290                 295                 300

Asp Asn Asp Glu Leu Lys Ile Asp Glu Glu Lys Ala Thr Leu Glu Asp
305                 310                 315                 320

Thr Leu Lys Lys Tyr Leu Gly Leu Asp Glu Val Thr Leu Ile Arg Cys
                325                 330                 335

Ala Gly Gly Asp Tyr Ile Asp Ala Gly Arg Glu Gln Trp Asn Asp Gly
            340                 345                 350

Ser Asn Thr Leu Ala Ile Ala Pro Gly Glu Val Val Tyr Asn Arg
        355                 360                 365

Asn His Thr Thr Asn Arg Leu Leu Glu Glu His Gly Ile Lys Leu His
    370                 375                 380

Val Ile Pro Ser Ser Glu Leu Ser Arg Gly Arg Gly Pro Arg Cys
385                 390                 395                 400

Met Ser Met Pro Leu Val Arg Glu Asp Ile
                405                 410

<210> SEQ ID NO 22
<211> LENGTH: 411
<212> TYPE: PRT
<213> ORGANISM: Staphylococcus aureus

<400> SEQUENCE: 22

Met Thr Asp Gly Pro Ile Lys Val Asn Ser Glu Ile Gly Ala Leu Lys
1               5                   10                  15

Thr Val Leu Leu Lys Arg Pro Gly Lys Glu Leu Glu Asn Leu Val Pro
            20                  25                  30

Asp Tyr Leu Asp Gly Leu Leu Phe Asp Ile Pro Tyr Leu Glu Val
        35                  40                  45

Ala Gln Lys Glu His Asp His Phe Ala Gln Val Leu Arg Glu Glu Gly
    50                  55                  60

Val Glu Val Leu Tyr Leu Glu Lys Leu Ala Ala Glu Ser Ile Glu Asn
65                  70                  75                  80

Pro Gln Val Arg Ser Glu Phe Ile Asp Asp Val Leu Ala Glu Ser Lys
                85                  90                  95

Lys Thr Ile Leu Gly His Glu Glu Ile Lys Ala Leu Phe Ala Thr
            100                 105                 110

Leu Ser Asn Gln Glu Leu Val Asp Lys Ile Met Ser Gly Val Arg Lys
        115                 120                 125
```

-continued

Glu Glu Ile Asn Pro Lys Cys Thr His Leu Val Glu Tyr Met Asp Asp
        130                 135                 140

Lys Tyr Pro Phe Tyr Leu Asp Pro Met Pro Asn Leu Tyr Phe Thr Arg
145                 150                 155                 160

Asp Pro Gln Ala Ser Ile Gly His Gly Ile Thr Ile Asn Arg Met Phe
                165                 170                 175

Trp Arg Ala Arg Arg Glu Ser Ile Phe Ile Gln Tyr Ile Val Lys
            180                 185                 190

His His Pro Arg Phe Lys Asp Ala Asn Ile Pro Ile Trp Leu Asp Arg
            195                 200                 205

Asp Cys Pro Phe Asn Ile Glu Gly Gly Asp Glu Leu Val Leu Ser Lys
        210                 215                 220

Asp Val Leu Ala Ile Gly Val Ser Glu Arg Thr Ser Ala Gln Ala Ile
225                 230                 235                 240

Glu Lys Leu Ala Arg Arg Ile Phe Glu Asn Pro Gln Ala Thr Phe Lys
                245                 250                 255

Lys Val Val Ala Ile Glu Ile Pro Thr Ser Arg Thr Phe Met His Leu
            260                 265                 270

Asp Thr Val Phe Thr Met Ile Asp Tyr Asp Lys Phe Thr Met His Ser
        275                 280                 285

Ala Ile Leu Lys Ala Glu Gly Asn Met Asn Ile Phe Ile Ile Glu Tyr
290                 295                 300

Asp Asp Val Asn Lys Asp Ile Ala Ile Lys Gln Ser Ser His Leu Lys
305                 310                 315                 320

Asp Thr Leu Glu Asp Val Leu Gly Ile Asp Ile Gln Phe Ile Pro
                325                 330                 335

Thr Gly Asn Gly Asp Val Ile Asp Gly Ala Arg Glu Gln Trp Asn Asp
            340                 345                 350

Gly Ser Asn Thr Leu Cys Ile Arg Pro Gly Val Val Thr Tyr Asp
        355                 360                 365

Arg Asn Tyr Val Ser Asn Asp Leu Leu Arg Gln Lys Gly Ile Lys Val
        370                 375                 380

Ile Glu Ile Ser Gly Ser Glu Leu Val Arg Gly Arg Gly Pro Arg
385                 390                 395                 400

Cys Met Ser Gln Pro Leu Phe Arg Glu Asp Ile
                405                 410

<210> SEQ ID NO 23
<211> LENGTH: 417
<212> TYPE: PRT
<213> ORGANISM: Pseudomonas plecoglossicida

<400> SEQUENCE: 23

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
            20                  25                  30

Thr Pro Ser Asn Cys Asp Glu Leu Leu Phe Asp Asp Val Ile Trp Val
        35                  40                  45

Asp Gln Ala Lys Arg Asp His Phe Asp Phe Val Thr Lys Met Arg Glu
    50                  55                  60

Arg Gly Val Asp Val Leu Glu Met His Asn Leu Leu Thr Asp Ile Val
65                  70                  75                  80

Gln Asn Pro Glu Ala Leu Lys Trp Ile Leu Asp Arg Lys Ile Thr Pro

```
            85                  90                  95
Asp Thr Val Gly Val Gly Leu Thr Asn Glu Val Arg Ser Trp Leu Glu
            100                 105                 110
Gly Gln Glu Pro Arg His Leu Ala Glu Phe Leu Ile Gly Gly Val Ala
            115                 120                 125
Gly Gln Asp Leu Pro Glu Ser Glu Gly Ala Ser Val Val Lys Met Tyr
            130                 135                 140
Asn Asp Tyr Leu Gly His Ser Ser Phe Ile Leu Pro Leu Pro Asn
145                 150                 155                 160
Thr Gln Phe Thr Arg Asp Thr Thr Cys Trp Ile Tyr Gly Gly Val Thr
            165                 170                 175
Leu Asn Pro Met Tyr Trp Pro Ala Arg Arg Gln Glu Thr Leu Leu Thr
            180                 185                 190
Thr Ala Ile Tyr Lys Phe His Pro Glu Phe Thr Lys Ala Asp Phe Gln
            195                 200                 205
Val Trp Tyr Gly Asp Pro Asp Gln Glu His Gly Gln Ala Thr Leu Glu
            210                 215                 220
Gly Gly Asp Val Met Pro Ile Gly Lys Gly Ile Val Leu Ile Gly Met
225                 230                 235                 240
Gly Glu Arg Thr Ser Arg Gln Ala Ile Gly Gln Leu Ala Gln Asn Leu
            245                 250                 255
Phe Ala Lys Gly Ala Val Glu Gln Val Ile Val Ala Gly Leu Pro Lys
            260                 265                 270
Ser Arg Ala Ala Met His Leu Asp Thr Val Phe Ser Phe Cys Asp Arg
            275                 280                 285
Asp Leu Val Thr Val Phe Pro Glu Val Val Arg Glu Ile Val Pro Phe
            290                 295                 300
Ile Ile Arg Pro Asp Glu Ser Lys Pro Tyr Gly Met Asp Val Arg Arg
305                 310                 315                 320
Glu Asn Lys Ser Phe Ile Glu Val Val Gly Glu Gln Leu Gly Val Lys
            325                 330                 335
Leu Arg Val Val Glu Thr Gly Gly Asn Ser Phe Ala Ala Glu Arg Glu
            340                 345                 350
Gln Trp Asp Asp Gly Asn Asn Val Val Ala Leu Glu Pro Gly Val Val
            355                 360                 365
Ile Gly Tyr Asp Arg Asn Thr Tyr Thr Asn Thr Leu Leu Arg Lys Ala
            370                 375                 380
Gly Ile Glu Val Ile Thr Ile Ser Ala Gly Glu Leu Gly Arg Gly Arg
385                 390                 395                 400
Gly Gly Gly His Cys Met Thr Cys Pro Ile Val Arg Asp Pro Ile Asn
            405                 410                 415
Tyr
```

<210> SEQ ID NO 24
<211> LENGTH: 417
<212> TYPE: PRT
<213> ORGANISM: Pseudomonas putida

<400> SEQUENCE: 24

```
Met Ser Ala Glu Lys Gln Lys Tyr Gly Val His Ser Glu Ala Gly Lys
1               5                   10                  15
Leu Arg Lys Val Met Val Cys Ala Pro Gly Leu Ala His Lys Arg Leu
            20                  25                  30
Thr Pro Ser Asn Cys Asp Glu Leu Leu Phe Asp Asp Val Ile Trp Val
```

```
            35                  40                  45
Asp Gln Ala Lys Arg Asp His Phe Asp Phe Val Thr Lys Met Arg Glu
 50                  55                  60

Arg Gly Val Asp Val Leu Glu Met His Asn Leu Leu Thr Asp Ile Val
 65                  70                  75                  80

Gln Asn Lys Asp Ala Leu Lys Trp Ile Leu Asp Arg Lys Ile Thr Pro
                 85                  90                  95

Asp Thr Val Gly Val Gly Leu Thr Asn Glu Val Arg Ser Trp Leu Glu
                100                 105                 110

Gly Leu Glu Pro Arg His Leu Ala Glu Phe Leu Ile Gly Gly Val Ala
            115                 120                 125

Gly Gln Asp Leu Pro Gln Ser Glu Gly Ala Asp Val Val Lys Met Tyr
        130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Gln Phe Thr Gly Ala Asp Phe Gln
        195                 200                 205

Val Trp Tyr Gly Asp Pro Asp Lys Asp His Gly Asn Ala Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Lys Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Ile Phe Pro Glu Val Val Lys Glu Ile Val Pro Phe
    290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Glu Gln Leu Gly Val Lys
                325                 330                 335

Leu Arg Val Val Glu Thr Gly Gly Asn Ser Phe Ala Ala Glu Arg Glu
            340                 345                 350

Gln Trp Asp Asp Gly Asn Asn Val Val Ala Val Glu Pro Gly Val Val
        355                 360                 365

Ile Gly Tyr Asp Arg Asn Thr Tyr Thr Asn Thr Leu Leu Arg Lys Ala
    370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asp
                405                 410                 415

Tyr

<210> SEQ ID NO 25
<211> LENGTH: 418
<212> TYPE: PRT
<213> ORGANISM: Pseudomonas aeruginosa
```

<400> SEQUENCE: 25

```
Met Ser Thr Glu Lys Thr Lys Leu Gly Val His Ser Glu Ala Gly Lys
1               5                   10                  15

Leu Arg Lys Val Met Val Cys Ser Pro Gly Leu Ala His Gln Arg Leu
            20                  25                  30

Thr Pro Ser Asn Cys Asp Glu Leu Phe Asp Asp Val Ile Trp Val
        35                  40                  45

Asn Gln Ala Lys Arg Asp His Phe Asp Phe Val Thr Lys Met Arg Glu
    50                  55                  60

Arg Gly Ile Asp Val Leu Glu Met His Asn Leu Leu Thr Glu Thr Ile
65                  70                  75                  80

Gln Asn Pro Glu Ala Leu Lys Trp Ile Leu Asp Arg Lys Ile Thr Ala
                85                  90                  95

Asp Ser Val Gly Leu Gly Leu Thr Ser Glu Leu Arg Ser Trp Leu Glu
            100                 105                 110

Ser Leu Glu Pro Arg Lys Leu Ala Glu Tyr Leu Ile Gly Gly Val Ala
        115                 120                 125

Ala Asp Asp Leu Pro Ala Ser Glu Gly Ala Asn Ile Leu Lys Met Tyr
    130                 135                 140

Arg Glu Tyr Leu Gly His Ser Ser Phe Leu Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Ala Asn Ala Glu Phe Glu
        195                 200                 205

Ile Trp Tyr Gly Asp Pro Asp Lys Asp His Gly Ser Ser Thr Leu Glu
    210                 215                 220

Gly Gly Asp Val Met Pro Ile Gly Asn Gly Val Val Leu Ile Gly Met
225                 230                 235                 240

Gly Glu Arg Ser Ser Arg Gln Ala Ile Gly Gln Val Ala Gln Ser Leu
                245                 250                 255

Phe Ala Lys Gly Ala Ala Glu Arg Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Lys Glu Ile Val Pro Phe
    290                 295                 300

Ser Leu Arg Pro Asp Ala Ser Ser Pro Tyr Gly Met Ser Ile Arg Arg
305                 310                 315                 320

Glu Glu Lys Thr Phe Leu Glu Val Val Ala Gly Ser Leu Gly Leu Lys
                325                 330                 335

Lys Leu Arg Val Val Glu Thr Gly Gly Asn Ser Phe Ala Ala Glu Arg
            340                 345                 350

Glu Gln Trp Asp Asp Gly Asn Asn Val Val Cys Leu Glu Pro Gly Val
        355                 360                 365

Val Val Gly Tyr Asp Arg Asn Thr Tyr Thr Asn Thr Leu Leu Arg Lys
    370                 375                 380

Ala Gly Val Glu Val Ile Thr Ile Ser Ala Ser Glu Leu Gly Arg Gly
385                 390                 395                 400

Arg Gly Gly Gly His Cys Met Thr Cys Pro Ile Ile Arg Asp Pro Ile
                405                 410                 415
```

Asp Tyr

<210> SEQ ID NO 26
<211> LENGTH: 402
<212> TYPE: PRT
<213> ORGANISM: Mycobacterium tuberculosis complex

<400> SEQUENCE: 26

Met Gly Val Glu Leu Gly Ser Asn Ser Glu Val Gly Ala Leu Arg Val
1               5                   10                  15

Val Ile Leu His Arg Pro Gly Ala Glu Leu Arg Arg Leu Thr Pro Arg
            20                  25                  30

Asn Thr Asp Gln Leu Leu Phe Asp Gly Leu Pro Trp Val Ser Arg Ala
        35                  40                  45

Gln Asp Glu His Asp Glu Phe Ala Glu Leu Leu Ala Ser Arg Gly Ala
    50                  55                  60

Glu Val Leu Leu Leu Ser Asp Leu Leu Thr Glu Ala Leu His His Ser
65                  70                  75                  80

Gly Ala Ala Arg Met Gln Gly Ile Ala Ala Val Asp Ala Pro Arg
                85                  90                  95

Leu Gly Leu Pro Leu Ala Gln Glu Leu Ser Ala Tyr Leu Arg Ser Leu
            100                 105                 110

Asp Pro Gly Arg Leu Ala His Val Leu Thr Ala Gly Met Thr Phe Asn
        115                 120                 125

Glu Leu Pro Ser Asp Thr Arg Thr Asp Val Ser Leu Val Leu Arg Met
    130                 135                 140

His His Gly Gly Asp Phe Val Ile Glu Pro Leu Pro Asn Leu Val Phe
145                 150                 155                 160

Thr Arg Asp Ser Ser Ile Trp Ile Gly Pro Arg Val Val Ile Pro Ser
                165                 170                 175

Leu Ala Leu Arg Ala Arg Val Arg Glu Ala Ser Leu Thr Asp Leu Ile
            180                 185                 190

Tyr Ala His His Pro Arg Phe Thr Gly Val Arg Arg Ala Tyr Glu Ser
        195                 200                 205

Arg Thr Ala Pro Val Glu Gly Gly Asp Val Leu Leu Leu Ala Pro Gly
    210                 215                 220

Val Val Ala Val Gly Val Gly Glu Arg Thr Thr Pro Ala Gly Ala Glu
225                 230                 235                 240

Ala Leu Ala Arg Ser Leu Phe Asp Asp Asp Leu Ala His Thr Val Leu
                245                 250                 255

Ala Val Pro Ile Ala Gln Gln Arg Ala Gln Met His Leu Asp Thr Val
            260                 265                 270

Cys Thr Met Val Asp Thr Asp Thr Met Val Met Tyr Ala Asn Val Val
        275                 280                 285

Asp Thr Leu Glu Ala Phe Thr Ile Gln Arg Thr Pro Asp Gly Val Thr
    290                 295                 300

Ile Gly Asp Ala Ala Pro Phe Ala Glu Ala Ala Lys Ala Met Gly
305                 310                 315                 320

Ile Asp Lys Leu Arg Val Ile His Thr Gly Met Asp Pro Val Val Ala
                325                 330                 335

Glu Arg Glu Gln Trp Asp Asp Gly Asn Asn Thr Leu Ala Leu Ala Pro
            340                 345                 350

Gly Val Val Val Ala Tyr Glu Arg Asn Val Gln Thr Asn Ala Arg Leu
        355                 360                 365

Gln Asp Ala Gly Ile Glu Val Leu Thr Ile Ala Gly Ser Glu Leu Gly
       370                         375                      380

Thr Gly Arg Gly Gly Pro Arg Cys Met Ser Cys Pro Ala Ala Arg Asp
385                         390                        395                  400

Pro Leu

<210> SEQ ID NO 27
<211> LENGTH: 409
<212> TYPE: PRT
<213> ORGANISM: Mycoplasma arthritidis

<400> SEQUENCE: 27

Met Ser Val Phe Asp Ser Lys Phe Lys Gly Ile His Val Tyr Ser Glu
1                 5                    10                15

Ile Gly Glu Leu Glu Thr Val Leu Val His Pro Gly Lys Glu Ile
          20                 25                30

Asp Tyr Ile Thr Pro Ala Arg Leu Asp Glu Leu Leu Phe Ser Ala Ile
                35                    40                45

Leu Glu Ser His Asp Ala Arg Lys Glu His Lys Glu Phe Val Ala Glu
 50                      55                    60

Leu Lys Lys Arg Gly Ile Asn Val Val Glu Leu Val Asp Leu Ile Val
65                     70                    75                80

Glu Thr Tyr Asp Leu Ala Ser Lys Glu Ala Lys Glu Lys Leu Leu Glu
                85                    90                95

Glu Phe Leu Asp Asp Ser Val Pro Val Leu Ser Asp Glu His Arg Ala
            100                  105              110

Ala Val Lys Lys Phe Leu Gln Ser Gln Lys Ser Thr Arg Ser Leu Val
      115                  120                125

Glu Tyr Met Ile Ala Gly Ile Thr Lys His Asp Leu Lys Ile Glu Ser
   130                  135                140

Asp Leu Glu Leu Ile Val Asp Pro Met Pro Asn Leu Tyr Phe Thr Arg
145                     150                  155              160

Asp Pro Phe Ala Ser Val Gly Asn Gly Val Thr Ile His Tyr Met Arg
                165                   170              175

Tyr Lys Val Arg Gln Arg Glu Thr Leu Phe Ser Arg Phe Val Phe Ser
            180                  185              190

Asn His Pro Lys Leu Val Asn Thr Pro Trp Tyr Tyr Asp Pro Ala Glu
      195                  200                205

Gly Leu Ser Ile Glu Gly Gly Asp Val Phe Ile Tyr Asn Asn Asp Thr
   210                  215                220

Leu Val Val Gly Val Ser Glu Arg Thr Asp Leu Gln Thr Ile Thr Leu
225                     230                  235              240

Leu Ala Lys Asn Ile Lys Ala Asn Lys Glu Cys Glu Phe Lys Arg Ile
                245                   250              255

Val Ala Ile Asn Val Pro Lys Trp Thr Asn Leu Met His Leu Asp Thr
            260                  265              270

Trp Leu Thr Met Leu Asp Lys Asp Lys Phe Leu Tyr Ser Pro Ile Ala
      275                  280                285

Asn Asp Val Phe Lys Phe Trp Asp Tyr Asp Leu Val Asn Gly Gly Asp
   290                  295                300

Ala Pro Gln Pro Val Asp Asn Gly Leu Pro Leu Glu Asp Leu Leu Lys
305                     310                  315              320

Ser Ile Ile Gly Lys Lys Pro Thr Leu Ile Pro Ile Ala Gly Ala Gly
                325                   330              335

```
Ala Ser Gln Ile Asp Ile Glu Arg Glu Thr His Phe Asp Gly Thr Asn
            340                 345                 350

Tyr Leu Ala Val Ala Pro Gly Ile Val Gly Tyr Ala Arg Asn Glu
            355                 360                 365

Lys Thr Asn Ala Ala Leu Glu Ala Ala Gly Ile Thr Val Leu Pro Phe
370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
            405

<210> SEQ ID NO 28
<211> LENGTH: 410
<212> TYPE: PRT
<213> ORGANISM: Artificial Sequence
<220> FEATURE:
<223> OTHER INFORMATION: Artificial full length of Mycoplasma
      phocicerebrale

<400> SEQUENCE: 28

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala

```
            275                 280                 285
Asn Asp Val Phe Lys Phe Trp Asp Tyr Asp Leu Val Asn Gly Gly Ala
    290                 295                 300
Glu Pro Gln Pro Lys Glu Asn Gly Leu Pro Leu Glu Gly Leu Leu Gln
305                 310                 315                 320
Ser Ile Ile Asn Lys Lys Pro Val Leu Ile Pro Ile Ala Gly Asn Asn
                325                 330                 335
Ala Ser His Ile Asp Ile Glu Arg Glu Thr His Phe Asp Gly Thr Asn
                340                 345                 350
Tyr Leu Ala Ile Lys Pro Gly Val Val Ile Gly Tyr Ala Arg Asn Glu
                355                 360                 365
Lys Thr Asn Ala Ala Leu Ala Ala Ala Gly Ile Lys Val Leu Pro Phe
                370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 29
<211> LENGTH: 410
<212> TYPE: PRT
<213> ORGANISM: Artificial Sequence
<220> FEATURE:
<223> OTHER INFORMATION: Artificial full length of Mycoplasma gateae

<400> SEQUENCE: 29

Met Ser Val Phe Asp Ser Lys Phe Asn Gly Ile His Val Tyr Ser Glu
1               5                   10                  15
Ile Gly Glu Leu Glu Ser Val Leu Val His Glu Pro Gly Arg Glu Ile
                20                  25                  30
Asp Tyr Ile Thr Pro Ala Arg Leu Asp Glu Leu Leu Phe Ser Ala Ile
                35                  40                  45
Leu Glu Ser His Asp Ala Arg Lys Glu His Lys Leu Phe Val Ser Glu
            50                  55                  60
Leu Lys Ala Asn Asp Ile Asn Val Val Glu Leu Thr Asp Leu Val Thr
65                  70                  75                  80
Glu Thr Tyr Asp Leu Ala Ser Gln Glu Ala Lys Asp Asn Leu Ile Glu
                85                  90                  95
Glu Phe Leu Glu Asp Ser Glu Pro Val Leu Thr Glu Glu Leu Lys Ser
                100                 105                 110
Val Val Arg Thr Tyr Leu Lys Ser Ile Lys Ser Thr Arg Glu Leu Ile
                115                 120                 125
Gln Met Met Met Ala Gly Ile Thr Lys Tyr Asp Leu Gly Ile Glu Ala
            130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Val Phe Ser
                180                 185                 190
Asn His Pro Lys Leu Val Asn Thr Pro Trp Tyr Tyr Asp Pro Ser Leu
                195                 200                 205
Lys Leu Ser Ile Glu Gly Gly Asp Val Phe Ile Tyr Asn Asn Asn Thr
            210                 215                 220
Leu Val Val Gly Val Ser Glu Arg Thr Asp Leu Glu Thr Val Thr Leu
```

```
225                 230                 235                 240
Leu Ala Lys Asn Ile Val Ala Asn Lys Glu Cys Glu Phe Lys Arg Ile
                245                 250                 255
Val Ala Ile Asn Val Pro Lys Trp Thr Asn Leu Met His Leu Asp Thr
                260                 265                 270
Trp Leu Thr Met Leu Asp Lys Asp Lys Phe Leu Tyr Ser Pro Ile Ala
                275                 280                 285
Asn Asp Val Phe Lys Phe Trp Asp Tyr Asp Leu Val Asn Gly Gly Glu
                290                 295                 300
Glu Pro Gln Pro Val Glu Asn Gly Leu Pro Leu Glu Gly Leu Leu Glu
305                 310                 315                 320
Ser Ile Ile Asn Lys Lys Pro Ile Leu Ile Pro Ile Ala Gly Glu Gly
                325                 330                 335
Ala Ser Gln Ile Asp Ile Glu Arg Glu Thr His Phe Asp Gly Thr Asn
                340                 345                 350
Tyr Leu Ala Ile Arg Pro Gly Val Val Ile Gly Tyr Ser Arg Asn Glu
                355                 360                 365
Lys Thr Asn Ala Ala Leu Glu Ala Ala Gly Ile Lys Val Leu Pro Phe
                370                 375                 380
His Gly Asn Gln Leu Ser Leu Gly Met Gly Asn Ala Arg Cys Met Ser
385                 390                 395                 400
Met Pro Leu Ser Arg Lys Asp Val Lys Trp
                405                 410

<210> SEQ ID NO 30
<211> LENGTH: 410
<212> TYPE: PRT
<213> ORGANISM: Artificial Sequence
<220> FEATURE:
<223> OTHER INFORMATION: Artificial full length of Mycoplasma phocidae

<400> SEQUENCE: 30

Met Ser Val Phe Asp Ser Lys Phe Asn Gly Ile His Val Tyr Ser Glu
1               5                   10                  15
Ile Gly Glu Leu Gln Thr Val Leu Val His Glu Pro Gly Arg Glu Ile
                20                  25                  30
Glu Tyr Ile Thr Pro Ala Arg Leu Asp Glu Leu Leu Phe Ser Ala Ile
                35                  40                  45
Leu Glu Ser His Asp Ala Arg Lys Glu His Gln Glu Phe Val Ala Glu
                50                  55                  60
Leu Lys Lys Asn Asn Ile Asn Val Val Glu Leu Thr Asp Leu Val Ser
65                  70                  75                  80
Glu Thr Tyr Asp Met Val Ser Lys Glu Lys Gln Glu Lys Leu Ile Glu
                85                  90                  95
Glu Phe Leu Glu Asp Ser Glu Pro Val Leu Ser Glu Glu His Lys Gly
                100                 105                 110
Leu Val Arg Lys Phe Leu Lys Ser Leu Lys Ser Ser Lys Glu Leu Ile
                115                 120                 125
Gln Tyr Met Met Ala Gly Ile Thr Lys His Asp Leu Asn Ile Glu Ala
                130                 135                 140
Asp His Glu Leu Ile Val Asp Pro Met Pro Asn Leu Tyr Phe Thr Arg
145                 150                 155                 160
Asp Pro Phe Ala Ser Val Gly Asn Gly Val Thr Ile His Tyr Met Arg
                165                 170                 175
Tyr Lys Val Arg Gln Arg Glu Thr Leu Phe Ser Arg Phe Ile Phe Ala
```

```
                    180                 185                 190
Asn His Pro Lys Leu Met Asn Thr Pro Leu Tyr Tyr Asn Pro Asp Met
        195                 200                 205

Lys Leu Ser Ile Glu Gly Gly Asp Val Phe Val Tyr Asn Asn Glu Thr
    210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
    370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 31
<211> LENGTH: 410
<212> TYPE: PRT
<213> ORGANISM: Mycoplasma salivarium

<400> SEQUENCE: 31

Met Ser Val Phe Ser Ser Lys Phe Asn Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ser Arg Leu Asp Glu Leu Leu Phe Ser Ala Ile
        35                  40                  45

Leu Glu Ser His Asp Ala Arg Lys Glu His Gln Glu Phe Val Ala Thr
    50                  55                  60

Leu Lys Lys Glu Lys Ile Asn Val Val Glu Leu Thr Asp Leu Val Thr
65                  70                  75                  80

Glu Thr Tyr Asp Leu Val Asp Gln Lys Thr Lys Asp Lys Leu Ile Asp
                85                  90                  95

Glu Phe Leu Glu Asp Ser Glu Pro Val Leu Thr Ala Glu Leu Lys Ala
            100                 105                 110

Thr Val Lys Lys Phe Leu Lys Ser Phe Lys Glu Thr Arg Lys Leu Ile
        115                 120                 125

Glu Val Met Met Ala Gly Ile Thr Lys Tyr Asp Leu Gly Ile Lys Ala
    130                 135                 140
```

```
Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Ile Phe Asn
        180                 185                 190

Asn His Pro Lys Leu Val Lys Thr Pro Trp Tyr Tyr Asp Pro Ala Met
    195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Ile Phe Lys Phe Trp Asp Tyr Asp Leu Val Asn Gly Gly Ala
        290                 295                 300

Asn Pro Gln Pro Lys Asp Asn Gly Leu Pro Leu Asp Lys Leu Leu Lys
305                 310                 315                 320

Ser Ile Ile Gly Lys Glu Pro Val Leu Ile Pro Ile Ala Gly His His
                325                 330                 335

Ala Thr Glu Ile Glu Val Ala Arg Glu Thr His Phe Asp Gly Thr Asn
                340                 345                 350

Tyr Leu Ala Ile Arg Pro Gly Val Val Ile Gly Tyr Ala Arg Asn Glu
            355                 360                 365

Lys Thr Asn Glu Ala Leu Lys Asp Ala Gly Ile Thr Val Leu Pro Phe
        370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 32
<211> LENGTH: 411
<212> TYPE: PRT
<213> ORGANISM: Mycoplasma spumans

<400> SEQUENCE: 32

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gly Phe Val Ala Glu
    50                  55                  60

Leu Lys Lys Gln Asn Val Asn Val Ile Glu Leu Thr Asp Leu Val Ala
65                  70                  75                  80

Glu Thr Tyr Glu Leu Ala Ser Lys Glu Ala Gln Ala Lys Leu Ile Glu
                85                  90                  95

Asp Phe Ile Glu Asp Ser Glu Pro Val Leu Asn Ala Glu Glu Ala Gln
            100                 105                 110
```

```
Ala Val Arg Lys Phe Leu Ser Glu Arg Lys Ser Thr Arg Glu Met Val
            115                 120                 125

Glu Tyr Met Met Ser Gly Leu Thr Lys Tyr Glu Leu Gly Leu Glu Ser
            130                 135                 140

Ala Asp Arg Glu Leu Ile Val Asp Pro Met Pro Asn Leu Tyr Phe Thr
145                 150                 155                 160

Arg Asp Pro Phe Ala Ser Val Gly Asn Gly Val Thr Ile His Tyr Met
                165                 170                 175

Lys Tyr Lys Val Arg Gln Arg Glu Thr Leu Phe Ala Lys Phe Val Phe
                180                 185                 190

Ser Asn His Pro Lys Leu Val Asn Thr Pro Arg Tyr Tyr Asp Pro Ser
                195                 200                 205

Met Lys Leu Pro Ile Glu Gly Gly Asp Val Phe Ile Tyr Asn Asn Glu
            210                 215                 220

Thr Leu Val Val Gly Cys Ser Glu Arg Thr Glu Leu Glu Thr Ile Thr
225                 230                 235                 240

Leu Leu Ala Lys Asn Ile Lys Ala Asn Lys Glu Val Glu Phe Lys Arg
                245                 250                 255

Ile Val Ala Ile Asn Val Pro Lys Trp Thr Asn Leu Met His Leu Asp
            260                 265                 270

Thr Trp Leu Thr Met Leu Asp Lys Asp Lys Phe Leu Tyr Ser Pro Ile
        275                 280                 285

Ala Asn Asp Val Phe Lys Phe Trp Asp Tyr Asp Leu Val Asn Gly Gly
            290                 295                 300

Glu Glu Pro Gln Pro Val Glu Asn Gly Leu Pro Leu Glu Glu Leu Leu
305                 310                 315                 320

Ala Ser Ile Ile Asn Lys Lys Pro Thr Leu Ile Pro Ile Ala Gly Glu
                325                 330                 335

Gly Ala Thr His Ile Asp Val Glu Arg Glu Thr His Phe Asp Gly Thr
                340                 345                 350

Asn Tyr Leu Ala Ile Ala Pro Ala Leu Ile Ile Gly Tyr Ser Arg Asn
            355                 360                 365

Glu Lys Thr Asn Ala Ala Leu Glu Lys Ala Gly Ile Thr Val Leu Pro
        370                 375                 380

Phe His Gly Asn Gln Leu Ser Leu Gly Met Gly Asn Ala Arg Cys Met
385                 390                 395                 400

Ser Met Pro Leu Ser Arg Lys Asp Val Lys Trp
                405                 410

<210> SEQ ID NO 33
<211> LENGTH: 410
<212> TYPE: PRT
<213> ORGANISM: Mycoplasma auris

<400> S

```
65                  70                  75                  80

Glu Thr Tyr Asp Leu Val Ser Gln Glu Leu Lys Asp Lys Leu Ile Glu
                85                  90                  95

Glu Phe Leu Asp Asp Ser Tyr Pro Val Leu Thr Glu Glu His Lys Lys
            100                 105                 110

Ala Val Arg Ser Phe Leu Lys Ser Arg Ser Ser Thr Arg Glu Leu Ile
        115                 120                 125

Glu Tyr Met Met Ala Gly Ile Thr Lys Tyr Asp Leu Gly Ile Glu Ala
    130                 135                 140

Glu Gly Asp Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asp
            180                 185                 190

Asn His Pro Lys Leu Val Asn Thr Pro Arg Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Met Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro His Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Tyr Phe Lys Phe Trp Asp Tyr Asp Leu Val Asn Gly Gly Ala
    290                 295                 300

Glu Pro Gln Pro Val Val Asn Glu Leu Pro Leu Asp Lys Leu Leu Glu
305                 310                 315                 320

Ser Ile Ile His Lys Lys Pro Ile Leu Ile Pro Ile Ala Gly Glu Gly
                325                 330                 335

Ala Ser Gln Ile Asp Leu Glu Arg Glu Thr His Phe Asp Gly Thr Asn
            340                 345                 350

Tyr Leu Val Leu Arg Pro Gly Val Val Val Gly Tyr Ala Arg Asn Glu
        355                 360                 365

Lys Thr Asn Ala Ala Leu Glu Ala Val Gly Ile Lys Val Leu Pro Phe
    370                 375                 380

Tyr Gly Asn Gln Leu Ser Leu Gly Met Gly Asn Ser Arg Cys Met Ser
385                 390                 395                 400

Met Pro Leu Ser Arg Lys Asp Val Lys Trp
                405                 410

<210> SEQ ID NO 34
<211> LENGTH: 410
<212> TYPE: PRT
<213> ORGANISM: Mycoplasma hyosynoviae

<400> SEQUENCE: 34

Met Ser Val Phe Asn Ser Lys Phe Lys Gly Ile His Val Tyr Ser Glu
1               5                   10                  15

Ile Gly Asp Leu Glu Ser Val Leu Val His Glu Pro Gly Lys Glu Ile
            20                  25                  30
```

Asp Tyr Ile Thr Pro Ser Arg Leu Asp Glu Leu Leu Phe Ser Ala Ile
             35                  40                  45

Leu Glu Ser Asn Asp Ala Arg Lys Glu His Lys Glu Phe Val Glu Ile
 50                  55                  60

Leu Lys Lys Glu Gly Val Asn Val Val Glu Leu Val Asp Leu Ile Ala
 65                  70                  75                  80

Glu Thr Ile Asp Leu Val Asp Ala Lys Lys Glu Ala Leu Ile Asp
                 85                  90                  95

Glu Tyr Ile Glu Asp Ser Glu Pro Val Asp Ala Lys Val Lys Pro
                100                 105                 110

Leu Val Lys Lys Leu Leu Leu Gly Ile Lys Asp Thr Lys Glu Leu Val
                115                 120                 125

Lys Leu Met Met Ala Gly Ile Thr Lys Tyr Asp Leu Glu Ile Glu Ser
130                 135                 140

Glu Lys Glu Leu Ile Ile Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Arg
                180                 185                 190

Asn His Pro Lys Leu Thr Ser Thr Pro Trp Tyr Tyr Asp Pro Ala Met
                195                 200                 205

Lys Leu Ser Ile Glu Gly Gly Asp Val Phe Ile Tyr Asn Asn Asp Thr
                210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
                275                 280                 285

Asn Asp Ile Phe Lys Phe Trp Asp Tyr Asp Leu Val Asn Gly Gly Ser
290                 295                 300

Glu Pro Gln Pro Lys Asp Asn Gly Leu Pro Leu Glu Lys Leu Leu Glu
305                 310                 315                 320

Ser Ile Ile Gly Lys Lys Pro Val Leu Ile Pro Ile Ala Gly Cys Cys
                325                 330                 335

Ala Ser Asp Ile Glu Ile Ala Arg Glu Thr His Phe Asp Gly Thr Asn
                340                 345                 350

Tyr Leu Ala Ile Lys Pro Gly Val Val Ile Gly Tyr Ala Arg Asn Glu
                355                 360                 365

Lys Thr Asn Lys Ala Leu Glu Lys Ala Gly Ile Lys Val Leu Pro Phe
                370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 35
<211> LENGTH: 409
<212> TYPE: PRT
<213> ORGANISM: Mycoplasma cloacale

<400> SEQUENCE: 35

```
Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Glu Phe Val Lys Ile
50                  55                  60

Leu Glu Ser Gln Gly Ile Asn Val Val Glu Leu Thr Asp Leu Ile Ala
65                  70                  75                  80

Glu Thr Tyr Glu Leu Ala Ser Glu Glu Ala Lys Asp Asn Leu Ile Glu
                85                  90                  95

Glu Phe Leu Asp Glu Ser Glu Pro Val Leu Ser Glu Glu His Arg Ile
            100                 105                 110

Leu Val Arg Asn Phe Leu Lys Gly Ile Thr Lys Thr Lys Glu Leu Val
            115                 120                 125

Lys Met Met Met Ala Gly Ile Thr Lys Tyr Asp Leu Gly Ile Glu Ala
            130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Glu
            180                 185                 190

Asn His Pro Lys Leu Val Ser Thr Pro Ile Tyr Tyr His Pro Ser Gln
            195                 200                 205

Gly Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Glu Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
            275                 280                 285

Asn Asp Val Phe Lys Phe Trp Asp Tyr Asp Leu Val Asn Gly Gly Asp
            290                 295                 300

Glu Pro Gln Pro Val Asp Asn Gly Leu Pro Leu Asn Glu Leu Leu Ala
305                 310                 315                 320

Ser Ile Ile Gly Glu Glu Pro Val Leu Val Pro Ile Ala Gly Glu Gly
                325                 330                 335

Ala Ser Lys Met Asp Ile Glu Arg Glu Thr His Phe Asp Gly Thr Asn
            340                 345                 350

Tyr Leu Ala Ile Ala Pro Gly Val Val Gly Tyr Ser Arg Asn Glu
            355                 360                 365

Lys Thr Asn Ala Ala Leu Glu Lys Ala Gly Ile Lys Val Leu Pro Phe
            370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
                405
```

```
<210> SEQ ID NO 36
<211> LENGTH: 412
<212> TYPE: PRT
<213> ORGANISM: Mycoplasma alkalescens

<400> SEQUENCE: 36

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly His Glu Ile
            20                  25                  30

Asp Tyr Ile Thr Pro Ser Arg Leu Asp Glu Leu Leu Phe Ser Ala Met
        35                  40                  45

Leu Glu Ser His Asp Ala Arg Lys Glu His Lys Gln Phe Val Ala Glu
    50                  55                  60

Leu Lys Ala Asn Asn Val Asn Val Ile Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu Asn Lys Ile
            100                 105                 110

Ala Val Arg Asp Phe Leu Lys Ser Arg Lys Thr Thr Arg Glu Leu Ile
        115                 120                 125

Glu Val Met Met Ala Gly Ile Thr Lys Tyr Asp Leu Gly Ile Lys Asn
    130                 135                 140

Cys Lys Cys Gln Asp Leu Val Val Asp Pro Met Pro Asn Leu Tyr Phe
145                 150                 155                 160

Thr Arg Asp Pro Phe Ala Ser Val Gly Asn Gly Ile Thr Ile His Tyr
                165                 170                 175

Met Arg Tyr Lys Val Arg Gln Arg Glu Thr Leu Phe Ser Arg Phe Ile
            180                 185                 190

Phe Ala Asn His Pro Lys Leu Val Asn Thr Pro Ile Tyr Tyr His Pro
        195                 200                 205

Ser Leu Lys Leu Ser Ile Glu Gly Gly Asp Val Phe Ile Tyr Asn Asn
    210                 215                 220

Asp Thr Leu Val Val Gly Val Ser Glu Arg Thr Asp Leu Glu Thr Ile
225                 230                 235                 240

Thr Leu Leu Ala Lys Asn Ile Val Ala Asn Lys Glu Cys Glu Phe Lys
                245                 250                 255

Arg Ile Val Ala Ile Asn Val Pro Lys Trp Thr Asn Leu Met His Leu
            260                 265                 270

Asp Thr Trp Leu Thr Met Leu Asp Lys Asp Lys Phe Leu Tyr Ser Pro
        275                 280                 285

Ile Ala Asn Asp Val Phe Lys Phe Trp Asp Tyr Asp Leu Val Asn Gly
    290                 295                 300

Gly Ala Glu Pro Lys Pro Val Glu Asn Gly Ser Ser Leu Glu Ala Ile
305                 310                 315                 320

Leu Glu Ser Ile Ile His Lys Lys Pro Ile Leu Ile Pro Ile Gly Gly
                325                 330                 335

Asp Ser Ala Ser Gln Ile Glu Val Glu Arg Glu Thr His Phe Asp Gly
            340                 345                 350

Thr Asn Tyr Leu Ala Ile Arg Pro Gly Val Val Ile Gly Tyr Ser Arg
        355                 360                 365

Asn Val Lys Thr Asn Ala Ala Leu Glu Ala Ala Gly Ile Lys Val Ile
    370                 375                 380
```

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
            405                 410

<210> SEQ ID NO 37
<211> LENGTH: 401
<212> TYPE: PRT
<213> ORGANISM: Mycoplasma iners

<400> SEQUENCE: 37

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
            35                  40                  45

Gln Glu His Lys Ser Phe Leu Lys Ile Leu Gln Asp Arg Gly Ile Lys
50                  55                  60

Thr Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
            100                 105                 110

Leu Ser Met Gln Gly Glu Pro Val Lys Met Val Arg Thr Met Met Ala
            115                 120                 125

Gly Val Ser Lys Gln Glu Leu Asn Val Glu Ser Glu Val Glu Leu Ile
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
            195                 200                 205

Gly Gly Asp Val Phe Ile Tyr Asn Lys Asp Thr Leu Val Ile Gly Val
210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
            275                 280                 285

Val Trp Glu Ile Asp Leu Ser Lys Pro Ile Glu Met Val Glu Thr Asn
290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val

```
              340                 345                 350
Val Val Gly Tyr Ser Arg Asn Val Lys Thr Glu Ala Ala Leu Arg Ala
            355                 360                 365

Ala Gly Val Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400

Lys

<210> SEQ ID NO 38
<211> LENGTH: 401
<212> TYPE: PRT
<213> ORGANISM: Mycoplasma gallinarum

<400> SEQUENCE: 38

Met Ser Lys Ile Arg Val Tyr Ser Glu Ile Gly Asn Leu Lys Lys Val
1               5                  10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile
        35                  40                  45

Glu Glu His Lys Arg Phe Val Lys Leu Leu Asp Arg Gly Ile Gln
    50                  55                  60

Ala Ile Gln Leu Ser Asp Leu Val Ala Glu Thr Tyr Val Lys Tyr Ala
65                  70                  75                  80

Thr Ala Glu Gln Lys Ala Ala Phe Ile Glu Lys Tyr Leu Asp Glu Ala
                85                  90                  95

Thr Pro Ala Leu Ser Ala Glu Asn Arg Glu Arg Ala Lys Lys Tyr Ile
            100                 105                 110

Leu Ser Leu Glu Met Gln Pro Val Lys Met Ile Arg Thr Met Met Ala
        115                 120                 125

Gly Leu Ser Lys Tyr Glu Leu Asn Val Glu Ser Asn Ile Glu Leu Ile
    130                 135                 140

Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ala Ile His Pro Glu Tyr
            180                 185                 190

Lys Glu Thr Pro His Trp Phe Asp Arg Leu Asp His Gly Ser Ile Glu
        195                 200                 205

Gly Gly Asp Val Phe Val Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Ile Tyr Ser Pro Asn Met Leu Ser Val Leu Lys
        275                 280                 285

Ile Trp Glu Ile Asp Leu Ala Lys Pro Ile Glu Met Val Glu Ser Asn
    290                 295                 300

Lys Ser Leu Thr Glu Val Leu Glu Ser Ile Ile Gly Glu Lys Pro Ile
```

```
                305                 310                 315                 320
Leu Ile Pro Ile Ala Gly Glu Gly Ala Ser Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Glu Lys Thr Glu Lys Ala Leu Lys Ala
                355                 360                 365

Ala Gly Ile Thr Val Leu Ser Phe Gly Asn Gln Leu Ser Leu Gly
                370                 375                 380

Met Gly Ser Ala Arg Cys Met Ser Met Pro Leu Val Arg Glu Asp Val
385                 390                 395                 400

Lys

<210> SEQ ID NO 39
<211> LENGTH: 405
<212> TYPE: PRT
<213> ORGANISM: Mycoplasma pirum

<400> SEQUENCE: 39

Met Asn Ser Asn Gln Lys Gly Ile His Val Tyr Ser Glu Ile Gly Lys
1               5                   10                  15

Leu Lys Glu Val Leu Val His Arg Pro Gly Arg Glu Leu Asp Phe Leu
                20                  25                  30

Asp Pro Thr Arg Leu Asp Glu Leu Phe Ala Ala Thr Leu Glu Ala
                35                  40                  45

Glu Thr Ala Arg Leu Glu His Asp Asn Phe Thr Asn Ala Leu Lys Asn
50                  55                  60

Gln Gly Val Thr Val Ile Glu Leu Ala Asp Leu Val Ala Gln Thr Tyr
65                  70                  75                  80

Ser Ser Ser Thr Pro Thr Ile Lys Ala Ala Phe Ile Asn Lys Tyr Leu
                85                  90                  95

Asp Glu Ala Thr Pro Ala Leu Thr Thr Lys Leu Arg Thr Leu Val Lys
                100                 105                 110

Asp Phe Leu Thr Lys Gln Lys Ser Val Arg Lys Met Val Asp Tyr Met
                115                 120                 125

Ile Gly Gly Ile Leu Ser Thr Asp Leu Asn Ile Lys Gly Lys Pro Glu
                130                 135                 140

Leu Ile Val Glu Pro Met Pro Asn Ala Tyr Phe Thr His Asp Pro Phe
145                 150                 155                 160

Ala Ser Val Gly Asn Gly Val Thr Leu His Tyr Met Lys His Asn Val
                165                 170                 175

Arg Arg Arg Glu Val Leu Phe Ser Glu Phe Ile Phe Asn Asn Asn Glu
                180                 185                 190

Arg Phe Gln Asn Thr Pro Arg Tyr Ile Val Pro Thr Lys Gly Leu Asp
                195                 200                 205

Ile Glu Gly Gly Asp Val Phe Val Tyr Asn Lys Asn Thr Leu Val Val
                210                 215                 220

Gly Val Ser Glu Arg Thr Lys Met Val Thr Ile Lys Glu Leu Ala Lys
225                 230                 235                 240

Asn Ile Leu Lys Asn Lys Glu Cys Leu Phe Lys Lys Ile Tyr Ala Ile
                245                 250                 255

Asn Val Pro Lys Met Pro Asn Leu Met His Leu Asp Thr Trp Leu Thr
                260                 265                 270

Met Leu Asp His Asn Lys Phe Leu Tyr Ser Pro Asn Met Leu Ser Val
```

```
                  275                 280                 285
Leu Lys Ile Trp Glu Ile Asp Ile Ser Ser Gly Lys Ser Ile Ser Ser
290                 295                 300

Pro Lys Glu Leu Asn Met Asp Leu Ser Lys Ala Leu Ser Ile Ile Ile
305                 310                 315                 320

Gly Lys Lys Pro Ile Leu Ile Pro Val Ala Gly Glu Asn Ala Ser Gln
                    325                 330                 335

Ile Asp Ile Asn Ile Glu Thr Asn Phe Asp Ala Thr Asn Tyr Leu Val
                340                 345                 350

Thr Gln Pro Gly Val Val Gly Tyr Ser Arg Asn Lys Lys Thr Glu
            355                 360                 365

Ala Ala Leu Ile Lys Ala Gly Ile Glu Val Ile Pro Phe Gln Gly Asn
            370                 375                 380

Gln Leu Ser Leu Gly Met Gly Ser Ala Arg Cys Met Ser Met Pro Leu
385                 390                 395                 400

Ile Arg Glu Asp Val
                405

<210> SEQ ID NO 40
<211> LENGTH: 404
<212> TYPE: PRT
<213> ORGANISM: Mycoplasma primatum

<400> SEQUENCE: 40

Met Ser Lys Ser Lys Ile Asn Val Tyr Ser Glu Tyr Gly Asn Leu Lys
1               5                   10                  15

Glu Val Leu Val His Thr Pro Gly Asp Glu Ile Arg Arg Ile Thr Pro
                20                  25                  30

Ser Arg Leu Asp Glu Leu Leu Phe Ser Ala Ile Leu Glu Pro Lys Ser
            35                  40                  45

Ala Ile Ala Glu His Lys Ser Phe Cys Gln Ile Leu Lys Asp Asn Lys
        50                  55                  60

Val Lys Ala Ile Gln Leu Asp Glu Leu Val Ala Ala Thr Tyr Lys Gly
65                  70                  75                  80

Val Ser Glu Ser Val Gln Asn Ser Phe Val Glu Arg Trp Leu Asp Glu
                85                  90                  95

Cys Glu Pro Lys Leu Glu Asn Asn Val Arg Pro Ile Val Lys Glu Tyr
                100                 105                 110

Leu Leu Lys Ala Ala Glu Gln Ser Val Lys Lys Met Ile Arg Ile Met
            115                 120                 125

Met Ala Gly Ile Asp Lys Arg Glu Ile Gly Val Glu Ser Glu Val Asp
        130                 135                 140

Phe Ile Val Asp Pro Met Pro Asn Leu Tyr Phe Thr Arg Asp Pro Phe
145                 150                 155                 160

Ala Ser Val Gly Asn Gly Ile Thr Leu His His Met Lys Tyr Val Val
                165                 170                 175

Arg Gln Arg Glu Thr Leu Phe Ser Glu Phe Ile Phe Asp Asn His Pro
            180                 185                 190

Asp Tyr Lys Phe Val Pro Arg Tyr Phe Asp Arg Asp Glu Gly Lys
        195                 200                 205

Ile Glu Gly Gly Asp Val Phe Ile Tyr Asn Ser Lys Thr Leu Val Val
        210                 215                 220

Gly Ile Ser Glu Arg Thr Asn Lys Asp Ala Ile Arg Ile Val Ala Lys
225                 230                 235                 240
```

```
Lys Ile Gln Ala Asn Ala Asp Ala Lys Phe Glu Lys Ile Phe Ala Ile
                245                 250                 255

Asn Val Pro Pro Met Pro Asn Leu Met His Leu Asp Thr Trp Leu Thr
260                 265                 270

Met Leu Asp Ser Asn Lys Phe Leu Tyr Ser Pro Asn Met Leu Ser Val
        275                 280                 285

Leu Lys Val Trp Glu Ile Asn Leu Asp Asp Pro Ala Leu Glu Trp Lys
290                 295                 300

Glu Ile Ser Gly Ser Leu Glu Ile Leu Thr Tyr Ile Ile Gly Lys
305                 310                 315                 320

Lys Pro Ile Leu Ile Pro Ile Ala Gly Lys Gly Ala Ser Gln Phe Glu
                325                 330                 335

Ile Asp Ile Glu Thr His Phe Asp Gly Thr Asn Tyr Leu Ala Ile Ala
                340                 345                 350

Pro Ser Val Val Ile Gly Tyr Ser Arg Asn Glu Leu Thr Glu Lys Ala
        355                 360                 365

Leu Lys Lys Ala Gly Val Lys Val Leu Ser Leu Asp Gly Asn Gln Leu
370                 375                 380

Ser Leu Gly Met Gly Ser Ala Arg Cys Met Ser Met Pro Leu Ile Arg
385                 390                 395                 400

Glu Asp Val Lys

<210> SEQ ID NO 41
<211> LENGTH: 401
<212> TYPE: PRT
<213> ORGANISM: Mycoplasma lipofaciens

<400> SEQUENCE: 41

Met Ser Lys Ile Asn Val Tyr Ser Glu Val Gly Val Leu Lys Glu Val
1               5                   10                  15

Leu Val His Thr Pro Gly Asp Glu Ile Arg Arg Val Ala Pro Ser Arg
                20                  25                  30

Leu Asp Glu Leu Leu Phe Ser Ala Ile Leu Glu Pro Gln Asp Ala Ile
        35                  40                  45

Ala Glu His Lys Arg Phe Ile Lys Ile Leu Glu Asp Asn Asn Ile Lys
    50                  55                  60

Val Ile Gln Leu Asp Glu Leu Val Ser Glu Thr Trp Glu Lys Ala Thr
65                  70                  75                  80

Ala Glu Gln Arg Asp Ala Phe Ile Glu Lys Trp Leu Asp Glu Ala Glu
                85                  90                  95

Pro Val Leu Asp Ala Lys Leu Arg Glu Thr Val Lys Lys Tyr Leu Leu
            100                 105                 110

Ser Leu Asn Pro Val Lys Lys Met Val Arg Thr Met Met Ala Gly Ile
        115                 120                 125

Asp Lys Lys Glu Leu Lys Ile Glu Leu Asp Arg Asp Leu Val Val Asp
130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Asn Ile His Pro Asp Tyr Lys Thr
            180                 185                 190

Thr Pro His Trp Phe Asp Arg Leu Asp Lys Gly Asn Ile Glu Gly Gly
        195                 200                 205
```

```
Asp Val Phe Ile Tyr Asn Lys Asp Thr Leu Val Leu Gly Val Ser Glu
        210                 215                 220

Arg Thr Asn Lys Asp Ala Val Met Thr Ile Ala Lys His Ile Gln Ser
225                 230                 235                 240

Asn Glu Gln Ala Lys Phe Lys Lys Leu Val Ala Ile Asn Val Pro Pro
                245                 250                 255

Met Pro Asn Leu Met His Leu Asp Thr Trp Leu Thr Met Val Asp His
                260                 265                 270

Asp Lys Phe Leu Tyr Ser Pro Asn Met Leu Ser Val Leu Lys Ile Trp
                275                 280                 285

Glu Ile Asp Leu Thr Pro Gly Lys Glu Ile Glu Met Val Glu Ser Thr
        290                 295                 300

Lys Ser Leu Ser Asp Met Leu Glu Ser Ile Ile Gly Lys Lys Pro Val
305                 310                 315                 320

Leu Ile Pro Ile Ala Gly Lys Asp Ala Ser Gln Leu Asp Ile Asp Ile
                325                 330                 335

Glu Thr His Phe Asp Gly Thr Asn Tyr Leu Thr Ile Arg Pro Gly Val
                340                 345                 350

Val Val Gly Tyr Ser Arg Asn Cys Leu Thr Glu Gln Ala Leu Lys Asp
                355                 360                 365

Ala Gly Val Thr Val Leu Ser Phe Asp Gly Asn Gln Leu Ser Leu Gly
        370                 375                 380

Met Gly Ser Ala Arg Cys Met Ser Met Pro Leu Val Arg Glu Asp Ile
385                 390                 395                 400

Lys

<210> SEQ ID NO 42
<211> LENGTH: 405
<212> TYPE: PRT
<213> ORGANISM: Mycoplasma felifaucium

<400> SEQUENCE: 42

Met Asn Lys Ile Asn Val Tyr Ser Glu Ile Gly Lys Leu Lys Glu Val
1               5                   10                  15

Leu Val His Thr Pro Gly Asn Glu Ile Arg Arg Ile Ser Pro Ser Arg
                20                  25                  30

Leu Asp Glu Leu Leu Phe Ser Ala Leu Leu Glu Pro Asn Phe Ala Ala
            35                  40                  45

Lys Glu His Thr Ala Phe Cys Glu Ile Leu Lys Glu Asn Gly Ile Lys
        50                  55                  60

Ala Ile Gln Leu Val Asp Leu Val Ser Asp Thr Trp Arg Ile Ala Ser
65                  70                  75                  80

Glu Lys Ala Lys Thr Glu Phe Ile Glu Arg Trp Leu Asp Glu Cys Glu
                85                  90                  95

Pro Lys Leu Asp Ser Asn Leu Arg Glu Ile Val Arg Lys His Ile Tyr
                100                 105                 110

Ala Ile Glu Lys Arg Ser Val Lys Arg Met Val Lys Thr Met Met Ala
            115                 120                 125

Gly Ile Glu Arg Arg Glu Leu Pro Val Thr Ser Lys Glu Val Ala Arg
        130                 135                 140

Glu Leu Val Val Asp Pro Met Pro Asn Leu Tyr Phe Thr Arg Asp Pro
145                 150                 155                 160

Phe Ala Ser Val Gly Asn Gly Ile Ser Leu His His Met Lys Tyr Val
                165                 170                 175
```

```
Thr Arg Gln Arg Glu Thr Ile Phe Ala Glu Phe Val Phe Gly Asn His
            180                 185                 190

Pro Asp Tyr Ile Asp Thr Pro Arg Trp Phe Asp Arg Ser Asp Asp Gly
        195                 200                 205

Arg Ile Glu Gly Gly Asp Val Phe Ile Tyr Gly Ser Lys Thr Leu Val
    210                 215                 220

Ile Gly Val Ser Glu Arg Thr Asn Lys Glu Ala Ile Lys Val Met Ala
225                 230                 235                 240

Lys Lys Ile Gln Ala Asn Lys Glu Ala Thr Phe Glu Lys Ile Tyr Ala
                245                 250                 255

Ile Asn Val Pro Pro Met Pro Asn Leu Met His Leu Asp Thr Trp Leu
            260                 265                 270

Thr Met Leu Asp Lys Asn Lys Phe Leu Tyr Ser Pro Asn Met Leu Ala
        275                 280                 285

Val Leu Gln Val Trp Glu Ile Asp Leu Lys Asp Pro Glu Leu Thr Trp
    290                 295                 300

His Glu Leu Ser Gly Ser Leu Glu Glu Ile Leu His Lys Ile Ile Gly
305                 310                 315                 320

Arg Lys Pro Ile Leu Ile Pro Ile Ala Gly His Gly Ala Gln Gln Ile
                325                 330                 335

Asp Ile Asp Ile Glu Thr His Phe Asp Gly Thr Asn Tyr Leu Ala Ile
            340                 345                 350

Ala Pro Gly Val Val Gly Tyr Asn Arg Asn Val Leu Thr Glu Arg
        355                 360                 365

Ala Leu Lys Lys Ala Gly Ile Lys Val Leu Ser Phe Glu Gly Asn Gln
    370                 375                 380

Leu Ser Leu Gly Met Gly Ser Ala Arg Cys Met Ser Met Pro Leu Ile
385                 390                 395                 400

Arg Glu Asn Leu Lys
                405

<210> SEQ ID NO 43
<211> LENGTH: 404
<212> TYPE: PRT
<213> ORGANISM: Mycoplasma imitans

<400> SEQUENCE: 43

Met Phe Asn Lys Ile Lys Val Tyr Ser Glu Ile Gly Arg Leu Arg Lys
1               5                   10                  15

Val Leu Val His Thr Pro Gly Lys Glu Leu Glu Tyr Val Thr Pro Gln
            20                  25                  30

Arg Leu Asp Glu Leu Leu Phe Ser Ser Leu Leu Asn Pro Val Lys Ala
        35                  40                  45

Arg Gln Glu His Glu Ala Phe Ile Lys Ile Leu Gln Asp Gln Gly Val
    50                  55                  60

Glu Cys Val Gln Leu Thr Thr Leu Thr Ala Gln Thr Phe Gln Ser Ala
65                  70                  75                  80

Thr Ser Glu Val Lys Glu Lys Phe Ile Asn Arg Trp Leu Asp Glu Cys
                85                  90                  95

Leu Pro Lys Leu Ser Asp Asp Asn Arg Ile Lys Val Tyr Ala Tyr Leu
            100                 105                 110

Lys Asp Leu Ser Ser Asp Pro Glu Val Met Ile Arg Lys Met Met Ser
        115                 120                 125

Gly Ile Leu Ala Lys Glu Val Asn Val Gln Ser Asp Val Glu Leu Ile
    130                 135                 140
```

```
Ala Asp Pro Met Pro Asn Leu Tyr Phe Thr Arg Asp Pro Phe Ala Ser
145                 150                 155                 160

Ile Gly Lys Gly Val Thr Leu His Ser Met Phe His Pro Thr Arg Lys
                165                 170                 175

Arg Glu Thr Ile Phe Ala Asp Phe Val Phe Ser His His Pro Glu Tyr
            180                 185                 190

Lys Gln Thr Pro Lys Tyr Tyr Ser Arg Leu Asn Glu Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Phe Leu Ala Glu Lys Leu
225                 230                 235                 240

Arg Glu Asn Tyr Glu Thr Thr Phe Glu Lys Ile Tyr Ala Ile Asn Val
                245                 250                 255

Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
        275                 280                 285

Ile Trp Glu Ile Asp Leu Thr His Glu Gln Leu Ser Trp Arg Glu Leu
290                 295                 300

Asn Glu Ser Leu Glu Glu Phe Leu Ser Met Val Ile Gly Lys Lys Ala
305                 310                 315                 320

Thr Thr Ile Pro Val Ala Gly Glu Asp Ser Thr Gln Ile Glu Ile Asp
                325                 330                 335

Val Glu Thr Asn Phe Asp Ala Thr Asn Phe Leu Val Ile Gln Pro Gly
            340                 345                 350

Val Val Val Gly Tyr Asp Arg Asn Tyr Lys Thr Asn Gln Ala Leu Val
        355                 360                 365

Asn Ala Gly Ile Lys Val Leu Ser Trp Asn Gly Asp Gln Leu Ser Leu
370                 375                 380

Gly Met Gly Ser Ala Arg Cys Met Ser Met Pro Leu Tyr Arg Asp Pro
385                 390                 395                 400

Ile Lys Lys Gly

<210> SEQ ID NO 44
<211> LENGTH: 401
<212> TYPE: PRT
<213> ORGANISM: Mycoplasma opalescens

<400> SEQUENCE: 44

Met Ser Lys Ile Asn Val Tyr Ser Glu Ile Gly Thr Leu Lys Glu Val
1               5                   10                  15

Leu Val His Thr Pro Gly Asp Glu Ile Arg Arg Val Ala Pro Ala Arg
                20                  25                  30

Leu Asp Glu Leu Leu Phe Ser Ala Ile Leu Glu Pro Asn His Ala Ile
            35                  40                  45

Ala Glu His Lys Ala Phe Ile Lys Ile Leu Glu Asp Asn Gly Ile Lys
        50                  55                  60

Val Ile Gln Leu Asp Glu Leu Val Val Gln Thr Trp Asn Gln Val Asp
65                  70                  75                  80

Glu Ala Thr Arg Lys Ala Phe Val Thr Lys Trp Leu Asp Glu Cys Glu
                85                  90                  95

Pro Lys Leu Glu Ser Asn Val Arg Val Glu Val Glu Lys Tyr Ile Tyr
            100                 105                 110
```

```
Ser Leu Ala Lys Glu Pro Lys Met Val Arg Thr Met Met Ala Gly
            115                 120                 125

Ile Ser Lys Glu Glu Leu Pro Leu Asn Val Asn Arg Pro Leu Val Val
130                 135                 140

Asp Pro Met Pro Asn Leu Tyr Phe Thr Arg Asp Pro Phe Ala Ser Val
145                 150                 155                 160

Gly Thr Gly Ile Ser Leu His His Met Lys Tyr Val Thr Arg Gln Arg
                165                 170                 175

Glu Thr Ile Phe Ala Gln Phe Val Phe Asp Asn His Lys Asp Tyr Asn
            180                 185                 190

Thr Val Pro Arg Trp Phe Asp Asn Lys Asp Gln Gly Arg Ile Glu Gly
            195                 200                 205

Gly Asp Val Phe Ile Tyr Asn Thr Lys Thr Leu Val Ile Gly Val Ser
            210                 215                 220

Glu Arg Thr Asp Lys Asp Ala Ile Lys Ile Met Ala Lys Lys Ile Gln
225                 230                 235                 240

Ala Asp Lys Asn Cys Lys Phe Glu Lys Ile Phe Ala Ile Asn Val Pro
                245                 250                 255

Pro Met Pro Asn Leu Met His Leu Asp Thr Trp Leu Thr Met Val Asp
            260                 265                 270

Arg Asn Lys Phe Leu Tyr Ser Pro Asn Met Leu Ser Val Leu Lys Val
            275                 280                 285

Trp Glu Ile Asp Leu Lys Asp Ala Ser Leu Ala Trp Lys Glu Ile Glu
            290                 295                 300

Gly Ser Leu Ser Gln Ile Leu Glu Lys Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Gln Ala Leu Lys Ala
            355                 360                 365

Ala Gly Val Lys Val Leu Ser Phe Glu Gly Asn Gln Leu Ser Leu Gly
            370                 375                 380

Met Gly Ser Ala Arg Cys Met Ser Met Pro Leu Ile Arg Glu Asp Leu
385                 390                 395                 400

Lys

<210> SEQ ID NO 45
<211> LENGTH: 425
<212> TYPE: PRT
<213> ORGANISM: Mycoplasma moatsii

<400> SEQUENCE: 45

Met Lys Lys Asn Ala Ile Asn Val Tyr Ser Glu Ile Gly Lys Leu Lys
1               5                   10                  15

Lys Val Leu Val His Arg Pro Gly Asp Glu Leu Lys Tyr Val Thr Pro
                20                  25                  30

Gln Arg Met Asp Glu Leu Leu Met Ser Ala Ile Glu Leu Glu Gln
            35                  40                  45

Ala Lys Glu Glu His Asp Ala Phe Thr Lys Ile Leu Arg Asp Asn Gly
        50                  55                  60

Val Glu Val Ile Glu Leu Ala Asp Leu Thr Ala Glu Met Tyr Asp Ser
65                  70                  75                  80
```

Leu Thr Pro Ser Glu Lys Asp Ala Phe Leu Asn Gln Trp Val Lys Glu
             85                  90                  95

Ala Ser Trp Gly Lys Lys Ser Ser Ile Asp Ala Leu Lys Ile Lys Lys
            100                 105                 110

Asn Leu Ser Lys Lys Val Phe Asp Tyr Val Lys Ser Ile Lys Pro Thr
            115                 120                 125

Arg Lys Met Ile Asp Lys Leu Met Ala Gly Val Leu Leu Ser Glu Ile
130                 135                 140

Gly Glu Lys Ser Ile Ile Leu Asn Lys Asp Lys Lys Asn Glu Met Val
145                 150                 155                 160

Ile Asp Leu Val Val Asp Pro Met Pro Asn Leu Tyr Phe Thr Arg Asp
                165                 170                 175

Pro Phe Ala Ser Val Gly Asn Gly Ile Thr Leu His Asn Met Lys Tyr
            180                 185                 190

Pro Thr Arg Lys Arg Glu Thr Ile Phe Ala Gln Trp Ile Phe Asn Lys
            195                 200                 205

His Pro Glu Tyr Lys Asp Val Pro Gln Phe Ile Ser Lys Arg Asp Gly
            210                 215                 220

Lys Glu Thr Ile Glu Gly Gly Asp Val Phe Ile Tyr Thr Lys Asp Val
225                 230                 235                 240

Leu Ala Ile Gly Val Ser Glu Arg Thr Asn Met Glu Ala Ile Leu Arg
                245                 250                 255

Ile Ala Thr Asn Ile Lys Lys Asp Lys Asn Cys Glu Phe Lys Lys Ile
            260                 265                 270

Val Ala Ile Asn Val Pro Pro Met Gly Asn Leu Met His Leu Asp Thr
            275                 280                 285

Trp Leu Thr Met Leu Asp Lys Asp Leu Phe Leu Tyr Ser Gly Asn Ile
290                 295                 300

Lys Ser Ala Leu Lys Val Trp Glu Ile Asp Leu Thr Lys Pro Ile Thr
305                 310                 315                 320

Pro Lys Ser Pro Lys Leu Ser Thr Ala Lys Leu Ala Asp Ile Leu Ala
            325                 330                 335

Lys Ile Val Gly Lys Lys Val Arg Met Ile Pro Ile Gly Gly Lys Asp
            340                 345                 350

Gly Asn Gln Met Asp Ile Asp Ile Glu Thr His Phe Asp Gly Thr Asn
            355                 360                 365

Tyr Leu Ala Ile Ala Pro Gly Val Val Gly Tyr His Arg Asn Arg
370                 375                 380

Lys Thr Gln Lys Ala Leu Glu Glu Ala Gly Val Lys Val Leu Ala Phe
385                 390                 395                 400

Gln Gly Asn Gln Leu Ser Leu Gly Met Gly Ser Ala Arg Cys Met Ser
            405                 410                 415

Met Pro Leu Val Arg Glu Glu Val Lys
            420                 425

<210> SEQ ID NO 46
<211> LENGTH: 399
<212> TYPE: PRT
<213> ORGANISM: Mycoplasma elephantis

<400> SEQUENCE: 46

Met Ser Gln Ile Asn Val Phe Ser Glu Ile Gly Gln Leu Lys Glu Val
1               5                   10                  15

Leu Val His Thr Pro Gly Asp Glu Ile Arg Arg Ile Ser Pro Lys Arg

```
            20                  25                  30
Tyr Asn Glu Leu Leu Phe Ser Ala Ile Leu Glu Ala Asp Val Ala Ile
        35                  40                  45

Lys Glu His Lys Ser Phe Val Lys Ile Leu Glu Glu Asn Asn Val Lys
 50                  55                  60

Val Ile Gln Leu Lys Asp Ile Leu Leu Glu Thr Trp Asn Ile Cys Ser
 65                  70                  75                  80

Lys Glu Ala Lys Asn Ile Phe Ile Asn Lys Trp Ile Glu Ala Gln
                 85                  90                  95

Pro Val Ile His Ser Ser Leu Lys Glu Lys Ile Lys Leu Phe Leu
                100                 105                 110

Lys Ser Lys Thr Pro Leu Glu Ile Ile Asp Ile Met Met Lys Gly Ile
            115                 120                 125

Leu Lys Gln Glu Leu Gly Ile Glu Tyr Lys His Glu Leu Ile Ile Asp
            130                 135                 140

Pro Met Pro Asn Leu Tyr Phe Thr Arg Asp Pro Phe Thr Ser Met Gly
145                 150                 155                 160

Ser Gly Ile Thr Ile Asn Asn Met Lys Tyr Gln Thr Arg Lys Arg Glu
                165                 170                 175

Thr Ile Phe Ser Glu Phe Ile Phe Asn Asn His Pro Lys Tyr Lys Asn
                180                 185                 190

Thr Pro Arg Trp Phe Asp Arg Phe Asp Ser Gly Asn Ile Glu Gly Gly
            195                 200                 205

Asp Leu Phe Val Tyr Thr Lys Glu Thr Ile Val Val Gly Val Ser Glu
            210                 215                 220

Arg Thr Lys Lys Lys Ala Ile Leu Lys Ile Ala Lys Asn Ile Gln Glu
225                 230                 235                 240

Asn Asn Asn Ser Phe Lys Lys Ile Val Ile Lys Val Pro Ile Met
                245                 250                 255

Gln Asn Leu Met His Leu Asp Thr Trp Ile Val Met Val Asp Phe Asp
            260                 265                 270

Lys Phe Ile Tyr Ser Pro Asn Val Thr Lys Ser Leu Lys Phe Trp Glu
            275                 280                 285

Ile Asp Leu Thr Lys Lys Pro Lys Phe Ile Gln Leu Lys Asn Glu Thr
            290                 295                 300

Leu Glu Asp Val Leu Tyr Arg Val Ile Gly Lys Lys Pro Ile Leu Ile
305                 310                 315                 320

Pro Val Ala Gly Glu Asn Ala Asn Gln Ile Asp Ile Asp Val Glu Thr
                325                 330                 335

His Phe Asp Ala Thr Asn Tyr Leu Thr Ile Arg Pro Gly Val Val Val
                340                 345                 350

Gly Tyr Ser Arg Asn Lys Lys Thr Glu Glu Ala Leu Ile Asn Ala Gly
            355                 360                 365

Val Lys Val Tyr Ala Phe Glu Gly Asn Gln Leu Ser Leu Gly Met Gly
            370                 375                 380

Ser Ala Arg Cys Met Ser Met Pro Leu Ile Arg Glu Asp Ile Ile
385                 390                 395
```

<210> SEQ ID NO 47
<211> LENGTH: 399
<212> TYPE: PRT
<213> ORGANISM: Mycoplasma testudinis

<400> SEQUENCE: 47

```
Met Lys Asn Ile Asn Val Tyr Ser Glu Val Gly Lys Leu Lys Glu Val
1               5                   10                  15
Val Val His Thr Pro Gly Glu Leu His Asn Val Ala Pro Ser Arg
            20                  25                  30
Leu Gln Glu Leu Leu Thr Ser Ala Val Leu Glu Pro Glu Val Ala Arg
            35                  40                  45
Lys Glu His Leu Lys Phe Ile Lys Ile Leu Asn Asp Tyr Gly Val Lys
        50                  55                  60
Val Ile Gln Ile Val Asp Leu Ile Thr Glu Thr Tyr Glu Ala Val Asp
65                  70                  75                  80
Ser Asn Lys Lys Glu Ala Phe Ile Asn Asn Trp Leu Asp Asn Ser Val
            85                  90                  95
Pro Lys Leu Thr Asp Lys Asn Arg Met Ile Leu Arg Asn Tyr Leu Thr
            100                 105                 110
Gln Phe Ser Thr Lys Ala Met Ile Arg Lys Met Ile Ser Gly Ile Arg
            115                 120                 125
Ala Lys Glu Leu Asn Leu Lys Thr Pro Ser Ala Leu Leu Val Asp Pro
        130                 135                 140
Met Pro Asn Leu Cys Phe Ala Arg Asp Thr Phe Ala Cys Val Gly Ser
145                 150                 155                 160
Ala Ile Ser Leu Ser Thr Met Lys His Pro Thr Arg Arg Glu Ala
            165                 170                 175
Leu Leu Thr Glu Phe Ile Phe Gln Asn His Pro Lys Tyr Lys Asp Val
            180                 185                 190
Ile Lys Tyr Phe Asp Ser Lys Asn Ser Lys Ala Thr Ile Glu Gly Gly
        195                 200                 205
Asp Ile Phe Val Tyr Asn Pro Lys Thr Leu Val Val Gly Asn Ser Glu
        210                 215                 220
Arg Thr Asn Met Gln Ala Cys Leu Leu Leu Ala Lys Lys Ile Gln Ser
225                 230                 235                 240
Asn Pro Asn Asn Lys Phe Glu Lys Ile Val Ile Asn Val Pro Pro
            245                 250                 255
Leu Pro His Leu Met His Leu Asp Thr Trp Leu Thr Met Val Asp Tyr
            260                 265                 270
Asp Lys Phe Ile Tyr Ser Pro Asn Ile Leu His Thr Leu Lys Phe Trp
        275                 280                 285
Val Ile Asp Leu Lys Lys Arg Lys Leu Glu Ala Val Glu Lys His Asn
        290                 295                 300
Thr Leu Lys Ala Met Leu Arg Met Ile Ile Lys Lys Glu Pro Ile Leu
305                 310                 315                 320
Ile Pro Val Gly Asp Val Gly Ala Asp Gln Leu Asp Ile Asp Leu Glu
            325                 330                 335
Thr His Phe Asp Ala Thr Asn Tyr Leu Ala Leu Ala Pro Gly Val Val
            340                 345                 350
Val Gly Tyr Asp Arg Asn Ile Lys Thr Gln Arg Ala Leu Glu Lys Ala
        355                 360                 365
Gly Val Lys Val Leu Ser Phe Ser Gly Asn Gln Leu Ser Leu Ala Met
        370                 375                 380
Gly Ser Ala Arg Cys Leu Ser Met Pro Leu Ile Arg Glu Glu Asn
385                 390                 395

<210> SEQ ID NO 48
<211> LENGTH: 410
<212> TYPE: PRT
```

<213> ORGANISM: Mycoplasma canadense

<400> SEQUENCE: 48

```
Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ser Glu
    50                  55                  60

Leu Lys Ala Asn Asp Ile Asn Val Val Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu His Lys Ala
            100                 105                 110

Ile Val Arg Lys Tyr Leu Lys Gly Ile Gln Pro Thr Arg Lys Leu Ile
        115                 120                 125

Glu Met Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Val Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ser
290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Gly Ile Lys Val Leu Pro Phe
370                 375                 380

His Gly Asn Gln Leu Ser Leu Gly Met Gly Asn Ala Arg Cys Met Ser
385                 390                 395                 400
```

Met Pro Leu Ser Arg Lys Asp Val Lys Trp
              405                 410

<210> SEQ ID NO 49
<211> LENGTH: 409
<212> TYPE: PRT
<213> ORGANISM: Mycoplasma anseris

<400> SEQUENCE: 49

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Ala Glu His Lys Lys Phe Val Ala Thr
    50                  55                  60

Leu Lys Glu Gln Gly Ile Asn Thr Val Glu Leu Thr Asp Leu Val Ala
65                  70                  75                  80

Glu Thr Tyr Asp Leu Ala Ser Gln Glu Ala Arg Asp Asn Leu Leu Glu
                85                  90                  95

Glu Phe Leu Asp Asp Ser Ala Pro Val Leu Ser Glu His Lys Glu
            100                 105                 110

Ile Val Arg Thr Tyr Leu Lys Gly Ile Lys Gly Thr Arg Lys Leu Ile
        115                 120                 125

Glu Thr Met Met Ala Gly Ile Thr Lys Tyr Asp Leu Gly Ile Glu Ala
    130                 135                 140

Glu Gln Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ser
            180                 185                 190

Asn His Pro Gln Leu Val Asn Thr Pro Trp Tyr Tyr Asn Pro Ala Glu
        195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Glu Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Thr Asn Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Val Asp Asn Gly Leu Pro Leu Asn Glu Leu Leu Lys
305                 310                 315                 320

Ser Ile Ile Gly Glu Glu Pro Ile Leu Ile Pro Ile Ala Gly Asp Gly
                325                 330                 335

Ala Thr Gln Ile Glu Ile Glu Arg Glu Thr His Phe Asp Gly Thr Asn
            340                 345                 350

Tyr Leu Ala Ile Ala Pro Gly Val Val Ile Gly Tyr Ser Arg Asn Glu
        355                 360                 365

-continued

Lys Thr Asn Ala Ala Leu Glu Ala Ala Gly Ile Lys Val Leu Pro Phe
370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
                405

<210> SEQ ID NO 50
<211> LENGTH: 401
<212> TYPE: PRT
<213> ORGANISM: Mycoplasma meleagridis

<400> SEQUENCE: 50

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ser Pro Ser Arg
                20                  25                  30

Leu Asp Glu Leu Leu Phe Ser Ala Ile Leu Gln Pro Glu Gln Ala Ile
            35                  40                  45

Lys Glu His Gln Ser Phe Val Lys Ile Leu Gln Asp Arg Gly Ile Lys
50                  55                  60

Val Ile Gln Leu Ser Asp Leu Val Ala Glu Thr Tyr Val Lys Tyr Ala
65                  70                  75                  80

Thr Ser Lys Glu Lys Glu Ser Phe Ile Glu Lys Trp Leu Asp Glu Ala
                85                  90                  95

Thr Pro Ala Leu Asn Ser Glu Asn Arg Ala Arg Val Lys Asn Tyr Ile
            100                 105                 110

Thr Ala Met Gln Gly Gln Pro Val Lys Met Val Arg Ala Met Met Ala
        115                 120                 125

Gly Val Ser Lys Gln Glu Leu Asn Ile Glu Ser Asp Val Glu Leu Ile
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Gln Thr Pro His Trp Phe Asp Arg Leu Asp Lys Gly Asn Ile Glu
        195                 200                 205

Gly Gly Asp Val Phe Ile Tyr Asn Lys Asp Thr Leu Val Ile Gly Val
210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Ile Trp Glu Ile Asp Leu Ser Lys Glu Ile Lys Met Val Glu Thr Ser
        290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile

```
                    325                 330                 335
Glu Thr His Phe Asp Gly Thr Asn Tyr Leu Thr Ile Ala Pro Gly Val
                340                 345                 350

Val Val Gly Tyr Ser Arg Asn Val Lys Thr Glu Ala Ala Leu Lys Ala
                355                 360                 365

Ala Gly Val Thr Val Tyr Ser Phe Asp Gly Asn Gln Leu Ser Leu Gly
                370                 375                 380

Met Gly Ser Gly Arg Cys Met Ser Met Pro Leu Val Arg Glu Asp Val
385                 390                 395                 400

Lys

<210> SEQ ID NO 51
<211> LENGTH: 404
<212> TYPE: PRT
<213> ORGANISM: Mycoplasma alvi

<400> SEQUENCE: 51

Met Ser Ile Lys Glu Asn Gly Ile His Val Tyr Ser Glu Ile Gly Lys
1               5                   10                  15

Leu Arg Asp Val Leu Val His Arg Pro Gly Arg Glu Leu Asn Phe Leu
                20                  25                  30

Asp Pro Ser Arg Leu Asp Glu Leu Leu Phe Ala Ala Thr Leu Glu Pro
            35                  40                  45

Glu Thr Ala Arg Leu Glu His Asp Asn Phe Thr Thr Val Leu Lys Asn
        50                  55                  60

Gln Gly Val Asn Val Ile Glu Leu Ala Asp Leu Val Ser Gln Thr Tyr
65                  70                  75                  80

Ser Lys Val Asp Ser Lys Val Lys Lys Glu Phe Ile Asp Gln Tyr Leu
                85                  90                  95

Asn Glu Ala Thr Pro Lys Leu Thr Ser Glu Leu Ser Lys Lys Val Tyr
                100                 105                 110

Asp Phe Leu Thr Lys Gln Lys Ser Asn Arg Glu Met Val Asp Phe Met
            115                 120                 125

Met Gly Gly Ile Leu Ser Ser Asp Leu Asn Ile Lys Gly Gln Pro Tyr
        130                 135                 140

Leu Ile Val Glu Pro Met Pro Asn Leu Tyr Phe Thr Arg Asp Pro Phe
145                 150                 155                 160

Ala Ser Val Gly Asn Gly Ala Thr Ile His Trp Met Lys His Asn Val
                165                 170                 175

Arg Arg Arg Glu Val Leu Phe Ala Asn Phe Ile Phe Lys Tyr Asn Glu
                180                 185                 190

Arg Phe Gln Asn Thr Pro Lys Tyr Ile Thr Pro Thr Lys Gly Leu Asp
            195                 200                 205

Ile Glu Gly Gly Asp Val Phe Val Tyr Asn Lys Lys Thr Leu Val Val
        210                 215                 220

Gly Val Ser Glu Arg Thr Lys Met Glu Thr Ile Lys Glu Leu Ala Lys
225                 230                 235                 240

Asn Ile Ser Lys Asn Lys Glu Cys Thr Phe Thr Lys Ile Tyr Ala Ile
                245                 250                 255

Asn Val Pro Lys Met Pro Asn Leu Met His Leu Asp Thr Trp Leu Thr
                260                 265                 270

Met Leu Asp Tyr Asn Lys Phe Leu Tyr Ser Pro Asn Met Leu Ser Val
            275                 280                 285

Leu Lys Val Trp Glu Ile Asn Ile Ser Asn Asn Lys Val Ser Ala Pro
```

```
                290                 295                 300
Lys Glu Leu Asn Val Asn Leu Glu Lys Ala Leu Ser Met Ile Ile Gly
305                 310                 315                 320

Lys Lys Pro Ile Leu Ile Pro Val Ala Gly Ala Asn Ala Ser Gln Ile
                325                 330                 335

Asp Ile Asn Ile Glu Thr Asn Phe Asp Ala Thr Asn Tyr Leu Val Ile
                340                 345                 350

Glu Pro Gly Val Val Gly Tyr Ser Arg Asn Lys Lys Thr Glu Glu
            355                 360                 365

Ala Leu Val Lys Ala Gly Ile Lys Val Leu Pro Phe His Gly Asn Gln
        370                 375                 380

Leu Ser Leu Gly Met Gly Ser Ala Arg Cys Met Ser Met Pro Leu Tyr
385                 390                 395                 400

Arg Glu Asp Val

<210> SEQ ID NO 52
<211> LENGTH: 410
<212> TYPE: PRT
<213> ORGANISM: Mycoplasma penetrans

<400> SEQUENCE: 52

Met Ser Ser Ile Asp Lys Asn Ser Leu Gly Asn Gly Ile Asn Val Tyr
1               5                   10                  15

Ser Glu Ile Gly Glu Leu Lys Glu Val Leu Val His Thr Pro Gly Asp
            20                  25                  30

Glu Ile Arg Tyr Thr Ala Pro Ser Arg Leu Glu Glu Leu Leu Phe Ser
        35                  40                  45

Ala Val Leu Lys Ala Asp Thr Ala Ile Glu Glu His Lys Gly Phe Val
    50                  55                  60

Lys Ile Leu Gln Asn Asn Gly Ile Lys Val Ile Gln Leu Cys Asp Leu
65                  70                  75                  80

Val Ala Glu Thr Tyr Glu Leu Cys Ser Lys Val Arg Asn Ser Phe
                85                  90                  95

Ile Glu Gln Tyr Leu Asp Glu Ala Leu Pro Val Leu Lys Lys Glu Ile
            100                 105                 110

Arg Pro Val Val Lys Asp Tyr Leu Leu Ser Phe Pro Thr Val Gln Met
        115                 120                 125

Val Arg Lys Met Met Ser Gly Ile Leu Ala Asn Glu Leu Asn Ile Lys
    130                 135                 140

Gln Asp Asn Pro Leu Ile Ile Asp Gly Met Pro Asn Leu Tyr Phe Thr
145                 150                 155                 160

Arg Asp Pro Phe Ala Ser Met Gly Asn Gly Val Ser Ile Asn Cys Met
                165                 170                 175

Lys Tyr Pro Thr Arg Lys Arg Glu Val Ile Phe Ser Arg Phe Val Phe
            180                 185                 190

Thr Asn Asn Pro Lys Tyr Lys Asn Thr Pro Arg Tyr Phe Asp Ile Val
        195                 200                 205

Gly Asn Asn Gly Thr Ile Glu Gly Gly Asp Ile Phe Ile Tyr Asn Ser
    210                 215                 220

Lys Thr Leu Val Ile Gly Asn Ser Glu Arg Thr Asn Phe Ala Ala Ile
225                 230                 235                 240

Glu Ser Val Ala Lys Asn Ile Gln Ala Asn Lys Asp Cys Thr Phe Glu
                245                 250                 255

Arg Ile Val Val Ile Asn Val Pro Pro Met Pro Asn Leu Met His Leu
```

```
                    260             265             270
Asp Thr Trp Leu Thr Met Leu Asp Tyr Asp Lys Phe Leu Tyr Ser Pro
            275             280             285

Asn Met Met Asn Val Leu Lys Ile Trp Glu Ile Asp Leu Asn Val Lys
            290             295             300

Pro Val Lys Phe Val Glu Lys Lys Gly Thr Leu Glu Glu Val Leu Tyr
305             310             315             320

Ser Ile Ile Asp Lys Lys Pro Ile Leu Ile Pro Ile Ala Gly Lys Gly
                325             330             335

Ala Asn Gln Leu Asp Ile Asp Ile Glu Thr His Phe Asp Gly Thr Asn
            340             345             350

Tyr Leu Thr Ile Ala Pro Gly Val Val Gly Tyr Glu Arg Asn Glu
            355             360             365

Lys Thr Gln Lys Ala Leu Val Glu Ala Gly Ile Lys Val Leu Ser Phe
            370             375             380

Asn Gly Ser Gln Leu Ser Leu Gly Met Gly Ser Ala Arg Cys Met Ser
385             390             395             400

Met Pro Leu Ile Arg Glu Asn Leu Lys Lys
                405             410

<210> SEQ ID NO 53
<211> LENGTH: 404
<212> TYPE: PRT
<213> ORGANISM: Mycoplasma fermentans

<400> SEQUENCE: 53

Met Lys Lys Ile Asn Val Tyr Ser Glu Tyr Gly Lys Leu Lys Glu Val
1               5               10              15

Leu Val His Thr Pro Gly Asp Glu Ile Arg Arg Ile Ala Pro Ser Arg
            20              25              30

Leu Asp Glu Leu Leu Phe Ser Ala Ile Leu Glu Pro Asp Ser Ala Ile
            35              40              45

Ala Glu His Lys Arg Phe Val Gln Leu Leu Lys Asp Asn Gly Ile Lys
    50              55              60

Val Ile Gln Leu Asp Glu Leu Phe Ala Lys Thr Phe Asp Leu Val Ser
65              70              75              80

Glu Ser Val Lys Gln Ser Phe Ile Glu Arg Trp Leu Asp Glu Cys Glu
            85              90              95

Pro Lys Leu Asp Ala Thr Leu Arg Ala Lys Val Lys Glu Tyr Ile Leu
            100             105             110

Glu Leu Lys Ala Lys Ser Ser Lys Lys Met Val Arg Val Met Met Ala
            115             120             125

Gly Ile Asp Lys Lys Glu Leu Gly Ile Glu Leu Asp Arg Asp Leu Val
            130             135             140

Val Asp Pro Met Pro Asn Leu Tyr Phe Thr Arg Asp Pro Phe Ala Ser
145             150             155             160

Val Gly Asn Gly Ile Ser Leu His His Met Lys Tyr Val Thr Arg Gln
                165             170             175

Arg Glu Thr Ile Phe Ser Glu Phe Ile Phe Asp Asn Asn Leu Asp Tyr
            180             185             190

Asn Thr Val Pro Arg Trp Phe Asp Arg Lys Asp Glu Gly Arg Ile Glu
            195             200             205

Gly Gly Asp Val Phe Ile Tyr Ser Ala Asp Thr Leu Val Val Gly Val
            210             215             220
```

```
Ser Glu Arg Thr Asn Lys Glu Ala Ile Asn Val Met Ala Arg Lys Ile
225                 230                 235                 240

Ala Ala Asp Lys Glu Val Lys Phe Lys Arg Ile Tyr Ala Ile Asn Val
            245                 250                 255

Pro Pro Met Pro Asn Leu Met His Leu Asp Thr Trp Leu Thr Met Leu
            260                 265                 270

Asp Lys Asn Lys Phe Leu Tyr Ser Pro Asn Met Leu Ser Val Leu Lys
            275                 280                 285

Val Trp Arg Ile Asp Leu Asn Asp Pro Asp Phe Val Trp His Glu Ile
        290                 295                 300

Glu Gly Ser Leu Glu Glu Ile Leu Glu Gln Ile Ile Gly Met Lys Pro
305                 310                 315                 320

Ile Leu Ile Pro Ile Ala Gly Lys Gly Ala Ser Gln Leu Asp Ile Asp
                325                 330                 335

Ile Glu Thr His Phe Asp Gly Thr Asn Tyr Leu Thr Ile Ala Pro Ser
                340                 345                 350

Val Val Val Gly Tyr Ser Arg Asn Glu Lys Thr Glu Lys Ala Leu Lys
            355                 360                 365

Ala Ala Lys Val Lys Val Leu Ser Phe Glu Gly Asn Gln Leu Ser Leu
        370                 375                 380

Gly Met Gly Ser Ala Arg Cys Met Ser Met Pro Leu Ile Arg Glu Asp
385                 390                 395                 400

Ile Lys Lys Lys

<210> SEQ ID NO 54
<211> LENGTH: 404
<212> TYPE: PRT
<213> ORGANISM: Mycoplasma pneumoniae

<400> SEQUENCE: 54

Met Lys Tyr Asn Ile Asn Val His Ser Glu Ile Gly Gln Leu Gln Thr
1               5                   10                  15

Val Leu Val His Thr Pro Gly Asn Glu Ile Arg Arg Ile Ser Pro Arg
            20                  25                  30

Arg Leu Asp Asp Leu Leu Phe Ser Ala Val Ile Glu Pro Asp Thr Ala
        35                  40                  45

Ile Gln Glu His Gln Thr Phe Cys Gln Leu Leu Gln Glu Gln Asn Ile
    50                  55                  60

Glu Val Val Gln Leu Thr Asp Leu Thr Ala Thr Thr Phe Asp Lys Ala
65                  70                  75                  80

Asn Ala Thr Ala Gln Asn Phe Ile Glu Thr Trp Leu Asp Gln Ala
                85                  90                  95

Glu Pro Lys Leu Thr Pro Glu His Arg Lys Val Ala Lys Gln Tyr Leu
            100                 105                 110

Leu Glu Gln Lys Ala Lys Ser Thr Leu Ser Met Val Arg Ser Met Met
        115                 120                 125

Gly Gly Ile Asp Lys Arg Lys Val Ala Ala Ala Asn Thr Ile Asn Gly
    130                 135                 140

Asp Phe Leu Val Asp Pro Met Pro Asn Leu Tyr Phe Thr Arg Asp Pro
145                 150                 155                 160

Phe Ala Ser Ile Gly His Gly Ile Ser Ile Asn Arg Met Lys Tyr Leu
                165                 170                 175

Thr Arg Arg Arg Glu Thr Leu Phe Ala Ser Phe Ile Phe Ala Asn His
            180                 185                 190
```

```
Pro Ile Ile Ala Ala Arg Lys Phe Tyr Phe Lys Pro Ile Asp Met Gly
            195                 200                 205

Thr Ile Glu Gly Gly Asp Ile Phe Val Tyr Asp Gln Gln Thr Val Val
210                 215                 220

Met Gly Leu Ser Glu Arg Thr Thr Glu Ala Ala Ile Asn Val Leu Ala
225                 230                 235                 240

Lys Lys Ile Gln Gln Asp Ser Ser Thr Ser Phe Lys Arg Ile Phe Val
            245                 250                 255

Ile Asn Val Pro Gln Leu Pro Asn Leu Met His Leu Asp Thr Trp Leu
            260                 265                 270

Thr Met Leu Asp Arg Asn Lys Phe Leu Tyr Ser Pro Asn Met Leu Ala
            275                 280                 285

Val Leu Lys Ala Trp Arg Ile Asp Phe Thr Asp Pro Ala Leu Lys Trp
290                 295                 300

Asn Glu Ile Ala Gly Asp Leu Ser Thr Ile Leu His Thr Ile Ile Gly
305                 310                 315                 320

Gln Lys Pro Met Leu Ile Pro Ile Ala Gly Ala Asp Ala Asn Gln Thr
            325                 330                 335

Glu Ile Asp Ile Glu Thr His Phe Asp Gly Thr Asn Tyr Leu Thr Ile
            340                 345                 350

Ala Pro Ser Val Val Val Gly Tyr Ala Arg Asn Lys Leu Thr His Gln
            355                 360                 365

Thr Leu Glu Ala Ala Gly Val Lys Val Ile Ala Phe Lys Gly Asn Gln
370                 375                 380

Leu Ser Leu Gly Met Gly Ser Ala Arg Cys Met Ser Met Pro Leu Val
385                 390                 395                 400

Arg Lys Pro Leu

<210> SEQ ID NO 55
<211> LENGTH: 414
<212> TYPE: PRT
<213> ORGANISM: Mycoplasma sp. CAG:877

<400> SEQUENCE: 55

Met Glu Lys Ile His Val Thr Ser Glu Ile Gly Pro Leu Lys Lys Val
1               5                   10                  15

Leu Leu His Arg Pro Gly Asn Glu Leu Leu Asn Leu Thr Pro Asp Thr
            20                  25                  30

Leu Ser Arg Leu Leu Phe Asp Asp Ile Pro Tyr Leu Pro Asp Ala Ile
            35                  40                  45

Lys Glu His Asp Glu Phe Ala Asp Ala Leu Arg Ala Asn Gly Val Glu
        50                  55                  60

Val Val Tyr Leu Glu Asn Leu Met Ala Asp Val Leu Asp Leu Ser Asp
65                  70                  75                  80

Glu Ile Arg Asp Lys Phe Ile Lys Gln Phe Ile Tyr Glu Ala Gly Ile
                85                  90                  95

Arg Thr Pro Lys Tyr Lys Tyr Leu Val Phe Asp Tyr Leu Asp Gln Ile
            100                 105                 110

Thr Asn Ser Lys Lys Leu Val Leu Lys Thr Met Glu Gly Ile Gln Ile
            115                 120                 125

Ser Asp Ile Pro Arg Arg Lys Arg Glu Ile Glu Lys Ser Leu Val Asp
        130                 135                 140

Leu Ile Glu Thr Glu Asp Glu Phe Ile Ala Asp Pro Met Pro Asn Leu
145                 150                 155                 160
```

Tyr Phe Thr Arg Asp Pro Phe Ala Ser Val Gly Glu Gly Ile Ser Leu
            165                 170                 175

Asn Lys Met Tyr Ser Val Thr Arg Asn Arg Glu Thr Ile Tyr Ala Glu
            180                 185                 190

Tyr Ile Phe Lys Tyr His Pro Asp Tyr Lys Asp Gln Ala Arg Leu Tyr
            195                 200                 205

Tyr Asp Arg Tyr Asn Pro Tyr His Ile Glu Gly Gly Asp Val Leu Asn
210                 215                 220

Ile Asn Asp His Val Leu Ala Ile Gly Ile Ser Gln Arg Thr Thr Ala
225                 230                 235                 240

Glu Ala Ile Asp Gln Ile Ala Lys Asn Leu Phe Lys Asp Pro Glu Cys
            245                 250                 255

Lys Ile Asp Thr Ile Leu Ala Phe Asn Ile Pro Glu Ser Arg Ala Phe
            260                 265                 270

Met His Leu Asp Thr Val Phe Thr Gln Val Asp Tyr Asp Lys Phe Thr
            275                 280                 285

Tyr His Pro Gly Ile Met Gly Thr Leu Gln Val Phe Glu Ile Thr Glu
            290                 295                 300

Gly Asp Pro Asn Ser Asp Glu Asp Leu Thr Val Thr Glu Ile Asn
305                 310                 315                 320

Ala Pro Leu Glu Glu Ile Leu Thr Lys Tyr Val Gly Arg Lys Val Thr
            325                 330                 335

Leu Ile Pro Cys Ala Gly Gly Asp Lys Val Ser Ala Glu Arg Glu Gln
            340                 345                 350

Trp Asn Asp Gly Ser Asn Thr Leu Cys Ile Ala Pro Gly Val Val Val
            355                 360                 365

Val Tyr Asp Arg Asn Asn Leu Thr Asn Ala Val Leu Arg Ser Tyr Gly
            370                 375                 380

Leu Lys Val Ile Glu Ile His Gly Ala Glu Leu Ser Arg Gly Arg Gly
385                 390                 395                 400

Gly Pro Arg Cys Met Ser Met Pro Leu Val Arg Glu Asp Ile
            405                 410

<210> SEQ ID NO 56
<211> LENGTH: 408
<212> TYPE: PRT
<213> ORGANISM: Mycoplasma sp. CAG:472

<400> SEQUENCE: 56

Met His Val Thr Ser Glu Ile Lys Lys Leu Lys Lys Val Leu Val His
1               5                   10                  15

Arg Pro Gly Lys Glu Leu Leu Asn Leu Thr Pro Asp Thr Leu Gly Arg
            20                  25                  30

Leu Leu Phe Asp Asp Ile Pro Tyr Leu Lys Asp Ala Ile Leu Glu His
            35                  40                  45

Asp Glu Phe Cys Gln Ile Leu Arg Asp Asn Asp Val Glu Val Val Tyr
        50                  55                  60

Leu Glu Asp Leu Met Ala Glu Thr Leu Asp Glu Asn Pro Gln Val Lys
65                  70                  75                  80

Pro Ser Phe Ile Arg Gln Phe Ile Tyr Glu Ala Gly Val Arg Thr Pro
            85                  90                  95

Lys Tyr Lys Asp Leu Leu Phe Asp Tyr Leu Met Ser Tyr Thr Asn Asn
            100                 105                 110

Lys Glu Leu Val Leu Lys Thr Met Glu Gly Ile Lys Val Ser Glu Val
            115                 120                 125

His Arg Asn Lys Gln Asp Ser Glu Tyr Ser Leu Val Asp Gln Ile Ser
    130                 135                 140

Glu Glu Thr Lys Phe Leu Ala Glu Pro Met Pro Asn Leu Tyr Phe Thr
145                 150                 155                 160

Arg Asp Pro Phe Ala Ser Val Gly Asp Gly Ile Ile Leu Asn Lys Met
            165                 170                 175

His Ser Val Thr Arg Ser Arg Glu Thr Ile Tyr Ala Tyr Tyr Ile Phe
        180                 185                 190

Asn Tyr His Pro Asp Tyr Met Asp Lys Val Pro Lys Tyr Tyr Asp Arg
    195                 200                 205

Glu Asn Pro Phe Ser Ile Glu Gly Gly Asp Val Leu Asn Leu Asn Glu
210                 215                 220

His Thr Leu Ala Ile Gly Ile Ser Gln Arg Thr Ser Ala Glu Ala Ile
225                 230                 235                 240

Asp Leu Val Ala Lys Asn Met Phe Asn Asp Glu Lys Cys Asn Ile Asp
            245                 250                 255

Thr Ile Leu Ala Phe Lys Ile Pro Glu Cys Arg Ala Phe Met His Leu
        260                 265                 270

Asp Thr Val Phe Thr Gln Ile Asp Ile Asp Lys Phe Tyr His Pro
    275                 280                 285

Gly Ile Met Asp Thr Leu Glu Val Phe Glu Ile Thr Lys Asn Glu Asp
290                 295                 300

Asp Leu Asp Glu Val Arg Val Ile Lys Lys Glu Gly Ser Leu Glu Asn
305                 310                 315                 320

Ile Leu Glu Glu Tyr Leu Gly Ile Asp Ile Thr Leu Ile Pro Cys Ala
            325                 330                 335

Gly Gly Asp Lys Ile Ala Ser Glu Arg Glu Gln Trp Asn Asp Gly Thr
        340                 345                 350

Asn Thr Leu Cys Ile Ala Pro Gly Val Val Val Tyr Asn Arg Asn
    355                 360                 365

Asn Ile Thr Asn Glu Val Leu Arg Glu Lys Gly Ile Lys Val Ile Glu
370                 375                 380

Met Asn Ser Ala Glu Leu Ser Arg Gly Arg Gly Pro Arg Cys Met
385                 390                 395                 400

Ser Met Pro Leu Glu Arg Glu Asp
            405

<210> SEQ ID NO 57
<211> LENGTH: 401
<212> TYPE: PRT
<213> ORGANISM: Artificial Sequence
<220> FEATURE:
<223> OTHER INFORMATION: Made in Lab - M. columbinum - M. gallinarum
      chimeric ADI

<400> SEQUENCE: 57

Met Ser Lys Ile Asn Val Tyr Ser Glu Ile Gly 65                  70                  75                  80
        Thr Ala Glu Gln Lys Ala Ala Phe Ile Glu Lys Tyr Leu Asp Glu Ala
                        85                  90                  95

Thr Pro Ala Leu Ser Ala Glu Asn Arg Glu Arg Ala Lys Lys Tyr Ile
                    100                 105                 110

Leu Ser Leu Glu Met Gln Pro Val Lys Met Ile Arg Thr Met Met Ala
                115                 120                 125

Gly Leu Ser Lys Tyr Glu Leu Asn Val Glu Ser Asn Ile Glu Leu Ile
            130                 135                 140

Ile Asp Pro Met Pro Asn Leu Tyr Phe Thr Arg Asp Pro Phe Ala Ser
        145                 150                 155                 160

Ala Gly Asn Gly Ile Ser Leu Asn Asn Met Lys Tyr Val Thr Arg Lys
                        165                 170                 175

Arg Glu Thr Ile Phe Ala Glu Phe Ile Phe Ala Thr His Pro Asp Tyr
                    180                 185                 190

Lys Thr Thr Pro His Trp Phe Asp Arg Leu Asp Glu Gly Asn Ile Glu
                195                 200                 205

Gly Gly Asp Val Phe Ile Tyr Asn Lys Asp Thr Leu Val Ile Gly Val
            210                 215                 220

Ser Glu Arg Thr Asn Lys Glu Ala Ile Leu Thr Ile Ala Lys Lys Ile
        225                 230                 235                 240

Lys Asn Asn Lys Glu Ala Lys Phe Lys Lys Ile Val Ala Ile Asn Val
                        245                 250                 255

Pro Pro Met Pro Asn Leu Met His Leu Asp Thr Trp Leu Thr Met Val
                    260                 265                 270

Asp Lys Asp Lys Phe Leu Tyr Ser Pro Asn Met Leu Ser Val Leu Lys
                275                 280                 285

Val Trp Glu Ile Asp Leu Ser Lys Glu Ile Glu Met Val Glu Thr Asn
            290                 295                 300

Lys Pro Leu Ala Asp Val Leu Glu Ser Ile Ile Gly Val Lys Pro Val
        305                 310                 315                 320

Leu Ile Pro Ile Ala Gly Lys Gly Ala Thr Gln Leu Asp Ile Asp Ile
                        325                 330                 335

Glu Thr His Phe Asp Gly Thr Asn Tyr Leu Thr Ile Ala Pro Gly Val
                    340                 345                 350

Val Val Gly Tyr Ser Arg Asn Ile Lys Thr Glu Ala Ala Leu Arg Ala
                355                 360                 365

Ala Gly Val Thr Val Leu Ser Phe Glu Gly Asn Gln Leu Ser Leu Gly
            370                 375                 380

Met Gly Ser Ala Arg Cys Met Ser Met Pro Leu Val Arg Glu Asp Val
        385                 390                 395                 400

Lys

<210> SEQ ID NO 58
<211> LENGTH: 401
<212> TYPE: PRT
<213> ORGANISM: Artificial Sequence
<220> FEATURE:
<223> OTHER INFORMATION: Made in Lab - M. columbinum - M. iners chimeric
      ADI

<400> SEQUENCE: 58

Met Ser Lys Ile Asn Val Tyr Ser Glu Ile Gly Glu Leu Lys Glu Val
1 5 10 15

Leu Val His Thr Pro Gly Asp Glu Ile Arg Arg Ile Ser Pro Ser Arg

```
            20                  25                  30
Leu Asp Glu Leu Leu Phe Ser Ala Ile Leu Glu Pro Asn Glu Ala Ile
             35                  40                  45

Lys Glu His Lys Gly Phe Leu Lys Ile Leu Gln Asp Lys Gly Ile Lys
         50                  55                  60

Val Ile Gln Leu Ser Asp Leu Val Ala Glu Thr Tyr Lys His Tyr Ala
 65                  70                  75                  80

Ser Glu Ala Glu Lys Glu Ala Phe Ile Glu Lys Tyr Leu Asp Glu Ala
                 85                  90                  95

Thr Pro Val Leu Ser Lys Asp Met Arg Ala Lys Val Lys Asn Tyr Ile
            100                 105                 110

Leu Ser Met Gln Gly Glu Pro Val Lys Met Val Arg Thr Met Met Ala
        115                 120                 125

Gly Val Ser Lys Gln Glu Leu Asn Val Glu Ser Glu Val Glu Leu Ile
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
            180                 185                 190

Lys Thr Thr Pro His Trp Phe Asp Arg Leu Asp Glu Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
    290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 59
<211> LENGTH: 401
<212> TYPE: PRT
<213> ORGANISM: Artificial Sequence
<220> FEATURE:
```

<223> OTHER INFORMATION: Made in Lab - M. columbinum - M. meleagridis chimeric ADI

<400> SEQUENCE: 59

```
Met Ser Lys Ile Asn Val Tyr Ser Glu Ile Gly Glu Leu Lys Glu Val
1               5                   10                  15

Leu Val His Thr Pro Gly Asp Glu Ile Arg Arg Ile Ser Pro Ser Arg
                20                  25                  30

Leu Asp Glu Leu Leu Phe Ser Ala Ile Leu Glu Pro Asn Glu Ala Ile
            35                  40                  45

Lys Glu His Lys Gly Phe Leu Lys Ile Leu Gln Asp Lys Gly Ile Lys
        50                  55                  60

Val Ile Gln Leu Ser Asp Leu Val Ala Glu Thr Tyr Val Lys Tyr Ala
65                  70                  75                  80

Thr Ser Lys Glu Lys Glu Ser Phe Ile Glu Lys Trp Leu Asp Glu Ala
                85                  90                  95

Thr Pro Ala Leu Asn Ser Glu Asn Arg Ala Arg Val Lys Asn Tyr Ile
                100                 105                 110

Thr Ala Met Gln Gly Gln Pro Val Lys Met Val Arg Ala Met Met Ala
            115                 120                 125

Gly Val Ser Lys Gln Glu Leu Asn Ile Glu Ser Asp Val Glu Leu Ile
130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
                180                 185                 190

Lys Thr Thr Pro His Trp Phe Asp Arg Leu Asp Glu Gly Asn Ile Glu
            195                 200                 205

Gly Gly Asp Val Phe Ile Tyr Asn Lys Asp Thr Leu Val Ile Gly Val
        210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
                260                 265                 270

Asp Lys Asp Lys Phe Leu Tyr Ser Pro Asn Met Leu Ser Val Leu Lys
            275                 280                 285

Val Trp Glu Ile Asp Leu Ser Lys Glu Ile Glu Met Val Glu Thr Asn
        290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Ile Lys Thr Glu Ala Ala Leu Arg Ala
            355                 360                 365

Ala Gly Val Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400
```

Lys

<210> SEQ ID NO 60
<211> LENGTH: 401
<212> TYPE: PRT
<213> ORGANISM: Artificial Sequence
<220> FEATURE:
<223> OTHER INFORMATION: Made in Lab - M. gallinarum - M. columbinum chimeric ADI

<400> SEQUENCE: 60

```
Met Ser L

```
Val Val Gly Tyr Ser Arg Asn Glu Lys Thr Glu Lys Ala Leu Lys Ala
        355                 360                 365

Ala Gly Ile Thr Val Leu Ser Phe Glu Gly Asn Gln Leu Ser Leu Gly
        370                 375                 380

Met Gly Ser Ala Arg Cys Met Ser Met Pro Leu Val Arg Glu Asp Val
385                 390                 395                 400

Lys

<210> SEQ ID NO 61
<211> LENGTH: 401
<212> TYPE: PRT
<213> ORGANISM: Artificial Sequence
<220> FEATURE:
<223> OTHER INFORMATION: Made in Lab - M. gallinarum - M. iners chimeric
      ADI

<400> SEQUENCE: 61

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile
        35                  40                  45

Glu Glu His Lys Arg Phe Val Lys Leu Leu Glu Asp Arg Gly Ile Gln
    50                  55                  60

Ala Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
            100                 105                 110

Leu Ser Met Gln Gly Glu Pro Val Lys Met Val Arg Thr Met Met Ala
        115                 120                 125

Gly Val Ser Lys Gln Glu Leu Asn Val Glu Ser Glu Val Glu Leu Ile
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Arg Lys
                165                 170                 175

Arg Glu Thr Ile Phe Ala Glu Phe Ile Phe Ala Ile His Pro Glu Tyr
            180                 185                 190

Lys Glu Thr Pro His Trp Phe Asp Arg Leu Asp His Gly Ser Ile Glu
        195                 200                 205

Gly Gly Asp Val Phe Val Tyr Asn Lys Asp Thr Leu Val Ile Gly Val
    210                 215                 220

Ser Glu Arg Thr Asn Lys Glu Ala Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Ile Tyr Ser Pro Asn Met Leu Ser Val Leu Lys
        275                 280                 285

Ile Trp Glu Ile Asp Leu Ala Lys Pro Ile Glu Met Val Glu Ser Asn
    290                 295                 300
```

```
Lys Ser Leu Thr Glu Val Leu Glu Ser Ile Ile Gly Glu Lys Pro Ile
305                 310                 315                 320

Leu Ile Pro Ile Ala Gly Gly Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Glu Lys Thr Glu Lys Ala Leu Lys Ala
                355                 360                 365

Ala Gly Ile Thr Val Leu Ser Phe Glu Gly Asn Gln Leu Ser Leu Gly
            370                 375                 380

Met Gly Ser Ala Arg Cys Met Ser Met Pro Leu Val Arg Glu Asp Val
385                 390                 395                 400

Lys

<210> SEQ ID NO 62
<211> LENGTH: 401
<212> TYPE: PRT
<213> ORGANISM: Artificial Sequence
<220> FEATURE:
<223> OTHER INFORMATION: Made in Lab - M. gallinarum - M. meleagridis
      chimeric ADI

<400> SEQUENCE: 62

Met Ser Lys Ile Arg Val Tyr Ser Glu Ile Gly Asn Leu Lys Lys Val
1

```
Pro Pro Met Pro Asn Leu Met His Leu Asp Thr Trp Leu Thr Met Val
            260                 265                 270
Asp Lys Asn Lys Phe Ile Tyr Ser Pro Asn Met Leu Ser Val Leu Lys
        275                 280                 285
Ile Trp Glu Ile Asp Leu Ala Lys Pro Ile Glu Met Val Glu Ser Asn
290                 295                 300
Lys Ser Leu Thr Glu Val Leu Glu Ser Ile Ile Gly Glu Lys Pro Ile
305                 310                 315                 320
Leu Ile Pro Ile Ala Gly Gly Ala Ser Gln Leu Asp Ile Asp Ile
                325                 330                 335
Glu Thr His Phe Asp Gly Thr Asn Tyr Leu Thr Ile Ala Pro Gly Val
            340                 345                 350
Val Val Gly Tyr Ser Arg Asn Glu Lys Thr Glu Lys Ala Leu Lys Ala
        355                 360                 365
Ala Gly Ile Thr Val Leu Ser Phe Glu Gly Asn Gln Leu Ser Leu Gly
370                 375                 380
Met Gly Ser Ala Arg Cys Met Ser Met Pro Leu Val Arg Glu Asp Val
385                 390                 395                 400
Lys
```

<210> SEQ ID NO 63
<211> LENGTH: 401
<212> TYPE: PRT
<213> ORGANISM: Artificial Sequence
<220> FEATURE:
<223> OTHER INFORMATION: Made in Lab - M. iners - M. columbinum chimeric ADI

<400> SEQUENCE: 63

```
Met Ser Lys Ile Asn Val Tyr Ser Glu Ile Gly Val Leu Lys Glu Val
1               5                   10                  15
Leu Val His Thr Pro Gly Asp Glu Ile Arg Arg Ile Ala Pro Ser Arg
            20                  25                  30
Leu As

```
Gly Gly Asp Val Phe Ile Tyr Asn Lys Asp Thr Leu Val Ile Gly Val
        210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
                260                 265                 270

Asp Lys Asn Lys Phe Leu Tyr Ser Pro Asn Met Leu Ser Val Leu Lys
            275                 280                 285

Val Trp Glu Ile Asp Leu Ser Lys Pro Ile Glu Met Val Glu Thr Asn
290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
                340                 345                 350

Val Val Gly Tyr Ser Arg Asn Val Lys Thr Glu Ala Ala Leu Arg Ala
            355                 360                 365

Ala Gly Val Thr Val Leu Ser Phe Glu Gly Asn Gln Leu Ser Leu Gly
370                 375                 380

Met Gly Ser Ala Arg Cys Met Ser Met Pro Leu Val Arg Glu Asp Val
385                 390                 395                 400

Lys

<210> SEQ ID NO 64
<211> LENGTH: 401
<212> TYPE: PRT
<213> ORGANISM: Artificial Sequence
<220> FEATURE:
<223> OTHER INFORMATION: Made in Lab - M. iners - M. gallinarum chimeric
      ADI

<400> S

```
Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Val Trp Glu Ile Asp Leu Ser Lys Pro Ile Glu Met Val Glu Thr Asn
    290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 65
<211> LENGTH: 401
<212> TYPE: PRT
<213> ORGANISM: Artificial Sequence
<220> FEATURE:
<223> OTHER INFORMATION: Made in Lab - M. iners - M. meleagridis
      chimeric ADI

<400> SEQUENCE: 65

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Ser Ala Ala Ile
        35                  40                  45

Gln Glu His Lys Ser Phe Leu Lys Ile Leu Gln Asp Arg Gly Ile Lys
    50                  55                  60

Thr Ile Gln Leu Ser Asp Leu Val Ala Glu Thr Tyr Val Lys Tyr Ala
65                  70                  75                  80

Thr Ser Lys Glu Lys Glu Ser Phe Ile Glu Lys Trp Leu Asp Glu Ala
                85                  90                  95

Thr Pro Ala Leu Asn Ser Glu Asn Arg Ala Arg Val Lys Asn Tyr Ile
            100                 105                 110
```

-continued

```
Thr Ala Met Gln Gly Gln Pro Val Lys Met Val Arg Ala Met Met Ala
        115                 120                 125

Gly Val Ser Lys Gln Glu Leu Asn Ile Glu Ser Asp Val Glu Leu Ile
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Val Trp Glu Ile Asp Leu Ser Lys Pro Ile Glu Met Val Glu Thr Asn
    290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys
```

<210> SEQ ID NO 66
<211> LENGTH: 401
<212> TYPE: PRT
<213> ORGANISM: Artificial Sequence
<220> FEATURE:
<223> OTHER INFORMATION: Made in Lab - M. meleagridis - M. columbinum chimeric ADI

<400> SEQUENCE: 66

```
Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Gln Pro Glu Gln Ala Ile
        35                  40                  45

Lys Glu His Gln Ser Phe Val Lys Ile Leu Gln Asp Arg Gly Ile Lys
    50                  55                  60
```

```
Val Ile Gln Leu Ser Asp Leu Val Ala Glu Thr Tyr Thr Tyr His Ala
 65                  70                  75                  80

Thr Gln Lys Glu Arg Glu Ala Phe Ile Glu Lys Trp Leu Asp Glu Ala
                 85                  90                  95

Glu Pro Ala Leu Thr Lys Asp Leu Arg Ala Lys Val Lys Ser Tyr Val
            100                 105                 110

Leu Ser Lys Glu Gly Thr Pro Val Ala Met Val Arg Thr Met Met Ala
        115                 120                 125

Gly Val Ser Lys Gln Glu Leu Asn Val Glu Ser Thr Glu Leu Val
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Gln Thr Pro His Trp Phe Asp Arg Leu Asp Lys Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Ile Trp Glu Ile Asp Leu Ser Lys Glu Ile Lys Met Val Glu Thr Ser
    290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Lys Ala
        355                 360                 365

Ala Gly Val Thr Val Tyr Ser Phe Asp Gly Asn Gln Leu Ser Leu Gly
    370                 375                 380

Met Gly Ser Gly Arg Cys Met Ser Met Pro Leu Val Arg Glu Asp Val
385                 390                 395                 400

Lys

<210> SEQ ID NO 67
<211> LENGTH: 401
<212> TYPE: PRT
<213> ORGANISM: Artificial Sequence
<220> FEATURE:
<223> OTHER INFORMATION: Made in Lab - M. meleagridis - M. gallinarum
      chimeric ADI

<400> SEQUENCE: 67

Met Ser Lys Ile Asn Val Tyr Ser Glu Ile Gly Val Leu Lys Glu Val
1               5                   10                  15

```
Leu Val His Thr Pro Gly Asp Glu Ile Arg Arg Ile Ser Pro Ser Arg
             20                  25                  30

Leu Asp Glu Leu Leu Phe Ser Ala Ile Leu Gln Pro Glu Gln Ala Ile
         35                  40                  45

Lys Glu His Gln Ser Phe Val Lys Ile Leu Gln Asp Arg Gly Ile Lys
     50                  55                  60

Val Ile Gln Leu Ser Asp Leu Val Ala Glu Thr Tyr Val Lys Tyr Ala
 65                  70                  75                  80

Thr Ala Glu Gln Lys Ala Ala Phe Ile Glu Lys Tyr Leu Asp Glu Ala
                 85                  90                  95

Thr Pro Ala Leu Ser Ala Glu Asn Arg Glu Arg Ala Lys Lys Tyr Ile
             100                 105                 110

Leu Ser Leu Glu Met Gln Pro Val Lys Met Ile Arg Thr Met Met Ala
         115                 120                 125

Gly Leu Ser Lys Tyr Glu Leu Asn Val Glu Ser Asn Ile Glu Leu Ile
130                 135                 140

Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                 165                 170                 175

Arg Glu Thr Ile Phe Ala Glu Phe Ile Phe Ser Ile His Pro Glu Tyr
             180                 185                 190

Lys Gln Thr Pro His Trp Phe Asp Arg Leu Asp Lys Gly Asn Ile Glu
         195                 200                 205

Gly Gly Asp Val Phe Ile Tyr Asn Lys Asp Thr Leu Val Ile Gly Val
210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Lys Ile Val Ala Ile Asn Val
                 245                 250                 255

Pro Pro Met Pro Asn Leu Met His Leu Asp Thr Trp Leu Thr Met Val
             260                 265                 270

Asp Lys Asn Lys Phe Leu Tyr Ser Pro Asn Met Leu Ser Val Leu Lys
         275                 280                 285

Ile Trp Glu Ile Asp Leu Ser Lys Glu Ile Lys Met Val Glu Thr Ser
290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile
                 325                 330                 335

Glu Thr His Phe Asp Gly Thr Asn Tyr Leu Thr Ile Ala Pro Gly Val
             340                 345                 350

Val Val Gly Tyr Ser Arg Asn Val Lys Thr Glu Ala Ala Leu Lys Ala
         355                 360                 365

Ala Gly Val Thr Val Tyr Ser Phe Asp Gly Asn Gln Leu Ser Leu Gly
370                 375                 380

Met Gly Ser Gly Arg Cys Met Ser Met Pro Leu Val Arg Glu Asp Val
385                 390                 395                 400

Lys

<210> SEQ ID NO 68
<211> LENGTH: 401
<212> TYPE: PRT
```

<213> ORGANISM: Artificial Sequence
<220> FEATURE:
<223> OTHER INFORMATION: Made in Lab - M. meleagridis - M. iners
      chimeric ADI

<400> SEQUENCE: 68

```
Met Ser Lys Ile Asn Val Tyr Ser Glu Ile Gly Val Leu Lys Glu

Met Gly Ser Gly Arg Cys Met Ser Met Pro Leu Val Arg Glu Asp Val
385                 390                 395                 400

Lys

<210> SEQ ID NO 69
<211> LENGTH: 281
<212> TYPE: PRT
<213> ORGANISM: Homo sapiens

<400> SEQUENCE: 69

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 70
<211> LENGTH: 168
<212> TYPE: PRT
<213> ORGANISM: Homo sapiens

<400> SEQUENCE: 70

Val Arg Glu Arg Gly Pro Gln Arg Val Ala Ala His Ile Thr Gly Thr
1               5                   10                  15

Arg Gly Arg Ser Asn Thr Leu Ser Ser Pro Asn Ser Lys Asn Glu Lys

```
                    20                  25                  30
Ala Leu Gly Arg Lys Ile Asn Ser Trp Glu Ser Ser Arg Ser Gly His
                35                  40                  45

Ser Phe Leu Ser Asn Leu His Leu Arg Asn Gly Glu Leu Val Ile His
    50                  55                  60

Glu Lys Gly Phe Tyr Tyr Ile Tyr Ser Gln Thr Tyr Phe Arg Phe Gln
 65                  70                  75                  80

Glu Glu Ile Lys Glu Asn Thr Lys Asn Asp Lys Gln Met Val Gln Tyr
                    85                  90                  95

Ile Tyr Lys Tyr Thr Ser Tyr Pro Asp Pro Ile Leu Leu Met Lys Ser
                100                 105                 110

Ala Arg Asn Ser Cys Trp Ser Lys Asp Ala Glu Tyr Gly Leu Tyr Ser
                115                 120                 125

Ile Tyr Gln Gly Gly Ile Phe Glu Leu Lys Glu Asn Asp Arg Ile Phe
            130                 135                 140

Val Ser Val Thr Asn Glu His Leu Ile Asp Met Asp His Glu Ala Ser
145                 150                 155                 160

Phe Phe Gly Ala Phe Leu Val Gly
                165
```

<210> SEQ ID NO 71
<211> LENGTH: 233
<212> TYPE: PRT
<213> ORGANISM: Homo sapiens

<400> SEQUENCE: 71

```
Met Ser Thr Glu Ser Met Ile Arg Asp Val Glu Leu Ala Glu Glu Ala
 1               5                  10                  15

Leu Pro Lys Lys Thr Gly Gly Pro Gln Gly Ser Arg Arg Cys Leu Phe
                20                  25                  30

Leu Ser Leu Phe Ser Phe Leu Ile Val Ala Gly Ala Thr Thr Leu Phe
            35                  40                  45

Cys Leu Leu His Phe Gly Val Ile Gly Pro Gln Arg Glu Glu Phe Pro
     50                  55                  60

Arg Asp Leu Ser Leu Ile Ser Pro Leu Ala Gln Ala Val Arg Ser Ser
 65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220
```

```
Gln Val Tyr Phe Gly Ile Ile Ala Leu
225                 230
```

```
<210> SEQ ID NO 72
<211> LENGTH: 281
<212> TYPE: PRT
<213> ORGANISM: Homo sapiens

<400> SEQUENCE: 72
```

```
Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280
```

```
<210> SEQ ID NO 73
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 73

Gly Ser Gly Ser
1
```

```
<210> SEQ ID NO 74
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 74

Gly Gly Ser Gly
1

<210> SEQ ID NO 75
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 75

Gly Gly Gly Ser
1

<210> SEQ ID NO 76
<211> LENGTH: 5
<212> TYPE: PRT
<213> ORGANISM: Artificial Sequence
<220> FEATURE:
<223> OTHER INFORMATION: Made in Lab - Linker

<400> SEQUENCE: 76

Gly Gly Gly Gly Ser
1               5

<210> SEQ ID NO 77
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 77

Gly Asn Gly Asn
1

<210> SEQ ID NO 78
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 78

Gly Gly Asn Gly
1

<210> SEQ ID NO 79
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 79

Gly Gly Gly Asn
1

<210> SEQ ID NO 80
```

```
<211> LENGTH: 5
<212> TYPE: PRT
<213> ORGANISM: Artificial Sequence
<220> FEATURE:
<223> OTHER INFORMATION: Made in Lab - Linker

<400> SEQUENCE: 80

Gly Gly Gly Gly Asn
1               5

<210> SEQ ID NO 81
<211> LENGTH: 7
<212> TYPE: PRT
<213> ORGANISM: Artificial Sequence
<220> FEATURE:
<223> OTHER INFORMATION: Made in Lab - Linker

<400> SEQUENCE: 81

Ala Glu Ala Ala Ala Lys Ala
1               5

<210> SEQ ID NO 82
<211> LENGTH: 12
<212> TYPE: PRT
<213> ORGANISM: Artificial Sequence
<220> FEATURE:
<223> OTHER INFORMATION: Made in Lab - Linker

<400> SEQUENCE: 82

Ala Glu Ala Ala Ala Lys Glu Ala Ala Ala Lys Ala
1               5                   10

<210> SEQ ID NO 83
<211> LENGTH: 6
<212> TYPE: PRT
<213> ORGANISM: Artificial Sequence
<220> FEATURE:
<223> OTHER INFORMATION: Made in Lab - Linker

<400> SEQUENCE: 83

Ala Pro Ala Pro Lys Pro
1               5

<210> SEQ ID NO 84
<211> LENGTH: 12
<212> TYPE: PRT
<213> ORGANISM: Artificial Sequence
<220> FEATURE:
<223> OTHER INFORMATION: Made in Lab - Linker

<400> SEQUENCE: 84

Ala Pro Ala Pro Lys Pro Glu Pro Ala Pro Lys Pro
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Made in Lab - Linker

<400> SEQUENCE: 85

Gly Gly Gly Gly Ser Gly Gly Gly Gly Ser
1               5                   10

<210> SEQ ID NO 86
<211> LENGTH: 5
```

```
<212> TYPE: PRT
<213> ORGANISM: Artificial Sequence
<220> FEATURE:
<223> OTHER INFORMATION: Made in Lab - Linker

<400> SEQUENCE: 86

Asp Gly Gly Gly Ser
1               5

<210> SEQ ID NO 87
<211> LENGTH: 5
<212> TYPE: PRT
<213> ORGANISM: Artificial Sequence
<220> FEATURE:
<223> OTHER INFORMATION: Made in Lab - Linker

<400> SEQUENCE: 87

Thr Gly Glu Lys Pro
1               5

<210> SEQ ID NO 88
<211> LENGTH: 4
<212> TYPE: PRT
<213> ORGANISM: Artificial Sequence
<220> FEATURE:
<223> OTHER INFORMATION: Made in Lab - Linker

<400> SEQUENCE: 88

Gly Gly Arg Arg
1

<210> SEQ ID NO 89
<211> LENGTH: 14
<212> TYPE: PRT
<213> ORGANISM: Artificial Sequence
<220> FEATURE:
<223> OTHER INFORMATION: Made in Lab - Linker

<400> SEQUENCE: 89

Glu Gly Lys Ser Ser Gly Ser Gly Ser Glu Ser Lys Val Asp
1               5                   10

<210> SEQ ID NO 90
<211> LENGTH: 18
<212> TYPE: PRT
<213> ORGANISM: Artificial Sequence
<220> FEATURE:
<223> OTHER INFORMATION: Made in Lab - Linker

<400> SEQUENCE: 90

Lys Glu Ser Gly Ser Val Ser Ser Glu Gln Leu Ala Gln Phe Arg Ser
1               5                   10                  15

Leu Asp

<210> SEQ ID NO 91
<211> LENGTH: 8
<212> TYPE: PRT
<213> ORGANISM: Artificial Sequence
<220> FEATURE:
<223> OTHER INFORMATION: Made in Lab - Linker

<400> SEQUENCE: 91

Gly Gly Arg Arg Gly Gly Gly Ser
1               5

<210> SEQ ID NO 92
```

```
<211> LENGTH: 9
<212> TYPE: PRT
<213> ORGANISM: Artificial Sequence
<220> FEATURE:
<223> OTHER INFORMATION: Made in Lab - Linker

<400> SEQUENCE: 92

Leu Arg Gln Arg Asp Gly Glu Arg Pro
1               5

<210> SEQ ID NO 93
<211> LENGTH: 12
<212> TYPE: PRT
<213> ORGANISM: Artificial Sequence
<220> FEATURE:
<223> OTHER INFORMATION: Made in Lab - Linker

<400> SEQUENCE: 93

Leu Arg Gln Lys Asp Gly Gly Gly Ser Glu Arg Pro
1               5                   10

<210> SEQ ID NO 94
<211> LENGTH: 16
<212> TYPE: PRT
<213> ORGANISM: Artificial Sequence
<220> FEATURE:
<223> OTHER INFORMATION: Made in Lab - Linker

<400> SEQUENCE: 94

Leu Arg Gln Lys Asp Gly Gly Gly Ser Gly Gly Gly Ser Glu Arg Pro
1               5                   10                  15

<210> SEQ ID NO 95
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 95 rccrccatgg                                                          10

<210> SEQ ID NO 96
<211> LENGTH: 6
<212> TYPE: PRT
<213> ORGANISM: Artificial Sequence
<220> FEATURE:
<223> OTHER INFORMATION: Made in Lab - Linker
<220> FEATURE:
<221> NAME/KEY: MOD_RES
<222> LOCATION: (1)..(1)
<223> OTHER INFORMATION: Xaa is any amino acid
<220> FEATURE:
<221> NAME/KEY: MOD_RES
<222> LOCATION: (3)..(3)
<223> OTHER INFORMATION: Xaa is any amino acid
<220> FEATURE:
<221> NAME/KEY: MOD_RES
<222> LOCATION: (5)..(5)
<223> OTHER INFORMATION: Xaa is any amino acid

<400> SEQUENCE: 96
```

```
Xaa Pro Xaa Pro Xaa Pro
1               5

<210> SEQ ID NO 97
<211> LENGTH: 12
<212> TYPE: PRT
<213> ORGANISM: Artificial Sequence
<220> FEATURE:
<223> OTHER INFORMATION: Made in Lab - Linker
<220> FEATURE:
<221> NAME/KEY: MOD_RES
<222> LOCATION: (1)..(1)
<223> OTHER INFORMATION: Xaa is any amino acid
<220> FEATURE:
<221> NAME/KEY: MOD_RES
<222> LOCATION: (3)..(3)
<223> OTHER INFORMATION: Xaa is any amino acid
<220> FEATURE:
<221> NAME/KEY: MOD_RES
<222> LOCATION: (5)..(5)
<223> OTHER INFORMATION: Xaa is any amino acid
<220> FEATURE:
<221> NAME/KEY: MOD_RES
<222> LOCATION: (7)..(7)
<223> OTHER INFORMATION: Xaa is any amino acid
<220> FEATURE:
<221> NAME/KEY: MOD_RES
<222> LOCATION: (9)..(9)
<223> OTHER INFORMATION: Xaa is any amino acid
<220> FEATURE:
<221> NAME/KEY: MOD_RES
<222> LOCATION: (11)..(11)
<223> OTHER INFORMATION: Xaa is any amino acid

<400> SEQUENCE: 97

Xaa Pro Xaa Pro Xaa Pro Xaa Pro Xaa Pro Xaa Pro
1               5                   10
```